US008026092B2

(12) United States Patent
Lemon et al.

(10) Patent No.: US 8,026,092 B2
(45) Date of Patent: Sep. 27, 2011

(54) REPLICATION COMPETENT HEPATITIS C VIRUS AND METHODS OF USE

(75) Inventors: Stanley M. Lemon, Galveston, TX (US); MinKyung Yi, Galveston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 494 days.

(21) Appl. No.: 10/580,979

(22) PCT Filed: Dec. 1, 2004

(86) PCT No.: PCT/US2004/040120
§ 371 (c)(1),
(2), (4) Date: Apr. 9, 2007

(87) PCT Pub. No.: WO2005/053516
PCT Pub. Date: Jun. 16, 2005

(65) Prior Publication Data
US 2007/0292840 A1    Dec. 20, 2007

Related U.S. Application Data

(60) Provisional application No. 60/525,989, filed on Dec. 1, 2003.

(51) Int. Cl.
*C12N 15/51* (2006.01)
*C12N 7/08* (2006.01)
(52) U.S. Cl. ............... 435/235.1; 424/228.1; 435/169.1; 435/70.1; 435/440
(58) Field of Classification Search ............... 424/228.1
See application file for complete search history.

(56) References Cited

U.S. PATENT DOCUMENTS

| | | |
|---|---|---|
| 5,766,906 A | 6/1998 | Lemon et al. |
| 5,846,767 A | 12/1998 | Halpin et al. |
| 5,874,565 A | 2/1999 | Rice et al. |
| 5,912,167 A | 6/1999 | Palmenberg et al. |
| 6,127,116 A | 10/2000 | Rice et al. |
| 6,392,028 B1 | 5/2002 | Rice, III et al. |
| 6,630,343 B1 | 10/2003 | Bartenschlager |
| 6,689,559 B2 | 2/2004 | Wimmer et al. |
| 6,921,634 B2 | 7/2005 | Lemon et al. |
| 6,930,095 B2 | 8/2005 | Bichko |
| 6,943,246 B2 | 9/2005 | Rice et al. |
| 7,049,428 B1 | 5/2006 | Rice, III et al. |
| 7,288,369 B2 | 10/2007 | Lemon et al. |
| 2002/0098202 A1 | 7/2002 | Wimmer et al. |
| 2002/0155582 A1 | 10/2002 | Lemon et al. |
| 2003/0073080 A1 | 4/2003 | Rice et al. |
| 2005/0153281 A1 | 7/2005 | Lemon et al. |
| 2008/0311576 A1 | 12/2008 | Lemon et al. |

FOREIGN PATENT DOCUMENTS

| | | |
|---|---|---|
| WO | WO 00/14263 | 3/2000 |
| WO | WO 02/059321 A2 | 8/2002 |
| WO | WO 02/059321 A3 | 8/2002 |
| WO | WO 2004/055216 A2 | 7/2004 |
| WO | WO 2004/055216 A3 | 7/2004 |
| WO | WO 2005/053516 | 6/2005 |

OTHER PUBLICATIONS

Franciscus A. In HCV Genotype & Quasispecies published by HCSP, Feb. 2006, pp. 1-3.*
Chamberlian et al. J. gene Virol. 1997, vol. 78, pp. 1341-1347.*
Iacovacci et al., "Molecular Characterization and Dynamics of Hepatitis C Virus Replication in Human Fetal Hepatocytes Infected In Vitro," *Hepatology*, 1997; 26(5):1328-1337.
Lanford et al., "Demonstration of in Vitro Infection of Chimpanzee Hepatocytes with Hepatitis C Virus Using Strand-Specific RT/PCR," *Virology*, 1994;202(2): 606-614.
Nakajima et al., "Characterization of Long-Term Cultures of Hepatitis C Virus," *Journal of Virology*, May 1996;70(5):3325-3329.
Shimizu et al., "Evidence for in vitro replication of hepatitis C virus genome in a human T-cell line," *Proc. Natl. Acad. Sci. USA*, Jun. 1992;89:5477-5481.
Shimizu et al., "Correlation between the infectivity of hepatitis C virus in vivo and its infectivity in vitro," *Proc. Natl. Acad. Sci. USA*, Jul. 1993;90:6037-6041.
U.S. Appl. No. 60/525,989, Lemon et al, Dec. 1. 2003.
Ausubel et al., eds., *Current Protocols in Molecular Biology*, vol. 1-4, John Wiley & Sons, U.S.; title page, publication page and table of contents only, 12 pgs. (1994).
Bartenschlager et al., "Replication of Hepatitis C Virus," *J. Gen. Virol.*, Jul. 2000; 81(7): 1631-1648.
Bartosch et al., "Infectious Hepatitis C Virus Pseudo-particles Containing Functional E1-E2 Envelope Protein Complexes," *J Exp Med*, Mar. 3, 2003;197(5):633-642.
Beard et al., "An Infectious Molecular Clone of a Japanese Genotype 1 b Hepatitis C Virus," *Hepatology*, Jul. 1999; 30(1):316-324.
Berger et al., "Secreted Placental Alkaline Phosphatase: A Powerful New Quantitative Indicator of Gene Expression in Eukaryotic Cells," *Gene*, Jun. 15, 1988; 66(1):1-10.
Bieniasz et al., "Highly Divergent Lentiviral Tat Proteins Activate Viral Gene Expression by a Common Mechanism," *Mol. Cell. Biol.*, Jul. 1999; 19(7):4592-9.
"BLAST," National Institutes of Health, Bethesda, MD [online]. Retrieved from Internet on Apr. 17, 2001. <URL:http://www.ncbi.nlm.nih.gov/gorf/b12.html>, 2 pgs.
Blight et al., "Efficient Initiation of HCV RNA Replication in Cell Culture," *Science*, Dec. 8, 2000; 290(5498):1972-1975.
Blight et al., "Highly Permissive Cell Lines for Subgenomic and Genomic Hepatitis C Virus RNA Replication," *J. Virol.*, Dec. 2002; 76(24):13001-13014.

(Continued)

*Primary Examiner* — Bao Li
(74) *Attorney, Agent, or Firm* — Mueting, Raasch & Gebhardt, P.A.

(57) ABSTRACT

The present invention provides replication competent polynucleotides that include a coding sequence encoding a hepatitis C virus polyprotein having adaptive mutations. The invention also includes methods for malting replication competent polynucleotides, identifying a compound that inhibits replication of a replication competent polynucleotide, selecting a replication competent polynucleotide, and detecting a replication competent polynucleotide.

37 Claims, 38 Drawing Sheets

OTHER PUBLICATIONS

Blight et al., "Efficient Replication of Hepatitis C Virus Genotype 1a RNAs in Cell Culture," *J. Virol.*, Mar. 2003; 77(5):3181-3190.

Bukh et al., "Sequence analysis of the 5' noncoding region of hepatitis C virus," *Proc. Nat. Acad. Sci. USA*, Jun. 1992;89: 4942-46.

Bukh et al., "Mutations that Permit Efficient Replication of Hepatitis C Virus RNA in Huh-7 Cells Prevent Productive Replication in Chimpanzees," *Proc. Natl. Acad. Sci. USA*, Oct. 29, 2002; 99(22):14416-14421.

Cai et al., "Robust Production of Infectious Hepatitis C Virus (HCV) from Stably HCV cDNA-Transfected Human Hepatoma Cells," *Journal of Virology*, Nov. 2005, 79(22):13963-13973.

Choo et al., "Genetic Organization and Diversity of the Hepatitis C Virus," *Proc. Natl. Acad. Sci. USA*, Mar. 1991; 88(6):2451-2455.

Cullen,"*Trans*-activation of Human Immunodeficiency Virus Occurs via a Bimodal Mechanism," *Cell*. Sep. 26, 1986 ;46(7):973-82.

Cullen, Bryan R., "HIV-1 Auxiliary Proteins: Making Connections in a Dying Cell," *Cell*, May 29, 1998; 93:685-92.

Date et al., "Genotype 2a Hepatitis C Virus Subgenomic Replicon Can Replicate in HepG2 and IMY-N9 Cells," *J. Biol. Chem.*, May 21, 2004; 279(21):22371-22376.

Duhamel et al., "Secondary structure content of the HDV ribozyme in 95% formamide," *Nucleic Acids Research*, 1996;24(20):3911-3917.

Enomoto et al., "There are Two Major Types of Hepatitis C Virus in Japan," *Biochem. Biophys. Res. Commun.*, Aug. 16, 1990; 170(3):1021-1025.

Evans et al., "Phosphorylation of hepatitis C virus nonstructural protein 5A modulates its protein interactions and viral RNA replication," *PNAS*, Aug. 31, 2004;101(35):13038-13043.

Forns et al., "Hepatitis C Virus Lacking the Hypervariable Region 1 of the Second Envelope Protein Is Infectious and Causes Acute Resolving or Persistent Infection in Chimpanzees," *PNAS*, Nov. 21, 2000; 97(24):13318-23.

Foy et al., "Regulation of Interferon Regulatory Factor-3 by the Hepatitis C Virus Serine Protease," *Science*, May 16, 2003; 300(5622):1145-1148.

Foy et al., "Control of antiviral defenses through hepatitis C virus disruption of retinoic acid-inducible gene-I signaling," *PNAS*, Feb. 22, 2005;102(8):2986-2991.

Frese et al., "Interferon-α inhibits hepatitis C virus subgenomic RNA replication by an MxA-independent pathway," *J. Gen. Virol.*, Apr. 2001; 82(pt.4):723-33.

Fried et al., "Peginterferon Alfa-2a Plus Ribavirin for Chronic Hepatitis C Virus Infection,"*N. Engl. J. Med.*, Sep. 26, 2002; 347(13):975-982.

Fujisawa et al., "The Indirect Association of Human T-cell Leukemia Virus *tax* Protein with DNA Results in Transcriptional Activation," *J. Virol.*, Aug. 1991; 65(8):4525-4528.

Gale et al., "Repression of the PKR Protein Kinase by the Hepatitis C Virus NS5A Protein: a Potential Mechanism of Interferon Resistance," *Clin. Diagn. Virol.*, Jul. 1998; 10(2-3):157-162.

Gale et al., "Evidence that hepatitis C virus resistance to Interferon is mediated through repression of the PKR protein kinase by the nonstructural 5A protein," *Virology*, 1997;230:217-227.

Graham et al., "A genotype 2b NS5B polymerase with novel substitutions supports replication of a chimeric HCV 1 b:2b replicon containing a genotype 1b NS3-5A background," *Antiviral Research*, Jan. 2006; 69(1):24-30.

Grobler et al., "Identification of a Key Determinant of Hepatitis C Virus Cell Culture Adaptation in Domain II of NS3 Helicase," *J. Biol. Chem.*, May 9, 2003; 278(19):16741-16746.

Gu et al., "Replication Studies Using Genotype 1a Subgenomic Hepatitis C Virus Replicons", *J. Virol.*, May 2003; 77(9):5352-5359.

Guo et al., "Identification of a Novel RNA Species in Cell Lines Expressing HCV Subgenomic Replicons," Abstract P045, 7th International Meeting on Hepatitis C Virus and Related Viruses (Molecular Virology and Pathogenesis), The Marriott Resort Hotel, Gold Coast, Queensland, Australia, Dec. 3-7, 2000; 1 pg.

Guo et al., "Effect of Alpha Interferon on the Hepatitis C Virus Replicon," *J. Virol.*, Sep. 2001; 75(18):8516-8523.

Hadzopoulou-Cladaras et al., "The *rev* (*trs/art*) Protein of Human Immunodeficiency Virus Type 1 Affects Viral mRNA and Protein Expression via a *cis*-acting Sequence in the *env* Region," *J. Virol.*, Mar. 1989; 63(3): 1265-1274.

Harlow et al., *Antibodies: A Laboratory Manual*, Cold Spring Harbor Laboratory Press, Cold Spring Harbor, NY; title page, publisher's page, and table of contents, 9 pages (1988).

Hayashi et al., "Molecular cloning and heterogeneity of the human hepatitis C virus (HCV) genome," *J. Hepatol.*, 1993;17 (Suppl. 3): S94-S107.

Heller et al., "An in vitro model of hepatitis C virion production," *PNAS*, Feb. 15, 2005;102(7:)2579-2583. Published online Feb. 8, 2005.

Honda et al., "Stability of a stem-loop involving the initiator AUG controls the efficiency of internal initiation of translation of hepatitis C virus RNA," *RNA*, 1996;2: 955-68.

Hsu et al., "Hepatitis C virus glycoproteins mediate pH-dependent cell entry of pseudotyped retroviral particles," *PNAS*, Jun. 10, 2003;100(12): 7271-7276.

Ikeda et al., "Human Hepatocyte Clonal Cell Lines that Support Persistent Replication of Hepatitis C Virus," *Virus Res.*, Aug. 1998; 56(2):157-167.

Ikeda et al., "Selectable Subgenomic and Genome-Length Dicistronic RNAs Derived from an Infectious Molecular Clone of the HCV-N Strain of Hepatitis C Virus Replicate Efficiently in Cultured Huh7 Cells," *J. Virol.*, Mar. 2002;76(6): 2997-3006.

Inchauspe et al., "Genomic Structure of the Human Prototype Strain H of Hepatitis C Virus: Comparison with American and Japanese Isolates", *Proc. Natl. Acad. Sci. USA*, Nov. 15, 1991; 88(22):10292-10296.

Kanda et al., "Generation of Infectious Hepatitis C Virus in Immortalized Human Hepatocytes," *Journal of Virology*, May 2006; 80(9):4633-4639.

Kato et al., "Replication of hepatitis C virus in cultured non-neoplastic human hepatocytes," *JPN. J. Cancer Research*, Aug. 1996;87:787-792.

Kato et al., "Susceptibility of Human T-Lymphotropic Virus Type I Infected Cell Line MT-2 to Hepatitis C Virus Infection," *Biochem. Biophys, Res. Commun.*, Jan. 1995; 206(3):863-869.

Kato et al., "Efficient Replication of the Genotype 2a Hepatitis C Virus Subgenomic Replicon," *Gastroenterology*, Dec. 2003; 125(6):1808-1817.

Kato, "Molecular Virology of Hepatitis C Virus," *Acta Medica Okayama*, 2001;55(3):133-159.

Kim et al., "Domains I and II in the 5' Nontranslated Region of the HCV Genome Are Required for RNA Replication," *Biochem. Biophys. Res. Comm.*, 2002; 290: 105-112.

Knowles et al., "Human hepatocellular carcinoma cell lines secrete the major plasma proteins and hepatitis B surface antigen," *Science*, Jul. 1980;209(25):497-499.

Kolykhalov et al., "Identification of a Highly Conserved Sequence Element at the 3' Terminus of Hepatitis C Virus Genome RNA," *J. Virol.*, Jun. 1996; 70(6):3363-71.

Kolykhalov et al., "Hepatitis C Virus-Encoded Enzymatic Activities and Conserved RNA Elements in the 3' Nontranslated Region Are Essential for Virus Replication In Vivo," *J. Virol.*, Feb. 2000; 74(4):2046-2051.

Krieger et al., "Enhancement of Hepatitis C Virus RNA Replication by Cell Culture-Adaptive Mutations," *J. Virol.*, May 2001; 75:4614-4624.

Lai et al., "Generation and Characterization of a Hepatitis C Virus NS3 Protease-Dependent Bovine Viral Diarrhea Virus," *J. Virol.*, Jul. 2000; 74(14):6339-6347.

Lanford et al., "Lack of Detection of Negative-Strand Hepatitis C Virus RNA in Peripheral Blood Mononuclear Cells and Other Extrahepatic Tissues by the Highly Strand-specific rTth Reverse Transcriptase PCR," *J. Virol.*, Dec. 1995; 69(12):8079-8083.

Lanford et al., "Anti-viral Effect and Virus-Host Interactions in Response to Alpha Interferon, Gamma Interferon, Poly(I)-Poly(C), Tumor Necrosis Factor Alpha, and Ribavirin in Hepatitis C Virus Subgenomic Replicons," *J. Virol.*, Jan. 2003, 77(2):1092-1104.

Le Pogam et al., "Comparison of DNA Enzyme Immunoassay and Line Probe Assays (Inno-LiPA HCV I and II) for Hepatitis C Virus Genotyping," *J. Clin. Microbiol.,* May 1998; 36(5):1461-1463.

Lemon, "Selection of Cell Culture-adapted Hepatitis C RNA," Grant Abstract for Grant No. 2U19A140035-050001 [online]. National Institute of Allergy and Infectious Diseases, National Institutes of Health; project dates Aug. 1, 1996 to Jul. 31, 2005. Retrieved from the Internet on Apr. 17, 2001; URL: <http://commons.cit.nih.gov/crisp/crisp_lib.getdoc?textkey=6340699&p_query=&ticket=1907498&p_audit_session_id=4197699&p_keywords=>, 2 pages.

Lemon, "The Southeastern Cooperative Hepatitis C Research Group," Grant Abstract for Grant No. 2U19A140035-05 [online]. National Institute of Allergy and Infectious Diseases, National Institutes of Health; project dates Aug. 1, 1996 to Jul. 31, 2005. Retrieved from the Internet on Apr. 17, 2001; URL: <http://commons.cit.nih.gov/crisp/crisp_lib.getdoc?textkey=6199426&p_query=&ticket=1907498&p_audit_session_id=4197699&p_keywords=>, 2 pages.

Li et al., "Cellular response to conditional expression of Hepatitis C virus core protein in Huh7 cultured human hepatoma cells," *Hepatology,* May 2002;35(5):1237-1246.

Li et al., "Immune evasion by hepatitis C virus NS3/4A protease-mediated cleavage of the Toll-like receptor 3 adaptor protein TRIF," *PNAS,* Feb. 22, 2005;102(8):2992-2997.

Lohmann et al. "Replication of Subgenomic Hepatitis C Virus RNAs in a Hepatoma Cell Line," *Science,* Jul. 2, 1999; 285(5424):110-113.

Lohmann et al., "Adaptation of Selectable HCV Replicon to a Human Hepatoma Cell Line," Abstract P038, 7th International Meeting on Hepatitis C Virus and Related Viruses (Molecular Virology and Pathogenesis), The Marriott Resort Hotel, Gold Coast, Queensland, Australia, Dec. 3-7, 2000; 1 pg.

Lohmann et al. "Mutations in Hepatitis C Virus RNAs Conferring Cell Culture Adaptation," *J. Virol.* Feb. 2001; 75(3):1437-49.

Lohmann et al., "Viral and Cellular Determinants of Hepatitis C Virus RNA Replication in Cell Culture," *J. Virol.,* Mar. 2003, 77(5):3007-3019.

McHutchison et al., "Current Therapy for Hepatitis C: Pegylated Interferon and Ribavirin," *Clin. Liver Dis.,* Feb. 2003; 7(1):149-161.

McKeating et al., "Diverse Hepatitis C Virus Glycoproteins Mediate Viral Infection in a CD81-Dependent Manner," *Journal of Virology,* Aug. 2004; 78(16):8496-8505.

Murray et al., "Persistent Replication of Hepatitis C Virus Replicons Expressing the β-Lactamase Reporter in Subpopulations of Highly Permissive Huh7 Cells," *Journal of Virology,* Mar. 2003, 77(5):2928-2935.

Nakano et al., "General Acid-Base Catalysis in the Mechanism of Hepatitis Delta Virus Ribozyme," *Science,* Feb. 25, 2000;287:1493-1497.

Naryshikin et al., "RNA Recognition and Regulation of HIV-1 Gene Expression by Viral Factor Tat," *Biochemistry,* 1998;63(5): 489-503.

National Center for Biotechnology Information, National Library of Medicine, National Institutes of Health, Bethesda, MD, GenBank Locus No. AB030907, Accession No. AB030907, "Hepatitis C virus type 2b gene for polyprotein, complete cds, isolate:JPUT971017," [online]. Retrieved from the Internet on Apr. 17, 2001:<URL: http://www.ncbi.nlm.nih.gov/entrez/query.fcgi?cmd=Retrieve&db=Nucleotide&list_uids=9757541&dopt=GenBank>, 8 pages.

National Center for Biotechnology Information, National Library of Medicine, National Institutes of Health, Bethesda, MD, GenBank Locus No. AF011751, Accession No. AFO11751, "Hepatitis C virus strain H77 pCV-H77C polyprotein gene, complete cds," [online]. Retrieved from the Internet on Apr. 26, 2001:<URL:http://www.ncbi.nlm.nih.gov/entrez/query.fcgi?cmd=Retrieve&db=Nucleotide&list_uids=2327070&dopt=GenBank>, 7 pages.

National Center for Biotechnology Information, National Library of Medicine, National Institutes of Health, Bethesda, MD, GenBank Locus No. AF033819, Accession No. AF033819, "HIV-1, complete genome," [online]. Retrieved from the Internet on Apr. 17, 2001:<URL: http://www.ncbi.nlm.nih.gov/entrez/query.fcgi?cmd=Retrieve&db=Nucleotide&list_uids=4558520&dopt=GenBank>, 9 pages.

National Center for Biotechnology Information, National Library of Medicine, National Institutes of Health, Bethesda, MD, GenBank Locus No. AF139594, Accession No. AF139594, "Hepatitis C virus strain HCV-N, complete genome," [online]. Retrieved from the Internet on Apr. 17, 2001:<URL: http://www.ncbi.nlm.nih.gov/entrez/query.fcgi?cmd=Retrieve&db=Nucleotide&list_uids=5532421&dopt=GenBank>, 7 pages.

National Center for Biotechnology Information, National Library of Medicine, National Institutes of Health, Bethesda, MD, GenBank Locus No. AF238481, Accession No. AF238481, "Hepatitis C virus 2a polyprotein gene, complete cds," [online]. Retrieved from the Internet on Apr. 17, 2001:<URL: http://www.ncbi.nlm.nih.gov/entrez/query.fcgi?cmd=Retrieve&db=Nucleotide&list_uids=7329200&dopt=GenBank>, 6 pages.

National Center for Biotechnology Information, National Library of Medicine, National Institutes of Health, Bethesda, MD, GenBank Locus No. SSE242652, Accession No. AJ242652, "Hepatitis C virus replicon I377/NS3-3'UTR," [online]. Retrieved from the Internet on Feb. 18, 2003:<URL: http://www.ncbi.nlm.nih.gov/entrez/query.fcgi?cmd=Retrieve&db=Nucleotide&list_uids=5441834&dopt=GenBank>, 7 pages.

National Center for Biotechnology Information, National Library of Medicine, National Institutes of Health, Bethesda, MD, GenBank Locus No. HCJ238799, Accession No. AJ238799, "Hepatitis C virus type 1b complete genome, isolate Con1," [online]. Retrieved from the Internet on Oct. 24, 2006:<URL: http://www.ncbi.nlm.nih.gov/entrez/viewer.fcgi?db=nucleotide&val=5420376>, 8 pages.

National Center for Biotechnology Information, National Library of Medicine, National Institutes of Health, Bethesda, MD, GenBank Locus No. HPCCGAA, Accession No. M67463, "Hepatitis C virus, complete genome," [online]. Retrieved from the Internet on Oct. 24, 2006:<URL: http://www.ncbi.nlm.nih.gov/entrez/viewer.fcgi?db=nucleotide&val=329737>, 7 pgs.

Neddermann et al., "Hyperphosphorylation of the Hepatitis C Virus NS5A Protein Requires an Active NS3 Protease, NS4A, NS4B, and NS5A Encoded on the Same Polyprotein," *Journal of Virology,* Dec. 1999;73(12):9984-9991.

Noguchi et al., "Cell lines from non-neoplastic liver and hepatocellular carcinoma tissue from a single patient," *In Vitro Cell Dev. Biol. Anim.,* Mar. 1996;32:135-137.

Noguchi et al., "Routes of transmission of hepatitis C virus in an endemic rural area of Japan—Molecular epidemiologic study of hepatitis C virus infection," *Scand J. Infect. Diseases,* 1997;29:23-28.

Ohno et al., "New Hepatitis C Virus (HCV) Genotyping System that Allows for Identification of HCV Genotypes 1a, 1b, 2a, 2b, 3a, 3b, 4, 5a, and 6a," *J. Clin. Microbiol.,* Jan. 1997; 35(1):201-207.

Pelletier, et al., "Internal Initiation of Translation of Eukaryotic mRNA Directed by a Sequence Derived from Poliovirus RNA," *Nature,* Jul. 28, 1988; 334(6180):320-325.

Perrotta et al., "Core Sequences and a Cleavage Site Wobble Pair Required for HDV Antigenomic Ribozyme Self-Cleavage," *Nucleic Acids Res.,* Apr. 1996; 24(7):1314-1321.

Pietschmann et al., "Persistent and transient replication of full-length hepatitis C virus genomes in cell culture," *J Virology,* 2002;76:4008-4021.

Pietschmann et al., "Characterization of Cell Lines Carrying Self-Replicating Hepatitis C Virus RNAs," *J. Virol,* Feb. 2001;75: 1252-64.

Rethwilm et al., "The Transcriptional Transactivator of Human Foamy Virus Maps to the *bel* 1 Genomic Region," *Proc. Natl. Acad. Sci. USA,* Feb. 1, 1991; 88(3):941-945.

Reynolds et al., "Unique features of internal initiation of hepatitis C virus RNA translation," *EMBO J.,* Sep. 1995;14(9): 6010-20.

Reynolds et al., "Internal initiation of translation of hepatitis C virus RNA: The ribosome entry site is at the authentic initiation codon," *RNA,* 1996; 2: 867-78.

Rijnbrand et al., "The influence of downstream protein-coding sequence on internal ribosome entry on hepatitis C virus and other flavivirus RNAs," *RNA,* Sep. 2001; 7(4):585-97.

Ryan et al., "Foot-and-Mouth Disease Virus 2A Oligopeptide Mediated Cleavage of an Artificial Polyprotein," *EMBO J.,* Feb. 15, 1994; 13(4):928-33.

Sandres et al., "Genetic Heterogeneity of Hypervariable Region 1 of the Hepatitis C Virus (HCV) Genome and Sensitivity of HCV to Alpha Interferon Therapy," *J. Virol.*, Jan. 2000; 74(2):661-668.

Scholle et al., "Virus-Host Cell Interactions during Hepatitis C Virus RNA Replication: Impact of Polyprotein Expression on the Cellular Transcriptome and Cell Cycle Association with Viral RNA Synthesis," *J. Virol*, Feb. 2004; 78(3):1513-1524.

Shimizu et al., "Infection of a Chimpanzee with Hepatitis C Virus Grown in Cell Culture,"*J. Gen. Virol.*, Jun. 1998; 79(Pt.6):1383-1386.

Silini et al., "Sequence Variation in the Hypervariable Region 1 of Hepatitis C Virus and Posttransplantation Recurrent Hepatitis," *Liver Transpl.*, Oct. 2003; 9(10):1040-1047.

Simmonds, "Variability of Hepatitis C Virus," *Hepatology*, Feb. 1995; 21(2):570-583.

Simmonds, "Viral Heterogeneity of the Hepatitis C Virus," *J. Hepatol.*, 1999; 31(Suppl.1):54-60.

Simmonds et al., "Classification of Hepatitis C Virus into Six Major Genotypes and a Series of Subtypes by Phylogenetic Analysis of the NS-5 Region," *J. Gen. Virol.*, Nov. 1993; 74(Pt 11):2391-2399.

Smith et al., "Variation of the Hepatitis C Virus 5' Non-Coding Region: Implications for Secondary Structure, Virus Detection and Typing", *J. Gen. Virol.*, Jul. 1995; 76 (Pt. 7):1749-1761.

Takeuchi et al., "Real-time Detection System for Quantification of Hepatitis C Virus Genome," *Gastroenterology*, Mar. 1999; 116(3):636-42.

Tatusova, et al. "BLAST 2 Sequences, a New Tool for Comparing Protein and Nucleotide Sequences," *FEMS Microbiol. Lett.*, May 15, 1999; 174(2):247-50.

Tautz et al., "Processing of Poly-ubiquitin in the Polyprotein of an RNA Virus," *Virology*, Nov. 1993; 197(1):74-85.

Tokita et al., "The Entire Nucleotide Sequences of Three Hepatitis C Virus Isolates in Genetic Groups 7-9 and Comparison with Those in the Other Eight Genetic Groups," *J. Gen. Virol.*, Aug. 1998; 79(Pt 8):1847-1857.

Whetter et al., "Analysis of Hepatitis A Virus Translation in a T7 Polymerase-expressing Cell Line," *Arch. Virol. Suppl.*, 1994; 9:291-8.

Whetter et al., "Low Efficiency of the 5' Nontranslated Region of Hepatitis A Virus RNA in Directing Cap-Independent Translation in Permissive Monkey Kidney Cells," *J. Virol.*, 1994; 68:5253-5263.

Wright-Minogue et al., "Cross-Genotypic Interaction Between Hepatitis C Virus NS3 Protease Domains and NS4A Cofactors," *J. Hepatol.*, Mar. 2000, 32(3):497-504.

Xu et al., "Synthesis of a novel hepatitis C virus protein by ribosomal frameshift," *EMBO J.*, Jul. 2001; 20(14):3840-3848.

Yamada et al., "Genetic Organization and Diversity of the 3' Noncoding Region of the Hepatitis C Virus Genome," *Virology*, Sep. 1, 1996; 223(1):255-261.

Yanagi et al., "Transcripts from a Single Full-length cDNA Clone of Hepatitis C Virus Are Infectious When Directly Transfected into the Liver of a Chimpanzee," *Proc. Natl. Acad. Sci. U S A*, Aug. 5, 1997; 94(16):8738-8743.

Yanagi et al., "In vivo Analysis of the 3' Untranslated Region of the Hepatitis C Virus after in vitro Mutagenesis of an Infectious cDNA Clone," *Proc. Natl. Acad. Sci. U S A*, Mar. 2, 1999; 96(5):2291-2295.

Yao et al., "Molecular Views of Viral Polyprotein Processing Revealed by the Crystal Structure of the Hepatitis C Virus Bifunctional Protease-Helicase," *Structure*, Nov. 1999, 7(11):1353-1363.

Yi et al., "Infectious Discistronic Hepatitis C Virus (HCV) RNA That Facilitates the Rescue of Virus from Synthetic RNA and the Monitoring of Viral Replication in Cultured Cells," presented at 7th International Meeting on Hepatitis C Virus and Related Viruses (Molecular Virology and Pathogenesis), The Marriott Resort Hotel, Gold Coast, Queensland, Australia, Dec. 3-7, 2000; abstract and poster (30 pages).

Yi et al., "Subgenomic Hepatitis C Virus Replicons Inducing Expression of a Secreted Enzymatic Reporter Protein," *Virology*, Dec. 20, 2002; 304(2):197-210.

Yi et al., "3' Nontranslated RNA Signals Required for Replication of Hepatitis C Virus RNA," *J. Virol.*, Mar. 2003; 77(6):3557-3568.

Yi et al., "Structure-Function Analysis of the 3' Stem-Loop of Hepatitis C Virus Genomic RNA and its Role in Viral RNA Replication," *RNA*, Mar. 2003, 9(3):331-345.

Yi et al., "Adaptive Mutations Producing Efficient Replication of Genotype 1a Hepatitis C Virus RNA in Normal Huh7 Cells," *Journal of Virology*, Aug. 2004;78(15): 7904-7915.

Yoo et al., "Transfection of a Differentiated Human Hepatoma Cell Line (Huh7) with In Vitro-transcribed Hepatitis C Virus (HCV) RNA and Establishment of a Long-term Culture Persistently Infected with HCV," *J. Virol.*, Jan. 1995; 69(1):32-38.

Zhong et al., "Robust hepatitis C virus infection in vitro," *PNAS*, Jun. 28, 2005; 102(26):9294-9299.

Zhu et al., "Replication of Hepatitis C Virus Subgenomes in Nonhepatic Epithelial and Mouse Hepatoma Cells," *J. Virol.*, Sep. 2003, 77(17):9204-9210.

Adams et al., "Complete Coding Sequence of Hepatitis C Virus Genotype 6a," *Biochemical and Biophysical Research Communications*, 1997; 234:393-396.

Bressanelli et al., "Crystal structure of the RNA-dependent RNA polymerase of hepatitis C virus," *PNAS*, Nov. 9, 1999; 96(23):13034-13039.

Bressanelli et al., "Structural Analysis of the Hepatitis C Virus RNA Polymerase in Complex with Ribonucleotides," *Journal of Virology*, Apr. 2002; 76(7):3482-3492.

Chamberlain et al., "Complete nucleotide sequence of a type 4 hepatitis C virus variant, the predominant genotype in the Middle East," *Journal of General Virology*, 1997; 78:1341-1347.

Cheney et al., "Mutations in NS5B Polymerase of Hepatitis C Virus: Impacts on in Vitro Enzymatic Activity and Viral RNA Replication in the Subgenomic Replicon Cell Culture," *Virology*, 2002; 297:298-306.

Love et al., "The Crystal Structure of Hepatitis C Virus NS3 Proteinase Reveals a Trypsin-like Fold and a Structural Zinc Binding Site," *Cell*, Oct. 18, 1996; 87:331-342.

Love et al., "Crystallographic Identification of a Noncompetitive Inhibitor Binding Site on the Hepatitis C Virus NS5B RNA Polymerase Enzyme," *Journal of Virology*, Jul. 2003; 77(13):7575-7581.

Marzio et al., "HIV-1 Tat transactivator recruits p300 and CREB-binding protein histone acetyltransferases to the viral promoter," *Proc. Natl. Acad. Sci. USA*, Nov. 1998; 95:13519-13524.

Simmonds et al., "A Proposed System for the Nomenclature of Hepatitis C Viral Genotypes," *Hepatology*, 1994; 19:1321-1324.

Simmonds et al., "Evolutionary analysis of variants of hepatitis C virus found in South-East Asia: comparison with classifications based upon sequence similarity," *Journal of General Virology*, 1996; 77:3013-3024.

Simmonds et al., "Consensus Proposals for a Unified System of Nomenclature of Hepatitis C Virus Genotypes," *Hepatology*, 2005; 42(4):962-973.

Smith et al., "Characteristics of Nucleotide Substitution in the Hepatitis C Virus Genome: Constraints on Sequence Change in Coding Regions at Both Ends of the Genome," *J. Mol. Evol.*, 1997; 45:238-246.

Yan et al., "Complex of NS3 protease and NS4A peptide of BK strain hepatitis C virus: A 2.2 Å resolution structure in a hexagonal crystal form," *Protein Science*, 1998; 7:837-847.

Reed et al., "Overview of Hepatitis C Virus Genome Structure, Polyprotein Processing, and Protein Properties," *Curr. Top. Microbiol. Immunol.*, 1999; 242:55-84.

U.S. Appl. No. 11/975,658, Oct. 19, 2007, Lemon et al.

Betti et al., "Characterization of HIV-1 Tat proteins mutated in the transactivation domain for prophylactic and therapeutic application," *Vaccine*, 2001; 19:3408-3419.

Rossi et al., "Inhibition of HIV-1 replication by a Tat transdominant negative mutant in human peripheral blood lymphocytes from healthy donors and HIV-1-infected patients," *Gene Therapy*, 1997; 4:1261-1269.

\* cited by examiner

Fig. 1
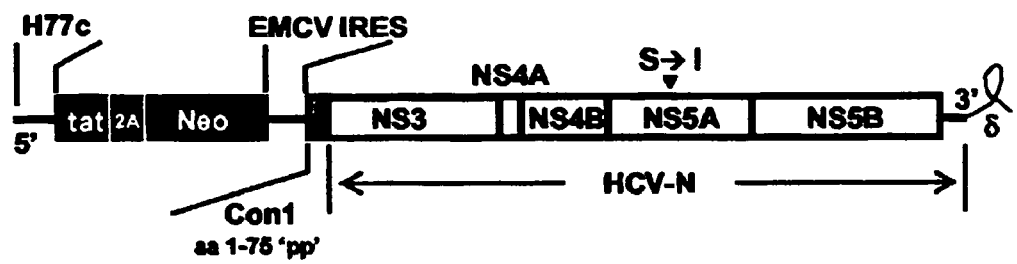
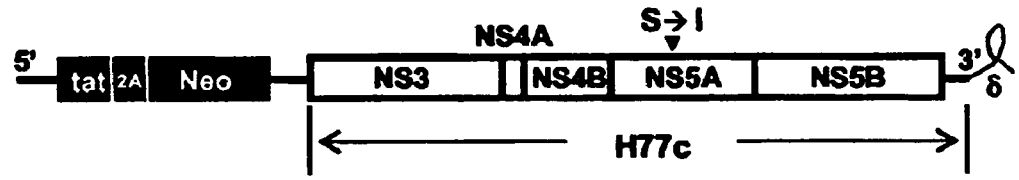
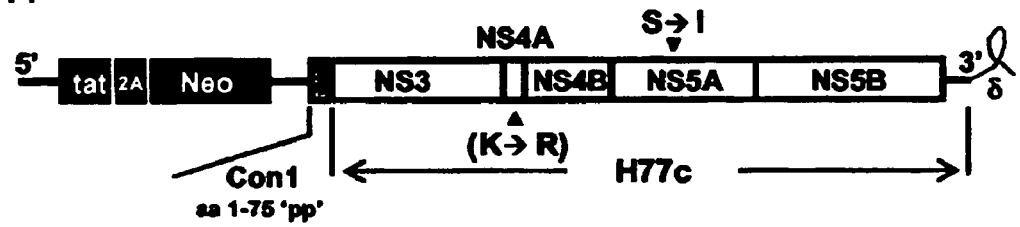

*Fig. 4A*
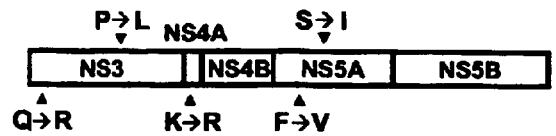
*Fig. 4B*
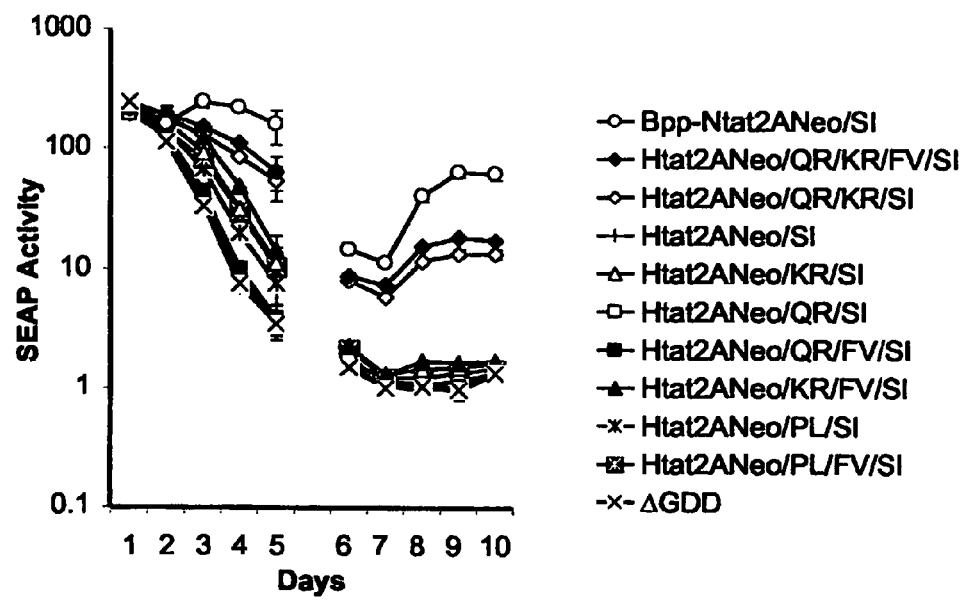
*Fig. 4C*
| SEAP | NS Substitutions | | | | |
|---|---|---|---|---|---|
| | 3p | 3h | 4A | 5A | 5A |
| − | | | | | SI |
| − | | KR | | | SI |
| − | QR | | | | SI |
| +++ | QR | | KR | | SI |
| − | QR | | | FV | SI |
| + | | KR | | FV | SI |
| +++ | QR | | KR | FV | SI |
| + | | PL | | | SI |
| + | | PL | | FV | SI |

*Fig.* 5
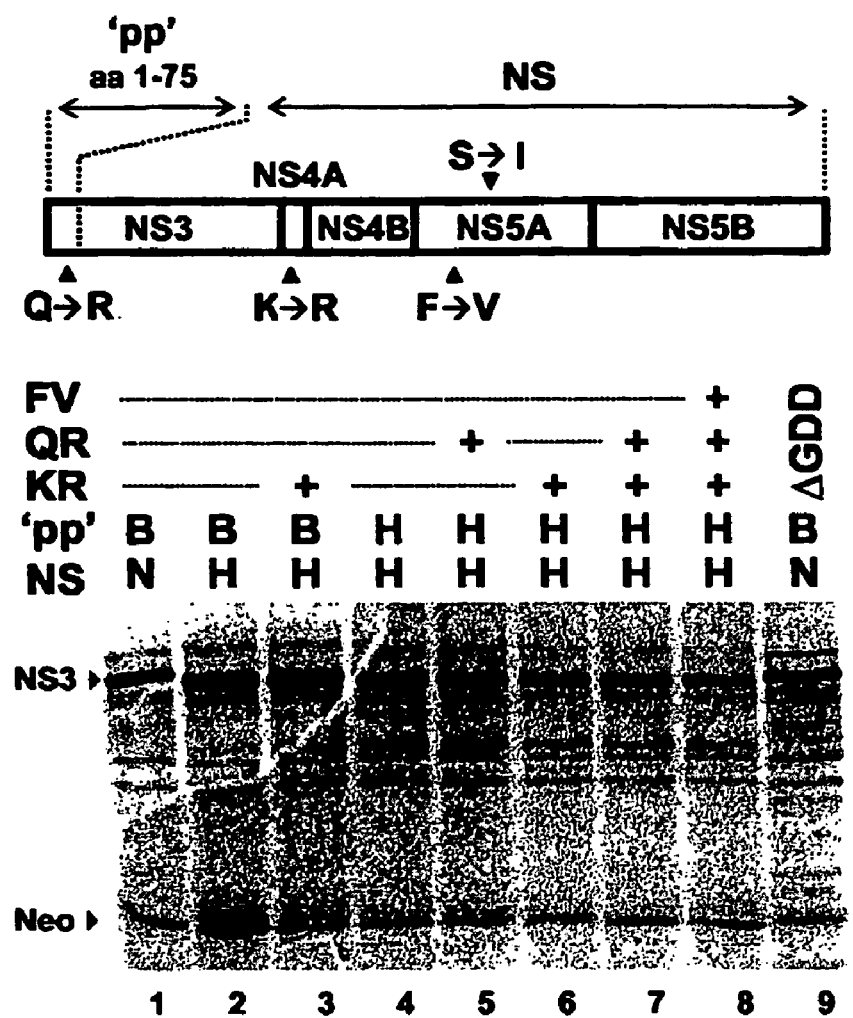

Fig. 9

```
        10         20         30         40         50         60         70         80
        |          |          |          |          |          |          |          |
   1 ACCTGGAAAA ACATGGAGCA ATCACAAGTA GCAATACAGC AGCTACCAAT GCTGCTTGTG CCTGGCTAGA AGCACAAGAG   80
  81 GAGGAGGAGG TGGGTTTTCC AGTCACACCT CAGTACCTT  TAAGACCAAT GACTTACAAG GCAGCTGTAG ATCTTAGCCA  160
 161 CTTTTTAAAA GAAAAGGGGG GACTGGAAGG GCTAATTCAC TCCCAAAGAA GACAAGATAT CCTTGATCTG TGGATCTACC  240
 241 ACACACAAGG CTACTTCCCT GATTAGCAGA ACTACACACC AGGGCCAGGG GTCAGATATC CACTGACCTT TGGATGTGTGC 320
 321 TACAAGCTAG TACCAGTTGA GCCAGATAAG ATAGAAGAGG CCAATAAAGG AGAGAACACC AGCTTGTTAC ACCCTGTGAG  400
 401 CCTGCATGGG ATGGATGACC CGGAGAGAGA AGTGTTAGAG TGGAGGTTTG ACAGCCGCCT AGCATTTCAT CACGTGCCCC  480
 481 GAGAGCTGCA TCCGGAGTAC TTCAAGAACT GCTGACATCG AGCTTGCTAC AAGGGACTTT CCGCTGGGGA CTTTCCAGGG  560
 561 AGGCGTGGCC TGGGCGGGAC TGGGGAGTGG CGAGCCCTCA GATCCTGCAT ATAAGCAGCT GCTTTTTGCC TGTACTGGGT  640
 641 CTCTCCGTT  AGACCAGATC TGAGCCTGGG AGCTCTCTGG CTAACTAGGG AACCCACTGC TTAAGCCTCA ATAaagcttc  720
 721 TGCATGCTGC TGCTGCTGCT GCTGCTGGGC CTGAGGCTAC AGCTCTCCCT GGGCATCATC CCAGTTGAGG AGGAGAACCC  800
 801 GGACTTCTGG AACCCGAGG  CAGCCGAGGC CCTGGGTGCC GCCAAGAAGC TGCAGCCTGC ACAGACAGCC GCCAAGAACC  880
 881 TCATCATCTT CCTGGGCGAT TGTCTACGGT GACACAGCT  AGGATCCTAA AGGGCAGAA  GAGATCCTAA GAAGGACAAA  960
 961 CTGGGGCCTG AGATACCCCT GGCCATGGAC CGCTTCCCAT GTCCAAGACA TACAATGTAG ACAAACATGT             1040
1041 GCCAGACAGT GGAGCCACAG CCTGTGAGCG GTCAAGGCA  ACTTCCAGAC CATTGGCTTG AGTGCAGCCG            1120
1121 CCCGCTTTAA CCAGTGCAAC ACGACAGCG  CTGAACGAGT CATCTCCGTG ATGAATCGGG CCAAGAAAGC AGGGAAGTCA 1200
1201 GTGGAGTGG  TAACCACCAC ACGAGTGCAG CAGCCCTCGC CAGCGCCCAC CTACGCCCAC ACGGTGAACC GCAACTGGTA 1280
1281 CTCGGACGCC GACGTGCCTG CCTCGGCCCG CCAGGAGGGG TGCCAGGACA TCGCTACGGA GCTCATCTCC AACATGGACA 1360
1361 TTGACGTGAT CCTAGGTGGA GGCGAAAGT  ACATGTTTCC CCAGACCCTG AGTACCCAGA TGACTACAGC            1440
1441 CAAGGTGGGA CCAGGCTGGA CGGGAAGAAT CTGGTGCAGG CATGGGAACC GAAGCGCCAG GGTGCCCGGT ATGTGTGAA  1520
1521 CCGCACTGAG CTCATGCAGG CTTCCCTGGA CCCGTCTGTG CCCGTCTGTT ACCCATCTCA TGGGTCTCTT TGAGCCTGGA GACATGAAAT 1600
1601 ACGAGATCCA CCGAGACTCC ACACTGGACC CCTCCCTGAT GGAGATGACA GAGGCTGCCC TGCGCCTGCT GAGCAGGAAC 1680
1681 CCCCGCGGCT TCTTCCCTCT CGTGGAGGGT GGTCGCATCG ACCATGGTCA TCATGAAAGC AGGGCTTACC CTCGTCACTG 1760
1761 TGAGACGATC ATGTTCGACG AGGCCATTGA GAGGGGCGGC ACCCATGGAG GCAGAGGAGA TCATGGTCAC CACGTGCGCC 1840
1841 CCGACCACTC CCACGTCTTC TCCTTCGGAG GCTACCCCT  TCCATGCGAG GTCCAGGCTA GCGAGGGAGC TGTGCTCAAG TGGCAAGGCC 1920
1921 CGGGACAGGA AGGCCTACAC TCCTTCCCTA GGTCCTCCTA TACGGAAACG GTCCAGTGC  CCCTGGACGA AGAGACAGA  2000
2001 TACCGAGAGC GAGAGGGGA  GCCCGGCGCC GGGCCCGCAG TCGGCAGCAG TCACGGCGTG CAGGAGCGAC CTTCATAGC  GCAGGCGAGG 2080
2081 ACGTGGCGGT GTTCGCGCGG GGCCCCGCGG CGCCCGACCG CGCACCTGGT TCACGGCGTG CCAGCACCGA GCACGTCATG 2160
2161 GCCTTCGCCG CCTGCCTGGA GCCCTACACC GCCTACACCC TGGGCGCCCC CGCCGGACC  ACCGACGCCG CGCACCCCG  2239
```

Fig. 10A

```
  1 TGAAGGTTGG GGTAAACACT CCGGCCTCTT AAGCCATTTC CTGTTTTTTT TTTTTTTTTT TCTTTTTTCT TTTCTTTCCT TTCCTTCTTT 100
101 TTTTCCTTTC TTTTTCCCTT CTTTAATGGT GGCTCCATCT TAGCCCTAGT CACGGCTAGC CCGTGAAAGGT TGTGAAAGCCG CATGACTGCA GAGAGTGCTG 200
201 ATACTGGCCT CTCTGCAGAT CATGT
```

Fig. 10B

```
  1 GCCAGCCCCC TGATGGGGGC GACACTCCAC CATGAATCAC TCCCCTGTGA GGAACTACTG TCTTCACGCA GAAAGCGTCT AGCCATGGCG TTAGTATGAG 100
101 TGTCGTGCAG CCTCCAGGAC CCCCCCTCCC GGGAGAGCCA TAGTGGTCTG CGGAACCGGT GAGTACACCG GAATTGCCAG GACGACCGGG TCCTTTCTTG 200
201 GATAAACCCG CTCAATGCCT GGAGATTTGG GCCTGCCCCC GCAAGACTGC TAGCCGAGTA GTGTTGGGTC GCGAAAGGCC TTGTGGTACT GCCTGATAGG 300
301 GTGCTTGCGA GTGCCCCGGG AGGTCTCGTA GACCGTGCAC C
```

```
8301 CGTACGGAGG AGGCAATTTA CCAATGTTGT GACCTGGACC CCCAAGCCCG CGTGGCCATC AAGTCCCTCA CTGAGAGGCT TTATGTTGGG GGCCCTCTTA 8400
8401 CCAATTCAAG GGGGAAAAC TGCGGCTACC GCAGGTGCCG CCGGAGCGGC GTACTGACAA CTAGCTGTGG TAACACCCTC ACTTGCTACA TCAAGGCCCG 8500
8501 GGCAGCCTGT CGAGCCGCAG GGCTCCAGGA CTGCACCATG CTCGTGTGTG GCGACGACTT AGTCGTTATC TGTGAAAGTG CGGGGTCCA GGAGGACGCG 8600
8601 GCGAGCCTGA GAGCCTTCAC GGAGGCTATG ACCAGGTACT CGGCCCCCC CCACAACCAG AATACGACTT GGAGCTTATA ACATCATGCT 8700
8701 CCTCCAACGT GTCAGTCGCC CACGACGGCG CTGGAAAGAG GGCTACTAC ACCCTCCGTG GGCGAGGATG ATACTGATGA AGAGCCGCGT GGGAGACAGC 8800
8801 AAGACACACT CCAGTCAATT CCTGGCTAGG CAACATAATC ATGTTTGCCC CCACACTGTG GGCGAGGATG TGGATCTACC CCCATTTCTT TAGCGTCCTC 8900
8901 ATAGCCAGGG ATCAGCTTGA ACAGGCTCTT AACTGTGAGA TCTACGGAGC CTGCTACTCC ATAGAACCAC TGGATCTACC TCCAATCATT CAAAGACTCC 9000
9001 ATGGCCTCAG CGCATTTTCA CTCCACAGTT ACTCTCCAGG TGAATCAAT AGGTGGCCG CATGCCTCAG AAAACTTGGG GTCCCGCCCT TGCGAGCTTG 9100
9101 GAGACACCGG GCCCAGAGCG TCCGCGCTAG GCTTCTGTCC AGAGGAGGCA GGGCTGCCAT ATGTGGCAAG TACCTCTTCA ACTGGGCAGT AAGAACAAAG 9200
9201 CTCAAACTCA CTCCAATAGC GGCCGCTTGG CGGCTGGACT TGTCCGGTTG GTTCACGGCT CCGATGAAGG CGGAGACAT TTATCACAGC GTGTCTCATG 9300
9301 CCCGGCCCCG CTGGTTCTGG TTTTGCCTAC TCCTGCTCGC TCAAGGGGTA GGCATCTACC TCCTTTCCTT CCGATGAAGG TTGGGTAAA CACTCCGGCC 9400
9401 TCTTAAGCCA ATCTTAGCCC TTTCCTGTTT TTTTTTTTT TCTTGCTTTT GTTCACGGCT TCCTTTTCTT CTTTTTTCTT TTTCTTTTTC CCTTCTTTAA 9500
9501 TGGTGGCTCC AFCTTAGCCC TAGTCACGGC TAGCTGTGAA AGTCCGTGA GCCCATGACT TGCAGAGAGT GCTGATACTG GCCTCTCTGC AGATCATGT 9599
       |        |        |        |        |        |        |        |        |        |
      10       20       30       40       50       60       70       80       90      100
```

```
1692/451                                                                      1722/461                                                                      1752/471
GGC TGT CCT GAG AGG TTG GCC AGC TGC CGA    CGC CTT ACC GAT TTT GCC CAG GGC TGG    CCT ATC AGT TAT GCC AAC GGA AGC GGC CTC
 G   C   P   E   R   L   A   S   C   R     R   L   T   D   F   A   Q   G   W     P   I   S   Y   A   N   G   S   G   L
1782/481                                                                      1812/491                                                                      1842/501
GAC GAA CGC CCC TAC TGC TGG TGG CAC TAC    CCA AGA CCT TGT GCG CCT ATT GTG AAG    AGC GTG TGT CCG GTA TAT TGC TTC ACT
 D   E   R   P   Y   C   W   W   H   Y     P   R   P   C   A   P   I   V   K     S   V   C   P   V   Y   C   F   T
1872/511                                                                      1902/521                                                                      1932/531
CCC AGC CCC GTG GTG GTG CTG CCA ACG GAC    AGG TCG GGC GCG CCT ATG TAC AGC GGT    GCA AAT GAT GAT GTC TTC GTC CTT AAC
 P   S   P   V   V   V   L   P   T   D     R   S   G   A   P   M   Y   S   G     A   N   D   D   V   F   V   L   N
1962/541                                                                      1992/551                                                                      2022/561
AAC ACC AGG CCA CCG CTG GGC AAT TGG TTC    GGT TGT TAC ACT TGG ATG TCA ACT GGA    TGC GGA GCG CCC CCT TGT GTC
 N   T   R   P   P   L   G   N   W   F     G   C   Y   T   W   M   S   T   G     C   G   A   P   P   C   V
2052/571                                                                      2082/581                                                                      2112/591
ATC GGA GGG GTG GGC AAC AAC ACC CTC CTC    TGC CCC ACT GAT TGC TTC AGG AAA CAT CCG    GAA GCC ACA TAC CGG ATA TTC AAA GTC AGG
 I   G   G   V   G   N   N   T   L   L     C   P   T   D   C   F   R   K   H   P     E   A   T   Y   R   I   F   K   V   R
2142/601                                                                      2172/611                                                                      2202/621
CCC TGG ATT ACA CCC AGG GTC GTC ATG TGC    TAC CCG TAT AGG CAC ACG CGG CCT TGT    ACC ATC AAT TAC CTG GAA GAC AGG ATC
 P   W   I   T   P   R   V   V   M   C     Y   P   Y   R   H   T   R   P   C     T   I   N   Y   L   E   D   R   I
2232/631                                                                      2262/641                                                                      2292/651
ATG TAC GTG GGA GGG GTC GCC GAG CAC CTG    GAA GCG GCC CGG GTC TGT GGG CGG GAA    CGC TGT GAT CTG TTG TCC TAC AGG AGG TCC
 M   Y   V   G   G   V   A   E   H   L     E   A   A   R   V   C   G   R   E     R   C   D   L   L   S   Y   R   R   S
2322/661                                                                      2352/671                                                                      2382/681
GAG CTC AGC CCG TTG CTG TTG TCC ACC ACA    CAG TGG CAG GTG CTC CCA TGT TCT TTC ACG    ACC CTG CCA GCC ATT AAG GCG ATC CTC ATC
 E   L   S   P   L   L   L   S   T   T     Q   W   Q   V   L   P   C   S   F   T     T   L   P   A   I   K   A   I   L   I
2412/691                                                                      2442/701                                                                      2472/711
CAC CTC CAC CAG AAC ATT GTG GAC GTG CAG    TAC TTG TAC GGG ATG GGG TCA AGC ATC    TCC TGG TCC ATC GCG TGG CTG TAC GTC GTT
 H   L   H   Q   N   I   V   D   V   Q     Y   L   Y   G   M   G   S   S   I     S   W   S   I   A   W   L   Y   V   V
2502/721                                                                      2532/731                                                                      2562/741
CTC CTG TTC CTT CTT GCC GAC GCA GAC GCG    GTC GTC TGC TTT TGT GGG TGC CGC ATG ATG TTA    ATA TCC CAA TAC CAG TAT CTG GAG AAC
 L   L   F   L   L   A   D   A   D   A     V   V   C   F   C   G   C   R   M   M   L     I   S   Q   Y   Q   Y   L   E   N
2592/751                                                                      2622/761                                                                      2652/771
CTC GTA ATA CTC AAT GCA GCA TCC CTG GCC    GGG ACG CAC CAC ATG ATG TCC TTC CTC CTC    TTC TTC TGC TTT GCG TGG TAT CTG AAG GGT
 L   V   I   L   N   A   A   S   L   A     G   T   H   H   M   M   S   F   L   L     F   F   C   F   A   W   Y   L   K   G
2682/781                                                                      2712/791                                                                      2742/801
AGG TGG GTG CCC GGA GCC GTG TAC GCC TTC    TAC GGG ATG TGG CCT CTT CTC CTG CTG    CTG GCG TTG CCT CAG CGG GCA TAC GCA CTG
 R   W   V   P   G   A   V   Y   A   F     Y   G   M   W   P   L   L   L   L     L   A   L   P   Q   R   A   Y   A   L
2772/811                                                                      2802/821                                                                      2832/831
GAC ACG GAG GTG GCC GCC TCG TGT GGT GGC    GTT GTT CTT GTC GGG CTT ATG GCG CTG    CTG ACG CGG TAT CTG TAT TAC ATC AGC
 D   T   E   V   A   A   S   C   G   G     V   V   L   V   G   L   M   A   L     L   T   R   Y   L   Y   Y   I   S
2862/841                                                                      2892/851                                                                      2922/861
TGG TGC ATG TGG TGG CTT CAG TAT TTT CTG    ACC AGA GTA GAA CAA CTG CTG CAC GTG    TGG GTT CCC CCC CTC AAC GTT CGG GGG CGC
 W   C   M   W   W   L   Q   Y   F   L     T   R   V   E   Q   L   L   H   V     W   V   P   P   L   N   V   R   G   R
2952/871                                                                      2982/881                                                                      3012/891
GAT GCC GTC ATC TTA TTA CTC ATG ATC ACC    CAC CCG ACC CTG GTA TTT GAC ATC ACC    AAA CTA CTC CTG GCC ATC TTC GGA CCC CTT TGG
 D   A   V   I   L   L   L   M   I   T     H   P   T   L   V   F   D   I   T     K   L   L   L   A   I   F   G   P   L   W
```

Fig. 11B-3

```
3042/901
ATT CTT CAA GCC AGT TTG CTT AAA GTC CCC         3072/911
I   L   Q   A   S   L   L   K   V   P           TAC TTC GTG CGC GTT CAA GGC CTT CTC CGG         3102/921
                                                Y   F   V   R   V   Q   G   L   L   R         ATC TGC GCG CTA GCG CCT CTC AAG ATA GCC GGA
3132/931                                                                                       I   C   A   L   A   P   L   K   I   A   G
GGT CAT TAC GTG CAA ATG GCC ATC AAG             3162/941
G   H   Y   V   Q   M   A   I   I   K           TTA GGG GCG CTT ACT GGC ACC TAT GTG TAT         3192/951
                                                L   G   A   L   T   G   T   Y   V   Y         AAC CAT CTC ACC ATC ACG CTT CGA GAC TGG GCG
3222/961                                                                                       N   H   L   T   I   T   L   R   D   W   A
CAC AAC GGC CTG CGA GAT ATC GCA GTG GCT         3252/971
H   N   G   L   R   D   I   A   V   A           GTG GAA CCA GTC GTC TTC CGA ATG GAG             3282/981
                                                V   E   P   V   V   F   R   M   E             ACC AAG CAT CTC ATC CCA GCC GGA GCA GAT ACC
3312/991                                                                                       T   K   H   L   I   P   A   G   A   D   T
GCC GCG TGC GGT GAC TGC GGT GAC ATC ATC         3342/1001
A   A   C   G   D   C   G   D   I   I           CCC GTC TCT GCC CGT CAG CAG ACG CAG CTC         3372/1011
                                                P   V   S   A   R   Q   Q   T   Q   L         CTG CTT GGG GGA ATG GTC TCC
                                                                                               L   L   G   G   M   V   S
3402/1021
AAG GGG TGG AGG TTG CTG GCG CCC ATC ATT         3432/1031
K   G   W   R   L   L   A   P   I   I           GCG TAC GCC ACT GCT ATA CTA                     3462/1041
                                                A   Y   A   T   A   I   L                     GGG TGT ATA ATC AGC ACT GGC CGG
                                                                                               G   C   I   I   S   T   G   R
3492/1051
GAC AAA AAC CAA GTG GAG GGT GAG GTC TCA         3522/1061
D   K   N   Q   V   E   G   E   V   S           CAG ACG GTG TGC CTG                             3552/1071
                                                Q   T   V   C   L                             GCA ACG TGC ATC GAC CTT GTA TGC TGG ACT
                                                                                               A   T   C   I   D   L   V   C   W   T
3582/1081
GTC TAC CAC GGG GCC GCC ACG GGA GCG ATC         3612/1091
V   Y   H   G   A   A   T   G   A   I           GCA TCA CCC AAG GGT ATG                         3642/1101
                                                A   S   P   K   G   M                         TAT ACC AAT GTG GAC CAA GAC CTT GTG GGC
                                                                                               Y   T   N   V   D   Q   D   L   V   G
3672/1111
TGG CCC GCT CCT CAA GGT TCC CGC TCA TTG         3702/1121
W   P   A   P   Q   G   S   R   S   L           ACA CCC TGT ACC TGT GTC GAC CTT                 3732/1131
                                                T   P   C   T   C   V   D   L                 TAC CTG GTC ACG CTC GAC GTC ATT
                                                                                               Y   L   V   T   L   D   V   I
3762/1141
CCC GTG CGC CGG CGA GAT AGC AGG GGT             3792/1151
P   V   R   R   R   D   S   R   G               AGC CTG CTT TCG CCC CGG ACC CGT GGA GTG         3822/1161
                                                S   L   L   S   P   R   T   R   G   V         TTG AAA ATA TCC TAC
                                                                                               L   K   I   S   Y
3852/1171
TGC CCC GCA GGA CAC GCC ATG AGA CTA TTC         3882/1181
C   P   A   G   H   A   M   R   L   F           AGG GCC GCG GCA GTG CGC GTG GCT                 3912/1191
                                                R   A   A   A   V   R   V   A                 AAA GCG GTG CCT GTG GAG AAC
                                                                                               K   A   V   P   V   E   N
3942/1201
CTA GGG ACA ACC ATG AGA AGA TCC CGG TTC         3972/1211
L   G   T   T   M   R   R   S   R   F           ACG GAC AAC TCC TCT GCA GCC                     4002/1221
                                                T   D   N   S   S   A   A                     CAG AGC TTC CCC CAC CTG CAT GCT
                                                                                               Q   S   F   P   H   L   H   A
4032/1231
CCC ACC GCG AGC GGC AAG AGC AGC ACC             4062/1241
P   T   A   S   G   K   S   S   T               CCG GCT GCG TAC GCA GCT GAT CCT AAT             4092/1251
                                                P   A   A   Y   A   A   D   P   N             GTG TTG GTG TAC AAG ACC CTC AAC ATT TGT
                                                                                               V   L   V   Y   K   T   L   N   I   C
4122/1261
GCT CTG GGC TTT GGT GCT ATG TCC TAC             4152/1271
A   L   G   F   G   A   M   S   Y               GCC CAT GGG GTT GAT CCT                         4182/1281
                                                A   H   G   V   D   P                         GGG GTG AGA ACA ATT ACC AGG GCT GCA
                                                                                               G   V   R   T   I   T   R   A   A
4212/1291
ACG CTG GGC TAC ACC AAG TAC TTC GGC             4242/1301
T   L   G   Y   T   K   Y   F   G               GCC GAC GGC GGG TGC TCA GGT                     4272/1311
                                                A   D   G   G   C   S   G                     GAC ATA ATA TGT CTG TCA GCA AGC CAC TCC
                                                                                               D   I   I   C   L   S   A   S   H   S
4302/1321
ATC ACG TAC ACC ATC TTG GGC ATC GGC             4332/1331
I   T   Y   T   I   L   G   I   G               ACT GTC CTT GAC CAA GCA GAG                     4362/1341
                                                T   V   L   D   Q   A   E                     GCG GGG GCG GCG CTC GTG GCT GCA CCC
                                                                                               A   G   A   A   L   V   A   A   P
ACG GAT GCC ACA TCC ATC GGC                     ACT GTC CTT GAC CAA GCA GAG                     GCG GGG GCG GCG CTC GTG GCT GCA CCC
T   D   A   T   S   I   G                       T   V   L   D   Q   A   E                     A   G   A   A   L   V   A   A   P
```

Fig. 11B-4

```
4392/1351
CCT CCG GGC TCC ACT GTG TCC CAT CCT GAG GTT GCT CTG TCC ACC ACC        4422/1361
 P   P   G   S   T   V   S   H   P   E   V   A   L   S   T   T        AAC ATC GAG GAG GTT GCT CTG TCC ACC ACC CCC TTT TAC GGC AAG GCT ATC
                                                                        N   I   E   E   V   A   L   S   T   T   P   F   Y   G   K   A   I
4482/1381
CCC CTC GAG GTG ATC AAG GGG AGA CAT TGC ATC TTC         4512/1391
 P   L   E   V   I   K   G   R   H   C   I   F          CTC ATC TTC TGC CAC TCA AAG AAG ACC AGC GGC        4542/1401
                                                         L   I   F   C   H   S   K   K   T   S   G          GAC GAG CTC GCC GCG GTG TCG GAT GCT ACC
                                                                                                            D   E   L   A   A   V   S   D   A   T
4572/1411
GGC ATC AAT GCC GTG GCC TAC TAC CGC GGT         4602/1421
 G   I   N   A   V   A   Y   Y   R   G          CTT GAC GTG TCT GTG ATC CCG ATC ACG        4632/1431
                                                 L   D   V   S   V   I   P   I   T         GAT GTT GTC TTC AGC CTT GAC CCT ACC CTC
                                                                                            D   V   V   F   S   L   D   P   T   L
4662/1441
ATG ACT GGC TTT ACC GGC GAC TTC GAC TCT         4692/1451
 M   T   G   F   T   G   D   F   D   S          GTG ATA GAC TGC AAC ACG TGC ACT CAG        4722/1461
                                                 V   I   D   C   N   T   C   T   Q         ACA GTC GAT GCT GTC ACT TAT AGA
                                                                                            T   V   D   A   V   T   Y   R
4752/1471
ACC ATT GAG ACA ACG CTC CCC CAG GAT         4782/1481
 T   I   E   T   T   L   P   Q   D          GCT GTC TCC AGG ACT CAA CGC CAA        4812/1491
                                             A   V   S   R   T   Q   R   Q         ACT GGC AGG GGC CCA ATC GAG CTC
                                                                                    T   G   R   G   P   I   E   L
4842/1501
TTT GTG GCA CCG CGC GAG CGC TCC GGC         4872/1511
 F   V   A   P   R   E   R   S   G          ATG TTC GAC CTA GTT GTC TCC GAC        4902/1521
                                             M   F   D   L   V   V   S   D         TAT GAC CGG CTC TGT GGG CTT GCT GAA TAT TGG GAG CTC
                                                                                    Y   D   R   L   C   G   L   A   E   Y   W   E   L
4932/1531
ACG CCC GCC GAG ACT ACA CGA CAT GCC         4962/1541
 T   P   A   E   T   T   R   H   A          GCG TAC ATG GCT GCC CTG AAC ACC        4992/1551
                                             A   Y   M   A   A   L   N   T         TGC CAG GAC CTG GGG CAT CTT TAC CTG GTA ACC CTC CAT GGG
                                                                                    C   Q   D   L   G   H   L   Y   L   V   T   L   H   G
5022/1561
GTC TTT ACG GGC CTC TGC CTA ATA GAT         5052/1571
 V   F   T   G   L   C   L   I   D          CAC TTT TTA TCC TGG TAC ATG        5082/1581
                                             H   F   L   S   W   Y   M         GAG AAC TTT CCT CTT AAA TAC ATC CAT
                                                                                E   N   F   P   L   K   Y   I   H
5112/1591
GCC ACC GTG TGC AGG CTG GCT CAA GCC         5142/1601
 A   T   V   C   R   L   A   Q   A          CCC CCA TCG TGG GAC CAG ATG CAG        5172/1611
                                             P   P   S   W   D   Q   M   Q         TTG ATC CGC AAA TAC ATC TGC ATG TCG
                                                                                    L   I   R   K   Y   I   C   M   S
5202/1621
CCA ACA CCC ACC CTA TAC AGA AAT GAA         5232/1631
 P   T   P   T   L   Y   R   N   E          GTT CAG AAT CAG GTT CAG ACG        5262/1641
                                             V   Q   N   Q   V   Q   T         ATC ACC AAA CCA GTG GCT GCT CTG
                                                                                I   T   K   P   V   A   A   L
5292/1651
GCC GAC CTG GGC GTG CTC ACG AGC TGG         5322/1661
 A   D   L   G   V   L   T   S   W          GTG CTC GTT GGC GGT CTG CTG        5352/1671
                                             V   L   V   G   G   L   L         GCC GCG TAT TGC CTG GAG TTC CTG
                                                                                A   A   Y   C   L   E   F   L
5382/1681
GTC ATA GTG GGC AGG ATC GTG TCC GGG         5412/1691
 V   I   V   G   R   I   V   S   G          AAG CCG GCA ATT ATA CCT GAG GTT        5442/1701
                                             K   P   A   I   I   P   E   V         CTC TAC CAG GAG TTC GAT GAG ATG GAA
                                                                                    L   Y   Q   E   F   D   E   M   E
5472/1711
TGC TCT CAG CAC TTA CCG TAC ATC CTC         5502/1721
 C   S   Q   H   L   P   Y   I   L          GGG ATG ATG GCT CTC GAG CAG TTC AAG        5532/1731
                                             G   M   M   A   L   E   Q   F   K         GGC GCC CTC GGC CTG CTG CAG AAT GCG TCC
                                                                                        G   A   L   G   L   L   Q   N   A   S
5562/1741
CGC CAT GCA GAG GCT GTT ATC ACC CCT GCT         5592/1751
 R   H   A   E   A   V   I   T   P   A          CAG AAA CTC TGG TGG AAG CAC ATG ATC TCG        5622/1761
                                                 Q   K   L   W   W   K   H   M   I   S         AAG GCG AAG CAC ATG TGG AAC TTC ATC AGT
                                                                                                K   A   K   H   M   W   N   F   I   S
5652/1771
GGG ATA CAA GCG CTG GGC GCC ATT GCC         5682/1781
 G   I   Q   A   L   G   A   I   A          GCC CCC AAC CCC AAC GTC GCC ACC        5712/1791
                                             A   P   N   P   N   V   A   T         ACA TTG ATG GCT TTT AGC AGC CCA
                                                                                    T   L   M   A   F   S   S   P
5742/1801
TAC TAC CAA CTG GGC GCG TCA ACG
 Y   Y   Q   L   G   A   S   T
```

Fig. 11B-5

```
5742/1801                               5772/1811
CTA ACC ACT GGC CAA ACC CTC CTC TTC AAC ATA TTG GGG TGG GTG GCT GCC CAG CTC GCC GCC CCC GGT GCC ACT GCC TTT GTG
 L   T   T   G   Q   T   L   L   F   N   I   L   G   W   V   A   A   Q   L   A   A   P   G   A   T   A   F   V
5832/1831                               5862/1841                               5892/1851
GGT GCT GGC CTA GGC GCC ATC GGC AGC GTT GGA CTG GGG AAG GTC CTC GAC GGA CTG GAC ATT CTT GCA GGG TAT GGC GCG GCG
 G   A   G   L   G   A   I   G   S   V   G   L   G   K   V   L   D   G   L   D   I   L   A   G   Y   G   A   A
5922/1861                               5952/1871                               5982/1881
GGA GCT CTT GTA GCA TTC GTC GGT GAG GTC CCC TCC ACG GAG GAC CTG GTC AAT CTG CTG CCC GCC ATC CTC AAC CGG CCT GGA
 G   A   L   V   A   F   V   G   E   V   P   S   T   E   D   L   V   N   L   L   P   A   I   L   N   R   P   G
6012/1891                               6042/1901                               6072/1911
GCC CTT GTA GTC GTG GTC TGC GCA GCA ATA CTG CGC CGG CAC GTT GGC CCG CGG CAC TAC ATG GCA GTG CAA GGG GCA GTG ATA
 A   L   V   V   V   V   C   A   A   I   L   R   R   H   V   G   P   R   H   Y   M   A   V   Q   G   A   V   I
6102/1921                               6132/1931                               6162/1941
GCC TTC GCC TCC CGG GGG CAG CAC TAC ATA GTG CCG GAG AGC GAT GCA GGG GCA TGG ATT GCC ACT CTA AGC GAC ATC
 A   F   A   S   R   G   Q   H   Y   I   V   P   E   S   D   A   G   A   W   I   A   T   L   S   D   I
6192/1951                               6222/1961                               6252/1971
CTC ACT GTA ACC CAG CTC ATA CAT CAG TGG ATA AGC CTG AAA GCC CAC ACT CGC TGT GGA GCT CGC CCA TGC TCC GGT GTC TCC
 L   T   V   T   Q   L   I   H   Q   W   I   S   L   K   A   H   T   R   C   G   A   R   P   C   S   G   V   S
6282/1981                               6312/1991                               6342/2001
TGG GAC TGG ATA TGC GGG TAT AGG CTG GTG CTC TTT AAG ACC ATG ATG ATG TGG AGT GCA GAG TAC ATG CCA CAA CTG CAC ATG
 W   D   W   I   C   G   Y   R   L   V   L   F   K   T   M   M   M   W   S   A   E   Y   M   P   Q   L   H   M
6372/2011                               6402/2021                               6432/2031
TGC CAG CGC GGG TAT AGG GGT GTC TGG CGA GGA GAC GGC ATT ATG CAG ATC CCA TCG AGA CTC GAG GAA TTT TTC ACA TGT GGA
 C   Q   R   G   Y   R   G   V   W   R   G   D   G   I   M   Q   I   P   S   R   L   E   E   F   F   T   C   G
6462/2041                               6492/2051                               6522/2061
AAC GGG ACG ATC AGG ATC GTC GGT GGT CCT CCT AGG AAC TGC AGG AGT GCA GAG GTG CTC CAC CAG GAA CAT CAG GAA TAC CTA
 N   G   T   I   R   I   V   G   G   P   P   R   N   C   R   S   A   E   V   L   H   E   Y   L
6552/2071                               6582/2081                               6612/2091
ACT CCC CTT GCG CGG TGC CCT TCC CGT CGT ACC TGC AGG AGG ATG GAG TGG AGG GAT TGC AGG AGG ATA GCC CCC CCC ATT AAC
 T   P   L   A   R   C   P   A   T   C   R   R   M   E   W   R   D   C   R   R   I   A   P   P   I   N
6642/2101                               6672/2111                               6702/2121
TAC GTA TCG GGT GTA ATG ACT GCG CTG TGG GCG CTG TGG AGG CAG ATC CCG TGC CCA GTA CAA TTG CCA GAG ATA AGG GAG TTG TTC ACA
 Y   V   S   G   V   M   T   A   L   W   A   L   W   R   Q   I   P   C   P   V   Q   L   P   E   I   R   E   L   F   T
6732/2131                               6762/2141                               6792/2151
CAC AGG TTT GCG CCC TTG TGC AAG CCC CTT CTG CGG GAG GAG GTA TCA TTC AGA GTA GAA CCC TAC TTT TTC CAC GAG GTG CAA TTA
 H   R   F   A   P   L   C   K   P   L   L   R   E   E   V   S   F   R   V   E   P   Y   F   H   E   V   Q   L
6822/2161                               6852/2171                               6882/2181
CAC CGG TGC GAG CCC ATG GCA TTG ACG GTG ATG CTC CAC TGG GAT GAT CCC TTG CTG CAC CAG GTG CAT CTT CAT CAA AGG
 H   R   C   E   P   M   A   L   T   V   M   L   H   W   D   D   P   L   L   H   E   Y   A   L   H   E   V   H
6912/2191                               6942/2201                               6972/2211
GCG AGA GGG TCA GAA GTA GCC TCT ATG CTC ACT AGG CAG CAG ATG GGC ATA ACA ACA GGG GAG GCG GCG TGC AGG GCG AGA AGG
 A   R   G   S   E   V   A   S   M   L   T   R   Q   Q   M   G   I   T   T   G   E   A   A   T   C   R   A   R   R
7002/2221                               7032/2231                               7062/2241
TCC CCT GAG GCC GAG GCG CTC AGC TCC TCG CTG TGG AGG CAG CAG CGC TCT AAG CTC AAG GCA ACT AAG CCC ACT AGG ATC ACC AGG GTT GAG TCA AAC AAC ATC AAA GTG
 S   P   D   A   E   A   L   S   S   S   L   W   R   Q   Q   R   S   K   L   K   A   T   R   S   P   T   R   I   T   R   V   E   S   N   N   I   T   R   K
```

```
8442/2701
GCG AGC GGC GTA CTG ACA ACT AGC TGT GGT    8472/2711
 A   S   G   V   L   T   T   S   C   G    AAC ACC CTC ACT TGC TAC ATC AAG GCC CGG
8532/2731                                   N   T   L   T   C   Y   I   K   A   R
TGC ACC ATG CTC GTG TGT GAC TTA           8502/2721
 C   T   M   L   V   C   D   L            GCA GCC TGT CGA GCC GCA GGG CTC CAG GAC
8622/2761                                   A   A   C   R   A   A   G   L   Q   D
GAG GCT ATG ACC AGG TAC TCC GCC CCC       8562/2741
 E   A   M   T   R   Y   S   A   P        GTC GTT ATC TGT GAA AGT GCG CTG AGA GCC TTC ACG
8712/2791                                   V   V   I   C   E   S   A   L   R   A   F   T
TCA GTC GCC CAC GAC GGC GCT GGA AAG AGG   8652/2771
 S   V   A   H   D   G   A   G   K   R    GGG GAC CCC CCC CAA CCA GAA TAC GAC TTG
8802/2821                                   G   D   P   P   Q   P   E   Y   D   L
AGA CAC ACT CCA GTC AAT TCC CTA GGC       8682/2781
 R   H   T   P   V   N   S   L   G        GAG CTT ATA ACA TCA TGC TCC GAG ACA GCA
8892/2851                                   E   L   I   T   S   C   S   E   T   A
AGC GTC CTC ATA AGA AGA CAA GCC AGG GAT CAG CTT GAA GCC  8772/2811
 S   V   L   I   R   R   Q   A   R   D   Q   L   E   A   CCC CTC GCG AGA GCC GCG TGG GAG ACA GCA
8982/2881                                                  P   L   A   R   A   A   W   E   T   A
CCA ATC ATT CAA CAG GCT CTT TCA CTC CAC AGT TAC TCT CCA GGT 8862/2841
 P   I   I   Q   Q   A   L   S   L   H   S   Y   S   P   G  GCG AGG ATG ATA CTG ATG ACC CAT TTC TTT
9072/2911                                                     A   R   M   I   L   M   T   H   F   F
AAA CTT GGG GTC CCG CCC TTG CGA GCT AGG  8952/2871
 K   L   G   V   P   P   L   R   A   R    TGC TAC TCC CTT AAC CAC CTC TCA GGT GCC ATA GAA CCA GAT CTA CCT
9162/2941                                   C   Y   S   L   N   H   L   S   G   A   I   E   P   D   L   P
TGT GGC AAG TAC CTC TTC AAC TGG GCA GTA  9042/2901
 C   G   K   Y   L   F   N   W   A   V    GAA ATC AAT AGG CTT CTG TCC AGA GGA CTG GAC TTG TCC GGT
9252/2971                                   E   I   N   R   L   L   S   R   G   L   D   L   S   G
TTC ACG GCT GGC TAC AGC GTG TCT CAT GCC   9132/2931
 F   T   A   G   Y   S   V   S   H   A    GCC CGG GCT AGG GCC CGG GCT AGG GCG
9342/3001                                   A   R   A   R   A   A   I   A
GCA GGG GTA GGC ATC TAC CTC CTC CCC       9222/2961
 A   G   V   G   I   Y   L   L   P        GCC GCT GGC CGG CTG GAC CTA CTC CTG GCT
9372/3011                                   A   A   G   R   L   D   L   L   L   A
CGA TGA                                   9312/2991
 R   *                                    TGG TTC TGG TTT TGC CTC CTC AGA
                                            W   F   W   F   C   L   L   R
                                          9402/3021
```

```
 8301 GCATCCGAAG GAGGACGCAC GTCCACTCGG ATGGCTAAGG GAGTCTAGAC TGGAATTCGT CGACGAGCTC CCTATAGTGA GTCGTATTAG AGGCCGACTT 8400
 8401 GGCCAAATTC GTAATCATGG GTAATTGTTAT TCATATGTGT TCCTGTGTG AAATTGTTAT CCGCTCACAA TTCCACACAA GGAAGCATAA AGTGTAAAGC 8500
 8501 CTGGGGTGCC TAATAGTGA GCTAACTCAC ATTAATTGCG TTGCGCTCAC TGCCCGCTTT CCAGTCGGGA AACCTGTCGT GCCAGCTGCA TTAATGAATC 8600
 8601 GGCCAACGCG CGGGGAGAGG CGGTTTGCGT ATTGGGCGCT CTTCCGCTTC GCTCGCTCACT GACTCGCTGC GCTCGGTCGT TCGGCTGCGG CGAGCGGTAT 8700
 8701 CAGCTCACTC AAAGGCGGTA ATACGGTTAT CCACAGAATC AGGGGATAAC GCAGGAAAGA ACATGTGAGC AAAAGGCCAG CAAAAGGCCA GGAACCGTAA 8800
 8801 AAAGGCCGCG TTGCTGGCGT TTTTCCATAG GCTCCGCCCC CCTGACGAGC ATCACAAAAA TCGACGCTCA AGTCAGAGGT GGCGAAACCC GACAGACTA 8900
 8901 TAAAGATACC AGGCGTTTCC CCCTGGAAGC TCCCTCGTGC GCTCTCCTGT TCCGACCCTG CCGCTTACCG GATACCTGTC CGCCTTTCTC CCTTCGGGAA 9000
 9001 GCGTGGCGCT TTCTCATAGC TCACGCTGTA GGTATCTCAG TTCGGTGTAG GTCGTTCGCT CCAAGCTGGG CTGTGTGCAC GAACCCCCCG TTCAGCCCGA 9100
 9101 CCGCTGCGCC TTATCCGGTA ACTATCGTCT TGAGTCCAAC CCGGTAAGAC ACGACTTATC GCCACTGGCA GCAGCCACTG GTAACAGGAT TAGCAGAGCG 9200
 9201 AGGTATGTAG GCGGTGCTAC AGAGTTCTTG AAGTGGTGGC CTAACTACGG CTACACTAGA AGGACAGTAT TTGGTATCTG CGCTCTGCTG AAGCCAGTTA 9300
 9301 CCTTCGGAAA AAGAGTTGGT AGCTCTTGAT CCGGCAAACA AACCACCGCT GGTAGCGGTG GTTTTTTTGT CTCACGCGTG CAGATTACGC GCAGAAAAGG 9400
 9401 ATCTCAAGAA GATCCTTTGA TCTTTTCTAC GGGGTCTGAC GCTCAGTGGA ACGAAAACTT CACGTTAAG GGATTTTGG TCATGAGATT ATCAAAAAGG 9500
 9501 AGGCACCTAT CTCAGCGATC TGTCTATTTC GTTCATCCAT AGTTGCCTGA CTCCCCGTCG TGTAGATAAC TACGATACGG GAGGGCTTAC CATCTGGCCC 9600
 9601 CAGTGCTGCA ATGATACCGC GAGACCCACG CTCACCGGCT CCAGATTTAT CAGCAATAAA CCAGCCAGCC GGAAGGGCCG AGCGCAGAAG TGGTCCTGCA 9700
 9701 ACTTTATCCG CCTCCATCCA GTCTATTAAT TGTTGCCGGG AAGCTAGAGT AAGTAGTTCG CCAGTTAATA GTTTGCGCAA CGTTGTTGCC ATTGCTACAG 9800
 9801 GCATCGTGGT GTCACGCTCG TCGTTTGGTA TGGCTTCATT CAGCTCCGGT TCCCAACGAT CAAGGCGAGT TACATGATCC CCCATGTTGT GCAAAAAAGC 9900
 9901 GGTTAGCTCC TTCGGTCCTC CGATCGTTGT CAGAAGTAAG TTGGCCGCAG TGTTATCACT CATGGTTATG GCAGCACTGC ATAATTCTCT TACTGTCATG 10000
10001 CCATCCGTAA GATGCTTTTC TGTGACTGGT GAGTACTCAA CCAAGTCATT CTGAGAATAG TGTATGCGGC GACCGAGTTG CTCTTGCCCG GCGTCAATAC 10100
10101 GGGATAATAC CGCGCCACAT AGCAGAACTT TAAAAGTGCT CATCATTGGA AAACGTTCTT CGGGGCGAAA ACTCTCAAGG ATCTTACCGC TGTTGAGATC 10200
10201 CAGTTCGATG TAACCCACTC GTGCACCCAA CTGATCTTCA GCATCTTTTA CTTTCACCAG CGTTTCTGGG TGAGCAAAAA CAGGAAGGCA AAATGCCGCA 10300
10301 AAAAAGGGAA TAAGGGCGAC ACGGAAATGT TGAATACTCA TACTCTTCCT TTTTCAATAT TATTGAAGCA TTTATCAGGG TTATTGTCTC ATGAGCGGAT 10400
10401 ACATATTTGA ATGTATTTAG AAAAATAAAC AAATAGGGGT TCCGCGCACA TTTCCCCGAA AAGTGCCACC TGACGCGCCC TGTAGCGGCG CATTAAGCGC 10500
10501 GGCGGGTGTG GTGGTTACGC GCAGCGTGAC CGCTACACTT GCCAGCGCCC TAGCGCCCGC TCCTTTCGCT TTCTTCCCTT CCTTTCTCGC CACGTTCGCC 10600
10601 GGCTTTCCCC GTCAAGCTCT AAATCGGGGC ATCCCTTTAG GGTTCCGATT TAGTGCTTTA CGGCACCTCG ACCCCAAAAA ACTTGATTAG GGTGATGGTT 10700
10701 CACGTAGTGG GCCATCGCCC TGATAGACGG TTTTTCGCCC TTTGACGTTG GAGTCCACGT TCTTTAATAG TGGACTCTTG TTCCAAACTG GAACAACACT 10800
10801 CAACCCTATC TCGGTCTATT CTTTTGATTT ATAAGGGATT TTGCCGATTT CGGCCTATTG GTTAAAAAAT GAGCTGATTT AACAAAAAT TAACGCGAAT 10900
10901 TTTAACAAAA TATTAACGTT TACAATTTC AGGTGGCACT TTTCGGGGAA ATGTGCGCGG AACCCCTATT TGTTTATTT TCTAAATACA TTCAAATATG 11000
11001 TATCCGCTCA TGAGACAATA ACCCTGATAA ATGCTTCAAT AATATTGAAA AAGGAAGAGT ATGAGTATTC AACATTTCCG TGTCGCCCTT ATTCCCTTTT 11100
11101 TTGCGGCATT TTGCCTTCCT GTTTTTGCTC ACCCAGAAAC GCTGGTGAAA GTAAAAGATG CTGAAGATCA GTTGGGTGCA CGAGTGGGTT ACATCGAACT 11200
```

Fig. 12B-1

```
2077/1
ATG GCG CCC ATC ACG TAC GCC CAG CAG              2107/11                              2137/21
M   A   P   I   T   Y   A   Q   Q              ACG AGA GGC CTC CTA GGG TGT ATA ATC ACT GGC CGG GAC AAA AAC CAA GTG
                                                T   R   G   L   L   G   C   I   I   T   G   R   D   K   N   Q   V
2167/31                                         2197/41                              2227/51
GAG GGT GAG GTC CAG ATC ATC GCT ACT             CAA ACC TTC CTG GCA ACG ATC ATC AAT GGG GTA TGC TGG ACT CAC GGG CCT CAA
E   G   E   V   Q   I   I   A   T              Q   T   F   L   A   T   I   I   N   G   V   C   W   T   H   G   P   Q
2257/61                                         2287/71                              2317/81
GGA ACG AGG ACC ATC GCA CCC AAG GGT             CCT GTC ATC CAG ATG TAT ACC TAC CTT GTG GGC GAT GTC CCC GCT CCT CGG CGA
G   T   R   T   I   A   P   K   G              P   V   I   Q   M   Y   T   Y   L   V   G   D   V   P   A   P   R   R
2347/91                                         2377/101                             2407/111
GGT TCC CGC TCA TTG ACA CCC ACC TGT             TCA TCC TCG GAC CTT TAC TGC CTG ACG CAC GCC GAT GTC CCC GCG GGA CAC
G   S   R   S   L   T   P   T   C              S   S   S   D   L   Y   C   L   T   H   A   D   V   P   A   G   H
2437/121                                        2467/131                             2497/141
GGT GAT AGC AGG GGT AGC CTG CTT TCG             CGG CCC ATT TCC TAC TTG AAA GGC GGT CCG CTG GAG AAC CTA CCC GCG ACA ATG
G   D   S   R   G   S   L   L   S              R   P   I   S   Y   L   K   G   G   P   L   E   N   L   P   A   T   M
2527/151                                        2557/161                             2587/171
GCC GTG GGC CTA TTC AGG GCC GTG TGC             ACC CGT GGA GTG GCT CCC CAG AGC GTG TTG ATC CCT GTT CAT GCT GCA ACC GGT
A   V   G   L   F   R   A   V   C              T   R   G   V   A   P   Q   S   V   L   I   P   V   H   A   A   T   G
2617/181                                        2647/191                             2677/201
AGA TCC CCG GTG TTC ACG GAC GAC AAC TCC TCT CCA CCA GCA GCG CCC AGC TTC CAG CTC GTG GCC CAC CTG GTT GGC ACC CCC ATC CGA
R   S   P   V   F   T   D   D   N   S   S   P   P   A   A   P   S   F   Q   L   V   A   H   L   V   G   T   P   I   R
2707/211                                        2737/221                             2767/231
AAG AGC ACC AAG GTC CCG GCT GCT ACG GGA TAC GCA CAG GGC GTG TTG AAG ACC AGG ATA ATC CTG CCC TCT GTT GCT GGC AGC CCC ACC TCC GTC
K   S   T   K   V   P   A   A   T   G   Y   A   Q   G   V   L   K   T   R   I   I   L   P   S   V   A   G   S   P   T   S   V
2797/241                                        2827/251                             2857/261
GCT GTG ATG TCC CAT CCT AAC ATC ATC ATC         CCT AAT GAT GTT GCT ATC GCG GGG GCA GAA GGA GAG ATC CCC TTT ACC ACT ACT TTT ACC
A   V   M   S   H   P   N   I   I   I          P   N   D   V   A   I   A   G   A   E   G   E   I   P   F   T   T   T   F   T
2887/271                                        2917/281                             2947/291
TAC TAC AAG TTC CTT GCC GAC GAT CAT GAC ATC TTC TCA GGA GGG TGC GGG GCT TAT GAC GGG GAC GAG GTT CTC ACG TGT TGC CCA ACC ACA TCC
Y   Y   K   F   L   A   D   D   H   D   I   F   S   G   G   C   G   A   Y   D   G   D   E   V   L   T   C   C   P   T   T   S
2977/301                                        3007/311                             3037/321
ATC TTG GGC ATC ACG GGA CTT CTT GAC GTT GAC TCA GGA CAA GCA GAG ACT GGG GCG GAT GTT CTC GCC ACT ACC CCT CCC ATG ACT CTC
I   L   G   I   T   G   L   L   D   V   D   S   G   Q   A   E   T   G   A   D   V   L   A   T   T   P   P   M   T   L
3067/331                                        3097/341                             3127/351
ACT GTG TCC CAT CCT AAC ATC GAG GAG GTT         GCT CTG TCC ACC AAG GGA GAG ATC CCC TTT TAC GGC AAG GCA GCT ATC CTC GAG GTG ATC
T   V   S   H   P   N   I   E   E   V          A   L   S   T   K   G   E   I   P   F   Y   G   K   A   A   I   L   E   V   I
3157/361                                        3187/371                             3217/381
AAG GGG AGA GAT CAT CTT CTG TGC CAC             TCA AAG AAG AAG TGC GAC GAG CTC GCA GCG AAG CTG GTC GCA TTG GGC ATC AAT GCC GTG
K   G   R   D   H   L   L   C   H              S   K   K   K   C   D   E   L   A   A   K   L   V   A   L   G   I   N   A   V
3247/391                                        3277/401                             3307/411
GCC TAC TAC CGC GGT CTT GAC GTC TCT             ATC CCG ACC AGC GGC GAT GTT GTC GTT TCG ACC GAT GCT CTC ATG ACT GGC TTT ACC
A   Y   Y   R   G   L   D   V   S              I   P   T   S   G   D   V   V   V   S   T   D   A   L   M   T   G   F   T
3337/421                                        3367/431                             3397/441
GGC GAC TTC GAC TCT GTG ATA GAC TGC             AAC ACG TGT GTC ACT CAG ACA GTC GAT TTC AGC CTT GAC CCT ACC TTT ACC ATT GAG ACA ACC
G   D   F   D   S   V   I   D   C              N   T   C   V   T   Q   T   V   D   F   S   L   D   P   T   F   T   I   E   T   T
```

```
4777/901
GGG AAC CAT GTT TCC CCC ACG CAC TAC GTG                                                 4807/911
 G   N   H   V   S   P   T   H   Y   V  CCG GAG AGC GAT GCA GCC GCC CGC GTC ACT         4837/921
4867/931                                  P   E   S   D   A   A   A   R   V   T  GCC ATA CTC AGC CTC ACT GTA ACC CAG
CTC CTG AGG CGA CTG CAT CAG TGG ATA AGC  4897/941                                  A   I   L   S   L   T   V   T   Q
 L   L   R   R   L   H   Q   W   I   S  TCG GAG TGT GAG ACT CCA TGC CAA CTG TCC         4927/951
4957/961                                  S   E   C   E   T   P   C   Q   L   S  TGG CTA AGG TTT CCT GAC ATC TGG GAT ATA TGC
GAG GTG CTG AGC GAC TTT AAG ACC TGG CTG  4987/971                                  W   L   R   F   P   D   I   W   D   I   C
 E   V   L   S   D   F   K   T   W   L  AAA GCC AAG GCT CTG ATG CCA CAA CTG GGG         5017/981
5047/991                                  K   A   K   A   L   M   P   Q   L   G  ATT CCC TTT GTG TCC CGC GGG TAT
AGG GGG GTC TGG CGA GGA GAC ATT ATG      5077/1001                                 I   P   F   V   S   R   G   Y
 R   G   V   W   R   G   D   I   M      CAC ACT CGC TGC CAC TGT GGA GCT ATG         5107/1011
5137/1021                                 H   T   R   C   H   C   G   A   M        ACT GGA CAT GTC AAA AAC GGG ACG CCT GCG
ATC GTC GGT CCT AGG ACC TGC AGG AAC ATG  5167/1031                                  T   G   H   V   K   N   G   T   P   A
 I   V   G   P   R   T   C   R   N   M  TGG AGT GGG AAC ACG GGC CCC TGT ACT           5197/1041
5227/1051                                 W   S   G   N   T   G   P   C   T         ACC ACG GGC TTC CAC TAC CTA CAC CAC CCC
CCG AAC TAT AAG TTC GCG CTG TGC CCG TGC  5257/1061                                  T   T   G   F   H   Y   L   H   H   P
 P   N   Y   K   F   A   L   C   P   C  TCT AGT GAG GTG CAG GTG GAC GGG GAC           5287/1071
5317/1081                                 S   S   E   V   Q   V   D   G   D         CGC CAA TTA TTA TAC CAC AGG TTT GCG CCC
ACT ACT GAC AAT CTT AAA TGC CCA TCG CAG  5347/1091                                  R   Q   L   L   Y   H   R   F   A   P
 T   T   D   N   L   K   C   P   S   Q  ATC CCA TCA TCG GAA TTT ACA GAA TTG           5377/1101
5407/1111                                 I   P   S   S   E   F   T   E   L         GAC GGG GTC GAT GGG GAC TCG GAG CCC GAA
CCT TGC AAG CCC TTG CTG CGG GAG GAG AGG  5437/1121                                  D   G   V   D   G   D   S   E   P   E
 P   C   K   P   L   L   R   E   E   R  TCA TTC AGA GTA GTA TAC CCG TAC CCG           5467/1131
5497/1141                                 S   F   R   V   V   Y   P   Y   P         GTG GGG GTC GGG GGG AGA GCA GAG GCG GAA
CCG GAC GTA GCC GTG TTG ACG ATG CTC      5527/1151                                  V   G   V   G   G   R   A   E   A   E
 P   D   V   A   V   L   T   M   L      ACT GAT GAT CCC CAT ATA TCT CTC AAG         5557/1161
5587/1171                                 T   D   D   P   H   I   S   L   K        GCC GGG AGA CAT GAC AAA AAC TGC GAG
CCT TCT ATG GCC AGC TCG AGC CAG CTG      5617/1181                                  A   G   R   H   D   K   N   C   E
 P   S   M   A   S   S   S   Q   L      CTG TCC GCT ATC ACC GGC AAC GGC              5647/1191
5677/1201                                 L   S   A   I   T   G   N   G            ACC GCC AAC TCA AAA GTG GTG ATT CTG
CTC ATA GAG GCT AAC CTC CTG AGG CAG      5707/1211                                  T   A   N   S   K   V   V   I   L
 L   I   E   A   N   L   L   R   Q      GAG ATG GGC GAG CAG GAG                     5737/1221
5767/1231                                 E   M   G   E   Q   E                     TCA GAG AAC TCT CGG AGA TTC GCC GCC CTG
TTC GAT CCG CTT GTG GCA GAG GAG GAG      5797/1241                                  S   E   N   S   R   R   F   A   A   L
 F   D   P   L   V   A   E   E   E      GAG GAG GTC GAG GAG                         5827/1251
5857/1271                                 E   E   V   E   E                         CGG AAG TCT GAA CGT GTC CAT GGC TGC CCG
CCC GTC TGG CGG TAC AAC CCG CCG CTA GTA  5887/1271                                  R   K   S   E   R   V   H   G   C   P
 P   V   W   R   Y   N   P   P   L   V  CGG CTA GTA                                 5917/1281
5947/1291                                 R   L   V                                 TAC GAA CCA CGT ACG CTC ACC TCT ACT
CTA CCA CCT CGG CCA CCT CCT GTG          5977/1301                                  Y   E   P   R   T   L   T   S   T
 L   P   P   R   P   P   P   V          CCG CCT GTG                                 6007/1311
6037/1321                                 P   P   V                                 ACC GAA TCA ACC CTA TCT ACT GCC GCC CCC
GAG CTT GCC ACC AAA AGT TTT GGC TCC      6067/1331                                  T   E   S   T   L   S   T   A   A   P
 E   L   A   T   K   S   F   G   S      TCA ACT TCC                                 6097/1341
                                          S   T   S                                ACA ACA ACG GGC ATT TCC GGC
                                                                                    T   T   T   G   I   S   G
```

```
7477/1801
AAT TCC TGG CTA GGC AAC ATA ATC ATG TTT GCC CCC ACA CTG TGG GCG AGG ATG ATA CTG
 N   S   W   L   G   N   I   I   M   F   A   P   T   L   W   A   R   M   I   L
                                                7507/1811
7567/1831                                                                7537/1821
AGG GAT CAG CTT GAA CAG GCT CTT AAC TGT GAG ATC TAC GGA ATC TAC ATA GAA ATG ACC CAT TTC TTT AGC GTC CTC ATA GCC
 R   D   Q   L   E   Q   A   L   N   C   E   I   Y   G   I   Y   I   E   M   T   H   F   F   S   V   L   I   A
7597/1841                                                    7627/1851
7657/1861                                                                7687/1871
CTC CAT GGC CTC AGC GCA TTT TCA CTC CAC AGT TAC TCT CCA GGT GAA ATC CCA CTA GAT CTA CCT CCA ATC ATT CAA AGA
 L   H   G   L   S   A   F   S   L   H   S   Y   S   P   G   E   I   P   L   D   L   P   P   I   I   Q   R
7717/1881
7747/1891                                                    7777/1901                        7717/1881
CCC TTG CGA GCT TGG AGA CAC CGG GCC CGG AGC GTC CGC GCT AGG CTT CTG TCC AGA GCC GCA TGC CTC AGA AAA CTT GGG GTC CCG
 P   L   R   A   W   R   H   R   A   R   S   V   R   A   R   L   L   S   R   A   A   C   L   R   K   L   G   V   P
7837/1921                                                    7867/1931                        7807/1911
TTC AAC TGG GCA GTA AGA ACA AAG CTC AAA CTC ACT CCA ATA GCG GCC CGG CTG GGC AGG CTA TGT GGC AAG TAC CTC
 F   N   W   A   V   R   T   K   L   K   L   T   P   I   A   A   R   L   G   R   A   I   C   G   K   Y   L
7927/1951                                                    7957/1961                        7897/1941
AGC GGG GGA GAC ATT TAT CAC AGC GTG TCT CAT GCC CGG CCC CGC CGG TGG TTC TGG GAC TTG TCC GGT TGG TTC ACG GCT GGC TAC
 S   G   G   D   I   Y   H   S   V   S   H   A   R   P   R   R   W   F   W   D   L   S   G   W   F   T   A   G   Y
8017/1981                        8047/1991                                                    7987/1971
TAC CTC CTC CCC AAC CGA TGA                      CTA CTC CTG TGC GCA GGG GTA GGC ATC
 Y   L   L   P   N   R   *                        L   L   L   C   A   G   V   G   I
                                                                                    8077/2001
```

Fig. 13A

```
   1 gccagccccc tgatggggc gacactccac catgaatcac tccctgtga ggaactactg
  61 tcttcacgca gaaagcgtct agccatggcg ttagtatgag tgtcgtgcag cctccaggac
 121 cccccctccc gggagagcca tagtggtctg cggaaccggt gagtacaccg gaattgccag
 181 gacgaccggg tcctttcttg gataaacccg ctcaatgcct ggagatttgg gcgtgccccc
 241 gcaagactgc tagccgagta gtgttgggtc gcgaaggcc ttgtggtact gcctgatagg
 301 gtgcttgcga gtgccccggg aggtctcgta gaccgtgcac catgagcacg aatcctaaac
 361 ctcaaagaaa aaccaaacgt aacaccaacc gtcgcccaca ggacgtcaag ttcccgggtg
 421 gcggtcagat cgttggtgga gtttacttgt tgccgcgcag gggccctaga ttgggtgtgc
 481 gcgcgacgag gaagacttcc gagcggtcgc aacctcgagg tagacgtcag cctatcccca
 541 aggcacgtcg gcccgagggc aggacctggg ctcagcccgg gtacccttgg ccctctatg
 601 gcaatgaggg ttgcgggtgg gcgggatggc tcctgtctcc ccgtggctct cggcctagct
 661 ggggccccac agaccccgg cgtaggtcgc gcaatttggg taaggtcatc gatacccta
 721 cgtgcggctt cgccgacctc atgggtaca taccgctcgt cggcgcccct cttggaggcg
 781 ctgccagggc cctggcgcat ggcgtccggg ttctggaaga cggcgtgaac tatgcaacag
 841 ggaaccttcc tggttgctct ttctctatct tccttctggc cctgctctct tgcctgactg
 901 tgcccgcttc agcctaccaa gtgcgcaatt cctcggggct ttaccatgtc accaatgatt
 961 gccctaactc gagtattgtg tacgaggcgg ccgatgccat cctgcacact ccggggtgtg
1021 tcccttgcgt tcgcgagggt aacgcctcga ggtgttgggt ggcggtgacc cccacggtgg
1081 ccaccaggga cggcaaactc cccacaacgc agcttcgacg tcatatcgat ctgcttgtcg
1141 ggagcgccac cctctgctcg gccctctacg tggggacct gtgcgggtct gtctttcttg
1201 ttggtcaact gtttaccttc tctcccaggc gccactggac gacgcaagac tgcaattgtt
1261 ctatctatcc cggccatata acgggtcatc gcatggcatg ggatatgatg atgaactggt
1321 ccctacggc agcgttggtg gtagctcagc tgctccggat cccacaagcc atcatggaca
1381 tgatcgctgg tgctcactgg ggagtcctgg cgggcatagc gtatttctcc atggtgggga
1441 actgggcgaa ggtcctggta gtgctgctgc tatttgccgg cgtcgacgcg gaaacccacg
1501 tcaccggggg aaatgccggc cgcaccacgg ctgggcttgt tggtctcctt acaccaggcg
1561 ccaagcagaa catccaactg atcaacacca acggcagttg gcacatcaat agcacggcct
1621 tgaattgcaa tgaaagcctt aacaccggct ggttagcagg gctcttctat caacacaaat
1681 tcaactcttc aggctgtcct gagaggttgg ccagctgccg acgccttacc gattttgccc
1741 agggctgggg tcctatcagt tatgccaacg gaagcggcct cgacgaacgc cctactgct
1801 ggcactaccc tccaagacct tgtggcattg tgcccgcaaa gagcgtgtgt ggccgggtat
1861 attgcttcac tcccagcccc gtggtggtgg aacgaccga caggtcgggc gcgcctacct
1921 acagctgggg tgcaaatgat acggatgtct tcgtccttaa caccaccagg ccaccgctgg
1981 gcaattggtt cggttgtacc tggatgaact caactggatt caccaaagtg tgcggagcgc
2041 ccccttgtgt catcggaggg gtgggcaaca acaccttgct ctgccccact gattgcttcc
2101 gcaaacatcc ggaagccaca tactctcggt gcggctccgg tcctggatt acacccaggt
2161 gcatggtcga ctaccgtat aggctttggc actatccttg taccatcaat tacaccatat
2221 tcaaagtcag gatgtacgtg ggaggggtcg agcacaggct ggaagcggcc tgcaactgga
2281 cgcggggcga acgctgtgat ctgaagaca gggacaggtc cgagctcagc ccgttgctgc
2341 tgtccaccac acagtggcag gtccttccgt gttctttcac gacctgcca gccttgtcca
2401 ccggcctcat ccacctccac cagaacattg tggacgtgca gtacttgtac ggggtagggt
2461 caagcatcgc gtcctgggcc attaagtggg agtacgtcgt tctcctgttc cttctgcttg
2521 cagacgcgcg cgtctgctcc tgcttgtgga tgatgttact catatcccaa gcggaggcgg
2581 ctttggagaa cctcgtaata ctcaatgcag catccctggc cgggacgcac ggtcttgtgt
2641 ccttcctcgt gttcttctgc tttgcgtggt atctgaaggg taggtgggtg cccggagcgg
2701 tctacgccct ctacgggatg tggcctctcc tcctgctcct gctggcgttg cctcagcggg
2761 catacgcact ggacacggag gtggccgcgt cgtgtggcgg cgttgttctt gtcgggttaa
2821 tggcgctgac tctgtcgcca tattacaagc gctatatcag ctggtgcatg tggtggcttc
2881 agtattttct gaccagagta gaagcgcaac tgcacgtgtg ggttcccccc ctcaacgtcc
2941 ggggggggcg cgatgccgtc atcttactca tgtgtgtagt acacccgacc ctggtatttg
3001 acatcaccaa actactcctg gccatcttcg gaccctttg gattcttcaa gccagtttgc
3061 ttaaagtccc ctacttcgtg cgcgttcaag gccttctccg gatctgcgcg ctagcgcgga
```

Fig. 13B

```
3121 agatagccgg aggtcattac gtgcaaatgg ccatcatcaa gttaggggcg cttactggca
3181 cctatgtgta taaccatctc accoctcttc gagactgggc gcacaacggc ctgcgagatc
3241 tggccgtggc tgtggaacca gtcgtcttct cccgaatgga gaccaagctc atcacgtggg
3301 gggcagatac cgccgcgtgc ggtgacatca tcaacggctt gcccgtctct gcccgtaggg
3361 gccaggagat actgcttggg ccagccgacg gaatggtctc caaggggtgg aggttgctgg
3421 cgcccatcac ggcgtacgcc cagcagacga gaggcctcct agggtgtata atcaccagcc
3481 tgactggccg ggacaaaaac caagtggagg gtgaggtcca gatcgtgtca actgctaccc
3541 aaaccttcct ggcaacgtgc atcaatgggg tatgctggac tgtctaccac ggggccggaa
3601 cgaggaccat cgcatcaccc aagggtcctg tcatccagat gtataccaat gtggaccaag
3661 accttgtggg ctggcccgct cctcaaggtt cccgctcatt gacaccctgt acctgcggct
3721 cctcggacct ttacctggtc acgaggcacg ccgatgtcat tcccgtgcgc cggcgaggtg
3781 atagcagggg tagcctgctt tcgccccggc ccatttccta cttgaaaggc tcctcggggg
3841 gtccgctgtt gtgccccgcg ggacacgccg tgggcctatt cagggccgcg gtgtgcaccc
3901 gtggagtggc taaagcggtg gactttatcc ctgtgagaa cctagggaca accatgagat
3961 ccccggtgtt cacggacaac tcctctccac cagcagtgcc ccagagcttc caggtggccc
4021 acctgcatgc tcccaccggc agcggtaaga gcaccaaggt cccggctgcg tacgcagccc
4081 agggctacaa ggtgttggtg ctcaacccct ctgttgctgc aacgctgggc tttggtgctt
4141 acatgtccaa ggcccatggg gttgatccta atatcaggac cggggtgaga acaattacca
4201 ctggcagccc catcacgtac tccacctacg gcaagttcct tgccgacgtc gggtgctcag
4261 gaggtgctta tgacataata atttgtgacg agtgccactc cacggatgcc atcccatct
4321 tgggcatcgg cactgtcctt gaccaagcag agactgcggg ggcgagactg gttgtgctcg
4381 ccactgctac ccctccgggc tccgtcactg tgtcccatcc taacatcgag gaggttgctc
4441 tgtccaccac cggagagatc ccctttacg gcaaggctat cccctcgag gtgatcaagg
4501 ggggaagaca tctcatcttc tgccactcaa agaagaagtg cgacgagctc gccgcgaagc
4561 tggtcgcatt gggcatcaat gccgtggcct actaccgcgg tcttgacgtg tctgtcatcc
4621 cgaccagcgg cgatgttgtc gtcgtgtcga ccgatgctct catgactggc tttaccggcg
4681 acttcgactc tgtgatagac tgcaacacgt gtgtcactca gacagtcgat ttcagccttg
4741 accctacctt taccattgag acaaccacgc tccccagga tgctgtctcc aggactcaac
4801 gccggggcag gactggcagg gggaagccag gcatctatag atttgtggca ccgggggagc
4861 gccctccgg catgtcgac tcgtccgtcc tctgtgagtg ctatgacgcg ggctgtgctt
4921 ggtatgagct cacgcccgcc gagactacag ttaggctacg agcgtacatg aacaccccgg
4981 ggcttccgt gtgccaggac catcttgaat tttgggaggg cgtctttacg ggcctcactc
5041 atatagatgc ccactttta tcccagacaa agcagagtgg ggagaacttt ccttacctgg
5101 tagcgtacca agccaccgtg tgcgctaggg ctcaagcccc tcccccatcg tgggaccaga
5161 tgtggaagtg tttgatccgc cttaaaccca ccctccatgg gccaacaccc ctgctataca
5221 gactgggcgc tgttcagaat gaagtcaccc tgaccgaccc aatcaccaaa tacatcatga
5281 catgcatgtc ggccgacctg gaggtcgtca cgagcacctg ggtgctcgtt ggcggcgtcc
5341 tggctgctct ggccgcgtat tgcctgtcaa caggctgcgt ggtcatagtg ggcaggatcg
5401 tcttgtccgg gaagccggca attatacctg acagggaggt tctctaccag gagttcgatg
5461 agatggaaga gtgctctcag cacttaccgt acatcgagca agggatgatg ctcgctgagc
5521 agttcaagca gaaggcccctc ggcctcctgc agaccgcgtc ccgccatgca gaggttatca
5581 ccctgctgt ccagaccaac tggcagaaac tcgaggtctt tgggcgaag cacatgtgga
5641 atttcatcag tgggatacaa tacttggcgg gcctgtcaac gctgcctggt aaccccgcca
5701 ttgcttcatt gatggctttt acagctgccg tcaccagccc actaaccact ggccaaaccc
5761 tcctcttcaa catattgggg gggtggtgg ctgcccagct cgccgccccc ggtgccgcta
5821 ctgcctttgt gggtgctggc ctagctggcg ccgccatcgg cagcgttgga ctggggaagg
5881 tcctcgtgga cattcttgca gggtatggcg cgggcgtggc gggagctctt gtagcattca
5941 agatcatgag cggtgaggtc ccctccacgg aggacctggt caatctgctg cccgccatcc
6001 tctcgcctgg agcccttgta gtcggtgtgg tctgcgcagc aatactgcgc cggcacgttg
6061 gcccgggcga gggggcagtg caatggatga accggctaat agccttcgcc tcccggggga
6121 accatgtttc ccccacgcac tacgtccgg agagcgatgc agccgcccgc gtcactgcca
6181 tactcagcag cctcactgta acccagctcc tgaggcgact gcatcagtgg ataagctcgg
6241 agtgtaccac tccatgctcc ggttcctgc taagggacat ctgggactgg atatgcgagg
6301 tgctgagcga ctttaagacc tggctgaaag ccaagctcat gccacaactg cctgggattc
6361 cctttgtgtc ctgccagcgc gggtataggg gggtctggcg aggagacggc attatgcaca
6421 ctcgctgcca ctgtggagct gagatcactg gacatgtcaa aaacgggacg atgaggatcg
6481 tcggtcctag gacctgcagg aacatgtgga gtgggacgtt ccccattaac gcctacacca
```

Fig. 13C

```
6541 cgggcccctg tactcccctt cctgcgccga actataagtt cgcgctgtgg agggtgtctg
6601 cagaggaata cgtggagata aggcgggtgg gggacttcca ctacgtatcg ggtatgacta
6661 ctgacaatct taaatgcccg tgccagatcc catcgcccga atttttcaca gaattggacg
6721 gggtgcgcct acacaggttt gcgcccctt gcaagccctt gctgcgggag gaggtatcat
6781 tcagagtagg actccacgag tacccggtgg ggtcgcaatt accttgcgag cccgaaccgg
6841 acgtagccgt gttgacgtcc atgctcactg atccctccca tataacagca gaggcggccg
6901 ggagaaggtt ggcgagaggg tcaccccctt ctatggccag ctcctcggct agccagctgt
6961 ccgctccatc tctcaaggca acttgcaccg ccaaccatga ctcccctgac gccgagctca
7021 tagaggctaa cctcctgtgg aggcaggaga tgggcggcaa catcaccagg gttgagtcag
7081 agaacaaagt ggtgattctg gactccttcg atccgcttgt ggcagaggag gatgagcggg
7141 aggtctccgt acctgcagaa attctgcgga agtctcggag attcgcccgg gccctgcccg
7201 tctgggcgcg gccggactac aacccccgc tagtagagac gtggaaaaag cctgactacg
7261 aaccacctgt ggtccatggc tgcccgctac cacctccacg gtcccctcct gtgcctccgc
7321 ctcggaaaaa gcgtacggtg gtcctcaccg aatcaaccct atctactgcc ttggccgagc
7381 ttgccaccaa aagttttggc agctcctcaa cttccggcat tacgggcgac aatacgacaa
7441 catcctctga gcccgcccct tctggctgcc cccccgactc cgacgttgag tcctattctt
7501 ccatgccccc cctggagggg gagcctgggg atccggatct cagcgacggg tcatggtcga
7561 cggtcagtag tggggccgac acggaagatg tcgtgtgctg ctcaatgtct tattcctgga
7621 caggcgcact cgtcaccccg tgcgctgcgg aagaacaaaa actgcccatc aacgcactga
7681 gcaactcgtt gctacgccat cacaatctgg tgtattccac cacttcacgc agtgcttgcc
7741 aaaggcagaa gaaagtcaca tttgacagac tgcaagttct ggacagccat taccaggacg
7801 tgctcaagga ggtcaaagca gcggcgtcaa aagtgaaggc taacttgcta tccgtagagg
7861 aagcttgcag cctgacgccc ccacattcag ccaaatccaa gtttggctat ggggcaaaag
7921 acgtccgttg ccatgccaga aaggccgtag cccacatcaa ctccgtgtgg aaagaccttc
7981 tggaagacag tgtaacacca atagacacta ccatcatggc caagaacgag gttttctgcg
8041 ttcagcctga aagggggggt cgtaagccag ctcgtctcat cgtgttcccc gacctgggcg
8101 tgcgcgtgtg cgagaagatg gccctgtacg acgtggttag caagctcccc ctggccgtga
8161 tgggaagctc ctacggattc caatactcac caggacagcg ggttgaattc ctcgtgcaag
8221 cgtggaagtc caagaagacc ccgatggggt tctcgtatga tacccgctgt tttgactcca
8281 cagtcactga gagcgacatc cgtacggagg aggcaattta ccaatgttgt gacctggacc
8341 cccaagcccg cgtggccatc aagtccctca ctgagaggct ttatgttggg ggccctctta
8401 ccaattcaag gggggaaaac tgcggctacc gcaggtgccg cgcgagcggc gtactgacaa
8461 ctagctgtgg taacaccctc acttgctaca tcaaggcccg ggcagcctgt cgagccgcag
8521 ggctccagga ctgcaccatg ctcgtgtgtg gcgacgactt agtcgttatc tgtgaaagtg
8581 cggggggtcca ggaggacgcg gcgagcctga gagccttcac ggaggctatg accaggtact
8641 ccgcccccc cggggacccc ccacaaccag aatacgactt ggagcttata acatcatgct
8701 cctccaacgt gtcagtcgcc cacgacggcg ctggaaagag ggtctactac cttacccgtg
8761 accctacaac cccccctcgcg agagccgcgt gggagacagc aagacacact ccagtcaatt
8821 cctggctagg caacataatc atgtttgccc ccacactgtg ggcgaggatg atactgatga
8881 cccattttctt tagcctcctc atagccaggc atcagcttga acaggctctt aactgtgaga
8941 tctacggagc ctgctactcc atagaaccac tggatctacc tccaatcatt caaagactcc
9001 atggcctcag cgcatttca ctccacagtt actctccagg tgaaatcaat agggtggccg
9061 catgcctcag aaaacttggg gtcccgccct tgcgagcttg gagacaccgg gcccggagcg
9121 tccgcgctag gcttctgtcc agaggaggca gggctgccat atgtggcaag tacctcttca
9181 actgggcagt aagaacaaag ctcaaactca ctccaatagc ggccgctggc cggctggact
9241 tgtccggttg gttcacggct gttctacacg ggggagacat ttatcacagc gtgtctcatg
9301 cccggccccg ctggttctgg ttttgcctac tcctgctcgc tgcagggta ggcatctacc
9361 tcctcccaa ccgatgaagg ttggggtaaa cactccggcc tcttaagcca tttcctgttt
9421 tttttttttt tttttttttt tttttcttt ttttttctt tcctttcctt cttttttcc
9481 tttctttttc ccttctttaa tggtggctcc atcttagccc tagtcacggc tagctgtgaa
9541 aggtccgtga gccgcatgac tgcagagagt gctgatactg gcctctctgc agatcatgt
```

Fig. 13D

MSTNPKPQRKTKRNTNRRPQDVKFPGGGQIVGGVYLLPRRGPRL
GVRATRKTSERSQPRGRRQPIPKARRPEGRTWAQPGYPWPLYGNEGCGWAGWLLSPRG
SRPSWGPTDPRRRSRNLGKVIDTLTCGFADLMGYIPLVGAPLGGAARALAHGVRVLED
GVNYATGNLPGCSFSIFLLALLSCLTVPASAYQVRNSSGLYHVTNDCPNSSIVYEAAD
AILHTPGCVPCVREGNASRCWVAVTPTVATRDGKLPTTQLRRHIDLLVGSATLCSALY
VGDLCGSVFLVGQLFTFSPRRHWTTQDCNCSIYPGHITGHRMAWDMMMNWSPTAALVV
AQLLRIPQAIMDMIAGAHWGVLAGIAYFSMVGNWAKVLVVLLLFAGVDAETHVTGGNA
GRTTAGLVGLLTPGAKQNIQLINTNGSWHINSTALNCNESLNTGWLAGLFYQHKFNSS
GCPERLASCRRLTDFAQGWGPISYANGSGLDERPYCWHYPPRPCGIVPAKSVCGPVYC
FTPSPVVVGTTDRSGAPTYSWGANDTDVFVLNNTRPPLGNWFGCTWMNSTGFTKVCGA
PPCVIGGVGNNTLLCPTDCFRKHPEATYSRCGSGPWITPRCMVDYPYRLWHYPCTINY
TIFKVRMYVGGVEHRLEAACNWTRGERCDLEDRDRSELSPLLLSTTQWQVLPCSFTTL
PALSTGLIHLHQNIVDVQYLYGVGSSIASWAIKWEYVVLLFLLLADARVCSCLWMMLL
ISQAEAALENLVILNAASLAGTHGLVSFLVFFCFAWYLKGRWVPGAVYALYGMWPLLL
LLLALPQRAYALDTEVAASCGGVVLVGLMALTLSPYYKRYISWCMWWLQYFLTRVEAQ
LHVWVPPLNVRGGRDAVILLMCVVHPTLVFDITKLLLAIFGPLWILQASLLKVPYFVR
VQGLLRICALARKIAGGHYVQMAIIKLGALTGTYVYNHLTPLRDWAHNGLRDLAVAVE
PVVFSRMETKLITWGADTAACGDIINGLPVSARRGQEILLGPADGMVSKGWRLLAPIT
AYAQQTRGLLGCIITSLTGRDKNQVEGEVQIVSTATQTFLATCINGVCWTVYHGAGTR
TIASPKGPVIQMYTNVDQDLVGWPAPQGSRSLTPCTCGSSDLYLVTRHADVIPVRRRG
DSRGSLLSPRPISYLKGSSGGPLLCPAGHAVGLFRAAVCTRGVAKAVDFIPVENLGTT
MRSPVFTDNSSPPAVPQSFQVAHLHAPTGSGKSTKVPAAYAAQGYKVLVLNPSVAATL
GFGAYMSKAHGVDPNIRTGVRTITTGSPITYSTYGKFLADGGCSGGAYDIIICDECHS
TDATSILGIGTVLDQAETAGARLVVLATATPPGSVTVSHPNIEEVALSTTGEIPFYGK
AIPLEVIKGGRHLIFCHSKKKCDELAAKLVALGINAVAYYRGLDVSVIPTSGDVVVVS
TDALMTGFTGDFDSVIDCNTCVTQTVDFSLDPTFTIETTTLPQDAVSRTQRRGRTGRG
KPGIYRFVAPGERPSGMFDSSVLCECYDAGCAWYELTPAETTVRLRAYMNTPGLPVCQ
DHLEFWEGVFTGLTHIDAHFLSQTKQSGENFPYLVAYQATVCARAQAPPPSWDQMWKC
LIRLKPTLHGPTPLLYRLGAVQNEVTLTHPITKYIMTCMSADLEVVTSTWVLVGGVLA

Fig. 13E

ALAAYCLSTGCVVIVGRIVLSGKPAIIPDREVLYQEFDEMEECSQHLPYIEQGMMLAE
QFKQKALGLLQTASRHAEVITPAVQTNWQKLEVFWAKHMWNFISGIQYLAGLSTLPGN
PAIASLMAFTAAVTSPLTTGQTLLFNILGGWVAAQLAAPGAATAFVGAGLAGAAIGSV
GLGKVLVDILAGYGAGVAGALVAFKIMSGEVPSTEDLVNLLPAILSPGALVVGVVCAA
ILRRHVGPGEGAVQWMNRLIAFASRGNHVSPTHYVPESDAAARVTAILSSLTVTQLLR
RLHQWISSECTTPCSGSWLRDIWDWICEVLSDFKTWLKAKLMPQLPGIPFVSCQRGYR
GVWRGDGIMHTRCHCGAEITGHVKNGTMRIVGPRTCRNMWSGTFPINAYTTGPCTPLP
APNYKFALWRVSAEEYVEIRRVGDFHYVSGMTTDNLKCPCQIPSPEFFTELDGVRLHR
FAPPCKPLLREEVSFRVGLHEYPVGSQLPCEPEPDVAVLTSMLTDPSHITAEAAGRRL
ARGSPPSMASSSASQLSAPSLKATCTANHDSPDAELIEANLLWRQEMGGNITRVESEN
KVVILDSFDPLVAEEDEREVSVPAEILRKSRRFARALPVWARPDYNPPLVETWKKPDY
EPPVVHGCPLPPPRSPPVPPPRKKRTVVLTESTLSTALAELATKSFGSSSTSGITGDN
TTTSSEPAPSGCPPDSDVESYSSMPPLEGEPGDPDLSDGSWSTVSSGADTEDVVCCSM
SYSWTGALVTPCAAEEQKLPINALSNSLLRHHNLVYSTTSRSACQRQKKVTFDRLQVL
DSHYQDVLKEVKAAASKVKANLLSVEEACSLTPPHSAKSKFGYGAKDVRCHARKAVAH
INSVWKDLLEDSVTPIDTTIMAKNEVFCVQPEKGGRKPARLIVFPDLGVRVCEKMALY
DVVSKLPLAVMGSSYGFQYSPGQRVEFLVQAWKSKKTPMGFSYDTRCFDSTVTESDIR
TEEAIYQCCDLDPQARVAIKSLTERLYVGGPLTNSRGENCGYRRCRASGVLTTSCGNT
LTCYIKARAACRAAGLQDCTMLVCGDDLVVICESAGVQEDAASLRAFTEAMTRYSAPP
GDPPQPEYDLELITSCSSNVSVAHDGAGKRVYYLTRDPTTPLARAAWETARHTPVNSW
LGNIIMFAPTLWARMILMTHFFSVLIARDQLEQALNCEIYGACYSIEPLDLPPIIQRL
HGLSAFSLHSYSPGEINRVAACLRKLGVPPLRAWRHRARSVRARLLSRGGRAAICGKY
LFNWAVRTKLKLTPIAAAGRLDLSGWFTAGYSGGDIYHSVSHARPRWFWFCLLLLAAG
VGIYLLPNR"

Fig. 14A

```
   1 gccagccccc tgatgggggc gacactccac catgaatcac tcccctgtga ggaactactg
  61 tcttcacgca gaaagcgtct agccatggcg ttagtatgag tgtcgtgcag cctccaggac
 121 cccccctccc gggagagcca tagtggtctg cggaaccggt gagtacaccg gaattgccag
 181 gacgaccggg tcctttcttg gataaacccg ctcaatgcct ggagatttgg gcgtgccccc
 241 gcaagactgc tagccgagta gtgttgggtc gcgaaaggcc ttgtggtact gcctgatagg
 301 gtgcttgcga gtgccccggg aggtctcgta gaccgtgcac catgagcacg aatcctaaac
 361 ctcaaagaaa aaccaaacgt aacaccaacc gtcgcccaca ggacgtcaag ttcccgggtg
 421 gcggtcagat cgttggtgga gtttacttgt tgccgcgcag gggccctaga ttgggtgtgc
 481 gcgcgacgag gaagacttcc gagcggtcgc aacctcgagg tagacgtcag cctatcccca
 541 aggcacgtcg gcccgagggc aggacctggg ctcagcccgg gtacccttgg cccctctatg
 601 gcaatgaggg ttgcgggtgg gcgggatggc tcctgtctcc ccgtggctct cggcctagct
 661 ggggccccac agaccccggg cgtaggtcgc gcaatttggg taaggtcatc gatacccttq
 721 cgtgcggctt cgccgacctc atggggtaca taccgctcgt cggcgcccct cttggaggcg
 781 ctgccagggc cctggcgcat ggcgtccggg ttctggaaga cggcgtgaac tatgcaacag
 841 ggaaccttcc tggttgctct ttctctatct tccttctggc cctgctctct tgcctgactg
 901 tgcccgcttc agcctaccaa gtgcgcaatt cctcggggct ttaccatgtc accaatgatt
 961 gccctaactc gagtgttgtg tacgaggcgg ccgatgccat cctgcacact ccggggtgtg
1021 tcccttgcgt tcgcgagggt aacgcctcga ggtgttgggt ggcggtgacc cccacggtgg
1081 ccaccaggga cggcaaactc cccacaacgc agcttcgacg tcatatcgat ctgcttgtcg
1141 ggagcgccac cctctgctcg gccctctacg tggggaccct gtgcgggtct gtctttcttg
1201 ttggtcaact gtttaccttc tctcccaggc accactggac gacgcaagac tgcaattgtt
1261 ctatctatcc cggccatata acgggtcatc gcatggcatg aatatgatg atgaactggt
1321 cccctacggc agcgttggtg gtagctcagc tgctccgaat cccacaagcc atcatggaca
1381 tgatcgctgg cgcccactgg ggagtcctgg cgggcataaa gtatttctcc atggtgggga
1441 actgggcgaa ggtcctggta gtgctgctgc tatttgccgg cgtcgacgcg gaaacccacg
1501 tcaccggggg aaatgccggc cgcaccacgg ctgggcttgt tggtctcctt acaccaggcg
1561 ccaagcagaa catccaactg atcaacacca acggcagttg gcacatcaat agcacggcct
1621 tgaactgcaa tgaaagcctt aacaccggct ggttagcagg gctcttctat cagcacaaat
1681 tcaactcttc aggctgtcct gagaggttgg ccagctgccg acgccttacc gattttgccc
1741 agggctgggg tcctatcagt tatgccaacg gaagcggcct cgacgaacgc cctactgct
1801 ggcactaccc tccaagacct tgtggcattg tcccgcaaa gagcgtgtgt ggcccggtat
1861 attgcttcac tcccagcccc gtggtggtgg aacgaccga caggtcgggc gcgcctacct
1921 acagctgggg tgcaaatgat acggatgtct tcgtccttaa caacaccagg ccaccgctgg
1981 gcaattggtt cggttgtacc tggatgaact caactggatt caccaaagtg tgcggagcgc
2041 ccccttgtgt catcggaggg gtgggcaaca acacctttgct ctgcccccact gattgcttcc
2101 gcaaatatcc ggaagccaca tactctcggt gcggctccgg tcccaggatt acacccaggt
2161 gcatggtcga ctacccgtat aggctttggc actatccttg taccatcaat tacaccatat
2221 tcaaagtcag gatgtacgtg ggaggggtcg agcacaggct ggaagcggcc tgcaactgga
2281 cgcggggcga acgctgtgat ctggaagaca gggacaggtc cgagctcagc ccgttgctgc
2341 tgtccaccac acagtggcag gtccttccgt gttctttcac gaccctgcca gccttgtcca
2401 ccggcctcat ccacctccac cagaacattg tggacgtgca gtacttgtac ggggtagggt
2461 caagcatcgc gtcctgggcc attaagtggg agtacgtcgt tctcctgttc cttctgcttg
2521 cagacgcgcg cgtctgttcc tgcttgtgga tgatgttact catatcccaa gcggaggcgg
2581 ctttggagaa cctcgtaata ctcaatgcag catccctggc cgggacgcat ggtcttgtgt
2641 ccttcctcgt gttcttctgc tttgcgtggt atctgaaggg taggtgggtg cccggagcgg
2701 tctacgccct ctacgggatg tggcctctcc tcctgctcct gctggcgttg cctcagcggg
2761 catacgcact ggacacggag gtggccgcgt cgtgtggcgg cgttgttctt gtcgggttaa
2821 tggcgctgac tctgtcgcca tattacaagc gctatatcag ctggtgcatg tggtggcttc
2881 agtatttct gaccagagta gaagcgcaac tgcacgtgtg ggttccccc ctcaacgtcc
2941 ggggggggcg cgatgccgtc atcttactca cgtgtgtagt acacccggcc ctggtatttg
3001 acatcaccaa actactcctg gccatcttcg gaccccttg gattcttcaa gccagtttgc
3061 ttaaagtccc ctacttcgtg cgcgttcaag gccttctccg gatctgcgcg ctagcgcgga
```

Fig. 14B

```
3121 agatagccgg aggtcattac gtgcaaatgg ccatcatcaa gttagggcg cttactggca
3181 cctgtgtgta taaccatctc gctcctcttc gagactgggc gcacaacggc ctgcgagatc
3241 tggccgtggc tgtggaacca gtcgtcttct cccgaatgga gaccaagctc atcacgtggg
3301 gggcagatac cgccgcgtgc ggtgacatca tcaacggctt gcccgtctct gcccgtaggg
3361 gccaggagat actgcttggg ccagccgacg gaatggtctc caaggggtgg aggttgctgg
3421 cgcccatcac ggcgtacgcc cagcagacga gaggcctcct agggtgtata atcaccagcc
3481 tgactggccg ggacaaaaac caagtggagg gtgaggtcca gatcgtgtca actgctaccc
3541 agaccttcct ggcaacgtgc atcaatgggg tatgctggac tgtctaccac ggggccggaa
3601 cgaggaccat cgcatcaccc aagggtcctg tcatccagac gtataccaat gtggatcaag
3661 acctcgtggg ctggcccgct cctcaaggtt cccgctcatt gacaccctgc acctgcggct
3721 cctcggacct ttacctggtc acgaggcacg ccgatgtcat tcccgtgcgc cggcgaggtg
3781 atagcagggg tagcctgctt tcgccccggc ccatttccta cttgaaaggc tcctcggggg
3841 gtccgctgtt gtgcccacg ggacacgccg tgggcctatt cagggccgcg gtgtgcaccc
3901 gtggagtggc taaggcggtg gactttatcc ctgtggagaa cctagagaca accatgagat
3961 ccccggtgtt cacggacaac tcctctccac cagcagtgcc ccagagcttc caggtggccc
4021 acctgcatgc tcccaccggc agcggtaaga gcaccaaggt cccggctgcg tacgcagcca
4081 agggctacaa ggtgttggtg ctcaacccct ctgttgctgc aacactgggc tttggtgctt
4141 acatgtccaa ggcccatggg gttgatccta atatcaggac cggggtgaga acaattacca
4201 ctggcagccc catcacgtac tccacctacg gcaagttcct tgccgacgcc gggtgctcag
4261 gaggtgctta tgacataata atttgtgacg agtgccactc cacggatgcc acatccatct
4321 cgggcatcgg cactgtcctt gaccaagcag agactgcggg ggcgagactg gttgtgctcg
4381 ccactgctac ccctccgggc tccgtcactg tgtcccatcc taacatcgag gaggtgctc
4441 tgtccaccac cggagagatc ccctttacg gcaaggctat cccctcgag gtgatcaagg
4501 ggggaagaca tctcatcttc tgccactcaa agaagaagtg cgacgagctc gccgcgaagc
4561 tggtcgcatt gggcatcaat gccgtggcct actaccgcgg tcttgacgtg tctgtcatcc
4621 cgaccagcgg cgatgttgtc gtcgtgtcga ccgatgctct catgactggc tttaccggcg
4681 acttcgactc tgtgatagac tgcaacacgt gtgtcactca gacagtcgat tttagccttg
4741 accctacctt taccattgag acaaccacgc tcccccagga tgctgtctcc aggactcaac
4801 gccggggcag gactggcagg gggaagccag gcatctatag atttgtggca ccggggagc
4861 gcccctccgg catgttcgac tcgtccgtcc tctgtgagtg ctatgacgcg ggctgtgctt
4921 ggtatgagct cacgcccgcc gagactacag ttaggctacg agcgtacatg aacacccgg
4981 ggcttcccgt gtgccaggac catcttggat tttgggaggg cgtctttacg ggcctcactc
5041 atatagatgc ccactttcta tcccagacaa agcagagtgg ggagaacttt ccttacctgg
5101 tagcgtacca agccaccgtg tgcgctaggg ctcaagcccc tcccccatcg tgggaccaga
5161 tgcggaagtg tttgatccgc cttaaaccca ccctccatgg gccaacaccc ctgctataca
5221 gactgggcgc tgttcagaat gaagtcaccc tgacgcaccc aatcaccaaa tacatcatga
5281 catgcatgtc ggccgacctg gaggtcgtca cgagcacctg ggtgctcgtt ggcggcgtcc
5341 tggctgctct ggccgcgtat tgcctgtcaa caggctgcgt ggtcatagtg ggcaggatcg
5401 tcttgtccgg gaagccggca attatacctg acagggaggt tctctaccag gagttcgatg
5461 agatggaaga gtgctctcag cacttaccgt acatcgagca agggatgatg ctcgctgagc
5521 agttcaagca gaaggccctc ggcctcctgc agaccgcgtc cgccatgca gaggttatca
5581 cccctgctgt ccagacccaac tggcagaaac tcgaggtctt tgggcgaag cacatgtgga
5641 atttcatcag tggatacaa tacttggcgg gcctgtcaac gctgcctggt aacccccgcca
5701 ttgcttcatt gatggctttt acagctgccg tcaccagccc actaaccact ggccaaaccc
5761 tcctcttcaa catattgggg gggtgggtgg ctgcccagct cgccgcccc ggtgccgcta
5821 ccgcctttgt gggcgctggc ttagctggcg ccgcactcga cagcgttgga ctggggaagg
5881 tcctcgtgga cattcttgca ggctatggcg cgggcgtggc gggagctctt gtggcattca
5941 agatcatgag cggtgaggtc ccctccacgg aggacctggt caatctgctg cccgccatcc
6001 tctcacctgg agcccttgca gtcggtgtgg tctttgcatc aatactgcgc cggcgtgttg
6061 gccggggcga ggggcagtg caatggatga accggctaat agccttcgcc tcccggggga
6121 accatgtttc ccccacacac tacgtgccgg agagcgatgc agccgcccgc gtcactgcca
6181 tactcagcag cctcactgta acccagctcc tgaggcgact gcatcagtgg ataagctcgg
6241 agtgtaccac tccatgctcc ggttcctggc taagggacat ctgggactgg atatgcgagg
6301 tgctgagcga ctttaagacc tggctgaaag ccaagctcat gccacaactg cctggggattc
6361 cctttgtgtc ctgccagcgc gggtataggg gggtctggcg aggagacggc attatgcaca
6421 ctcgctgcca ctgtggagct gagatcactg gacatgtcaa aaacgggacg atgaggatcg
6481 tcggtcctag gacctgcaag aacatgtgga gtgggacgtt cttcattaat gcctacacca
```

Fig. 14C

```
6541 cgggcccctg tactccccctt cctgcgccga actataagtt cgcgctgtgg agggtgtctg
6601 cagaggaata cgtggagata aggcgggtgg gggacttcca ctacgtatcg ggcatgacta
6661 ctgacaatct caaatgcccg tgccagatcc catcgcccga attttcaca gaattggacg
6721 gggtgcgcct acataggttt gcgcccccctt gcaagcccctt gctgcgggag gaggtatcat
6781 tcagagtagg actccacgag tacccggtgg ggtcgcaatt accttgcgag cccgaaccgg
6841 acgtagccgt gttgacgtcc atgctcactg atccctccca tataacagca gaggcggccg
6901 ggagaaggtt ggcgagaggg tcacccccctt ctatggccag ctcctcggct agccagctgt
6961 ccgctccatc tctcaaggca acttgcaccg ccaaccatga ctcccctgac gccgagctca
7021 tagaggctaa cctcctgtgg aggcaggaga tgggcggcaa catcaccagg gttgagtcag
7081 agaacaaagt ggtgattctg gactccttcg atccgcttgt ggcagaggag gatgagcggg
7141 aggtctccgt acccgcagaa attctgcgga agtctcggag attcgcccca gccctgcccg
7201 tctgggcgcg gccggactac aacccctgc tagtagagac gtggaaaaag cctgactacg
7261 aaccacctgt ggtccatggc tgcccgctac cacctccacg gtcccctcct gtgcctccgc
7321 ctcggaaaaa gcgtacggtg gtcctcaccg aatcaaccct acctactgcc ttggccgagc
7381 ttgccaccaa aagttttggc agctcctcaa cttccggcat tacgggcgac aatacgacaa
7441 catcctctga gcccgccct tctggctgcc cccccgactc cgacgttgag tcctattctt
7501 ccatgccccc cctggagggg gagcctgggg atccggatct cagcgacggg tcatggtcga
7561 cggtcagtag tggggccgac acggaagatg tcgtgtgctg ctcaatgtct tattcctgga
7621 caggcgcact cgtcaccccg tgcgctgcgg aggaacaaaa actgcccatc aacgcactga
7681 gcaactcgtt gctacgccat cacaatctgg tgtattccac cacttcacgc agtgcttgcc
7741 aaaggaagaa gaaagtcaca tttgacagac tgcaagttct ggacagccat taccaggacg
7801 tgctcaagga ggtcaaagca gcggcgtcaa aagtgaaggc taacttgcta tccgtagagg
7861 aagcttgcag cctggcgccc ccacattcag ccaaatccaa gtttggctat ggggcaaaag
7921 acgtccgttg ccatgccaga aaggccgtag cccacatcaa ctccgtgtgg aaagaccttc
7981 tggaagacag tgtaacacca atagacacta ccatcatggc caagaacgag gttttctgcg
8041 ttcagcctga gaaggggggt cgtaagccag ctcgtctcat cgtgttcccc gacctgggcg
8101 tgcgcgtgtg cgagaagatg gccctgtacg acgtggttag caagctcccc ttggccgtga
8161 tgggaagctc ctacggattc caatactcac caggacagcg ggttgaattc ctcgtgcaag
8221 cgtggaagtc caagaagacc ccgatgggc tctcgtatga tacccgctgt tttgactcca
8281 cagtcactga gagcgacatc cgtacggagg aggcaattta ccaatgttgt gacctggacc
8341 cccaagcccg cgtggccatc aagtccctca ctgagaggct ttatgttggg ggcccctctta
8401 ctaattcaag gggggaaaac tgcggctacc gcaggtgccg cgcgagcaga gtactgacaa
8461 ctagctgtgg taacaccctc actcgctaca tcaaggcccg ggcagcctgt cgagccgcag
8521 ggctccagga ctgcaccatg ctcgtgtgtg gcgacgactt agtcgttatc tgtgaaagtg
8581 cggggtcca ggaggacgcg gcgagcctga gagccttcac ggaggctatg accaggtact
8641 ccgcccccc cggggacccc ccacaaccag aatacgactt ggagcttata acatcatgct
8701 cctccaacgt gtcagtcgcc cacgacggcg ctggaaagag ggtctactac cttacccgtg
8761 accctacaac cccccctcgcg agagccgcgt gggagacagc aagacacact ccagtcaatt
8821 cctggctagg caacataatc atgtttgccc ccacactgtg ggcgaggatg atactgatga
8881 cccacttctt tagcgtcctc atagccaggg atcagcttga acaggctctc aactgcgaga
8941 tctacggagc ctgctactcc atagaaccac tggatctacc tccaatcatt caaagactcc
9001 atggcctcag cgcattttca ctccacagtt actctccagg tgaaattaat agggtggccg
9061 catgcctcag aaaacttggg gtcccgcccct tgcgagcttg agacaccgg gcctggagcg
9121 tccgcgctag gcttctggcc agaggaggca aggctgccat atgtggcaag tacctcttca
9181 actgggcagt aagaacaaag ctcaaactca ctccgataac ggccgctggc cggctggact
9241 tgtccggctg gttcacggct ggctacagcg gggagacat ttatcacagc gtgtctcatg
9301 cccggccccg ctggttctgg ttttgcctac tcctgcttgc tgcagggta ggcatctacc
9361 tcctccccaa ccgatgaaga ttgggctaac cactccaggc caataggcca ttccct
```

Fig. 14D

MSTNPKPQRKTKRNTNRRPQDVKFPGGGQIVGGVYLLPRRGPRL
GVRATRKTSERSQPRGRRQPIPKARRPEGRTWAQPGYPWPLYGNEGCGWAGWLLSPRG
SRPSWGPTDPRRRSRNLGKVIDTLTCGFADLMGYIPLVGAPLGGAARALAHGVRVLED
GVNYATGNLPGCSFSIFLLALLSCLTVPASAYQVRNSSGLYHVTNDCPNSSVVYEAAD
AILHTPGCVPCVREGNASRCWVAVTPTVATRDGKLPTTQLRRHIDLLVGSATLCSALY
VGDLCGSVFLVGQLFTFSPRHHWTTQDCNCSIYPGHITGHRMAWNMMMNWSPTAALVV
AQLLRIPQAIMDMIAGAHWGVLAGIKYFSMVGNWAKVLVVLLLFAGVDAETHVTGGNA
GRTTAGLVGLLTPGAKQNIQLINTNGSWHINSTALNCNESLNTGWLAGLFYQHKFNSS
GCPERLASCRRLTDFAQGWGPISYANGSGLDERPYCWHYPPRPCGIVPAKSVCGPVYC
FTPSPVVVGTTDRSGAPTYSWGANDTDVFVLNNTRPPLGNWFGCTWMNSTGFTKVCGA
PPCVIGGVGNNTLLCPTDCFRKYPEATYSRCGSGPRITPRCMVDYPYRLWHYPCTINY
TIFKVRMYVGGVEHRLEAACNWTRGERCDLEDRDRSELSPLLLSTTQWQVLPCSFTTL
PALSTGLIHLHQNIVDVQYLYGVGSSIASWAIKWEYVVLLFLLLADARVCSCLWMMLL
ISQAEAALENLVILNAASLAGTHGLVSFLVFFCFAWYLKGRWVPGAVYALYGMWPLLL
LLLALPQRAYALDTEVAASCGGVVLVGLMALTLSPYYKRYISWCMWWLQYFLTRVEAQ
LHVWVPPLNVRGGRDAVILLTCVVHPALVFDITKLLLAIFGPLWILQASLLKVPYFVR
VQGLLRICALARKIAGGHYVQMAIIKLGALTGTCVYNHLAPLRDWAHNGLRDLAVAVE
PVVFSRMETKLITWGADTAACGDIINGLPVSARRGQEILLGPADGMVSKGWRLLAPIT
AYAQQTRGLLGCIITSLTGRDKNQVEGEVQIVSTATQTFLATCINGVCWTVYHGAGTR
TIASPKGPVIQTYTNVDQDLVGWPAPQGSRSLTPCTCGSSDLYLVTRHADVIPVRRRG
DSRGSLLSPRPISYLKGSSGGPLLCPTGHAVGLFRAAVCTRGVAKAVDFIPVENLETT
MRSPVFTDNSSPPAVPQSFQVAHLHAPTGSGKSTKVPAAYAAKGYKVLVLNPSVAATL
GFGAYMSKAHGVDPNIRTGVRTITTGSPITYSTYGKFLADAGCSGGAYDIIICDECHS
TDATSISGIGTVLDQAETAGARLVVLATATPPGSVTVSHPNIEEVALSTTGEIPFYGK
AIPLEVIKGGRHLIFCHSKKKCDELAAKLVALGINAVAYYRGLDVSVIPTSGDVVVVS
TDALMTGFTGDFDSVIDCNTCVTQTVDFSLDPTFTIETTTLPQDAVSRTQRRGRTGRG
KPGIYRFVAPGERPSGMFDSSVLCECYDAGCAWYELTPAETTVRLRAYMNTPGLPVCQ
DHLGFWEGVFTGLTHIDAHFLSQTKQSGENFPYLVAYQATVCARAQAPPPSWDQMRKC
LIRLKPTLHGPTPLLYRLGAVQNEVTLTHPITKYIMTCMSADLEVVTSTWVLVGGVLA

Fig. 14E

ALAAYCLSTGCVVIVGRIVLSGKPAIIPDREVLYQEFDEMEECSQHLPYIEQGMMLAE
QFKQKALGLLQTASRHAEVITPAVQTNWQKLEVFWAKHMWNFISGIQYLAGLSTLPGN
PAIASLMAFTAAVTSPLTTGQTLLFNILGGWVAAQLAAPGAATAFVGAGLAGAALDSV
GLGKVLVDILAGYGAGVAGALVAFKIMSGEVPSTEDLVNLLPAILSPGALAVGVVFAS
ILRRRVGPGEGAVQWMNRLIAFASRGNHVSPTHYVPESDAAARVTAILSSLTVTQLLR
RLHQWISSECTTPCSGSWLRDIWDWICEVLSDFKTWLKAKLMPQLPGIPFVSCQRGYR
GVWRGDGIMHTRCHCGAEITGHVKNGTMRIVGPRTCKNMWSGTFFINAYTTGPCTPLP
APNYKFALWRVSAEEYVEIRRVGDFHYVSGMTTDNLKCPCQIPSPEFFTELDGVRLHR
FAPPCKPLLREEVSFRVGLHEYPVGSQLPCEPEPDVAVLTSMLTDPSHITAEAAGRRL
ARGSPPSMASSSASQLSAPSLKATCTANHDSPDAELIEANLLWRQEMGGNITRVESEN
KVVILDSFDPLVAEEDEREVSVPAEILRKSRRFAPALPVWARPDYNPLLVETWKKPDY
EPPVVHGCPLPPPRSPPVPPPRKKRTVVLTESTLPTALAELATKSFGSSSTSGITGDN
TTTSSEPAPSGCPPDSDVESYSSMPPLEGEPGDPDLSDGSWSTVSSGADTEDVVCCSM
SYSWTGALVTPCAAEEQKLPINALSNSLLRHHNLVYSTTSRSACQRKKKVTFDRLQVL
DSHYQDVLKEVKAAASKVKANLLSVEEACSLAPPHSAKSKFGYGAKDVRCHARKAVAH
INSVWKDLLEDSVTPIDTTIMAKNEVFCVQPEKGGRKPARLIVFPDLGVRVCEKMALY
DVVSKLPLAVMGSSYGFQYSPGQRVEFLVQAWKSKKTPMGLSYDTRCFDSTVTESDIR
TEEAIYQCCDLDPQARVAIKSLTERLYVGGPLTNSRGENCGYRRCRASRVLTTSCGNT
LTRYIKARAACRAAGLQDCTMLVCGDDLVVICESAGVQEDAASLRAFTEAMTRYSAPP
GDPPQPEYDLELITSCSSNVSVAHDGAGKRVYYLTRDPTTPLARAAWETARHTPVNSW
LGNIIMFAPTLWARMILMTHFFSVLIARDQLEQALNCEIYGACYSIEPLDLPPIIQRL
HGLSAFSLHSYSPGEINRVAACLRKLGVPPLRAWRHRAWSVRARLLARGGKAAICGKY
LFNWAVRTKLKLTPITAAGRLDLSGWFTAGYSGGDIYHSVSHARPRWFWFCLLLLAAG
VGIYLLPNR"

REPLICATION COMPETENT HEPATITIS C VIRUS AND METHODS OF USE

CONTINUING APPLICATION DATA

This application is a U.S. National Stage Application of International Application No. PCT/US2004/040120, filed Dec. 1, 2004, which claims the benefit of U.S. Provisional Application Serial No. 60/525,989, filed Dec. 1, 2003, both of which are incorporated by reference herein.

GOVERNMENT FUNDING

The present invention was made with government support under Grant Nos. U19-AI40035-07 and N01-AI25488, awarded by the National Institute of Allergy and Infectious Diseases. The Government has certain rights in this invention.

BACKGROUND

Hepatitis C virus is the most common cause of chronic viral hepatitis within the United States, infecting approximately 4 million Americans and responsible for the deaths of 8,000-10,000 persons annually due to progressive hepatic fibrosis leading to cirrhosis and/or the development of hepatocellular carcinoma. Hepatitis C virus is a single stranded, positive-sense RNA virus with a genome length of approximately 9.6 kb. It is currently classified within a separate genus of the flavivirus family, the genus *Hepacivirus*. The hepatitis C virus genome contains a single large open reading frame (ORF) that follows a 5' non-translated RNA of approximately 342 bases containing an internal ribosome entry segment (IRES) directing cap-independent initiation of viral translation. The large ORF encodes a polyprotein which undergoes post-translational cleavage, under control of cellular and viral proteinases. This yields a series of structural proteins which include a core or nucleocapsid protein, two envelope glycoproteins, E1 and E2, and at least six nonstructural replicative proteins. These include NS2 (which with the adjacent NS3 sequence demonstrates cis-active metalloproteinase activity at the NS2/NS3 cleavage site), NS3 (a serine proteinase/NTPase/RNA helicase), NS4A (serine proteinase accessory factor), NS4B, NS5A, and NS5B (RNA-dependent RNA polymerase).

With the exception of the 5' non-translated RNA, there is substantial genetic heterogeneity among different stains of hepatitis C virus. Phylogenetic analyses have led to the classification of hepatitis C virus strains into a series of genetically distinct "genotypes," each of which contains a group of genetically related viruses. The genetic distance between some of these genotypes is large enough to suggest that there may be biologically significant serotypic differences as well. There is little understanding of the extent to which infection with a virus of any one genotype might confer protection against viruses of a different genotype.

The currently available therapy of interferon in combination with ribavirin has poor response rate against most prevalent strains of HCV, genotype 1a and 1b. Establishment of selectable subgenomic replicon systems has advanced the study of HCV RNA replication. However, only replicons of genotype 1b strains are readily available, and extension of replicon systems to other genotypes has been largely unsuccessful. Considering the nature of high genetic variability of HCV, HCV replication systems derived from other genotypes will be very helpful in the effort of drug discovery. In support with this notion, chimeric replicons containing a genotype 1a polymerase in the background of a genotype 1b replicon were more resistant to interferon treatment in vitro than the replicon derived from a genotype 1b HCV. Extension of replicon system to other genotypes are also necessary to understand the mechanism of HCV RNA replication and the contribution of variable sequences in that process.

Recently two groups reported the generation of genotype 1a replication system using highly permissive sublines of Huh-7 cells. Blight et al. (J. Virol. 77, 3181-3190 (2003)) were able to select G418 resistant colonies supporting replication of genotype 1a derived subgenomic replicons in a hyper-permissive Huh7 subline, Huh-7.5, that was generated by curing an established G418-resistant replicon cell line of the cubgenomic Con1 replicon RNA that had been used to select it by treatment with interferon-alpha (Blight et al., J. Virol., 76, 13001-13014 (2002)). Sequence analysis of replicating HCV RNAs inside of such selected cell lines showed that the most common critical mutations were located at amino acid position 470 of NS3 (P1496L) within domain II of the NS3 helicase, and the NS5A mutation (S2204I). In other case, Grobler et al. (J. Biol. Chem., 278,16741-16746 (February 2003)), used a systematic mutational approach to reach the similar conclusion that both P1496L and S2204I combination was necessary to get genotype 1a replication in a highly permissive Huh-7 subline which was selected in an independent but similar way. However, genotype 1a RNAs with these two enhanced mutations does not undergo replication in the Huh-7 cell line, indicating limited usefulness of this system.

SUMMARY

The present invention provides replication competent polynucleotides. The replication competent polynucleotides include a 5' non-translated region (NTR), a 3' NTR, and a first coding sequence present between the 5'NTR and 3' NTR and encoding a hepatitis C virus polyprotein. The 5' NTR, the 3' NTR, and the nucleotide sequence encoding the polyprotein may be genotype 1a. The polyprotein includes an isoleucine at about amino acid 2204, and further includes an adaptive mutation. The adaptive mutation can be an arginine at about amino acid 1067, an arginine at about amino acid 1691, a valine at about amino acid 2080, an isoleucine at about amino acid 1655, an arginine at about amino acid 2040, an arginine at about amino acid 1188, or a combination thereof. The polyprotein may be a subgenomic polyprotein. The polyprotein may include the cleavage products core, E1, E2, P7, NS2, NS3, NS4A, NS4B, NS5A, and NS5B. The replication competent polynucleotides may further include a second coding sequence. The second coding sequence can encode, for instance, a marker or a transactivator. The replication competent polynucleotides may further include a nucleotide sequence having cis-acting ribozyme activity, wherein the nucleotide sequence is located 3' of the 3' NTR.

Also provided by the present invention are methods for making a replication competent polynucleotide, and the resulting replication competent polynucleotide. The methods include providing a polynucleotide having a 5' NTR, 3' NTR, a first coding sequence present between the 5'NTR and 3'NTR and encoding a hepatitis C virus polyprotein. Typically, the 5' NTR, polyprotein, and 3' NTR are genotype 1a. The polyprotein includes a serine at about amino acid 2204, a glutamine at about amino acid 1067, a lysine at about amino acid 1691, a phenylalanine at about amino acid 2080, a valine at about amino acid 1655, a lysine at about amino acid 2040, or a glycine at about amino acid 1188. The method also includes altering the coding sequence such that the polyprotein encoded thereby includes an isoleucine at amino acid 2204, and an adaptive mutation. The polyprotein may be a subgenomic polyprotein. The polyprotein may include the cleavage products core, E1, E2, P7, NS2, NS3, NS4A, NS4B, NS5A, and NS5B.

The present invention further provides methods for identifying a compound that inhibits replication of a replication competent polynucleotide. The method includes contacting a cell containing a replication competent polynucleotide with a compound, incubating the cell under conditions wherein the replication competent polynucleotide replicates in the absence of the compound, and detecting the replication competent polynucleotide, wherein a decrease of the replication competent HCV polynucleotide in the cell contacted with the compound compared to the replication competent polynucleotide in a cell not contacted with the compound indicates the compound inhibits replication of the replication competent polynucleotide. The detecting of the replication competent polynucleotide can include, for instance, nucleic acid amplification or identifying a marker encoded by the replication competent polynucleotide or by the cell containing the replication competent polynucleotide.

Also provided by the present invention are methods for selecting a replication competent polynucleotide. The method includes incubating a cell containing a polynucleotide including a 5' NTR, a 3'NTR, and a first coding sequence present between the 5' NTR and 3' NTR and encoding a hepatitis C virus polyprotein, and a second coding sequence. The polyprotein includes an isoleucine at about amino acid 2204, and further includes an adaptive mutation. The second coding sequence encodes a selectable marker conferring resistance to a selecting agent that inhibits replication of a cell that does not express the selectable marker. The method also includes detecting a cell that replicates in the presence of the selecting agent, wherein the presence of such a cell indicates the polynucleotide is replication competent. The method may further include obtaining a virus particle produced by the cell, exposing a second cell to the isolated virus particle and incubating the second cell in the presence of the selecting agent, and detecting a second cell that replicates in the presence of the selecting agent, wherein the presence of such a cell indicates the replication competent polynucleotide in the first cell produces an infectious virus particle.

The present invention also provides methods for detecting a replication competent polynucleotide, including incubating a cell containing a replication competent polynucleotide. The replication competent polynucleotide includes a 5' NTR, a 3' NTR, and a first coding sequence present between the 5' NTR and 3' NTR and encoding a hepatitis C virus polyprotein, and a second coding sequence encoding a transactivator. The cell includes a transactivated coding region and an operator sequence operably linked to the transactivated coding region, and the transactivated coding region encodes a detectable marker, wherein the transactivator alters transcription of the transactivated coding region. The method further includes detecting the detectable marker, wherein the presence of the detectable marker indicates the cell includes a replication competent polynucleotide.

Definitions

As used herein, the term "replication competent polynucleotide" refers to a polynucleotide that replicates when present in a cell. For instance, a complementary polynucleotide is synthesized. As used herein, the term "replicates in vitro" indicates the polynucleotide replicates in a cell that is growing in culture. The cultured cell can be one that has been selected to grow in culture, including, for instance, an immortalized or a transformed cell. Alternatively, the cultured cell can be one that has been explanted from an animal. "Replicates in vivo" indicates the polynucleotide replicates in a cell within the body of an animal, for instance a primate (including a chimpanzee) or a human. In some aspects of the present invention, replication in a cell can include the production of infectious viral particles, i.e., viral particles that can infect a cell and result in the production of more infectious viral particles.

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, including for instance coding sequences, and non-coding sequences such as regulatory sequences and/or non-translated regions. A polynucleotide can be obtained directly from a natural source, or can be prepared with the aid of recombinant, enzymatic, or chemical techniques. A polynucleotide can be linear or circular in topology and can be, for example, a portion of a vector, such as an expression or cloning vector, or a fragment.

The terms "coding region" and "coding sequence" are used interchangeably and refer to a polynucleotide region that encodes a polypeptide and, when placed under the control of appropriate regulatory sequences, expresses the encoded polypeptide. The boundaries of a coding region are generally determined by a translation start codon at its 5' end and a translation stop codon at its 3' end. A coding region can encode one or more polypeptides. For instance, a coding region can encode a polypeptide that is subsequently processed into two or more polypeptides. A regulatory sequence or regulatory region is a nucleotide sequence that regulates expression of a coding region to which it is operably linked. Nonlimiting examples of regulatory sequences include promoters, transcription initiation sites, translation start sites, internal ribosome entry sites, translation stop sites, and terminators. "Operably linked" refers to a juxtaposition wherein the components so described are in a relationship permitting them to function in their intended manner. A regulatory sequence is "operably linked" to a coding region when it is joined in such a way that expression of the coding region is achieved under conditions compatible with the regulatory sequence.

"Polypeptide" as used herein refers to a polymer of amino acids and does not refer to a specific length of a polymer of amino acids. Thus, for example, the terms peptide, oligopeptide, protein, polyprotein, proteinase, and enzyme are included within the definition of polypeptide. This term also includes post-expression modifications of the polypeptide, for example, glycosylations, acetylations, phosphorylations and the like. A "hepatitis C virus polyprotein" refers to a polypeptide that is post-translationally cleaved to yield more than one polypeptide.

The terms "5' non-translated RNA," "5' non-translated region," "5' untranslated region" and "5' noncoding region" are used interchangeably, and are terms of art (see Bukh et al., Proc. Nat. Acad. Sci. USA, 89, 4942-4946 (1992)). The term refers to the nucleotides that are at the 5' end of a replication competent polynucleotide.

The terms "3' non-translated RNA," "3' non-translated region," and "3' untranslated region" are used interchangeably, and are terms of art. The term refers to the nucleotides that are at the 3' end of a replication competent polynucleotide.

Unless otherwise specified, "a," "an," "the," and "at least one" are used interchangeably and mean one or more than one.

BRIEF DESCRIPTION OF THE FIGURES

FIG. 1. Organization of the selectable subgenomic dicistronic HCV replicons, Bpp-Ntat2ANeo/SI (identical to Ntat2Aneo/SI in Yi et al., Virol., 302, 197-210 (2002)), Htat2ANeo/SI, and Bpp-Htat2ANeo/SI, in which most of the nonstructural protein-coding region and the 3' NTR are derived from the H77c HCV genotype 1a sequence. The two large ORFs are shown as rectangles, with nontranslated RNA segments shown as lines. The segment of the 3' ORF labeled 'pp' ('proximal protease') encodes the amino terminus of the NS3 protein (residues 1 to 75). 'Bpp' indicates that this region is derived from the HCV Con1 sequence. Both replicons contain the S2204I mutation in NS5A (S→I). 'δ' Indicates the hepatitis delta ribozyme sequence introduced downstream of the 3' terminus of the HCV sequence that produces an exact 3' end.

FIG. 4. Impact of adaptive mutations on replication competence of the subgenomic genotype 1a replicon, Htat2ANeo/SI. (A) Location of various adaptive mutations within the second ORF (derived entirely from the genotype 1a H77sequence): Q1067R, P1496L (NS3); K1691R (NS4A); and F2080V and S2204I (NS5A). (B) Transient HCV RNA replication assay. SEAP activity in culture supernatants collected at 12-24 hr intervals following electroporation of En5-3 cells carrying the indicated combinations of the adaptive mutations shown in panel A. Cells were also transfected with genotype 1b Bpp-Ntat2ANeo/SI replicon RNA as a reference. (C) Summary of the replication phenotypes of genotype 1a replicon Htat2ANeo RNAs containing various combinations of adaptive mutations: (−) no detectable replication, (+) modest increase in SEAP expression above background days 3-5, and (+++)>10-fold increase in SEAP expression above background 7 days after transfection in the transient replication assay (see panel B). SI, S2204 adaptive mutation; QR, Q1067R adaptive mutation; PL, P1496L adaptive mutation; KR, K1691R adaptive mutation; and FV, F2080V adaptive mutation.

FIG. 5. Adaptive mutations within the polyprotein do not influence the efficiency of polyprotein translation under control of the EMCV IRES. Shown is an SDS-PAGE gel loaded with products of in vitro translation reactions programmed with RNAs derived from Bpp-Ntat2ANeo (lane1), Bpp-Htat2ANeo (lanes 2 and 3), Htat2ANeo (lanes 4 to 8), or Bpp-Ntat2ANeo/ΔGDD (lane 9) RNAs carrying various combinations of adaptive mutations (Q1067R, K1691R, F2080V, or S2204I) as indicated. The schematic at the top of the figure indicates the location of these mutations within the polyprotein. 'pp' indicates the RNA segment encoding the amino terminal 75 residues of NS3, while 'NS' indicates the remainder of the RNA segment encoding the nonstructural proteins. H=genotype 1a H77 sequences, B=genotype 1b Con1 sequences, and N=genotype 1b HCV-N sequences. Location of NS3 and Neo product is indicated at the side of gel.

FIG. 9. Nucleotide sequence of HIVSEAP (SEQ ID NO:7). The HIV long terminal repeat (LTR) is depicted at nucleotides 1-719, and secretory alkaline phosphatase is encoded by the nucleotides 748-2239.

FIG. 10. 10A, nucleotide sequence of a 3' NTR (SEQ ID NO:8); 10B, nucleotide sequence of a 5' NTR (SEQ ID NO:9).

Figure 11A-1:
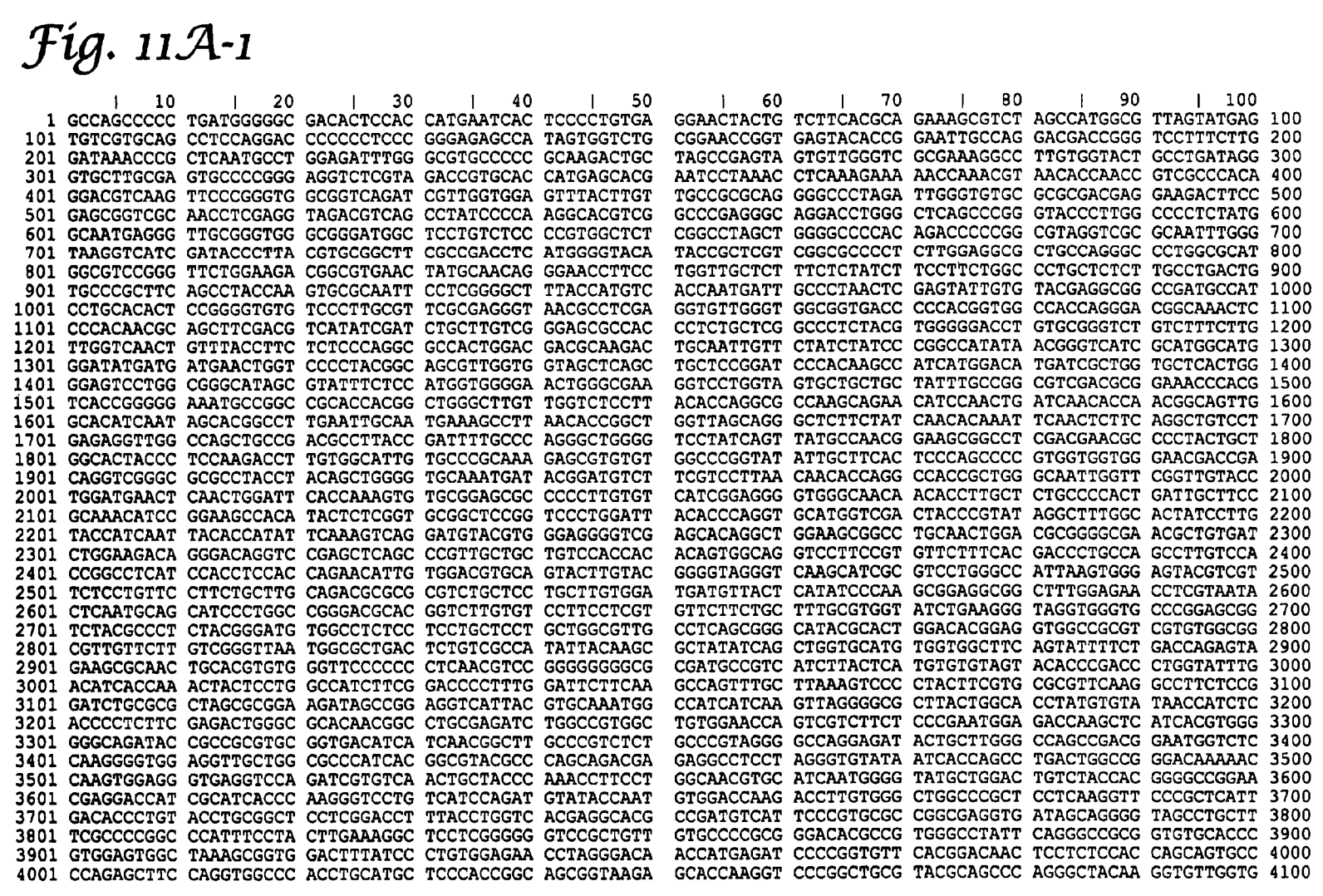
Figure 11A-2:
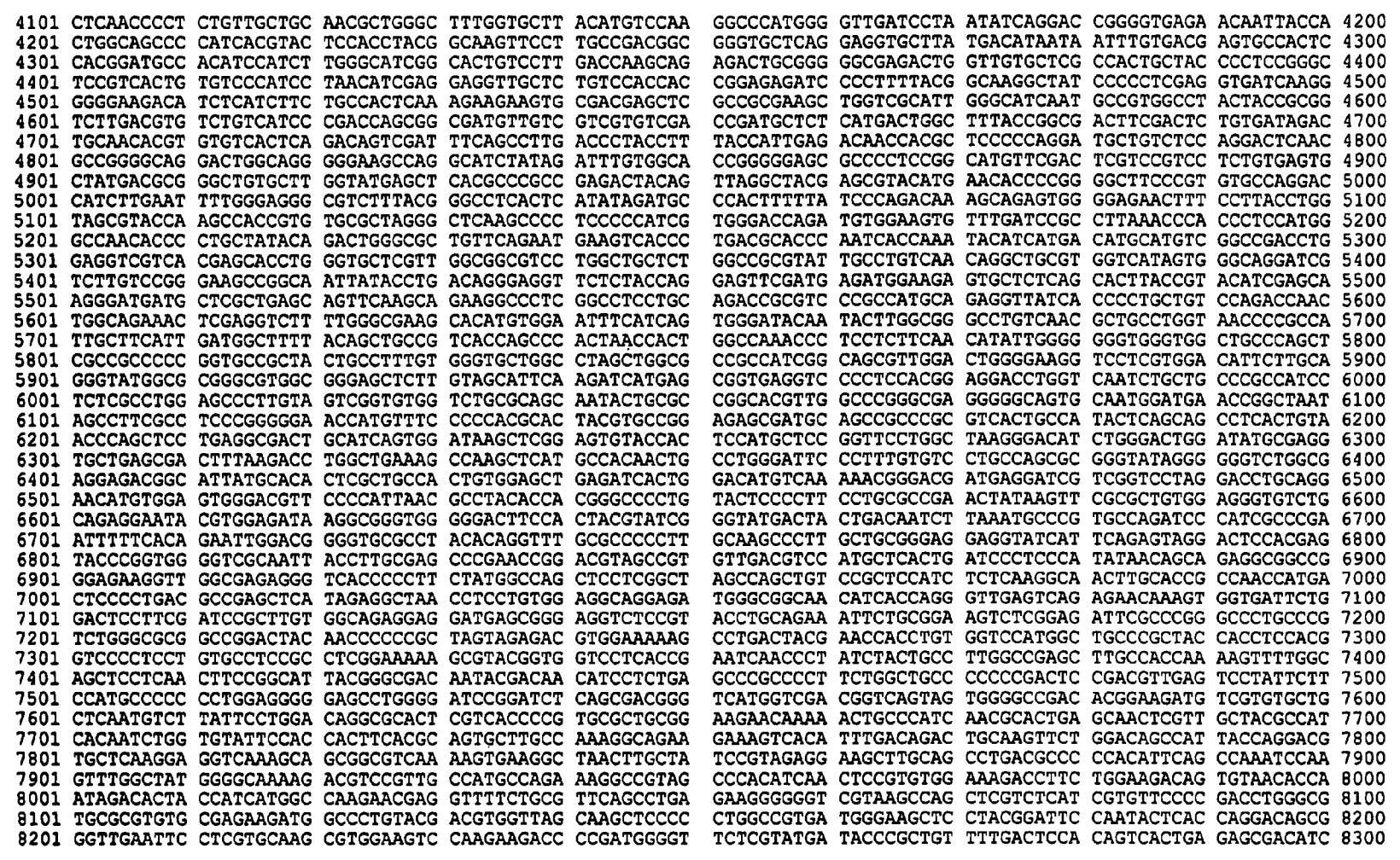
Figure 11B-1:
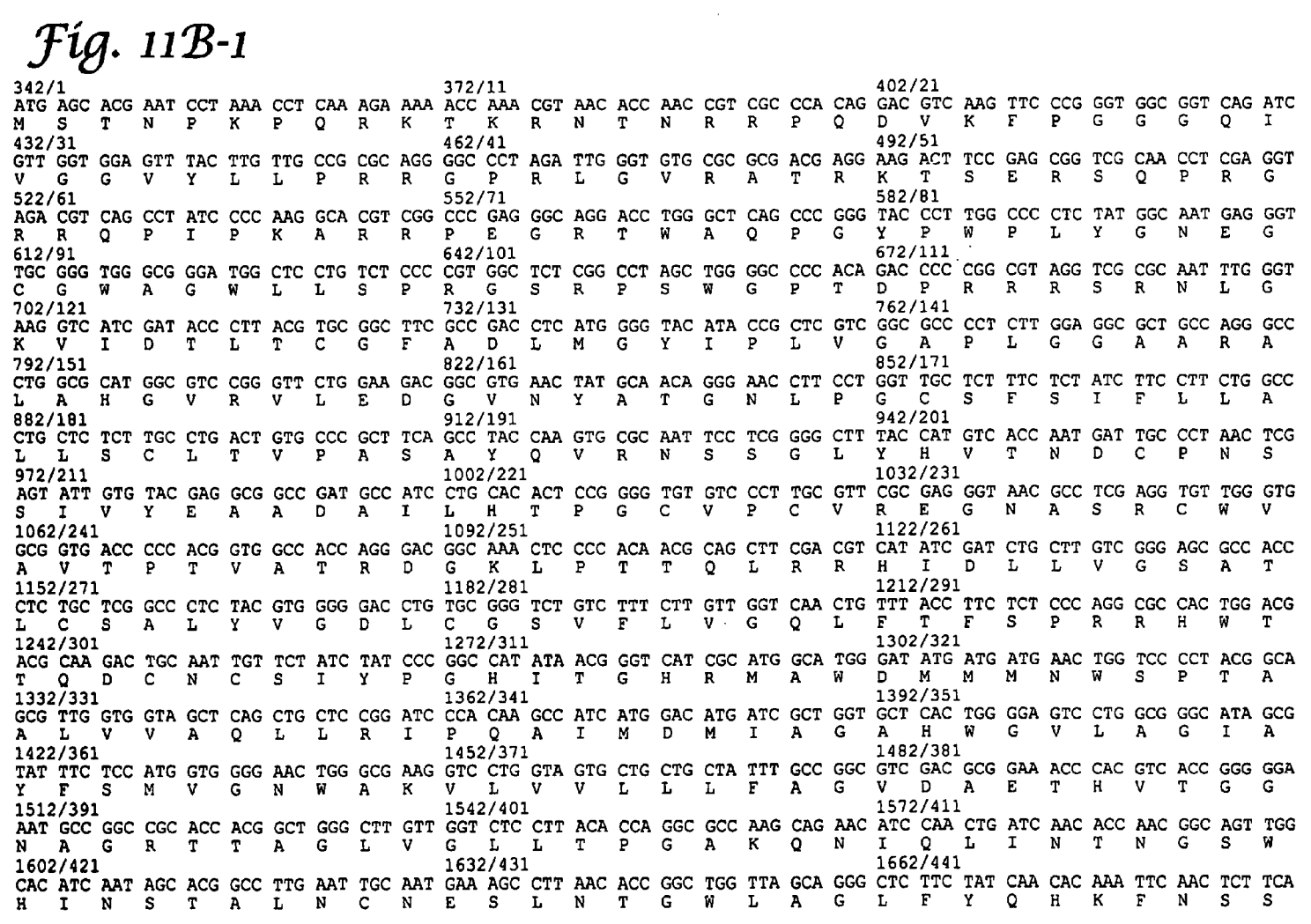
Figure 11B-6:
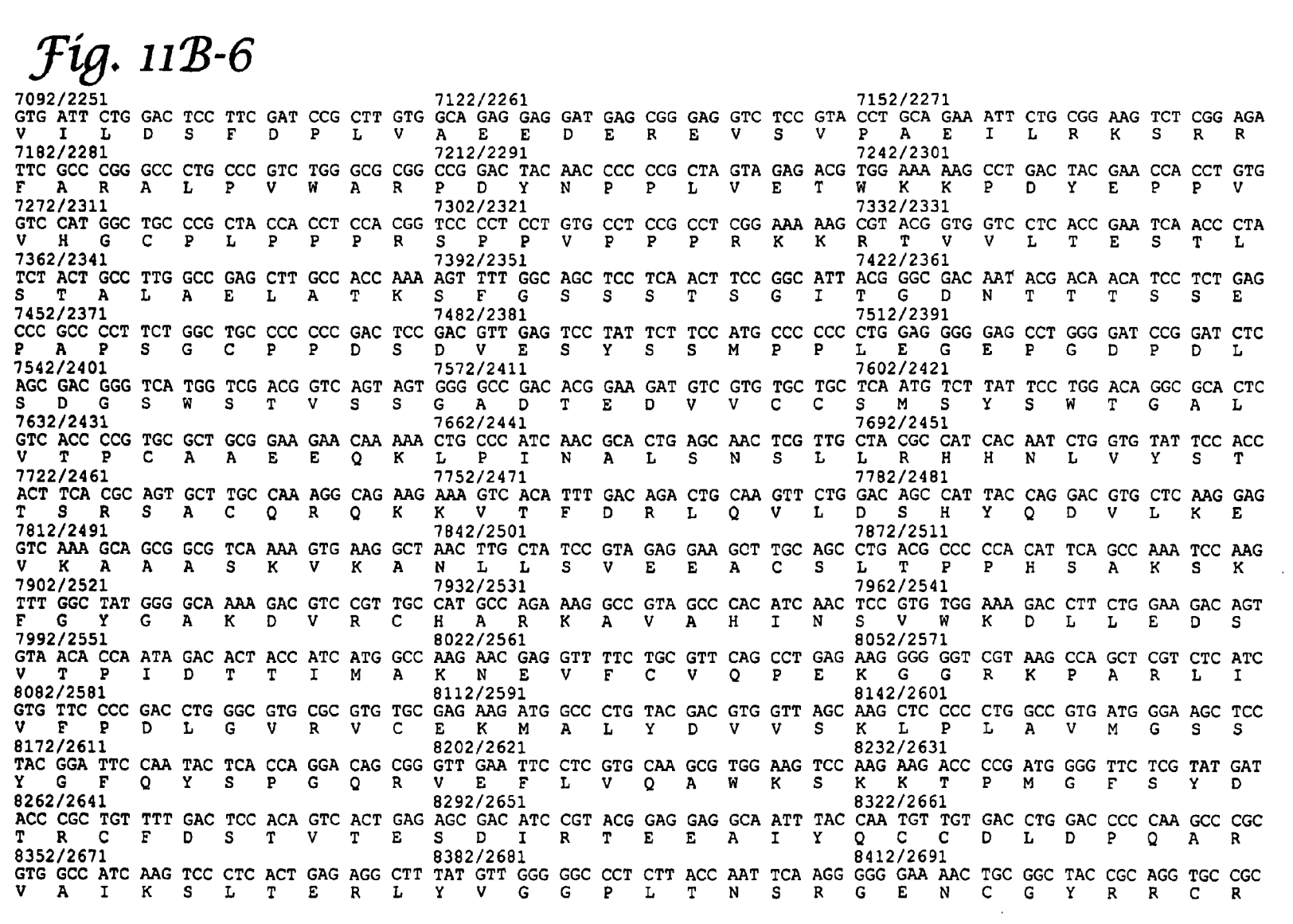

FIG. 11. 11A, nucleotide sequence of a genomic length (full length) hepatitis C virus, genotype 1a (SEQ ID NO:11); 11B, the amino acid sequence of the HCV polyprotein (SEQ ID NO:12) encoded by the coding region present in SEQ ID NO:11.

Figure 12A-1:
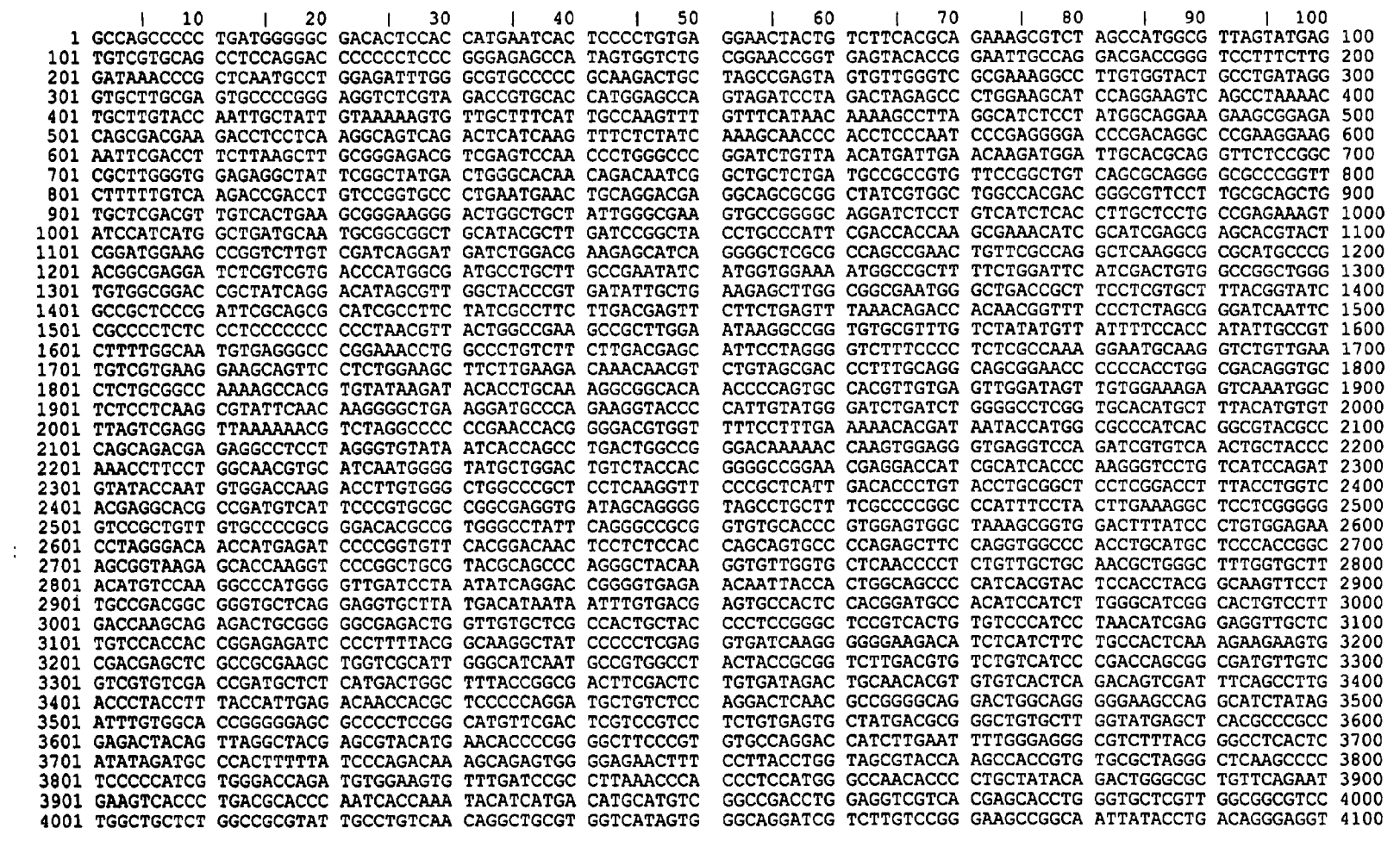
Figure 12A-2:
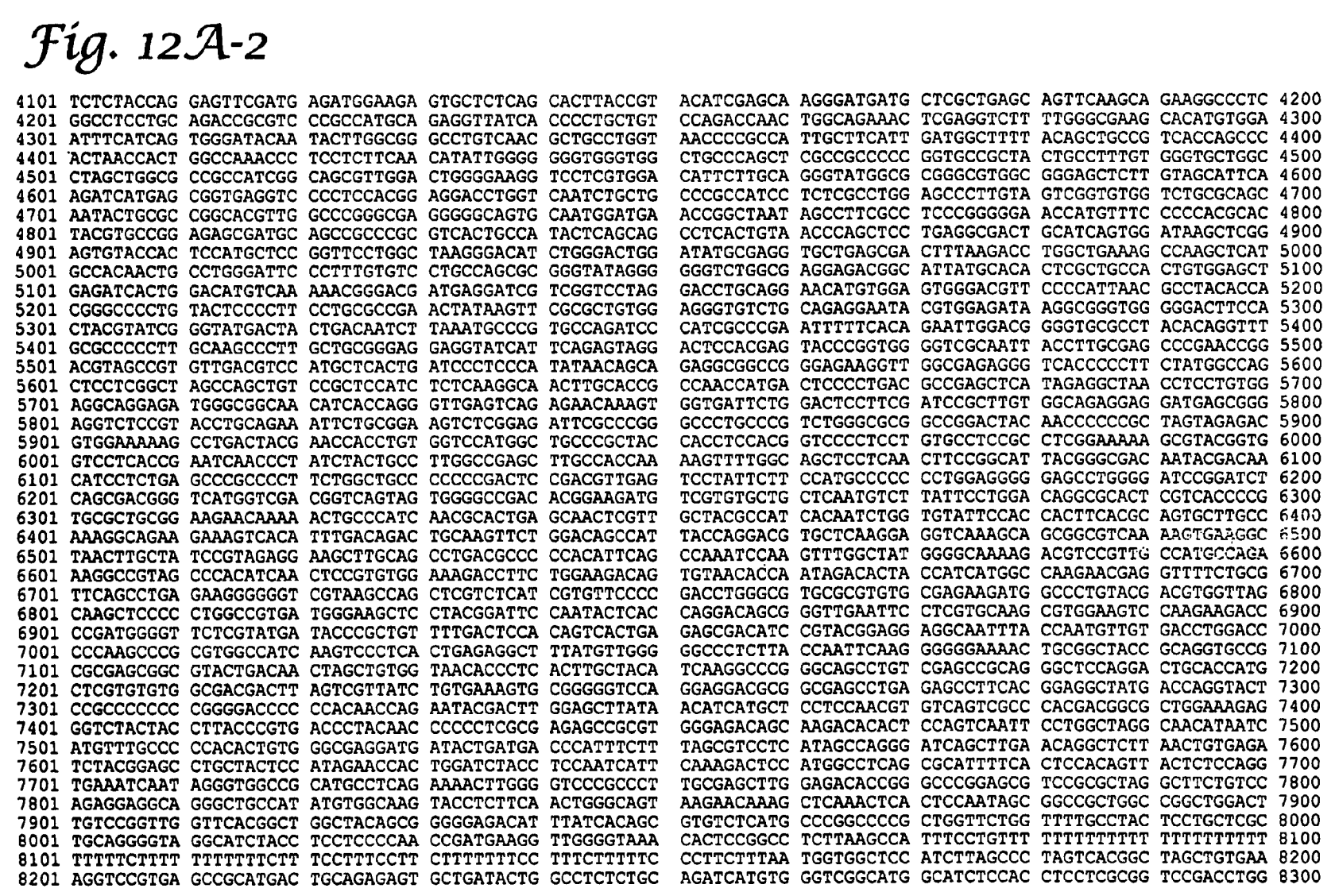
Figure 12B-2:
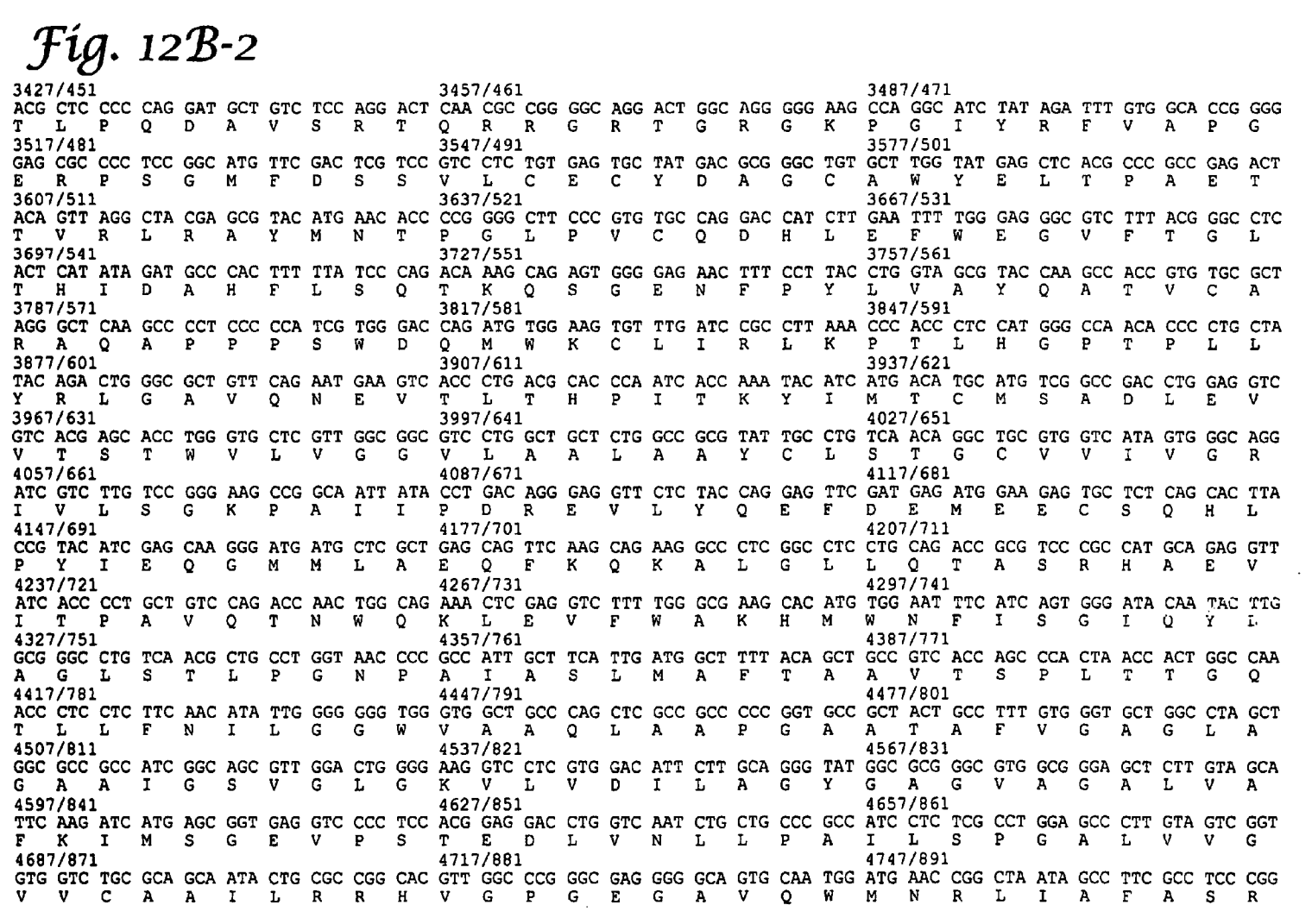
Figure 12B-4:
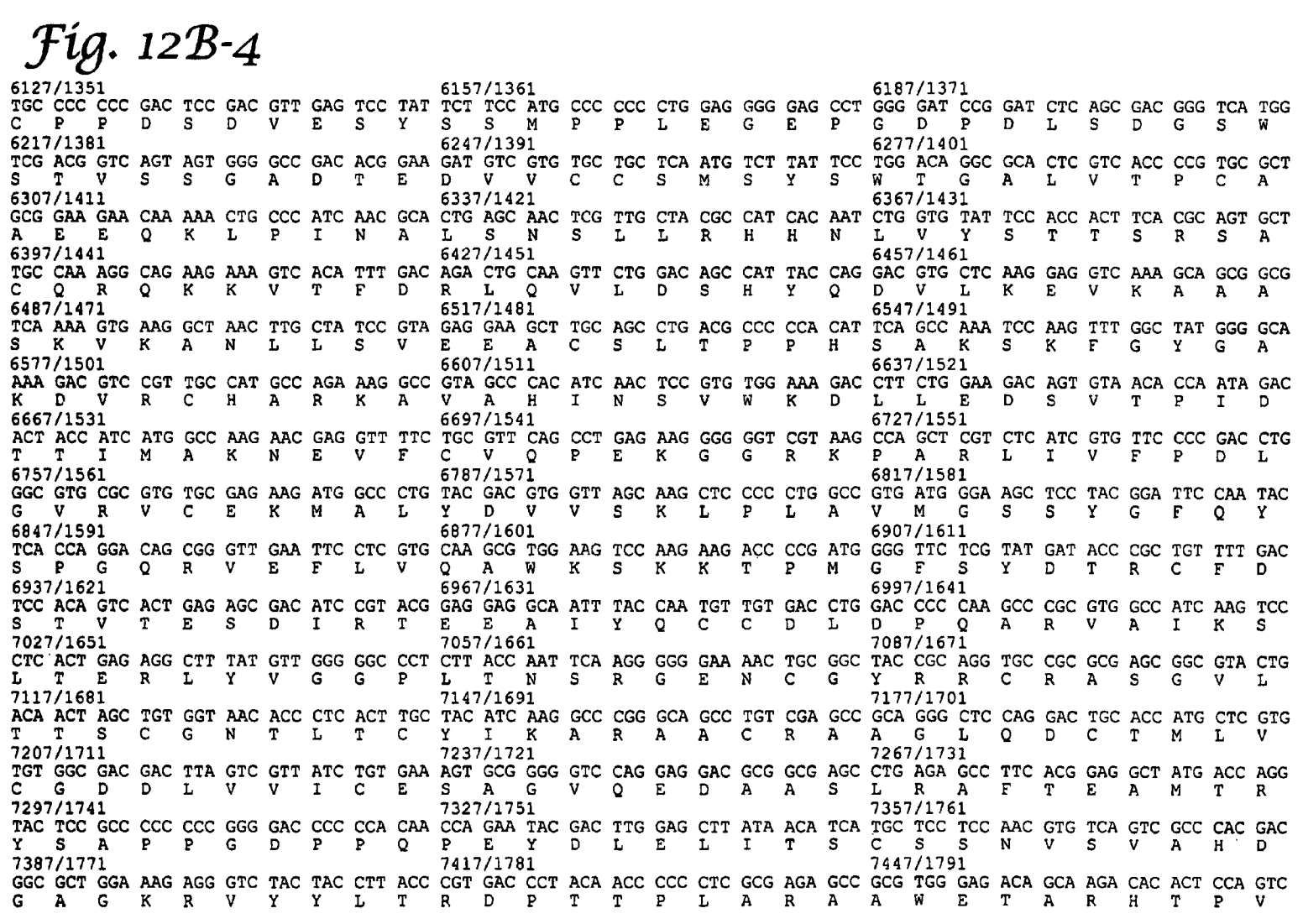

FIG. 12. 12A, nucleotide sequence of Htat2ANeo (SEQ ID NO:13), where nucleotide 1-341 are the SNTR, nucleotides 342-1454 are the tat2ANeo (termination codon at 1455-1457), nucleotides 1458-2076 are the EMCV IRES, nucleotides 2080-8034 encode the HCV polyprotein (initiation codon at nucleotides 2077-2079 and termination codon at nucleotides 8035-8037), nucleotides 8038-8259 are the 3' NTR, and nucleotides 8260-8345 are the HDV delta ribozyme (plasmid vector sequences are shown at nucleotides 8346-11240); 12B, the amino acid sequence of the HCV polyprotein (SEQ ID NO:14) encoded by the coding region present in SEQ ID NO:13.

FIG. 13. Nucleotide (SEQ ID NO:1) of Hepatitis C virus strain H77 and amino acid sequence (SEQ ID NO:2) encoded by nucleotides 342-9377.

FIG. 14. Nucleotide (SEQ ID NO:3) of Hepatitis C virus strain H and amino acid sequence (SEQ ID NO:4) encoded by nucleotides 342-9377.

DETAILED DESCRIPTION OF PREFERRED EMBODIMENTS OF THE INVENTION

Figure 2:
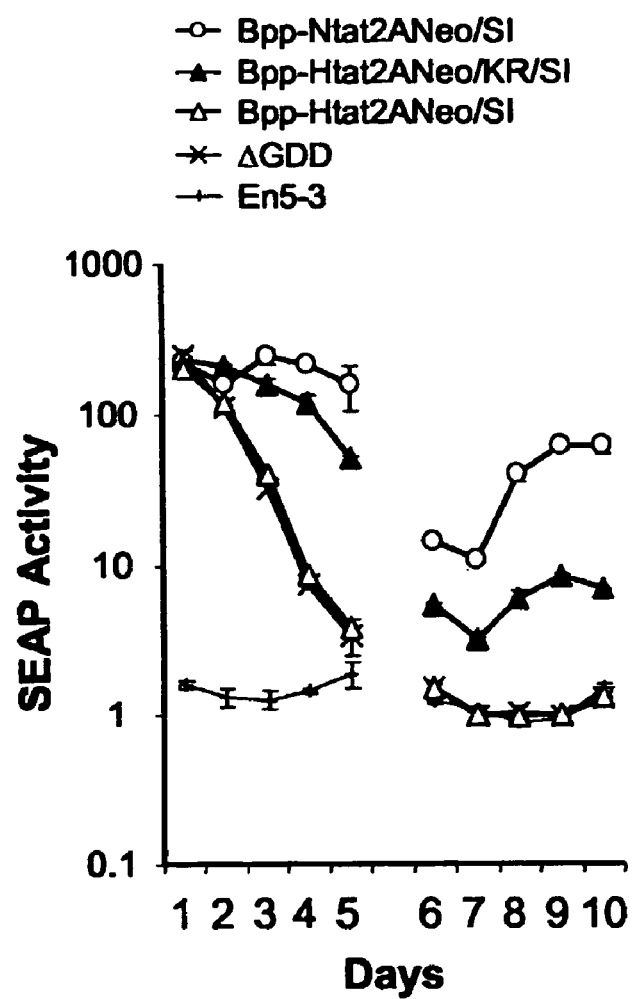
FIG. 2. Transient HCV RNA replication assay. Shown is the expression of SEAP by En5-3 cells following transfection with the chimeric 1a replicon Bpp-Htat2ANeo/SI and Bpp-Htat2ANeo/KR/SI, which carries an additional K1691R mutation in NS3 that was identified following selection of G418-resistant cells following transfection with Bpp-Htat2ANeo/SI. As controls, SEAP expression is shown following transfection of cells with the highly replication competent 1b replicon, Bpp-Ntat2ANeo/SI, and a related replication defective ΔGDD mutant; also shown in SEAP expression by normal En5-3 cells. Results shown represent the mean values obtained from triplicate cultures transfected with each RNA. SI, S2204 adaptive mutation; KR, K1691R adaptive mutation.

The present invention provides replication competent polynucleotides. The polynucleotides include a 5' non-translated region (NTR), a 3' NTR, and a coding sequence present between the 5' NTR and 3' NTR. The replication competent polynucleotides of the present invention are based on hepatitis C virus (HCV), a positive-strand virus. While the ability of a polynucleotide to replicate typically requires the presence of the positive-strand RNA polynucleotide in a cell, it is understood that the term "replication competent polynucleotide" also includes the complement thereof (i.e., the negative-sense RNA), and the corresponding DNA sequences of the positive-sense and the negative-sense RNA sequences. Optionally, a replication competent polynucleotide may be isolated. "Isolated" means a biological material, for instance a polynucleotide, polypeptide, or virus particle, that has been removed from its natural environment. For instance, a virus that has been removed from an animal or from cultured cells in which the virus was propagated is an isolated virus. An isolated polypeptide or polynucleotide means a polypeptide or polynucleotide that has been either removed from its natural environment, produced using recombinant techniques, or chemically or enzymatically synthesized. A "purified" biological material is one that is at least 60% free, preferably 75% free, and most preferably 90% free from other components with which it is naturally associated.

The coding sequence encodes a hepatitis C virus polyprotein. In some aspects of the invention, the HCV polyprotein can yield the following polypeptides; core (also referred to as C or nucleocapsid), E1, E2, P7, NS2, NS3, NS4A, NS4B, NS5A, and NS5B. Optionally, a full length HCV polyprotein also yields protein F (see Xu et al., *EMBO J.*, 20, 3840-3848 (2001). in some aspects of the present invention, an HCV polyprotein is shortened and yields a subset of polypeptides, and typically does not include polypeptides encoded by the amino terminal end of the full length HCV polyprotein. Thus, a hepatitis C virus polyprotein may encode the polypeptides E1, E2, P7, NS2, NS3, NS4A, NS4B, NS5A, and NS5B; E2, P7, NS2, NS3, NS4A, NS4B, NS5A, and NS5B; P7, NS2, NS3, NS4A, NS4B, NS5A, and NS5B; NS2, NS3, NS4A, NS4B, NS5A, and NS5B; or NS3, NS4A, NS4B, NS5A, and NS5B. The hepatitis C virus encoding such a shortened HCV polyprotein may be referred to as a subgenomic hepatitis C virus, and the shortened HCV polyprotein may be referred to as a subgenomic HCV polyprotein. In other aspects of the invention, a replication competent polynucleotide encodes an HCV polyprotein that does not include polypeptides present in an internal portion of a hepatitis C virus polyprotein. Thus, a subgenomic hepatitis C virus polyprotein may encode, for instance, the polypeptides NS3, NS4A, NS4B, and NS5B.

In those aspects of the invention where the replication competent polynucleotide includes a coding region that encodes less than a full length HCV polyprotein, the 5' end of the coding region encoding the HCV polyprotein may further include about 33 to about 51 nucleotides, or about 36 to about 48 nucleotides, that encode the first about 11 to about 17, or about 12 to about 16, amino acids of the core polypeptide. The result is a fusion polypeptide made up of amino terminal amino acids of the core polypeptide and the first polypeptide encoded by the first cleavage product of the polyprotein, e.g., E1, or E2, or P7, or NS2, etc.

A polyprotein that can yield the core, E1, E2, P7, NS2, NS3, NS4A, NS4B, NS5A, and NS5B polypeptides (a full length polyprotein) is typically between about 3000 and 3033 amino acids in length, preferably about 3011 amino acids in length. The relationship between such a polyprotein and the corresponding residues of the individual polypeptides resulting after post-translational processing is shown in Table 1. This numbering system is used herein when referring to a full length polyprotein, and when referring to a polyprotein that contains a portion of the full length polyprotein. For instance, in those aspects of the invention where the replication competent polynucleotide includes a coding sequence encoding an HCV polyprotein that yields the cleavage products NS3, NS4A, NS4B, NS5A, and NS5B and there is no fusion polypeptide made up of amino terminal amino acids of the core polypeptide and the cleavage product NS3, the first amino acid of the NS3 polypeptide is considered to be about residue number 1027. A person of ordinary skill in the art recognizes that this numbering system can vary between members of different genotypes, and between members of the same genotype, thus the numbers shown in Table 1 are approximate, and can vary by 1, 2, 3, 4, or about 5.

TABLE 1

Correspondence between amino acids of polyprotein and individual polypeptides after processing.

| Amino acids of HCV polyprotein[a] | Corresponding polypeptide after processing |
|---|---|
| 1-191 | Core |
| 192-383 | E1 |
| 384-746 | E2 |
| 747-809 | P7 |
| 810-1026 | NS2 |
| 1027-1657 | NS3 |
| 1658-1711 | NS4A |
| 1712-1972 | NS4B |
| 1973-2420 | NS5A |
| 2421-3011 | NS5B |

[a]Refers to the approximate amino acid number prior to cleavage of the polyprotein where the first amino acid is the first amino acid of the polyprotein expressed by the HCV at Genbank Accession number AF011751 and Genbank Accession number M67463.

A replication competent polynucleotide of the present invention includes at least one adaptive mutation. As used herein, an adaptive mutation is a change in the amino acid sequence of the polyprotein that increases the ability of a replication competent polynucleotide to replicate compared to a replication competent polynucleotide that does not have the adaptive mutation. One adaptive mutation that a replication competent polynucleotide of the present invention typically includes is an isoleucine at about amino acid 2204, which is about amino acid 232 of NS5A. Most clinical HCV isolates and molecularly cloned laboratory HCV strains include a serine at this position, and this mutation has been referred to in the art as S2204I. In most replication competent polynucleotides, the location of this adaptive mutation can also be determined by locating the amino acid sequence SSSA beginning at about amino acid 2200 in the HCV polyprotein, where the amino acid immediately following the SSSA sequence is isoleucine.

A replication competent polynucleotide of the present invention may also include one or more of the adaptive mutations described herein, or a combination thereof. The first such adaptive mutation is an arginine at about amino acid 1067, which is about amino acid 41 of NS3. Most clinical HCV isolates and molecularly cloned laboratory HCV strains include a glutamine at this position, thus this mutation can be referred to as Q1067R. In most replication competent polynucleotides, the location of this adaptive mutation can also be determined by locating the amino acid sequence STAT beginning at about amino acid 1063 in the HCV polyprotein, where the amino acid immediately following the STAT sequence is arginine. The second adaptive mutation is an arginine at about amino acid 1691, which is about amino acid 34 of NS4A. Most clinical HCV isolates and molecularly cloned laboratory HCV strains include a lysine at this position, thus this mutation can be referred to as K1691R. In most replication competent polynucleotides, the location of this adaptive mutation can also be determined by locating the amino acid sequence VLSG beginning at about amino acid 1687 in the HCV polyprotein, where the amino acid immediately following the VLSG sequence is arginine. The third adaptive mutation is a valine at about amino acid 2080, which is about amino acid 108 of NS5A. Most clinical HCV isolates and molecularly cloned laboratory HCV strains include a phenylalanine at this position, thus this mutation can be referred to as F2080V. In most replication competent polynucleotides, the location of this adaptive mutation can also be determined by locating the amino acid sequence ALWR beginning at about amino acid 2081 in the HCV polyprotein, where the amino acid immediately before the ALWR sequence is valine. A fourth adaptive mutation is an isoleucine at about amino acid 1655, which is about amino acid 629 of NS3. Most clinical HCV isolates and molecularly cloned laboratory HCV strains include a valine at this position, thus this mutation can be referred to as V1655I. In most replication competent polynucleotides, the location of this adaptive mutation can also be determined by locating the amino acid sequence ADLE beginning at about amino acid 2051 in the HCV polyprotein, where the amino acid immediately after the ADLE sequence is isoleucine. A fifth adaptive mutation is an arginine at about amino acid 2040, which is about amino acid 68 of NS5A. Most clinical HCV isolates and molecularly cloned laboratory HCV strains include a lysine at this position, thus this mutation can be referred to as K2040R. In most replication competent polynucleotides, the location of this adaptive mutation can also be determined by locating the amino acid sequence GHVXN beginning at about amino acid 2037 in the HCV polyprotein, where the X in the amino acid is arginine. A sixth adaptive mutation is an arginine at about amino acid 1188, which is about amino acid 162 of NS3. Most clinical HCV isolates and molecularly cloned laboratory HCV strains include a glycine at this position, thus this mutation can be referred to as G1188R. In most replication competent polynucleotides, the location of this adaptive mutation can also be determined by locating the amino acid sequence VCTR beginning at about amino acid 1184 in the HCV polyprotein. In some aspects, the replication competent polynucleotide of the present invention includes the Q1067R and K1691R adaptive mutations, as well as the S2204I adaptive mutation. These adaptive mutations are summarized in Table 2. A person of ordinary skill in the art recognizes that the precise location of these cell culture adaptive mutations can vary between members of different genotypes, and between members of the same genotype, thus the numbers shown in Table 2 are approximate, and can vary by 1, 2, 3, 4, or about 5.

TABLE 2

Adaptive Mutations

| Symbol[1] | Protein/Residue[2] | Mutation[3] |
|---|---|---|
| QR | NS3/41 | Q1067R |
| GR | NS3/162 | G1188R |
| VI | NS3/629 | V1655I |
| KR | NS4A/34 | K1691R |
| KR[5A] | NS5A/68 | K2040R |
| FV | NS5A/108 | F2080V |
| SI | NS5A/232 | S2204I |

[1]Symbol used to designate presence in RNA transcripts.
[2]Residue refers to position in protein after post-translational cleavage of the H77c polyprotein (GenBank accession AF011751).
[3]Number refers to position of mutation in H77c polyprotein before post-translational cleavage (GenBank accession AF011751).

There are many other adaptive mutations known to the art, and the replication competent polynucleotides of the present invention may include one or more of those adaptive mutations. Examples of known adaptive mutations can be found in, for instance, Bartenschlager (U.S. Pat. No. 6,630,343), Blight et al. (Science, 290, 1972-1975 (2000)), Lohmann et al., (Abstract P038, 7th International Meeting on Hepatitis C virus and Related viruses (Molecular Virology and Pathogenesis), Dec. 3-7 (2000)), Guo et al. (Abstract P045, 7th International Meeting on Hepatitis C virus and Related viruses (Molecular Virology and Pathogenesis), Dec. 3-7 (2000)), Blight et al., (J. Virol. 77, 3181-3190 (2003)), Gu et al., (J. Virol. 77, 5352-5359 (2003)), and Grobler et al., (J. Biol. Chem., 278,16741-16746 (February 2003).

It is expected that polynucleotides encoding an HCV polyprotein can be obtained from different sources, including molecularly cloned laboratory strains, for instance cDNA clones of HCV, and clinical isolates. Examples of molecularly cloned laboratory strains include the HCV that is encoded by pCV-H77C (Yanagi et al., *Proc. Natl. Acad. Sci. USA*, 94, 8738-8743 (1997), Genbank accession number AF011751, SEQ ID NO:1), and pHCV-H (Inchauspe et al., *Proc. Natl. Acad. Sci. USA*, 88, 10292-10296 (1991), Genbank accession number M67463, SEQ ID NO:3). Clinical isolates can be from a source of infectious HCV, including tissue samples, for instance from blood, plasma, serum, liver biopsy, or leukocytes, from an infected animal, including a human or a primate. It is also expected that the polynucleotide encoding the HCV polyprotein present in a replication competent polynucleotide can be prepared by recombinant, enzymatic, or chemical techniques. The nucleotide sequence of molecularly cloned laboratory strains and clinical isolates can be modified to encode an HCV polyprotein that includes the S22041 adaptive mutation and one or more of the adaptive mutations described herein. Such methods are routine and known to the art and include, for instance, PCR mutagenesis.

The present invention further includes replication competent polynucleotides encoding an HCV polyprotein having similarity with the amino acid sequence of SEQ ID NO:2, SEQ ID NO:4 (in the case of a full length polyprotein), or a portion thereof (in the case of an HCV polyprotein encoding, for instance, NS3, NS4A, NS4B, NS5A, and NS5B, and not encoding core, E1, E2, P7, and NS2). The similarity is referred to as structural similarity and is generally determined by aligning the residues of the two amino acid sequences (i.e., a candidate amino acid sequence and the amino acid sequence of SEQ ID NO:2, SEQ ID NO:4, or a portion thereof) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence is the amino acid sequence being compared to an amino acid sequence present in SEQ ID NO:2, SEQ ID NO:4, or a portion thereof. A candidate amino acid sequence can be isolated from a cell infected with a hepatitis C virus, or can be produced using recombinant techniques, or chemically or enzymatically synthesized. Preferably, two amino acid sequences are compared using the Blastp program of the BLAST 2 search algorithm, as described by Tatusova, et al. (*FEMS Microbiol Lett* 1999, 174:247-250), and available through the World Wide Web at the internet site maintained by the National Center for Biotechnology Information, National Institutes of Health. Preferably, the default values for all BLAST 2 search parameters are used, including matrix=BLOSUM62; open gap penalty=11, extension gap penalty=1, gap x_dropoff=50, expect=10, wordsize=3, and optionally, filter on. In the comparison of two amino acid sequences using the BLAST search algorithm, structural similarity is referred to as "identities." An HCV polyprotein may include an amino acid sequence having a structural similarity with SEQ ID NO:2, SEQ ID NO:4, or a portion thereof, of at least about 90%, for example 91%, 92%, 93% identity, and so on to 100% identity. A replication competent polynucleotide having a 5' NTR of SEQ ID NO:9, a 3' NTR of SEQ ID NO:8, and HCV polyprotein with structural similarity with SEQ ID NO:2, SEQ ID NO:4, or a portion thereof, is replication competent in a cell derived from a human hepatoma such as Huh-7 and Huh-7.5. An HCV polyprotein having structural similarity with the amino acid sequence of SEQ ID NO:2, SEQ ID NO:4, or a portion thereof, includes the S2204I adaptive mutation and one or more of the adaptive mutations described herein. Such an HCV polyprotein may optionally include other adaptive mutations.

In some aspects, the coding sequence of a replication competent polynucleotide of the present invention that encodes a hepatitis C virus polyprotein is not a specific genotype. For instance, a polynucleotide encoding an HCV polyprotein present in a replication competent polynucleotide of the present invention can be genotype 1a, 1b, 1c, 2a, 2b, 2c, 3a, 3b, 4, 5a, or 6a (as defined by Simmonds, *Hepatology*, 21, 570-583 (1995)). In other aspects, the HCV polyprotein is genotype 1a. Methods for determining the genotype of a hepatitis C virus are routine and known to the art and include, for instance, serotyping the virus particle using antibody, and/or evaluation of the nucleotide sequence by, for instance, polymerase chain reaction assays (see Simmonds, *J. Hepatol.*, 31(Suppl. 1), 54-60 (1999)).

The present invention includes polynucleotides encoding an amino acid sequence having similarity to an HCV polyprotein. The similarity is referred to as structural similarity and is determined by aligning the residues of two polynucleotides (e.g., the nucleotide sequence of the candidate coding region and nucleotides 342-9377 of SEQ ID NO:1 or nucleotides 342-9377 of SEQ ID NO:3) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate coding region is the coding region being compared to a coding region present in SEQ ID NO:1 (e.g., nucleotides 342-9377 of SEQ ID NO:1). A candidate nucleotide sequence can be isolated from a cell, or can be produced using recombinant techniques, or chemically or enzymatically synthesized. Preferably, two nucleotide sequences are compared using the Blastn program of the BLAST 2 search algorithm, as described by Tatusova, et al. (*FEMS Microbiol Lett* 1999, 174:247-250), and available through the World Wide Web at the internet site maintained by the National Center for Biotechnology Information, National Institutes of Health. Preferably, the default values for all BLAST 2 search parameters are used, including reward for match=1, penalty for mismatch=-2, open gap penalty=5, extension gap penalty=2, gap x_dropoff=50, expect=10, wordsize=11, and optionally, filter on. In the comparison of two nucleotide sequences using the BLAST search algorithm, structural similarity is referred to as "identities."

The present invention also includes polynucleotides encoding the HCV polyproteins described herein, including, for instance, the polyproteins having the amino acid sequence shown in SEQ ID NO:2 and SEQ ID NO:4. An example of the class of nucleotide sequences encoding each of these polyproteins are nucleotides 342-9377 of SEQ ID NO:1 and nucleotides 342-9377 of SEQ ID NO:3, respectively. These classes of nucleotide sequences are large but finite, and the nucleotide sequence of each member of the class can be readily determined by one skilled in the art by reference to the standard genetic code.

A replication competent polynucleotide of the present invention includes a 5' non-translated region (NTR) (see Smith et al., *J. Gen. Virol.*, 76, 1749-1761 (1995)). A 5' NTR is typically about 341 nucleotides in length. A replication competent polynucleotide of the present invention also includes a 3' NTR. A 3' NTR typically includes, from 5' to 3', nucleotides of variable length and sequence (referred to as the variable region), a poly-pyrimidine tract (the poly U-UC region), and a highly conserved sequence of about 100 nucleotides (the conserved region) (see, for instance, Lemon et al., U.S. Published Application US 2003 0125541, and Yi and Lemon, J. Virol., 77, 3557-3568 (2003)). The variable region begins at about the first nucleotide following the stop codon of the HCV polyprotein, and generally ends immediately before the nucleotides of the poly U-UC region. The poly U-UC region is a stretch of predominantly U residues, CU residues, or $C(U)_n$-repeats. When the nucleotide sequence of a variable region is compared between members of the same genotype, there is typically a great deal of similarity; however, there is typically very little similarity in the nucleotide sequence of the variable regions between members of different genotypes (see, for instance, Yamada et al., *Virology*, 223, 255-261 (1996)).

It is expected that a 5' NTR and a 3' NTR can be obtained from different sources, including molecularly cloned laboratory strains, for instance cDNA clones of HCV, and clinical isolates. Examples of molecularly cloned laboratory strains include the HCV that is encoded by pCV-H77C (Yanagi et al., *Proc. Natl. Acad. Sci. USA,* 94, 8738-8743 (1997), Genbank accession number AF011751, SEQ ID NO:1, where nucleotides 1-341 are the 5' NTR and nucleotides 9378-9599 are the 3' NTR), and pHCV-H (Inchauspe et al., *Proc. Natl. Acad. Sci. USA,* 88, 10292-10296 (1991), Genbank accession number M67463, SEQ ID NO:3, where nucleotides 1-341 are the 5' NTR and nucleotides 9378-9416 are the 3' NTR). Clinical isolates can be from a source of infectious HCV, including tissue samples, for instance from blood, plasma, serum, liver biopsy, or leukocytes, from an infected animal, including a human or a primate. It is also expected that the polynucleotide encoding the HCV polyprotein present in a replication competent polynucleotide can be prepared by recombinant, enzymatic, or chemical techniques.

In some aspects, a 5' NTR and a 3' NTR of a replication competent polynucleotide of the present invention is not a specific genotype. For instance, a 5' NTR and a 3' NTR present in a replication competent polynucleotide of the present invention can be genotype 1a, 1b, 1c, 2a, 2b, 2c, 3a, 3b, 4, 5a, or 6a (as defined by Simmons, *Hepatology,* 21, 570-583 (1995)). In other aspects, the HCV polyprotein is genotype 1a. Methods for determining the genotype of a 5' NTR and a 3' NTR are routine and known to the art and include evaluation of the nucleotide sequence for specific nucleotides that are characteristic of a specific genotype.

In some aspects of the invention a replication competent polynucleotide includes a second coding region. The second coding sequence may be present in the 3' NTR, for instance, in the variable region of the 3' NTR. In some aspects of the invention, the second coding region is present in the variable region such that the variable region is not removed. Alternatively, the second coding region replaces the variable region in whole or in part. In some aspects of the invention, for instance, when the HCV has the genotype 1a, the second coding region is inserted in the variable region between nucleotides 5 and 6 of the sequence 5' CUCUUAAGC 3', where the sequence shown corresponds to the positive-strand.

In some aspects of the invention, the second coding region is present in a replication competent polynucleotide downstream of the 5' NTR, and upstream of the first coding region, i.e., the coding region encoding a HCV polyprotein. For instance, the first nucleotide of the second coding region may be immediately downstream and adjacent to the last nucleotide of the 5' NTR. Alternatively, the first nucleotide of the second coding region may be further downstream of the last nucleotide of the 5' NTR, for instance, about 2 to about 51 nucleotides, about 33 to about 51 nucleotides, or about 36 to about 48 nucleotides downstream of the last nucleotide of the 5' NTR. Typically, when the first nucleotide of the second coding region is not immediately downstream of the last nucleotide of the 5' NTR, the nucleotides in between the 5' NTR and the second coding region encode the amino terminal amino acids of the HCV core polypeptide. For instance, the 5' end of the second coding region may further include about 33 to about 51 nucleotides, or about 36 to about 48 nucleotides, that encode the first about 11 to about 17, or about 12 to about 16, amino acids of the core polypeptide. The result is a fusion polypeptide made up of amino terminal amino acids of the core polypeptide and the polypeptide encoded by the second coding region (see, for instance, Yi et al., Virol., 304, 197-210 (2002), and U.S. Published Application US 2003 0125541). Without intending to be limiting, it is believed the presence of the nucleotiodes from the core coding sequence act to enhance translation the polypeptide encoded by the second coding region.

In those aspects of the invention where the second coding region present in a replication competent polynucleotide is present downstream of the 5' NTR and upstream of the coding region encoding the HCV polyprotein, the replication competent polynucleotide typically includes a regulatory region operably linked to the downstream coding region, e.g., the coding region encoding the HCV polyprotein. Preferably, the regulatory region provides for the translation of the downstream coding region. The size of the regulatory region may be from about 400 nucleotides to about 800 nucleotide, more preferably, about 600 nucleotides to about 700 nucleotides. Typically, the regulatory region is an IRES. Examples of IRES elements are described herein.

The second coding region can encode a polypeptide including, for instance, a marker, including a detectable marker and/or a selectable marker. Examples of detectable markers include molecules having a detectable enzymatic activity, for instance, secretory alkaline phosphatase, molecules having a detectable fluorescence, for instance, green or red or blue fluorescent protein, and molecules that can be detected by antibody. Examples of selectable markers include molecules that confer resistance to antibiotics able to inhibit the replication of eukaryotic cells, including the antibiotics kanamycin, ampicillin, chloramphinicol, tetracycline, blasticidin, neomycin, and formulations of phleomycin D1 including, for example, the formulation available under the tradename ZEOCIN (Invitrogen, Carlsbad, Calif.). Coding sequences encoding such markers are known to the art. Other examples of polypeptides that can be encoded by the second coding region include a transactivator, and/or a fusion polypeptide. Preferably, when the polypeptide is a fusion polypeptide, the second coding region includes nucleotides encoding a marker, more preferably, nucleotides encoding a fusion between a transactivator and a marker. Transactivators are described herein below. Optionally, the coding region can encode an immunogenic polypeptide. A replication competent polynucleotide containing a second coding region is typically dicistronic, i.e., the coding region encoding the HCV polyprotein and the second coding region are separate.

An "immunogenic polypeptide" refers to a polypeptide which elicits an immunological response in an animal. An immunological response to a polypeptide is the development in a subject of a cellular and/or antibody-mediated immune response to the polypeptide. Usually, an immunological response includes but is not limited to one or more of the following effects: the production of antibodies, B cells, helper T cells, suppressor T cells, and/or cytotoxic T cells, directed specifically to an epitope or epitopes of the polypeptide fragment.

A transactivator is a polypeptide that affects in trans the expression of a coding region, preferably a coding region integrated in the genomic DNA of a cell. Such coding regions are referred to herein as "transactivated coding regions." The cells containing transactivated coding regions are described in detail herein below. Transactivators useful in the present invention include those that can interact with a regulatory region, preferably an operator sequence, that is operably linked to a transactivated coding region. As used herein, the term "transactivator" includes polypeptides that interact with an operator sequence and either prevent transcription from initiating at, activate transcription initiation from, or stabilize a transcript from, a transactivated coding region operably linked to the operator sequence. Examples of useful transactivators include the HIV tat polypeptide (see, for example, the polypeptides MEPVDPRLEPWKHPGSQPKTACTNCY-CKKCCFHCQVCFITKALGISYGRK KRRQRRRAHQN-SQTHQASLSKQPTSQPRGDPrGPKE (SEQ ID NO:5) which is encoded by nucleotides 5377 to 5591 and 7925 to 7970 of Genbank accession number AF033819), and MEPVDPRLEPWKHPGSQPKTACTNCYCK-KCCFHCQVCFITKALGISYGRK KRRQRRRPPQG-SQTHQVSLSKQPTSQSRGDPTGPKE (SEQ ID NO:10). The HIV tat polypeptide interacts with the HIV long terminal repeat (LTR). Other useful transactivators include human T cell leukemia virus tax polypeptide (which binds to the operator sequence tax response element, Fujisawa et al., *J. Virol.*, 65, 4525-4528 (1991)), and transactivating polypeptides encoded by spumaviruses in the region between env and the LTR, such as the bel-1 polypeptide in the case of human foamy virus (which binds to the U3 domain of these viruses, Rethwilm et al., *Proc. Natl. Acad. Sci. USA*, 88, 941-945 (1991)). Alternatively, a post-transcriptional transactivator, such as HIV rev, can be used. HIV rev binds to a 234 nucleotide RNA sequence in the env gene (the rev-response element, or RRE) of HIV (Hadzopolou-Cladaras et al., *J. Virol.*, 63, 1265-1274 (1989)).

Other transactivators that can be used are those having similarity with the amino acid sequence of SEQ ID NO:5 or SEQ ID NO:10. The similarity is generally determined as described herein above. A candidate amino acid sequence that is being compared to an amino acid sequence present in SEQ ID NO:5 or SEQ ID NO:10 can be isolated from a virus, or can be produced using recombinant techniques, or chemically or enzymatically synthesized. Preferably, two amino acid sequences are compared using the Blastp program of the BLAST 2 search algorithm, as described herein above. Preferably, a transactivator includes an amino acid sequence having a structural similarity with SEQ ID NO:5 or SEQ ID NO:10, of at least about 90%, at least about 94%, at least about 96%, at least about 97%, at least about 98%, or at least about 99% identity. Typically, an amino acid sequence having a structural similarity with SEQ ID NO: 5 or SEQ ID NO:10 has tat activity. Whether such a polypeptide has activity can be evaluated by determining if the amino acid sequence can interact with an HIV LTR, preferably alter transcription from a coding sequence operably linked to an HIV LTR. Useful HIV LTRs are described herein.

Active analogs or active fragments of a transactivator can be used in the invention. An active analog or active fragment of a transactivator is one that is able to interact with an operator sequence and either prevent transcription from initiating at, activate transcription initiation from, or stabilize a transcript from, a transactivated coding region operably linked to the operator sequence.

Active analogs of a transactivator include polypeptides having conservative amino acid substitutions that do not eliminate the ability to interact with an operator and alter transcription. Substitutes for an amino acid may be selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, aspartate, and glutamate. The positively charged (basic) amino acids include arginine, lysine, and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$.

Active fragments of a transactivator include a portion of the transactivator containing deletions or additions of about 1, about 2, about 3, about 4, or at least about 5 contiguous or noncontiguous amino acids such that the resulting transactivator will alter expression of an operably linked transactivated coding region. A preferred example of an active fragment of the HIV tat polypeptide includes amino acids amino acids 1-48 of SEQ ID NO: 5, or amino acids 1-48 of SEQ ID NO:10.

In those aspects of the invention where the second coding region encodes a fusion polypeptide, the fusion polypeptide can further include amino acids corresponding to a cis-active proteinase. When the fusion polypeptide is a fusion between a transactivator and a marker, preferably the fusion polypeptide also includes amino acids corresponding to a cis-active proteinase. Preferably the amino acids corresponding to a cis-active proteinase are present between the amino acids corresponding to the transactivator and the marker. A cis-active proteinase in this position allows the amino acids corresponding to the transactivator and the marker to be physically separate from each other in the cell within which the replication competent polynucleotide is present. Examples of cis-active proteinases that are useful in the present invention include the cis-active 2A proteinase of foot-and-mouth disease (FMDV) virus (see, for example, U.S. Pat. No. 5,846,767 (Halpin et al.) and U.S. Pat. No. 5,912,167 (Palmenberg et al.)), ubiquitin (see, for example, Tauz et al., *Virology*, 197, 74-85 (1993)), and the NS3 recognition site GADTEDV-VCCSMSY (SEQ ID NO:6) (see, for example, Lai et al., *J. Virol.*, 74, 6339-6347 (2000)).

Active analogs and active fragments of cis-active proteinases can also be used. Active analogs of a cis-acting proteinase include polypeptides having conservative amino acid substitutions that do not eliminate the ability of the proteinase to catalyze cleavage. Active fragments of a cis-active proteinase include a portion of the cis-active proteinase containing deletions or additions of one or more contiguous or noncontiguous amino acids such that the resulting cis-active proteinase will catalyze the cleavage of the proteinase.

In some aspects of the invention, the second coding region may further include an operably linked regulatory region. Preferably, a regulatory region located 5' of the operably linked coding region provides for the translation of the coding region.

A preferred regulatory region located 5' of an operably linked second coding region is an internal ribosome entry site (IRES). An IRES allows a ribosome access to mRNA without a requirement for cap recognition and subsequent scanning to the initiator AUG (Pelletier, et al., *Nature*, 334, 320-325 (1988)). An IRES is located upstream of the translation initiation codon, e.g., ATG or AUG, of the coding sequence to which the IRES is operably linked. The distance between the IRES and the initiation codon is dependent on the type of IRES used, and is known to the art. For instance, poliovirus IRES initiates a ribosome translocation/scanning process to a downstream AUG codon. For other IRES elements, the initiator codon is generally located at the 3' end of the IRES sequence. Examples of an IRES that can be used in the invention include a viral IRES, preferably a picornaviral IRES or a flaviviral IRES. Examples of poliovirus IRES elements include, for instance, poliovirus IRES, encephalomyocarditis virus IRES, or hepatitis A virus IRES. Examples of preferred flaviviral IRES elements include hepatitis C virus IRES, GB virus B IRES, or a pestivirus IRES, including but not limited to bovine viral diarrhea virus IRES or classical swine fever virus IRES. Other IRES elements with similar secondary and tertiary structure and translation initiation activity can either be generated by mutation of these viral sequences, by cloning of analogous sequences from other viruses (including picornaviruses), or prepared by enzymatic synthesis techniques.

The size of the second coding region is not critical to the invention. It is expected there is no lower limit on the size of the second coding region, and that there is an upper limit on the size of the second coding region. This upper limit can be easily determined by a person skilled in the art, as second coding region that are greater than this upper limit adversely affect replication of a replication competent polynucleotide. The second coding region is typically at least about 10 nucleotides, at least about 20 nucleotides, at least about 30 nucleotides, or at least about 40 nucleotides.

A replication competent polynucleotide may also include a nucleotide sequence having cis-acting ribozyme activity. Such a ribozyme is typically present at the 3' end of the 3' NTR of a replication competent polynucleotide, and generates a precise 3' terminal end of the replication competent polynucleotide when it is an RNA molecule by cleaving the junction between the replication competent polynucleotide and the ribozyme. This can be advantageous when the replication competent polynucleotide is to be used for a transient transfection. Since the ribozyme catalyzes its own removal from the RNA molecule, this type of ribozyme is present only when a replication competent polynucleotide is a DNA molecule.

The replication competent polynucleotide of the invention can be present in a vector. When a replication competent polynucleotide is present in a vector the polynucleotide is DNA, including the 5' non-translated RNA and the 3' non-translated RNA, and, if present, the second coding sequence. Methods for cloning and/or inserting hepatitis C virus sequences into a vector are known to the art (see, e.g., Yanagi et al., *Proc. Natl. Acad. Sci., USA,* 94, 8738-8743 (1997); and Rice et al., (U.S. Pat. No. 6,127,116)). Such constructs are often referred to as molecularly cloned laboratory strains, and an HCV that is inserted into a vector is often referred to as a cDNA clone of the HCV. If the RNA encoded by the HCV is able to replicate in vivo, the HCV present in the vector is referred to as an infectious cDNA clone. A vector is a replicating polynucleotide, such as a plasmid, phage, cosmid, or artificial chromosome to which another polynucleotide may be attached so as to bring about the replication of the attached polynucleotide. A vector can provide for further cloning (amplification of the polynucleotide), i.e., a cloning vector, or for expression of the polypeptide encoded by the coding region, i.e., an expression vector. The term vector includes, but is not limited to, plasmid vectors, viral vectors, cosmid vectors, or artificial chromosome vectors. Preferably the vector is a plasmid. Preferably the vector is able to replicate in a prokaryotic host cell, for instance *Escherichia coli*. Preferably, the vector can integrate in the genomic DNA of a eukaryotic cell.

An expression vector optionally includes regulatory sequences operably linked to the replication competent polynucleotide such that it is transcribed to produce RNA molecules. These RNA molecules can be used, for instance, for introducing a replication competent polynucleoitde into a cell that is in an animal or growing in culture. The terms "introduce" and "introducing" refer to providing a replication competent polynucleotide to a cell under conditions that the polynucleotide is taken up by the cell in such a way that it can then replicate. The replication competent polynucleotide can be present in a virus particle, or can be a nucleic acid molecule, for instance, RNA. The invention is not limited by the use of any particular promoter, and a wide variety are known. Promoters act as regulatory signals that bind RNA polymerase in a cell to initiate transcription of a downstream (3' direction) HCV. The promoter used in the invention can be a constitutive or an inducible promoter. A preferred promoter for the production of replication competent polynucleotide as an RNA molecule is a T7 promoter.

The present invention includes methods for identifying a replication competent polynucleotide, including detecting and/or selecting for cells containing a replication competent polynucleotide. Typically, the cells used in this aspect of the invention are primate or human cells growing in culture. Useful cultured cells will support the replication of the polynucleotides of the present invention, and include primary human or chimpanzee hepatocytes, peripheral mononuclear cells, cultured human lymphoid cell lines (for instance lines expressing B-cell and T-cell markers such as Bjab and Molt-4 cells), and continuous cell lines derived from such cells, including HPBMa10-2 and Daudi (Shimizu et al., *J. Gen. Virol.,* 79, 1383-1386 (1998), and MT-2 (Kato et al., *Biochem. Biophys. Res. Commun.,* 206, 863-869 (1995)). Other useful cells include those derived from a human hepatoma cells, for instance, Huh-7 (see, for instance, Lohmann et al. (*Science,* 285, 110-113 (1999)), Huh-7.5 (see, for instance, Blight et a., *J. Virol.,* 76, 13001-13014 (2002), and Blight et al., *J. Virol.,* 77, 3183-3190 (2003)), HepG2 and IMY-N9 (Date et al., *J. Biol. Chem.,* 279, 22371-22376 (2004)), and PH5CH8 (Ikeda et al., *Virus Res.,* 56, 157-167 (1998)). In general, useful cells include those that support replication of HCV RNA, including, for instance, replication of the HCV encoded by pCV-H77C, replication of the HCV encoded by pHCV-N as modified by Beard et al. (*Hepatol.,* 30, 316-324 (1999)), or replication of such an HCV modified to contain one or more adaptive mutations.

In some aspects of the invention, the cultured cell includes a polynucleotide that includes a coding region, the expression of which is controlled by a transactivator. Such a coding region is referred to herein as a transactivated coding region. A transactivated coding region encodes a marker, such as a detectable marker, for example, secretory alkaline phosphatase (SEAP), an example of which is encoded by nucleotides 748-2239 of SEQ ID NO:7 (see FIG. 9). Typically, a cultured cell that includes a polynucleotide having a transactivated coding region is used in conjunction with a replication competent polynucleotide of the present invention that includes a coding region encoding a transactivator.

The polynucleotide that includes the transactivated coding region can be present integrated into the genomic DNA of the cell, or present as part of a vector that is not integrated. Methods of modifying a cell to contain an integrated DNA are known to the art (see, for instance, Lemon et al., U.S. Published Application US 2003 0125541, and Yi et al., Virol., 302, 197-210 (2002)).

Operably linked to the transactivated coding region is an operator sequence. The interaction of a transactivator with an operator sequence can alter transcription of the operably linked transactivated coding region. In those aspects of the invention where a transactivator increases transcription, there is typically low transcription, or, essentially no transcription, of the transactivated coding region in the absence of a transactivator. An operator sequence can be present upstream (5') or downstream (3') of a transactivated coding region. An operator sequence can be a promoter, or can be a nucleotide sequence that is present in addition to a promoter.

In some aspects of the invention, the operator sequence that is operably linked to a transactivated coding sequence is an HIV long terminal repeat (LTR). An example of an HIV LTR is depicted at nucleotides 1-719 of SEQ ID NO:7. Also included in the present invention are operator sequences having similarity to nucleotides 1-719 of SEQ ID NO:7. The similarity between two nucleotides sequences may be determined by aligning the residues of the two polynucleotides (i.e., the nucleotide sequence of the candidate operator sequence and the nucleotide sequence of nucleotides 1-719 of SEQ ID NO:7) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate operator sequence can be isolated from a cell, or can be produced using recombinant techniques, or chemically or enzymatically synthesized. Preferably, two nucleotide sequences are compared using the Blastn program of the BLAST 2 search algorithm, as described by Tatusova, et al. (*FEMS Microbiol Lett* 1999, 174:247-250), and available at http://www.ncbi.nlm.nih.gov/gorf/b12.html. Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on. In the comparison of two nucleotide sequences using the BLAST search algorithm, structural similarity is referred to as "identities." Preferably, an operator sequence includes a nucleotide sequence having a structural similarity with the nucleotides 1-719 of SEQ ID NO:7 of at least about 90%, at least about 95%, or at least about 99% identity. Typically, an operator sequence having structural similarity with the nucleotides 1-719 of SEQ ID NO:7 has transcriptional activity. Whether such an operator sequence has transcriptional activity can be determined by evaluating the ability of the operator sequence to alter transcription of an operably linked coding sequence in response to the presence of a polypeptide having tat activity, preferably, a polypeptide including the amino acids of SEQ ID NO:5 or SEQ ID NO:10.

A selecting agent may be used to inhibit the replication of cultured cells that support the replication of polynucleotides of the present invention. Examples of selecting agents include antibiotics, including kanamycin, ampicillin, chloramphinicol, tetracycline, neomycin, and formulations of phleomycin D1. A selecting agent can act to prevent replication of a cell, or kill a cell, while the agent is present and the cell does not express a molecule that provides resistance to the selecting agent. Typically, the molecule providing resistance to a selecting agent is expressed in the cell by a replication competent polynucleotide of the present invention. Alternatively, the molecule providing resistance to a selecting agent is expressed by the cell but the expression of the molecule is controlled by a replication competent polynucleotide of the present invention that is present in the cell. The concentration of the selecting agent is typically chosen such that a cell does not replicate if it does not contain a molecule providing resistance to a selecting agent. The appropriate concentration of a selecting agent varies depending on the particular selecting agent, and can be easily determined by one having ordinary skill in the art using known techniques.

When a polynucleotide is introduced into a cell that is growing in culture, the polynucleotide can be introduced using techniques known to the art. Such techniques include, for instance, liposome and non-liposome mediated transfection. Non-liposome mediated transfection methods include, for instance, electroporation.

In some aspects of the invention, when a replication competent polynucleotide is identified using cultured cells, its ability to replicate may be verified by introducing the replication competent polynucleotide into a cell present in an animal, preferably a chimpanzee. When the cell is present in the body of an animal, the replication competent polynucleotide can be introduced by, for instance, subcutaneous, intramuscular, intraperitoneal, intravenous, or percutaneous intrahepatic administration, preferably by percutaneous intrahepatic administration. Methods for determining whether a replication competent polynucleotide is able to replicate in a chimpanzee are known to the art (see, for example, Yanagi et al., *Proc. Natl. Acad. Sci. USA*, 94, 8738-8743 (1997)). In general, the demonstration of infectivity is based on the appearance of the virus in the circulation of the chimpanzee over the days and weeks following the intrahepatic injection of the replication competent polynucleotide. The presence of the virus can be confirmed by reverse transcription-polymerase chain reaction (RT-PCR) detection of the viral RNA, by inoculation of a second chimpanzee with transfer of the hepatitis C virus infection as indicated by the appearance of liver disease and seroconversion to hepatitis C virus in ELISA tests, or possibly by the immunologic detection of components of the hepatitis C virus (e.g., the core protein) in the circulation of the inoculated animal. It should be noted that seroconversion by itself is generally not a useful indicator of infection in an animal injected with a viral RNA produced using a molecularly cloned laboratory strain, as this RNA may have immunizing properties and be capable of inducing HCV-specific antibodies to proteins translated from an input RNA that is non-replicating. Similarly, the absence of seroconversion does not exclude the possibility of viral replication and infection of a chimpanzee with HCV.

Whether a polynucleotide is replication competent can be determined using methods known to the art, including methods that use nucleic acid amplification to detect the result of increased levels of replication. For instance, transient transfection of a cell with a replication competent polynucleotide permits measurement of the production of additional polynucleotides. Methods for transient transfection of a cell with a replication competent polynucleotide and for assay of subsequent replication are known to the art. In some aspects of the invention, another method for detecting a replication competent polynucleotide includes measuring the production of viral particles by a cell. The measurement of viral particles can be accomplished by passage of supernatant from media containing a cell culture that may contain a replication competent polynucleotide, and using the supernatant to infect a second cell. Detection of the polynucleotide or viral particles in the second cell indicates the initial cell contains a replication competent polynucleotide. The production of infectious virus particles by a cell can also be measured using antibody that specifically binds to an HCV viral particle. As used herein, an antibody that can "specifically bind" an HCV viral particle is an antibody that interacts only with the epitope of the antigen (e.g., the viral particle or a polypeptide that makes up the particle) that induced the synthesis of the antibody, or interacts with a structurally related epitope. "Epitope" refers to the site on an antigen to which specific B cells and/or T cells respond so that antibody is produced. An epitope could include about 3 amino acids in a spatial conformation which is unique to the epitope. Generally an epitope includes at least about 5 such amino acids, and more usually, consists of at least about 8-10 such amino acids. Antibodies to HCV viral particles can be produced as described herein.

In another aspect, identifying a replication competent polynucleotide includes incubating a cultured cell that includes a polynucleotide of the present invention. In those aspects of the invention where the replication competent polynucleotide includes a second coding region encoding a detectable marker, cells containing the replication competent polynucleotide can be identified by observing individual cells that contain the detectable marker. Alternatively, if the detectable marker is secreted by the cell, the presence of the marker in the medium in which the cell is incubated can be detected. Methods for observing the presence or absence of a detectable marker in a cell or in liquid media are known to the art.

Another aspect of the invention provides for the positive selection of cells that include a replication competent polynucleotide. In this aspect of the invention, a replication competent polynucleotide typically includes a second coding sequence encoding a selectable marker, and the cell which includes the replication competent polynucleotide is incubated in the presence of a selecting agent. Those cells that can replicate in the presence of the selecting agent contain a polynucleotide that is replication competent. The cells that can replicate are detected by allowing resistant cells to grow in the presence of the selecting agent, and observing, for instance, the presence of colonies and/or the expression of a marker, such as SEAP.

In some aspects, the method may further include isolating virus particles from the cells that contain a replication competent polynucleotide and exposing a second cell to the isolated virus particle under conditions such that the virus particle is introduced to the cell. After providing time for expression of the selectable marker, the second cell is then incubated with the selecting agent. The presence of a cell that replicates indicates the replication competent polynucleotide produces infectious virus particles.

In another aspect, the invention provides a method for detecting a replication competent polynucleotide. The method includes incubating a cell that contains a replication competent polynucleotide of the present invention. The polynucleotide may include a second coding region encoding a selectable or detectable marker. Optionally, the polynucleotide may include a transactivator that interacts with the operator sequence present in the cell. In this aspect, the cell may include a transactivated coding region and an operator sequence operably linked to the transactivated coding region. The method further includes detecting the presence of increased amounts of the replication competent polynucleotide, or the presence or absence of the marker encoded by the second coding sequence or the transactivated coding region present in the cell. The presence of increased amounts of the replication competent polynucleotide or the marker indicates the cell includes a replication competent polynucleotide.

The methods described above for identifying a replication competent polynucleotide can also be used for identifying a variant replication competent polynucleotide, i.e., a replication competent polynucleotide that is derived from a replication competent polynucleotide of the present invention. A variant replication competent polynucleotide may have a faster replication rate than the parent or input polynucleotide. The method takes advantage of the inherently high mutation rate of RNA replication. It is expected that during continued culture of a replication competent polynucleotide in cultured cells, the polynucleotide of the present invention may mutate, and some mutations will result in polynucleotides with greater replication rates. The method includes identifying a cell that has greater expression of a polypeptide encoded by a replication competent polynucleotide. A polynucleotide of the present invention that replicates at a faster rate will result in more of the polynucleotide in the cell, or will result in more of the polypeptide(s) that is encoded by the second coding region present in the polynucleotide. For instance, when a replication competent polynucleotide encodes a selectable marker, a cell containing a variant polynucleotide having a greater replication rate will be resistant to higher levels of an appropriate selecting agent. When a polynucleotide encodes a transactivator, a cell containing a variant polynucleotide having a greater replication rate than the parent or input polynucleotide will express higher amounts of the transactivated coding region that is present in the cell.

A cDNA molecule of a variant replication competent polynucleotide can be cloned using methods known to the art (see, for instance, Yanagi et al., *Proc. Natl. Acad. Sci., USA*, 94, 8738-8743 (1997)). The nucleotide sequence of the cloned cDNA can be determined using methods known to the art, and compared with that of the input RNA. This allows identification of mutations that have occurred in association with passage of the replication competent polynucleotide in cell culture. For example, using methods known to the art, including longrange RT-PCR, extended portions of a variant replication competent polynucleotide genome can be obtained. Multiple clones could be obtained from each segment of the genome, and the dominant sequence present in the culture determined. Mutations that are identified by this approach can then be reintroduced into the background of the cDNA encoding the parent or input polynucleotide.

The present invention also provides methods for identifying a compound that inhibits replication of a replication competent polynucleotide. The method includes contacting a cell containing a replication competent polynucleotide with a compound and incubating the cell under conditions that permit replication of the replication competent polynucleotide in the absence of the compound. After a period of time sufficient to allow replication of the polynucleotide, the replication competent polynucleotide is detected. A decrease in the presence of replication competent polynucleotide in the cell contacted with the compound relative to the presence of replication competent polynucleotide in a cell not contacted by the compound indicates the compound inhibits replication of the polynucleotide. A compound that inhibits replication of such a polynucleotide includes compounds that completely prevent replication, as well as compounds that decrease replication. Preferably, a compound inhibits replication of a replication competent polynucleotide by at least about 50%, more preferably at least about 75%, most preferably at least about 95%.

The compounds added to a cell can be a wide range of molecules and is not a limiting aspect of the invention. Compounds include, for instance, a polyketide, a non-ribosomal peptide, a polypeptide, a polynucleotide (for instance an antisense oligonucleotide or ribozyme), other organic molecules, or a combination thereof. The sources for compounds to be screened can include, for example, chemical compound libraries, fermentation media of Streptomycetes, other bacteria and fungi, and extracts of eukaryotic or prokaryotic cells. When the compound is added to the cell is also not a limiting aspect of the invention. For instance, the compound can be added to a cell that contains a replication competent polynucleotide. Alternatively, the compound can be added to a cell before or at the same time that the replication competent polynucleotide is introduced to the cell.

Typically, the ability of a compound to inhibit replication of a replication competent polynucleotide is measured using methods described herein. For instance, methods that use nucleic acid amplification to detect the amount of a replication competent polynucleotide in a cell can be used. Alternatively, methods that detect or select for a marker encoded by a replication competent polynucleotide or encoded by a cell containing a replication competent polynucleotide can be used.

In some aspects of the invention, the replication competent polynucleotide of the invention can be used to produce viral particles. Preferably, the viral particles are infectious. For instance, a cell that includes a replication competent polynucleotide can be incubated under conditions that allow the polynucleotide to replicate, and the viral particles that are produced can be isolated using methods routine and known to the art. The viral particles can be used as a source of virus particles for various assays, including evaluating methods for inactivating particles, excluding particles from serum, identifying a neutralizing compound, and as an antigen for use in detecting anti-HCV antibodies in an animal. An example of using a viral particle as an antigen includes use as a positive-control in assays that test for the presence of anti-HCV antibodies.

For instance, the activity of compounds that neutralize or inactivate the particles can be evaluated by measuring the ability of the molecule to prevent the particles from infecting cells growing in culture or in cells in an animal. Inactivating compounds include detergents and solvents that solubilize the envelope of a viral particle. Inactivating compounds are often used in the production of blood products and cell-free blood products. Examples of compounds that can be neutralizing include a polyketide, a non-ribosomal peptide, a polypeptide (for instance, an antibody), a polynucleotide (for instance, an antisense oligonucleotide or ribozyme), or other organic molecules. Preferably, a neutralizing compound is an antibody, including polyclonal and monoclonal antibodies, as well as variations thereof including, for instance, single chain antibodies and Fab fragments.

Viral particles produced by replication competent polynucleotide of the invention can be used to produce antibodies. Laboratory methods for producing polyclonal and monoclonal antibodies are known in the art (see, for instance, Harlow E. et al. *Antibodies: A laboratory manual* Cold Spring Harbor Laboratory Press, Cold Spring Harbor (1988) and Ausubel, R. M., ed. *Current Protocols in Molecular Biology* (1994)), and include, for instance, immunizing an animal with a virus particle. Antibodies produced using the viral particles of the invention can be used to detect the presence of viral particles in biological samples. For instance, the presence of viral particles in blood products and cell-free blood products can be determined using the antibodies.

The present invention further includes methods of treating an animal including administering neutralizing antibodies. The antibodies can be used to prevent infection (prophylactically) or to treat infection (therapeutically), and optionally can be used in conjunction with other molecules used to prevent or treat infection. The neutralizing antibodies can be mixed with pharmaceutically acceptable excipients or carriers. Suitable excipients include but are not limited to water, saline, dextrose, glycerol, ethanol, or the like and combinations thereof. In addition, if desired, neutralizing antibodies and pharmaceutically acceptable excipients or carriers may contain minor amounts of auxiliary substances such as wetting or emulsifying agents, pH buffering agents, and/or adjuvants which enhance the effectiveness of the neutralizing antibodies. Such additional formulations and modes of administration as are known in the art may also be used.

The virus particles produced by replication competent polynucleotide of the invention can be used as a source of viral antigen to measure the presence and amount of antibody present in an animal. Assays are available that measure the presence in an animal of antibody directed to HCV, and include, for instance, ELISA assays and recombinant immunoblot assay. These types of assays can be used to detect whether an animal has been exposed to HCV, and/or whether the animal may have an active HCV infection. However, these assays do not use virus particles, but rather individual or multiple viral polypeptides expressed from recombinant cDNA that are not in the form of virus particles. Hence they are generally unable to detect potentially important antibodies directed against surface epitopes of the envelope polypeptides, nor are they typically measures of functionally important viral neutralizing antibodies. Such antibodies are generally detected with the use of infectious virus particles, such as those that are produced in this system. The use of infectious viral particles as antigen in assays that detect the presence of specific antibodies by virtue of their ability to block the infection of cells with HCV viral particles, or that possibly bind to whole virus particles in an ELISA assay or radioimmunoassay, will allow the detection of functionally important viral neutralizing antibodies.

The present invention also provides a kit for identifying a compound that inhibits replication of a replication competent polynucleotide. The kit includes a replication competent polynucleotide as described herein, and a cell that contains a polynucleotide including a transactivated coding sequence encoding a detectable marker and an operator sequence operably linked to the transactivated coding sequence in a suitable packaging material. Optionally, other reagents such as buffers and solutions needed to practice the invention are also included. Instructions for use of the packaged materials are also typically included.

As used herein, the phrase "packaging material" refers to one or more physical structures used to house the contents of the kit. The packaging material is constructed by well known methods, preferably to provide a sterile, contaminant-free environment. The packaging material may include a label which indicates that the replication competent polynucleoitde can be used for identifying a compound that inhibits replication of such a polynucleotide. In addition, the packaging material may contain instructions indicating how the materials within the kit are employed. As used herein, the term "package" refers to a solid matrix or material such as glass, plastic, and the like, capable of holding within fixed limits the replication competent virus and the vertebrate cell.

The present invention is illustrated by the following examples. It is to be understood that the particular examples, materials, amounts, and procedures are to be interpreted broadly in accordance with the scope and spirit of the invention as set forth herein.

EXAMPLES

Materials and Methods

Cells. Huh7 cells were grown in Dulbecco's modified Eagle's medium (Gibco BRL, Carlsbad, Calif.) supplemented with 10% fetal calf serum, penicillin and streptomycin. En5-3 is a clonal cell line derived from Huh7 cells by stable transformation with the plasmid pLTR-SEAP (Yi et al., Virology, 304,197-210 (2002)). These cells were cultured in Dulbecco's modified Eagle's medium (Gibco BRL) supplemented with 10% fetal calf serum, 2 µg/ml blasticidin (Invitrogen), penicillin and streptomycin. Cell lines were passaged once or twice per week. G418 at a concentration of 250 µg/ml was used to select colonies from En5-3 cells transfected with replicon RNAs containing 1a sequences.

Plasmids. The plasmid pBpp-Htat2ANeo was constructed by replacing the BsrGI-XbaI fragment of pBpp-Ntat2ANeo/SI (identical to Ntat2ANeo/SI as described by Yi et al. (Yi et al., Virology, 304,197-210 (2002)) with the analogous segment of pH77c (GenBank AF011751) (Yanagi et al., Proc Natl Acad Sci USA, 94, 8738-43 (1997)) engineered to contain a BsrGI site at the corresponding location by Quick-Change (Stratagene, La Jolla, Calif.) mutagenesis. This fragment swap results in the NS3-NS5B sequence in pBpp-Htat2ANeo being identical to that of pH77c, with the exception of the RNA encoding the N-terminal 75 amino acid residues of NS3 that retains the genotype 1b Con1 sequence. Since Bpp-Ntat2ANeo/SI was originally engineered to contain the genotype 1a 5' nontranslated RNA (5' NTR) sequence (Yi et al., Virology, 304,197-210 (2002)), the resulting pBpp-Htat2ANeo construct possesses both a genotype 1a 5' NTR and 1a 3'NTR sequence. Overlapping PCR was used to fuse an anti-genomic hepatitis delta ribozyme sequence directly to the 3' end of the genotype 1a 3'NTR, in order to generate a self-cleaving 3' sequence with the exact 3' terminal nucleotide of HCV (Perrotta and Been, Nucleic Acids Res, 24,1314-21 (1996)). Derivatives of pBpp-Htat2ANeo containing the adaptive mutations K1691R or S2204I were created by Quick-Change (Stratagene) mutagenesis.

To construct pBpp-H34A-Ntat2ANeo/SI, an EcoRI restriction site was created in pBpp-Ntat2ANeo/SI near the 3' end of the NS4A coding region by Quick-Change mutagenesis. After digestion of the resulting plasmid with BsrGI and EcoRI, the excised HCV segment was replaced with the equivalent sequence from pH77c which had been amplified by PCR using primers pairs containing terminal BsrGI and EcoRI sites, respectively. To construct the plasmid Hpp-H34A-Ntat2ANeo, DNA fragments representing the encephalomyocarditis virus (EMCV) internal ribosome entry site (IRES) sequence and the genotype 1a H77c NS3 protein-coding sequence were fused by overlapping PCR. The resulting fragment was digested with KpnI at a site located within the EMCV IRES and BsrGI at the site created within the modified pH77c NS3 region (see above), then inserted in place of the corresponding fragment in pBpp-H34A-Ntat2ANeo/SI. The adaptive mutations, Q1067R or G1188R, were introduced into pHpp-H34A-Ntat2ANeo/SI in a similar fashion, using cDNA fragments prepared by RT-PCR of template RNAs isolated from independent G418-resistant replicon cell lines selected after transfection of En5-3 cells with Hpp-H34A-Ntat2ANeo RNA. pHtat2ANeo/SI was constructed by replacing the BsrGI-XbaI fragment of pHpp-H34A-Ntat2ANeo/SI with that of pBpp-Htat2ANeo/SI. A similar strategy was used to construct pHtat2ANeo/QR/SI, pHtat2ANeo/KR/SI, and pHtat2ANeo/QR/KR/SI. Quick-Change (Stratagene) mutagenesis was used to introduce the P1496L, F2080V and K2040R mutations into replicon constructs derived from pHtat2ANeo/SI.

Modified pH77c plasmids containing adaptive mutations were created by replacing the BsrGI-XbaI fragment with the corresponding fragment from the pHtat2ANeo plasmid derivative containing the indicated mutation, except for the Q1067R mutation which was introduced by Quick-Change (Stratagene) mutagenesis. Each mutation was confirmed by sequence analysis. For use as controls, replication-incompetent subgenomic and genome-length genotype 1a constructs (Htat2ANeo/QR/VI/KR5A/SI/AAG and H77/QR/VI/KR/KR5A/SI/AAG) were created by replacing residues 2737-2739 of NS5B ('GDD') with 'AAG' using a similar strategy. Each mutation was confirmed by sequence analysis.

RNA transcription and transfection. RNA was synthesized with T7 MEGAScript reagents (Ambion, Austin, Tex.), after linearizing plasmids with XbaI. Following treatment with RNase-free DNase to remove template DNA and precipitation of the RNA with lithium chloride, the RNA was transfected into Huh7 cells or En5-3 cells by electroporation. Briefly, 5 µg RNA was mixed with $2\times10^6$ cells suspended in 500 µl phosphate buffered saline, in a cuvette with a gap width of 0.2 cm (Bio-Rad). Electroporation was with two pulses of current delivered by the Gene Pulser II electroporation device (Bio-Rad), set at 1.5 kV, 25 µF, and maximum resistance. For transient replication assays, no G418 was added to the media. Transfected cells were transferred to two wells of a 6-well tissue culture plate, and culture medium removed completely every 24 hrs and saved at 4° C. for subsequent SEAP assay. The cells were washed twice with PBS prior to re-feeding with fresh culture medium. Since the culture medium was replaced every 24 hours in these transient assays, the SEAP activity measured in these fluids reflected the daily production of SEAP by the cells. Cells were split 5 days after transfection. Samples of media were stored at 4° C. until assayed for SEAP activity at the conclusion of the experiment.

Alkaline phosphatase assay. SEAP activity was measured in 10 µl aliquots of transfected cell supernatant culture fluids using the Phospha-Light Chemiluminescent Reporter Assay (Applied Biosystems/Tropix, Foster City, Calif.) with the manufacturer's suggested protocol reduced in scale. The luminescent signal was read using a TD-20/20 Luminometer (Turner Designs, Inc., Sunnyvale, Calif.).

Sequence analysis of cDNA from replicating HCV RNAs. HCV RNA was extracted from cells, converted to cDNA and amplified by PCR as described previously (Yi et al., J Virol, 77, 57-68 (2003)). First-strand cDNA synthesis was carried out with Superscript II reverse transcriptase (Gibco-BRL); pfu-Turbo DNA polymerase (Stratagene) was used for PCR amplification of the DNA. The amplified DNAs were subjected to direct sequencing using an ABI 9600 automatic DNA sequencer.

In vitro translation. In vitro transcribed RNA, prepared as described above, was used to program in vitro translation reactions in rabbit reticulocyte lysate (Promega, Madison, Wis.). Approximately 1 µg RNA, 2 µl of [$^{35}$S]-methionine (1,000 Ci/mmol at 10 mCi/ml), and 1 µl of an amino acid mixture lacking methionine were included in each 50 µl reaction mixture. Translation was carried out at 30° C. for 90 minutes. Translation products were separated by SDS-PAGE followed by autoradiography or PhosphorImager (Molecular Dynamics) analysis.

Indirect immunofluorescence. Cells were grown on chamber slides until 70-80% confluent, washed 3 times with PBS, and fixed in methanol/acetone (1:1 V/V) for 10 min at room temperature. A 1:20 dilution of a primary, murine monoclonal antibody to core or NS5A (Maine Biotechnology Services, Portland, Me.) was prepared in PBS containing 3% bovine serum albumin, and incubated with the fixed cells for 1 hour at room temperature. Following additional washes with PBS, specific antibody binding was detected with a goat anti-mouse IgG FITC-conjugated secondary antibody (Sigma, St. Louis, Mo.) diluted 1:70. Cells were washed with PBS, counterstained with DAPI, and mounted in Vectashield mounting medium (Vector Laboratories, Burlingame, Calif.) prior to examination by a Zeiss AxioPlan2 Fluorescence microscope.

Northern analysis for HCV RNA. Replicon-bearing cells were seeded into 10 cm dishes at a density of $5 \times 10^5$ cells/dish, and harvested the RNA 4 days later. Total cellular RNA was extracted with Trizol reagent (Gibco-BRL) and quantified by spectrophotometry at 260 nm. Thirty μg of the total RNA extracted from each well was loaded onto a denaturing agarose-formaldehyde gel, subjected to electrophoresis and transferred to positively-charged Hybond-N+ nylon membranes (Amersham-Pharmacia Biotec) using reagents provided with the NorthemMax Kit (Ambion). RNAs were immobilized on the membranes by UV-crosslinking. The membrane was hybridized with a mixture of [$^{32}$P]-labeled antisense riboprobe complementary to the 3'-end of the HCV NS5B sequence (nucleotides 8990-9275) derived from pH77C or pHCV-N, and the hybridized probe was detected by exposure to X-ray film.

Results

Transient replication of 1a replicon containing chimeric NS3-coding sequence. In contrast to genotype 1b HCV, several previous reports suggest that it is difficult to generate subgenomic genotype 1a replicons that are capable of efficient replication in Huh7 cells (Blight et al., Science, 290: 1972-4 (2000), Guo et al., J Virol, 75, 8516-23 (2001), Ikeda et al., J Virol, 76, 2997-3006 (2002), Lanford et al., J Virol, 77,1092-104 (2003)). Similar results were encountered with a dicistronic SEAP reporter replicon constructed from the H77c infectious molecular clone (Yanagi et al., Proc Natl Acad Sci USA, 94, 8738-43 (1997)) that encoded both the HIV tat protein and neomycin phosphotransferase in the upstream cistron. The organization of this latter replicon, Htat2ANeo/SI (FIG. 1), was similar to that of the efficiently replicating, genotype 1b Bpp-Ntat2ANeo/SI replicon (FIG. 1), referred to previously simply as "Ntat2ANeo/SI" (Yi et al., Virology, 304,197-210 (2002)). Most of the HCV polyprotein-coding sequence in Bpp-Ntat2ANeo/SI was derived from the genotype 1b HCV-N strain of HCV (Beard et al., Hepatol., 30, 316-24 (1999)), but the "Bpp" prefix used here and throughout this communication refers to the presence of 225 nucleotides (nts) of sequence that are derived from the Con1 strain of HCV at the extreme 5' end of the polyprotein coding region ("pp" indicates the 5' proximal protease-coding region, FIG. 1). In contrast, all of the HCV sequence in Htat2ANeo/SI (FIG. 1) is derived from the genotype 1a H77c virus, including both the 5'NTR and 3'NTR sequences. Unlike Bpp-Ntat2ANeo/SI RNA, Htat2ANeo/SI RNA did not transduce the selection of G418-resistant colonies, nor induce secretion of SEAP above that observed with a replication-incompetent NS5B-deletion mutant (ΔGDD) when transfected into En5-3 cells (stably transformed Huh7 cells that express SEAP under control of the HIV long terminal repeat promoter) (Yi et al., Virology, 304,197-210 (2002)). in a transient replication assay. This was the case even though the replicon was engineered to contain the genotype 1b adaptive mutation, S2204I, within NS5A (FIG. 1). The absence of apparent replication of Htat2ANeo/SI RNA was striking given the fact that it was derived from a well-documented infectious molecular clone of the H77c strain of HCV (Yanagi et al., Proc Natl Acad Sci USA, 94, 8738-43 (1997)).

Recent reports suggest that the EMCV IRES-driven translation of the second cistron in dicistronic, subgenomic RNAs such as those shown in FIG. 1 may be reduced when the translated RNA sequence is derived from genotype 1a virus, rather than genotype 1b (Gu et al., J Virol, 77, 5352-9 (2003), Guo et al., J Virol, 75, 8516-23 (2001), Lanford et al., J Virol, 77,1092-104 (2003)). However, even when translation of the second cistron is rendered more efficient by replacing the 5' 225 nts of the genotype 1a NS3 sequence with related sequence from the Con1 genotype 1b virus, replication typically has not been observed when the remainder of the replicon sequence is derived from a genotype 1a virus (Guo et al., J Virol, 75, 8516-23 (2001), Lanford et al., J Virol, 77,1092-104 (2003)). However, Gu et al. (Gu et al., J Virol, 77, 5352-9 (2003)) recently described the successful selection of a replication competent, chimeric replicon in which the 5' 225 nts of the NS3 coding sequence was derived from genotype 1b virus, and the remainder of the second cistron from genotype 1a HCV (construction of chimeric replicons being simplified by a unique BsrG1 site within the genotype 1b Con1 virus sequence, 225 nts downstream from the 5' end of the NS3 region). This replicon also contained 5' NTR sequence derived from genotype 1b virus, and had a single base change within the genotype 1a 3' NTR sequence. The results of Gu et al. (Gu et al., J Virol, 77, 5352-9 (2003)) suggest that the inclusion of the Con1 sequence at the 5' end of the NS3 region may in some way facilitate replication of the 1a RNA. This hypothesis is strengthened by observations made with genotype 1b replicons derived from HCV-N. Those described previously, including Bpp-Ntat2ANeo/SI RNA, were constructed by ligation of HCV-N sequence to a Con1 replicon at the BsrG1 site (Guo et al., J Virol, 75, 8516-23 (2001), Ikeda et al., J Virol, 76, 2997-3006 (2002), Yi et al., Virology, 304,197-210 (2002)), and thus they contain 5' proximal NS3 sequence (proximal protease sequence or 'pp', FIG. 1) derived from the Con1 virus. Although this chimeric Con1/HCV-N RNA replicates significantly more efficiently than the originally-described Con1 replicons, the replacement of the 5' proximal NS3 sequence in Bpp-Ntat2ANeo/SI with sequence from HCV-N (resulting in Npp-Ntat2ANeo/SI) virtually ablated its replication phenotype in transient transfection assays, although it remained possible to select G418-resistant colonies at a low frequency following transfection.

To formally assess the ability of the 5' proximal genotype 1b NS3 sequence to enhance genotype 1a RNA replication, the 5' 225 nts of NS3 coding region in Htat2ANeo/SI were replaced with the Con1 sequence, generating Bpp-Htat2ANeo/SI (FIG. 1). The construct was also modified by replacing the XbaI restriction site at the 3' end of the HCV sequence with the hepatitis delta virus ribozyme sequence (Perrotta and Been, Nucleic Acids Res, 24,1314-21 (1996)). We have shown previously that the presence of the 4 extraneous nts at the 3' end of the replicon RNA that results from run-off transcription of XbaI-digested plasmid DNA reduces the replication competence of genotype 1b RNAs by 2-3 fold (Yi and Lemon, Rna, 9, 331-45 (2003)). The inclusion of the ribozyme resulted in self-cleaving RNA transcripts capable of generating the exact 3' terminal HCV RNA sequence. Nonetheless, this modified Bpp-Htat2ANeo/SI RNA still remained incapable of inducing the expression of SEAP in transfected EN5-3 cells beyond that observed following transfection of the ΔGDD RNA. Transfection resulted only in an initial burst in SEAP expression due to translation of the input replicon RNA, without the sustained SEAP expression that is indicative of RNA replication (FIG. 2). However, the Bpp-Htat2ANeo/SI RNA was capable of transducing the selection of G418-resistant cell colonies supporting replication of the RNA over a period of 3-4 weeks following transfection of the cells.

The sequence of replicon RNAs extracted from two independent G418-resistant cell clones selected following the transfection of En5-3 cells with Bpp-Htat2ANeo RNA was analyzed. The presence of a single Lys to Arg mutation located within the NS4A region, at residue 1691 (K1691R) of the polyprotein in both cell clones was determined. This residue is located just beyond the 3' limits of the NS4A cofactor peptide sequence which participates in forming a noncovalent complex with NS3 and enhances its protease activity (Wright-Minogue et al., J Hepatol, 32, 497-504 (2000), Yao et al., Structure Fold Des, 7, 1353-63 (1999)). To determine whether the K1691R mutation facilitated replication of the chimeric genotype 1b/1a RNA in En5-3 cells, this mutation was introduced into the parental Bpp-Htat2ANeo/SI construct, thereby creating Bpp-Htat2ANeo/KR/SI (see Table 2 for a list of all adaptive mutations identified in these studies, as well as the symbols used to indicate their presence in constructs). As shown in FIG. 2, this single mutation significantly enhanced the replication capacity of the RNA, allowing replication to be detected by a sustained increase in SEAP expression following transient transfection of EN5-3 cells in the absence of G418 (FIG. 2). Since the level of SEAP production has been shown to correlate closely with intracellular replicon RNA abundance in this reporter system (Yi et al., Virology, 304,197-210 (2002), Yi et al., J Virol, 77, 57-68 (2003)) we conclude that K1691R is an adaptive mutation. Interestingly, this mutation has been shown previously to confer an enhanced replication phenotype on Con1 replicons (Lohmann et al., J Virol, 77, 3007-19 (2003)), whereas the sequence of HCV-N is naturally Arg at this position (Beard et al., Hepatol., 30, 316-24 (1999)). Our results stand in contrast to those reported by Gu et al. (Gu et al., J Virol, 77, 5352-9 (2003)), who identified several mutations within the NS3, NS5A, and NS5B sequences of chimeric genotype 1b-1a RNAs. None of these mutations appeared to enhance the ability of the chimeric RNA to replicate or transduce colony selection.

The 5' 225 nts of the genotype 1a NS3 sequence down modulate replicon amplification. The results described above, as well as those of Gu et al. (Gu et al., J Virol, 77, 5352-9 (2003)) suggest that first 225 nts of the genotype 1a NS3 sequence have a negative impact on the replication of subgenomic HCV replicons. This could occur by down modulation of EMCV IRES-directed translation of the nonstructural proteins (Guo et al., J Virol, 75, 8516-23 (2001)), or by directly influencing replication itself, possibly by influencing an NS3-related function. To address this issue, the identification of additional adaptive mutations capable of compensating for the presence of the 5' proximal genotype 1a protease sequence was sought. Thus additional chimeric replicons containing the entire genotype 1a NS3/4A sequence within the background of Bpp-Ntat2ANeo/SI (Hpp-H34A-Ntat2ANeo/SI, FIG. 3A) were constructed. Also constructed was a variant of this construct in which the first 225 nts of the NS3/4A sequence was replaced with Con1 sequence (Bpp-H34A-Ntat2ANeo/SI, FIG. 3A). In both chimeric RNAs, the sequence extending from NS4B to the 3'NTR was derived entirely from the genotype 1b HCV-N strain. While the replicon containing the entire genotype 1a NS3/4A sequence (Hpp-H34A-NtatNeo/SI) did not show evidence of replication in a transient transfection assay, the variant containing the first 225 nts of the Con1 sequence (Bpp-H34A-NtatNeo/SI) replicated as well as the reference Bpp-Ntat2ANeo/SI replicon (FIG. 3B). This result confirms that the 5' 225 nucleotides of the genotype 1a NS3 sequence have a negative effect on RNA replication in En5-3 cells, and also indicates that the downstream genotype 1a NS3/4A sequence functions well in this context.

Interestingly, despite the lack of detectable RNA replication in the transient assay, selection of stable G418-resistant cell clones following transfection of Hpp-H34A-Ntat2ANeo/SI RNA was possible. Sequencing of replicon RNAs derived from two independent cell clones revealed only a single potentially adaptive mutation in each: Q1067R and G1188R, both of which are located within RNA encoding the NS3 protease (FIG. 3A). The Q1067R mutation is of particularly interest, since it is within the 5' 225 nucleotides of the NS3 region. When introduced into Hpp-H34A-Ntat2ANeo/SI, both the Q1067R and (to a lesser extent) the G1188R mutations enhanced replication of the RNA to a level that was detectable in the transient assay (FIG. 3B), indicating that both are adaptive mutations and capable of compensating, in part, for the presence of the genotype 1a protease sequence. However, neither of these mutations, when introduced into a replicon containing only genotype 1a sequence (Htat2ANeo/SI), was able to enhance replication to the point where it was evident in the transient assay (Htat2ANeo/QR/SI, FIG. 4).

Transient replication of a genotype 1a replicon in normal Huh7 cells. To determine whether the K1691R and Q1067R mutations might work cooperatively to confer a transient replication phenotype on the genotype 1a replicon RNA, both were introduced into Htat2ANeo and assessed the ability of the modified RNA to replicate in transfected En5-3 cells. Surprisingly, the combination of the K1691R and Q1067R mutations (in addition to the S2204I mutation in NS5A) conferred a relatively robust replication phenotype on the genotype 1a RNA, such that replication was easily detectable in the transient transfection assay using the SEAP reporter system (Htat2ANeo/QR/KR/SI, FIG. 4B). Using an approach similar to that taken in the preceding experiments, an additional adaptive mutation (F2080V) within the NS5A-coding region (F2080V) was subsequently identified, when cells transfected with Htat2ANeo/QR/KR/SI RNA were subjected to G418 selection pressure. This mutation resulted in slightly greater replication efficiency when introduced into the genotype 1a replicon containing K1691R and Q1067R in addition to S22041(Htat2ANeo/QR/KR/FV/SI, FIG. 4B). However, F2080V had relatively little effect when added to replicons containing only K1691R or Q1067R (in addition to S2204I) (FIG. 4B). Minimally increased secretion of SEAP above the ΔGDD background was observed during the first 5 days after transfection with Htat2ANeo/KR/FV/SI, but this was no longer apparent after 6 days. The replication phenotype of Htat2ANeo/QR/FV/SI was indistinguishable from that of the replication incompetent ΔGDD mutant in this assay (FIG. 4B). These results are summarized in FIG. 4C.

To facilitate a comparison of these results with those reported previously by Blight et al. (Blight et al., J Virol, 77, 3181-90 (2003)), the adaptive P1496L mutation identified by this group within the helicase domain of NS3 following transfection of a genotype 1a replicon was introduced into the highly permissive Huh7 subline, Huh-7.5. Consistent with the previous report, a 1a replicon bearing this mutation P1496L demonstrated only minimal evidence of replication in the transient assay (which utilizes En5-3 cells that are comparable to normal Huh7 cells in terms of their permissiveness for HCV RNA replication) (Htat2ANeo/PL/SI, FIG. 4B). The addition of the NS5A mutation, F2080V, failed to noticeably enhance the replication capacity of this RNA (Htat2ANeo/PL/FV/SI, FIG. 4B). SEAP expression induced by genotype 1a replicons containing both Q1067R and K1691R was approximately 10-fold that induced by replicons containing P1496L. Since SEAP production from En5-3 cells correlates closely with the intracellular abundance of replicon RNA (Yi et al., Virology, 304,197-210 (2002)), these results suggest that the protease domain mutations make a greater contribution to replication competence of the genotype 1a replicon.

Adaptive mutations within NS3 do not affect EMCV IRES-driven translation of the second cistron. As mentioned above, previous reports indicate that the EMCV-driven translation of the second cistron is reduced in genotype 1a replicons in comparison to replicons containing the genotype 1b Con1 sequence (Gu et al., J Virol, 77, 5352-9 (2003), Guo et al., J Virol, 75, 8516-23 (2001), Lanford et al., J Virol, 77,1092-104 (2003)). Although the mechanism is uncertain, the effect appears to be due to the genotype 1a sequence encoding the amino terminus of NS3. Since the adaptive Q1067R mutation is located within this region, we asked whether it or other mutations that enhance 1a replicon amplification do so by improving EMCV IRES-driven translation of the HCV nonstructural proteins. To test this hypothesis, in vitro translation reactions were programmed with genotype 1b and 1a replicon RNAs containing various adaptive mutations, and compared the production of proteins encoded by the second cistron with neomycin phosphotransferase produced from the first cistron. As shown in FIG. 5, the synthesis of NS3 was modestly reduced with replicons containing genotype 1a H77c sequence in the 5' proximal protease region (compare NS3 abundance in lanes 4-8 with that in other lanes). However, it was not increased by any of the adaptive mutations, including Q1067R. This result indicates that the difficulty of establishing replication competent Ia replicons is more likely due to the intrinsic property of the 1a sequence, than to an incompatibility of the HCV and EMCV sequences in this region leading to reduced activity of the EMCV IRES. Nonetheless, the reduced level of translation of the genotype 1a nonstructural proteins that is evident in FIG. 5 may contribute to the poor replication phenotype of these RNAs.

Figure 6A:
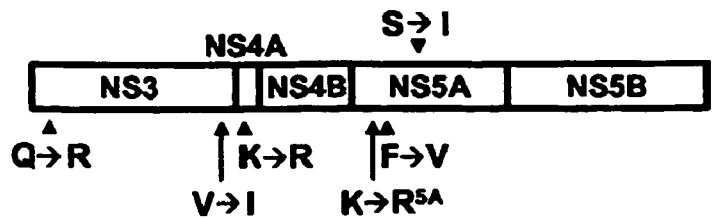
FIG. 6. Impact of additional adaptive mutations on replication competence of the subgenomic genotype 1a replicon, Htat2ANeo/QR/KR/SI (see FIG. 4). (A) Location of various adaptive mutations within the second ORF (derived entirely from the genotype 1a H77sequence): Q1067R, V1655I (NS3); K1691R (NS4A); and K2040R ($KR^{54}$), F2080V and S2204I (NS5A). (B) Transient HCV RNA replication assay. SEAP activity in culture supernatants collected at 12-24 hr intervals following electroporation of En5-3 cells with the 1a replicon Htat2ANeo carrying the indicated combinations of the adaptive mutations shown in panel A. Cells were also transfected with genotype 1b Bpp-Ntat2ANeo/SI replicon RNA as a reference. QR, Q1067R adaptive mutation; VI, V1655I adaptive mutation; KR, K1691R adaptive mutation; $KR^{54}$, K2040 adaptive mutation; FV, F2080V adaptive mutation; and SI, S2204I adaptive mutation.
Figure 6B:
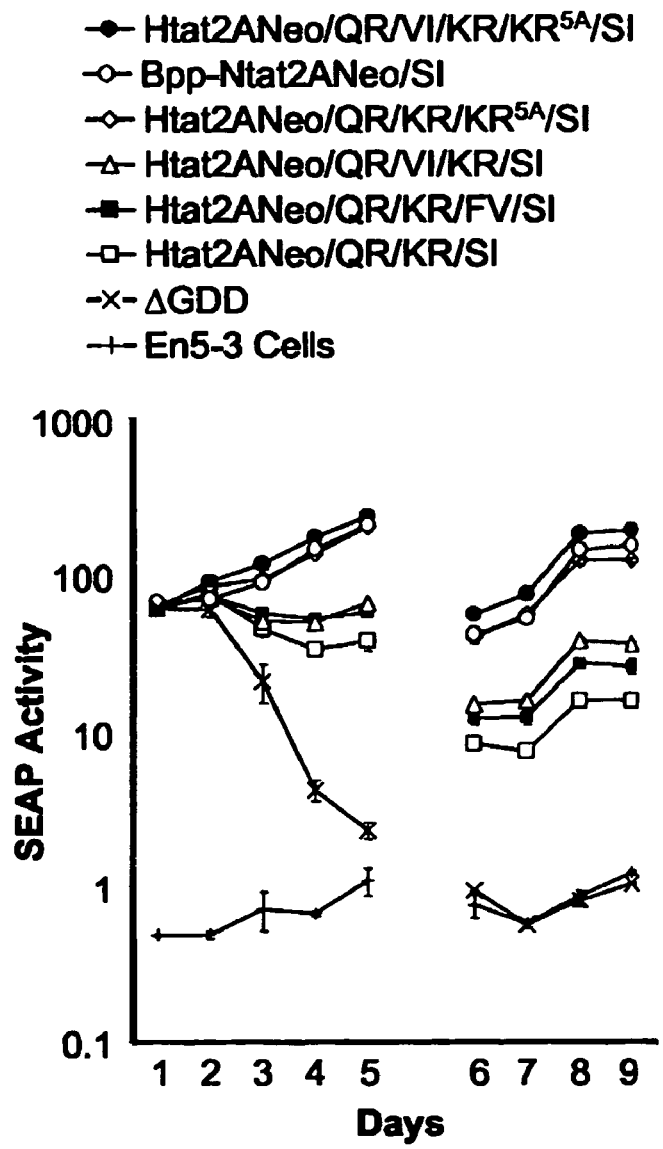

An additional adaptive NS5A mutation further augments replication competence. Although the F2080V mutation in NS5A provided only a slight additional replication advantage to subgenomic genotype 1a RNAs containing the Q1067R, K1691R and S2204I mutations (FIG. 4), additional mutations were subsequently identified concurrently near the C-terminus of NS3 (V1655I) and within NS5A (K2040R) in RNAs replicating within a G418-resistant cell line selected following transfection with the subgenomic Htat2ANeo/QR/KR/SI replicon. As shown in FIG. 6, both of these mutations enhanced the replication capacity of genotype 1a RNA. Addition of the V1655I mutation resulted in a modest enhancement of Htat2ANeo/QR/KR/SI replication, leading to a replication phenotype slightly better that observed with the addition of the F2080V mutation. In contrast, the addition of the K2040R mutation in NS5A resulted in a dramatic increase in replication competence, rendering the replication phenotype of the genotype 1a RNA equivalent to that of the standard genotype 1b HCV-N replicon used in these studies, Bpp-Ntat2ANeo/SI (FIG. 6B). A genotype 1 a replicon containing both of these adaptive mutations in addition to those identified earlier replicated with slightly greater efficiency than this reference genotype 1b RNA in the transient assay (FIG. 6B, Htat2ANeo/QR/VI/KR/KR5A/SI). These results were confirmed in independent experiments.

Robust replication of genome-length genotype 1a RNA with adaptive mutations. Encouraged by the above results, we assessed the in vitro replication competence of genome length, genotype 1a H77c RNA engineered to contain the adaptive mutations described above. As with the dicistronic, subgenomic RNAs, we placed the hepatitis delta ribozyme sequence at the 3' end of the cloned infectious cDNA sequence in pH77c in order to generate RNA transcripts containing an exact HCV 3' terminus. As these genomic RNAs encoded no selectable marker or reporter protein product, their replication was assessed in transfected Huh7 and En5-3 cells by northern blot analysis in comparison with related subgenomic RNAs. Subgenomic and genome-length replication-incompetent H77 mutant RNAs, in which the GDD motif had been replaced with AAG, served as negative controls for this experiment. For En5-3 cells transfected with the subgenomic RNAS, we also determined levels of SEAP expression.

Figure 7:
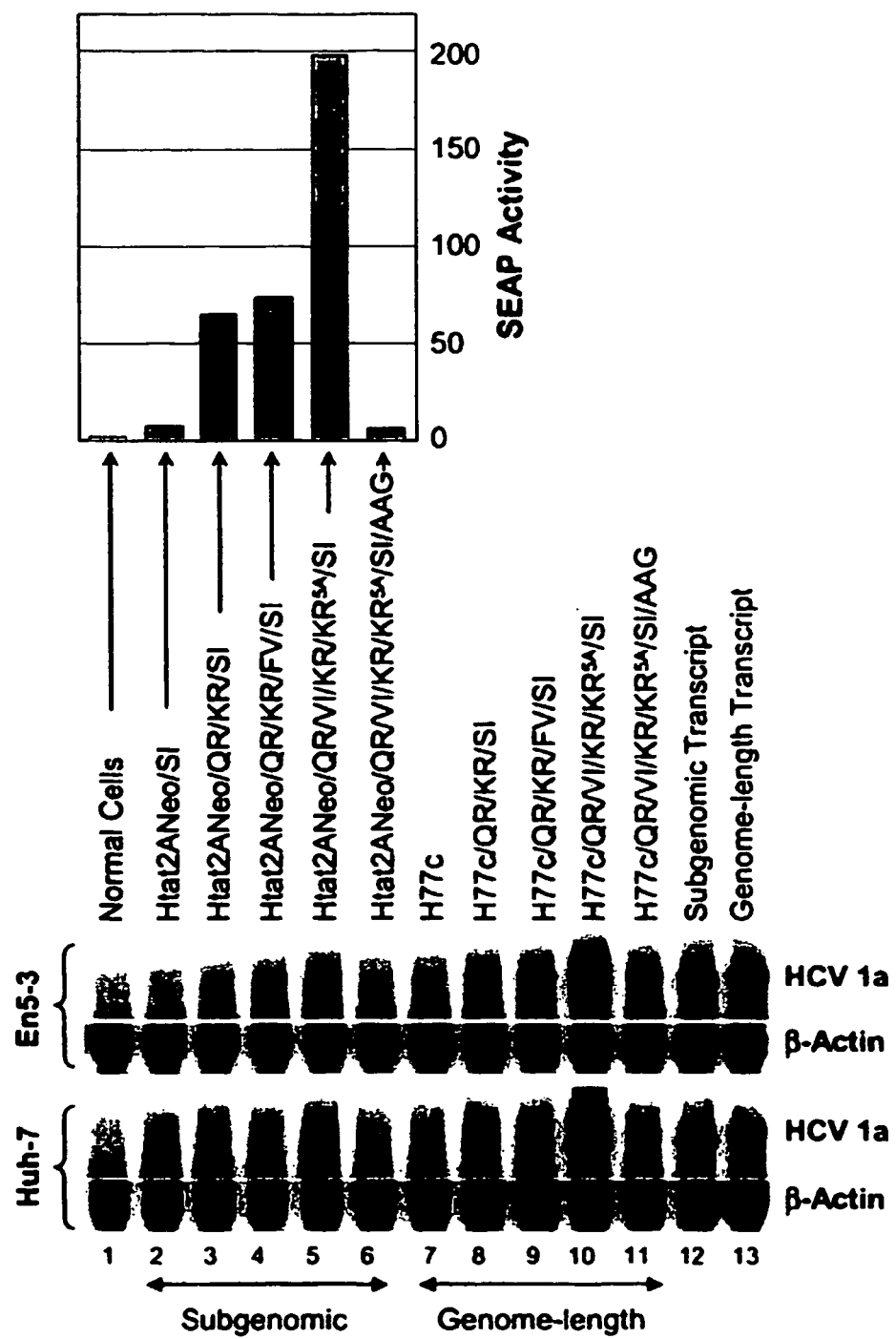
FIG. 7. Northern analysis of HCV RNA abundance 4 days following transfection of normal Huh7 or En5-3 cells with the indicated dicistronic subgenomic and monocistronic genome length HCV RNAs: (lane 1), normal cells; (lane 2), the subgenomic replicon, Htat2ANeo/SI; (lanes 2-5), Htat2ANeo/SI replicon RNAs carrying the indicated combinations of mutations; (lane 6), nonreplicating Htat2ANeo/QR/VI/KR// KR5A/SI/AAG; (lanes 7) genome-length H77c RNA; (lanes 8-10), genome-length H77c RNA containing the indicated combinations of mutations; (lane 11), genome-length H77 RNA containing the lethal NS5B mutation; (lanes 12 and 13) subcontrol genomic and genome-length synthetic RNA transcripts. Blots were probed with a genotype 1a probe derived from the NS5B coding sequence for detection of HCV-specific sequence (top panels); blots were also probed for b-actin message to assess RNA loading (lower panels). At the top of the figure is shown the En5-3 cell culture supernatant fluid SEAP activity induced by replicating subgenomic RNAs at the time of cell harvest. SI, S2204 adaptive mutation; QR, Q1067R adaptive mutation; KR, K1691R adaptive mutation; and FV, F2080V adaptive mutation.

As expected, the unmodified H77c RNA showed no evidence of replication, even though it has been shown previously to be infectious in chimpanzees when inoculated into liver (FIG. 7, compare lane 7 with the replication defective 1a genomic RNA in lane 11). The introduction of the Q1067R (NS3) mutation, alone or in combination with S2204I (NS5A), was insufficient to confer a detectable level of replication in Huh7 cells. However, when all three mutations were introduced (Q1067R, K1691R and S2204I), the H77c RNA acquired a relatively efficient replication phenotype with readily detectable amplification of the RNA in northern blots of cell lysates prepared 4 days after transfection of either Huh7 or En5-3 cells (FIG. 7, lane 8). Replication of the genome-length RNA was slightly increased by the further addition of the F2080V (NS5A) mutation (FIG. 7, lane 9). However, consistent with the data presented in FIG. 6, the inclusion of both the V1655I mutation in NS3 and the K2040R mutation conferred a substantially more robust replication phenotype on genome-length H77c, when present in combination with other adaptive mutations in NS3, NS4A and NS5A (H77c/QR/VI/KR/KR5A/SI, FIG. 7, compares lane10 and 11). This experiment thus confirmed the adaptive effects of these mutations. Northern blotting indicated that the replication capacity of genome-length genotype 1a RNAs containing adaptive mutations was significantly greater than the comparable subgenomic, dicistronic genotype 1a replicons, for which the RNA signal 4 days after transfection was low and near the limits of detection in northern blots (FIG. 7, compare lanes 3 to 6 with lanes 8 to 11). These findings are consistent with those reported previously by Blight et al. (*J. Virol.*, 77, 3181-3190 (2003)), and indicate that the inclusion of heterologous sequences in the dicistronic replicons impairs RNA replication competence. Subgenomic replicon RNA was detected unambiguously only in cells transfected with Htat2ANeo/QR/VI/KR/KR5A/SI, the RNA that generated the highest level of SEAP expression (FIG. 7, compare lane 5 and 6).

As a further measure of the replication competence of these modified genome-length H77c RNAs, we also examined transfected En5-3 cells for the presence of core or NS5A proteins using an indirect immunofluorescence method. Introduction of both the K1691R (NS4A) and S2204I mutations resulted in detectable antigen expression 4 days after transfection, albeit only in a very low percentage of cells (less than 0.01%). However, strong expression of both the core and NS5A proteins was observed in approximately 30% of En5-3 cells 4 days after transfection of RNA containing all four adaptive mutations. Increased replication efficiency of genotype 1a RNAs correlated with a greater proportion of cells supporting the replication of HCV RNA, evidenced by the presence of viral antigen.

Discussion

Subgenomic, dicistronic, selectable HCV RNA replicons derived from genotype 1b viruses replicate efficiently in cultured cells (Blight et al, Science, 290:1972-1974 (2000), Guo et al., J. Virol., 75:8516-8523 (2001), Ikeda et al., J. Virol., 76:2997-3006 (2002), Krieger et al., J. Virol., 75:4614-4624 (2001), Lohmann et al., J. Virol., 75:1437-1449 (2001), and Lohmann et al., Science 285:110-113 (1999)). These novel RNAs have facilitated the study of HCV RNA replication and substantially accelerated antiviral drug discovery efforts. The Huh7 cell line, derived from a human hepatoma, appears to be uniquely permissive and supportive of the replication of these HCV RNAs, although recent studies suggest that other types of cells may also be permissive for HCV RNA replication (Zhu et al., J. Virol., 77:9204-9210 (2003)). However, despite the success of genotype 1b replicons, it has been difficult to generate RNAs that replicate efficiently in any cell type from other genotypes of HCV, including genotype 1a, (Blight et al, Science, 290:1972-1974 (2000), Guo et al., J. Virol., 75:8516-8523 (2001), Ikeda et al., J. Virol., 76:2997-3006 (2002), and Lanford et al., J. Virol., 77:1092-104 (2003)). This surprising observation indicates that significant biological differences exist between genotype 1a and 1b viruses, despite the fact that the nucleotide sequences of genotype 1a viruses are relatively closely related to those of genotype 1b (~90-93% identity). This biological difference raises the likelihood that antiviral agents that are found to be active against the genotype 1b virus may have significantly lesser activity against genotype 1a viruses. Considering these observations and the relatively high genetic variability that exists between different HCV genotypes, the development of cell culture systems supporting replication of viral RNAs from other genotypes will be important for validating in vitro efficacy of candidate antiviral agents across a range of genetically distinct HCV genotypes, as well as developing a better overall understanding of these viruses.

Genotype 1a viruses are the most prevalent types of HCV in the United States, and like genotype 1b virus they are relatively refractory to treatment with interferon (Fried et al., N Engl J Med, 347, 975-82 (2002), McHutchison and Fried, Clin Liver Dis, 7, 149-61 (2003)). Thus far, a detectable level of genotype 1a RNA replication has been reported only in specially isolated, highly permissive Huh7 human hepatoma cell sublines (e.g., Huh-7.5 cells) generated by eliminating the replication of genotype 1b RNA replicons from established replicon cell lines using interferon-α002B0 in vitro (Blight et al., J Virol, 77, 3181-90 (2003), Grobler et al., J Biol Chem, 278,16741-6 (2003)). These previously described genotype 1a RNAs possess cell culture-adaptive mutations that enhance their replication in these special cells, including those selected during the isolation of antibiotic-resistant cell lines containing these 1a replicons (Blight et al., J Virol, 77, 3181-90 (2003), Grobler et al., J Biol Chem, 278,16741-6 (2003)). However, the published reports suggest that these previously described genotype 1a RNAs do not replicate to a detectable level in standard Huh7 cells, and that their capacity for replication in cultured cells is thus limited. In contrast, genotype 1a HCV RNAs are reported here that replicate in a highly efficient manner in normal Huh7 cells.

Figure 8A:
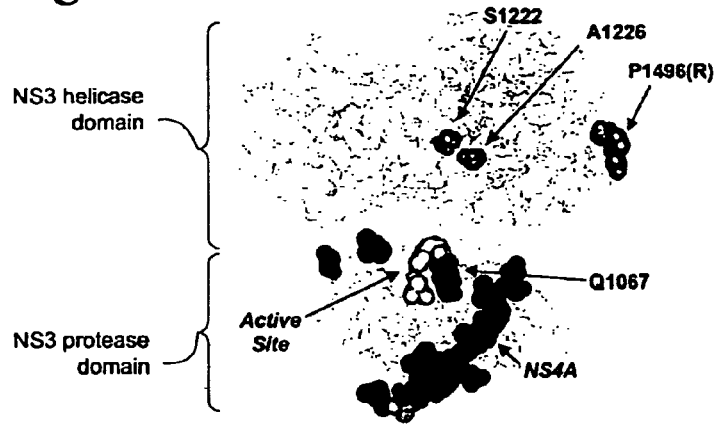
FIG. 8. Structure of the NS3/4A serine protease/helicase enzyme complex derived from the genotype 1b BK strain of HCV (PDP ICU1), with the locations of adaptive mutations highlighted. (A) Wire diagram of structure showing the NS3 helicase domain (H) and the protease domain (P). The NS4A cofactor polypeptide (NS4A) is shown in space-filling view, with the NS3 protease active site residues (Active Site) shown in space-filling view. Adaptive mutations identified in this study (Q1067, G1188, V1655, and K1691) cluster near the protease active site or at sites involved in substrate recognition, including the mutations in the NS3 protease domain at Gln-1067, Gly-1188 and near the carboxyl terminus of NS3 in the helicase domain at Val-1655. The NS4A adaptive mutation at Lys-1691 is just beyond the surface of the protease, at the site of exit of the NS4A strand. Adaptive mutations within the NS3 helicase domain that were identified in other studies, S1222, A1226, and P1496 are shown in space-filling view, and are not close to the protease active site. (B) Space-filling view of the structure shown in panel A, in which the adaptive mutations and active site have similar shading. The NS3/4A adaptive mutations identified in this study (Q1067R, G1188R, V1655I, and K1691R) all occur at solvent accessible residues on this side of the molecule. (C) Flip-view of the structure shown in panel B, rotated approximately 180 degrees. The helicase adaptive mutations identified in previous studies are located on the surface of the helicase, distant from the protease active site. Note that in the sequence of the genotype 1b BK strain of HCV, Pro-1496 is Arg (referred to as P1496(R) in the figure, and Lys-1691 is Ser (referred to as K1691(S) in the figure).
Figure 8B:
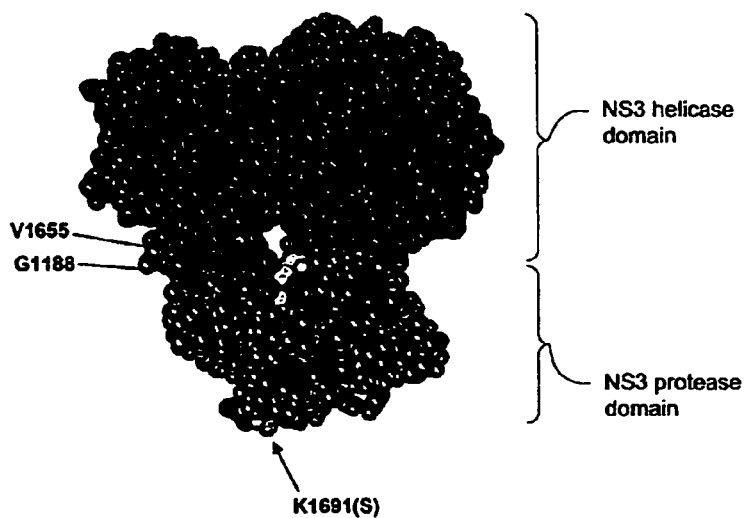
Figure 8C:
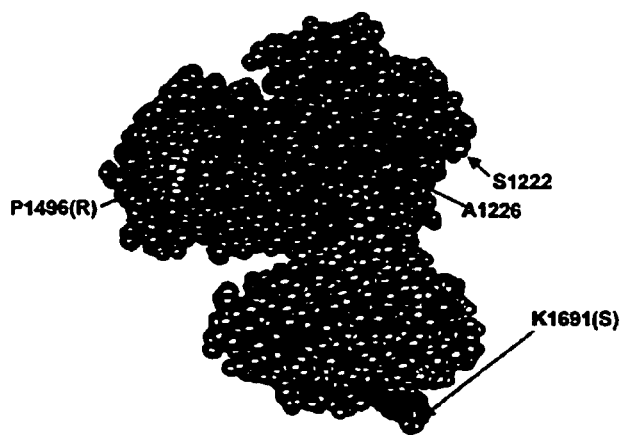

Our results suggest that the highly efficient replication of genotype 1a RNAs requires at least three adaptive mutations located within the NS3, NS4A and NS5A proteins. It is evident that these mutations are mutually reinforcing in their ability to enhance the replication of the genotype 1a RNAs, even though they were identified individually under different circumstances. It was found that the introduction of the S2204I mutation in NS5A, which is known to promote the replication of genotype 1b virus RNAs in Huh7 cells (Blight et al., Science, 290:1972-4 (2000)), was not sufficient for subgenomic replicons composed entirely of the genotype 1a sequence to initiate replication in Huh7 cells. However, it made possible the selection of G418-resistant cell colonies following transfection of a chimeric replicon RNA, in which sequence from the infectious molecular clone of the genotype 1a H77c virus encoded all of the nonstructural proteins other than the N-terminal 75 amino acid residues of NS3 which were derived from the genotype 1b Con1 sequence (FIG. 1, Bpp-Htat2ANeo/SI). The HCV RNAs replicating in these cells contained a single mutation within the NS4A-coding region (K1691R) that enhanced the replication capacity of the original chimeric replicon RNA (FIG. 2). These results suggest that a restriction to the replication of genotype 1a virus in Huh7 cells may reside within the serine protease domain of NS3, since substitution of the N-terminal domain of the genotype 1a protease with that from the Con1 genotype 1b virus allowed the initiation of replication and the selection of G418-resistant cells. A similar conclusion can be drawn from the results reported by Gu et. al. (Gu et al., J Virol, 77, 5352-9 (2003)). Thus, it is interesting that the adaptive mutation K1691R resides within NS4A very close to the surface of the NS3/4A protease complex that it helps to form (FIG. 8).

Figure 3A:
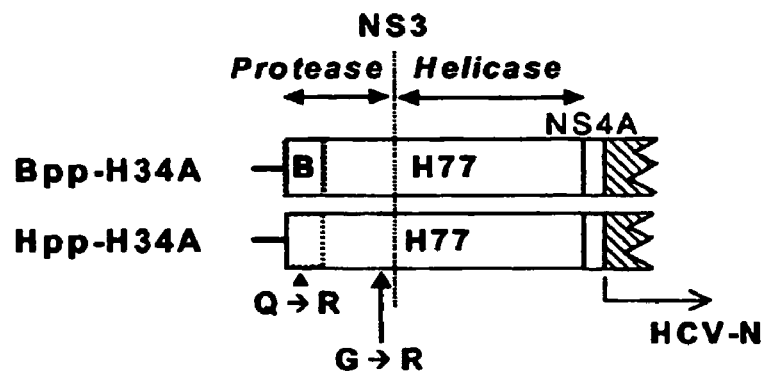
FIG. 3. (A) Schematic depicting the organization of the 5' end of the second ORF in subgenomic chimeric replicons containing most (Bpp-H34A-Ntat2ANeo/SI) or all (Hpp-H34A-Ntat2ANeo/SI) of the H77 genotype 1a NS34A-coding sequence in the background of the genotype 1b Bpp-Ntat2ANeo/SI. Genotype 1a sequence (H77) is shown as an open box, genotype 1b sequence (Con1 or HCV-N) as a shaded box. 'Bpp' indicates the presence of genotype 1b sequence from the Con1 strain of HCV in the 5' proximal protease coding sequence, whereas 'Hpp' indicates that this sequence is derived from the genotype 1a H77 sequence. Approximate locations are shown for the adaptive mutations Q1067R (Q→R) and G1188R (G→R), identified in G418-resistant cell clones selected following transfection of Hpp-H34A-Ntat2ANeo/SI. (B) SEAP activity present in supernatant culture fluids collected at 24 hr intervals following transfection of En5-3 cells with various chimeric 1a-1b replicons including Bpp-H34A-Ntat2ANeo/SI, Hpp-H34A-Ntat2ANeo/SI, Hpp-H34A-Ntat2ANeo/QR/SI, and Hpp-H34A-Ntat2ANeo/GR/SI. Control cells were transfected with Bpp-Ntat2ANeo/SI and the replication defective ΔGDD mutant. See legend to FIG. 2 for further details. SI, S2204 adaptive mutation; QR, Q1067R adaptive mutation; and GR, G1188R adaptive mutation.
Figure 3B:
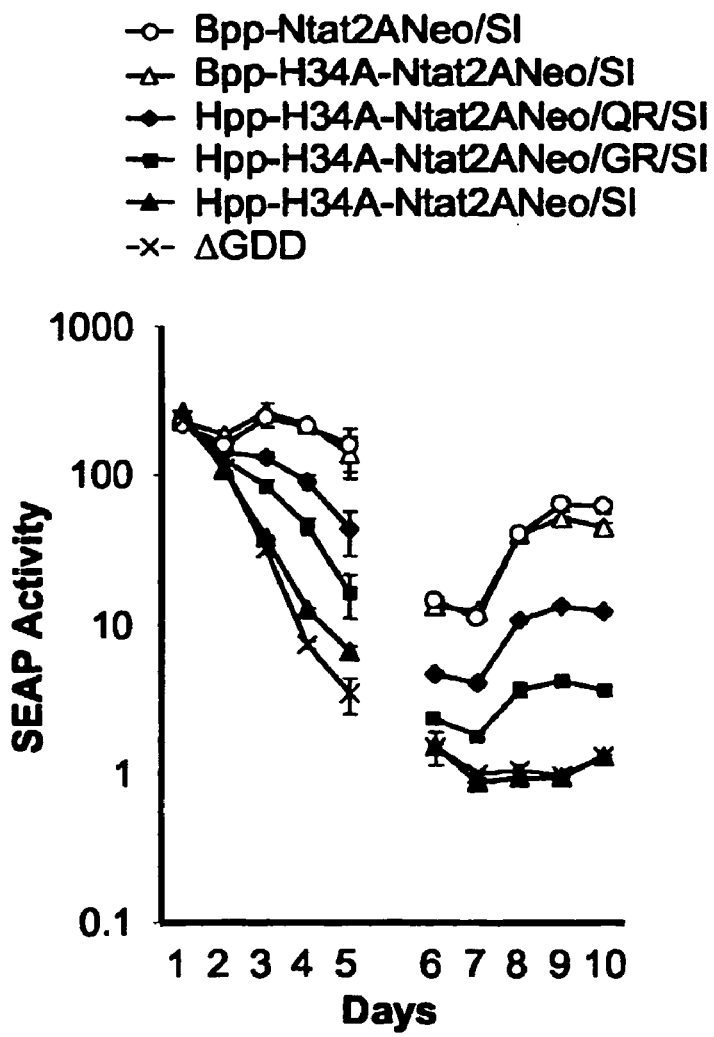

In an effort to better understand this restriction, a second chimeric replicon containing the complete genotype 1a NS34A sequence within the background of a genotype 1b replicon was constructed. This RNA (Hpp-H34A-Ntat2ANeo/SI) did not undergo detectable replication in the transient transfection system utilized in these studies (FIG. 3). However, it was capable of transducing the selection of G418-resistant cell colonies following transfection and antibiotic selection. Analysis of the sequence of the HCV RNAs replicating within these cells identified a second, cell culture-adaptive mutation within the N-terminal region of the NS3 protease (Q1067R), providing further evidence that a primary restriction to replication of genotype 1a virus resides within this domain. Yet additional evidence for this comes from the replication phenotype of the Bpp-H34A-Ntat2ANeo/SI replicon, which also contains all of the genotype 1a NS3/4A sequence except for the N-terminal 75 amino acid resides, and which demonstrated a robust replication phenotype in the transient transfection assay. Thus there appears to be no restriction to replication deriving from inclusion of the genotype 1a NS3 helicase domain, nor for that matter any part of the protease domain except for its N-terminus.

Further work demonstrated that the K1691R and Q1067R mutations worked cooperatively: neither by itself was capable of conferring the capacity for efficient replication on a replicon composed entirely of genotype 1a sequence, but a combination of the two (in addition to the genotype 1b S2204I adaptive mutation) resulted in RNA replication that could be readily detected in the transient transfection assay (FIG. 4). That these mutations should act cooperatively in their effects on replication, as indicated by the data shown in FIG. 4, is consistent with their location in the polyprotein, since the NS4A protease cofactor domain interacts primarily with residues within the N-terminal domain of the NS3 protease (Wright-Minogue et al., J Hepatol, 32, 497-504 (2000), Yao et al., Structure Fold Des, 7, 1353-63 (1999)).

Additional adaptive mutations were identified and verified through an iterative series of experiments involving RNA transfection, isolation of G418-resistant cells, and analysis of the sequence of efficiently replicating genotype 1a RNAs.

Also demonstrated was that the S2204I mutation did indeed facilitate the replication of the genotype 1a RNA, as its removal from the efficiently replicating subgenomic RNAs substantially reduced their replication competence in the transient transfection assay. The genotype 1a adaptive mutations identified herein are summarized in Table 2. They can be grouped functionally into two groups: K2040R, F2080V, and S2204I, which are all located within NS5A (a common site of genotype 1b adaptive mutations), and Q1067R, G1188R, V1655I, and K1691R, which are all located in or otherwise associated with the protease domain of NS3. While to some extent solvent exposed, both G1188R and Q1067R are close to the active site of the protease (FIG. 8), and would both add a significant charge difference to the active face of the protein. V1655I is particularly interesting. It is located near the extreme C-terminus of the NS3 protein, downstream of the helicase domain, and close to the protease active site in the crystal structure of the NS3/4A complex (Yao et al., Structure Fold Des, 7, 1353-63 (1999)). In the P3 position of the NS3/4A cleavage site, V1655 is certain to play a role in substrate recognition during the cis-active cleavage of the polyprotein at the NS3/4A junction and it remains within the substrate-binding pocket in the crystal structure. The potential impact of the K1691R mutation, within NS4A, on the conformation of the protease active site is much less certain, but it is in close proximity to the NS4A cofactor domain, as mentioned above, and intercalation of this domain into the NS3 protease is well known to modulate the activity of the protease.

Significantly, all of these NS3 and NS4A mutations are located at some distance from other genotype 1a adaptive mutations in NS3 that have been described in the literature (see FIG. 8). These mutations, located at S1222, A1226 and P1496, are all within the helicase domain of NS3 (Blight et al., J Virol, 77, 3181-90 (2003), Grobler et al., J Biol Chem, 278,16741-6 (2003)). While on the surface of the protein, they are located on the side opposite the solvent exposed surfaces containing the G1188, V1655, and Q1067 residues (FIG. 8). Thus, it is possible that they facilitate genotype 1a RNA replication by a different mechanism than those mutations that cluster near the active site of the protease. At least the P1496L mutation identified by both Blight et al. (Blight et al., J Virol, 77, 3181-90 (2003)) and Grobler et al. (Grobler et al., J Biol Chem, 278,16741-6 (2003)) appears to be substantially less active in conferring replication capacity on the genotype 1a H77c RNA. This was demonstrated by the lack of detectable replication of RNA replicons containing this mutation (Htat2ANeo/PL/SI and Htat2ANeo/PL/FV/SI) in the transient transfection experiment summarized in FIG. 4.

What role could mutations near the active site of the NS3 protease play in promoting the replication of genotype 1a HCV RNA in Huh7 cells? It is unlikely that these mutations work by enhancing translation of the nonstructural proteins under control of the EMCV IRES in the context of the subgenomic replicon, since we observed no difference in translation of these proteins in vitro in reticulocyte lysates programmed with these RNAs (FIG. 5). More importantly, they enhance the replication of genomic H77c RNA lacking any heterologous sequence in Huh7 cells (see FIG. 7). These mutations do not seem likely to promote replication by favorably influencing the ability of the protease to process the viral polyprotein, since the polyprotein segment expressed in the Htat2ANeo derivatives is derived entirely from the same H77c genome, and this replicates very efficiently in chimpanzee liver. However, this does remain a formal possibility that needs to be excluded in future studies. It is possible, instead, that these mutations promote interactions of the NS3/4A complex with specific cellular proteins that play a role in assembly of the viral replicase complex, or otherwise influence replication by disabling innate cellular antiviral defenses.

Foy et al. (Foy et al., Science, 300, 1145-8 (2003)) recently demonstrated that expression of the NS3/4A protease effectively blocked activation of interferon regulatory factor 3 (IRF3) in Huh7 cells infected with Sendai virus, thereby preventing the induction of synthesis of interferon-$\beta$ and other antiviral cytokines. This immuno-evasive action of NS3 was reversed by a specific ketoamide inhibitor of the NS3/4A protease, and was dependent upon the protease activity of NS3/4A, indicating that NS3/4A is likely to cleave a cellular protein involved in IRF3 signaling following viral infection. While Foy et al. (Foy et al., Science, 300, 1145-8 (2003)) demonstrated that both genotype 1a and genotype 1b proteases are capable of blocking IRF3 activation, it is intriguing to consider that the adaptive mutations within NS3/4A may promote its ability to direct such a cleavage, thereby enhancing replication of the virus by lessening cellular antiviral defenses.

The second group of adaptive mutations identified within NS5A, K2040R, F2080V, and S2204I (Table 2), are likely to function in a fashion similar to NS5A adaptive mutations identified in genotype 1b replicons, which include S2204I. Although their specific mechanism of action is not known, they may either promote the ability of NS5A to assemble a functional replicase complex in Huh7 cells, or perhaps augment the immunomodulatory actions that have been proposed for this viral protein through its interactions with double-stranded RNA stimulated protein kinase R (PKR) (Gale et al., Clin Diagn Virol, 10, 157-62 (1998)). The contribution of these adaptive mutations to the replication of the genotype 1a RNA in these studies appears to be additive to that of the NS3/4A mutations (FIGS. 3 and 6), not synergistic as shown for the combination of Q1067R and K1691R (FIG. 3).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Sequence Listing Free Text

| | |
|---|---|
| SEQ ID NO: 1 | Nucleotide sequence of Hepatitis C virus strain H77 |
| SEQ ID NO: 2 | Amino acid sequence of HCV polyprotein encoded by nucleotides 342-9377 of SEQ ID NO: 1. |

-continued

| Sequence Listing Free Text | |
|---|---|
| SEQ ID NO: 3 | Nucleotide sequence of Hepatitis C virus strain H |
| SEQ ID NO: 4 | Amino acid sequence of HCV polyprotein encoded by nucleotides 342-9377 of SEQ ID NO: 3. |
| SEQ ID NO: 5 | HIV tat polypeptide |
| SEQ ID NO: 6 | NS3 recognition site |
| SEQ ID NO: 7 | Nucleotide sequence of HIV SEAP, HIV long terminal repeat (LTR) is depicted at nucleotides 1-719, and secretory alkaline phosphatase is encoded by the nucleotides 748-2239. |
| SEQ ID NO: 8 | Nucleotide sequence of a 3'NTR. |
| SEQ ID NO: 9 | Nucleotide sequence of a 5'NTR |
| SEQ ID NO: 10 | HIV tat polypeptide |
| SEQ ID NO: 11 | genomic length hepatitis C virus, genotype 1a |
| SEQ ID NO: 12 | HCV polyprotein encoded by the coding region present in SEQ ID NO: 11. |
| SEQ ID NO: 13 | nucleotide sequence of Htat2ANeo |
| SEQ ID NO: 14 | HCV polyprotein encoded by the coding region present in SEQ ID NO: 13. |

What is claimed is:

1. An isolated polynucleotide encoding a replication competent hepatitis C virus genotype 1a replicon comprising:
   a 5' non-translated region (NTR), a 3' NTR, and a first coding sequence present between the 5' NTR and 3' NTR and encoding a hepatitis C virus polyprotein, wherein the polyprotein comprises an amino acid sequence having at least about 95% identity to amino acids 1-3011 of SEQ ID NO:2, and wherein the amino acid sequence of the polyprotein comprises at least three adaptive mutations relative to the amino acid positions using SEQ ID NO: 2 as a reference sequence, wherein the adaptive mutations comprise an isoleucine at about amino acid 2204 of the polyprotein and at least two adaptive mutations selected from the group of an arginine at about amino acid 1067 of the polyprotein, an arginine at about amino acid 1691 of the polyprotein, a valine at about amino acid 2080 of the polyprotein, an isoleucine at about amino acid 1655 of the polyprotein, an arginine at about amino acid 2040 of the polyprotein, an arginine at about amino acid 1188 of the polyprotein, and a combination thereof.

2. The isolated polynucleotide of claim 1 further comprising a second coding sequence.

3. The isolated polynucleotide of claim 2 wherein the second coding sequence encodes a marker.

4. The isolated polynucleotide of claim 2 wherein the second coding sequence encodes a transactivator.

5. The isolated polynucleotide of claim 1 wherein the hepatitis C virus polyprotein is a subgenomic hepatitis C virus polyprotein.

6. The isolated polynucleotide of claim 1 wherein the hepatitis C virus polyprotein comprises cleavage products core, E1, E2, P7, NS2, NS3, NS4A, NS4B, NS5A, and NS5B.

7. The isolated polynucleotide of claim 1 further comprising a nucleotide sequence having cis-acting ribozyme activity, wherein the nucleotide sequence is located 3' of the 3' NTR.

8. The isolated polynucleotide of claim 1 wherein the adaptive mutations are an isoleucine at amino acid 2204 of the polyprotein, an arginine at amino acid 1067 of the polyprotein, an arginine at amino acid 1691 of the polyprotein, a valine at amino acid 2080 of the polyprotein, an isoleucine at amino acid 1655 of the polyprotein, an arginine at amino acid 2040 of the polyprotein, and an arginine at amino acid 1188 of the polyprotein.

9. A method for making an isolated polynucleotide encoding a replication competent hepatitis C virus genotype 1a replicon comprising:
   providing a polynucleotide comprising a 5' NTR, 3' NTR, and a first coding sequence present between the 5' NTR and 3' NTR and encoding a hepatitis C virus polyprotein, wherein the polyprotein comprises an amino acid sequence having at least about 95% identity to amino acids 1-3011 of SEQ ID NO:2, and wherein the amino acid sequence of the polyprotein comprises a serine at about amino acid 2204 of the polyprotein, a glutamine at about amino acid 1067 of the polyprotein, a lysine at about amino acid 1691 of the polyprotein, a phenylalanine at about amino acid 2080 of the polyprotein, a valine at about amino acid 1655 of the polyprotein, a lysine at about amino acid 2040 of the polyprotein, or a glycine at about amino acid 1188 of the polyprotein; and altering the coding sequence such that the polyprotein encoded thereby comprises at least three adaptive mutations relative to the amino acid positions using SEQ ID NO: 2 as a reference sequence, wherein the adaptive mutations comprise an isoleucine at about amino acid 2204 of the polyprotein and at least two adaptive mutations selected from the group consisting of an arginine at about amino acid 1067 of the polyprotein, an arginine at about amino acid 1691 of the polyprotein, a valine at about amino acid 2080 of the polyprotein, an isoleucine at about amino acid 1655 of the polyprotein, an arginine at about amino acid 2040 of the polyprotein, an arginine at about amino acid 1188 of the polyprotein, and a combination thereof.

10. The method of claim 9 wherein the hepatitis C virus polyprotein is a subgenomic hepatitis C virus polyprotein.

11. The method of claim 9 wherein the hepatitis C virus polyprotein comprises cleavage products core, E1, E2, P7, NS2, NS3, NS4A, NS4B, NS5A, and NS5B.

12. A replication competent hepatitis C virus genotype 1a replicon produced by the method of claim 9.

13. A method for identifying a compound that inhibits replication of a replication competent hepatitis C virus genotype 1a replicon, the method comprising:

contacting a cell comprising a replication competent hepatitis C virus genotype 1a replicon with a compound, the replication competent hepatitis C virus genotype 1a replicon comprising a 5' NTR, 3' NTR, and a first coding sequence present between the 5' NTR and 3' NTR and encoding a hepatitis C virus polyprotein, wherein the hepatitis C virus polyprotein comprises an amino acid sequence having at least about 95% identity to amino acids 1-3011 of SEQ ID NO:2, and wherein the amino acid sequence of the polyprotein comprises at least three adaptive mutations relative to the amino acid positions using SEQ ID NO: 2 as a reference sequence, wherein the adaptive mutations comprise an isoleucine at about amino acid 2204 of the polyprotein and at least two adaptive mutations selected from the group of an arginine at about amino acid 1067 of the polyprotein, an arginine at about amino acid 1691 of the polyprotein, a valine at about amino acid 2080 of the polyprotein, an isoleucine at about amino acid 1655 of the polyprotein, an arginine at about amino acid 2040 of the polyprotein, an arginine at about amino acid 1188 of the polyprotein, and a combination thereof;

incubating the cell under conditions wherein the replication competent hepatitis C virus genotype 1a replicon replicates in the absence of the compound; and detecting the replication competent hepatitis C virus genotype 1a replicon, wherein a decrease of the replication competent hepatitis C virus genotype 1a replicon in the cell contacted with the compound compared to the replication competent hepatitis C virus genotype 1a replicon in a cell not contacted with the compound indicates the compound inhibits replication of the replication competent hepatitis C virus genotype 1a replicon.

14. The method of claim 13 wherein detecting the replication competent hepatitis C virus genotype 1a replicon comprises nucleic acid amplification.

15. The method of claim 13 wherein the replication competent hepatitis C virus genotype 1a replicon further comprises a second coding sequence encoding a marker, and wherein detecting the replication competent hepatitis C virus genotype 1a replicon comprises identifying the marker.

16. The method of claim 13 wherein the replication competent hepatitis C virus genotype 1a replicon further comprises a second coding sequence encoding a transactivator, wherein the cell comprises a polynucleotide comprising a transactivated coding sequence encoding a detectable marker and an operator sequence operably linked to the transactivated coding sequence, wherein the transactivator interacts with the operator sequence and alters expression of the transactivated coding sequence, and wherein detecting the replication competent hepatitis C virus genotype 1a replicon in the cell comprises detecting the detectable marker encoded by the transactivated coding sequence.

17. The method of claim 13 wherein the cell is a human hepatoma cell.

18. The method of claim 13 wherein the hepatitis C virus polyprotein is a subgenomic hepatitis C virus polyprotein.

19. The method of claim 13 wherein the hepatitis C virus polyprotein comprises cleavage products core, E1, E2, P7, NS2, NS3, NS4A, NS4B, NS5A, and NS5B.

20. A method for selecting a replication competent hepatitis C virus genotype 1a replicon, the method comprising:

incubating a cell in the presence of a selecting agent, wherein:

the cell comprises a polynucleotide comprising a 5' non-translated region (NTR), a 3' NTR, and a first coding sequence present between the 5' NTR and 3' NTR and encoding a hepatitis C virus polyprotein, and a second coding sequence, wherein the polyprotein comprises an amino acid sequence having at least about 95% identity to amino acids 1-3011 of SEQ ID NO:2, and wherein the amino acid sequence of the polyprotein comprises at least three adaptive mutations relative to the amino acid positions using SEQ ID NO: 2 as a reference sequence, wherein the adaptive mutations comprise an isoleucine at about amino acid 2204 of the polyprotein and at least two adaptive mutations selected from the group of an arginine at about amino acid 1067 of the polyprotein, an arginine at about amino acid 1691 of the polyprotein, a valine at about amino acid 2080 of the polyprotein, an isoleucine at about amino acid 1655 of the polyprotein, an arginine at about amino acid 2040 of the polyprotein, an arginine at about amino acid 1188 of the polyprotein, and a combination thereof;

the second coding sequence encodes a selectable marker conferring resistance to the selecting agent; and the selecting agent inhibits replication of a cell that does not express the selectable marker; and detecting a cell that replicates in the presence of the selecting agent, wherein the presence of such a cell indicates the polynucleotide is replication competent.

21. The method of claim 20 wherein the selecting agent is an antibiotic.

22. The method of claim 20 wherein the cell is a human hepatoma cell.

23. The method of claim 20 wherein the cell is a first cell, the method further comprising:

obtaining a virus particle produced by the first cell;

exposing a second cell to the isolated virus particle and incubating the second cell in the presence of the selecting agent; and detecting a second cell that replicates in the presence of the selecting agent, wherein the presence of such a cell indicates the replication competent hepatitis C virus genotype 1a replicon in the first cell produces an infectious virus particle.

24. The method of claim 20 wherein the hepatitis C virus polyprotein is a subgenomic hepatitis C virus polyprotein.

25. The method of claim 20 wherein the hepatitis C virus polyprotein comprises cleavage products core, E1, E2, P7, NS2, NS3, NS4A, NS4B, NS5A, and NS5B.

26. A method for detecting a replication competent hepatitis C virus genotype 1a replicon, the method comprising:

incubating a cell comprising a replication competent hepatitis C virus genotype 1a replicon, wherein:

the replication competent hepatitis C virus genotype 1a replicon comprises a 5' non-translated region (NTR), a 3' NTR, and a first coding sequence present between the 5' NTR and 3' NTR and encoding a hepatitis C virus polyprotein, and a second coding sequence encoding a transactivator, wherein the polyprotein comprises an amino acid sequence having at least about 95% identity to amino acids 1-3011 of SEQ ID NO:2, and wherein the amino acid sequence of the polyprotein comprises at least three adaptive mutations relative to the amino acid positions using SEQ ID NO: 2 as a reference sequence, wherein the adaptive mutations comprise an isoleucine at about amino acid 2204 of the polyprotein and at least two adaptive mutations selected from the group of an arginine at about amino acid 1067 of the polyprotein, an arginine at about amino acid 1691 of the polyprotein, a valine at about amino acid 2080 of the polyprotein, an isoleucine at about amino acid 1655 of the polyprotein, an arginine at about amino acid 2040 of the polyprotein, an arginine at about amino acid 1188 of the polyprotein, and a combination thereof;

the cell comprises a transactivated coding region and an operator sequence operably linked to the transactivated coding region; and the transactivated coding region encodes a detectable marker, wherein the transactivator alters transcription of the transactivated coding region; and detecting the detectable marker, wherein the presence of the detectable marker indicates the cell comprises a replication competent hepatitis C virus genotype 1a replicon.

27. The method of claim 26 wherein the hepatitis C virus polyprotein is a subgenomic hepatitis C virus polyprotein.

28. The method of claim 26 wherein the hepatitis C virus polyprotein comprises cleavage products core, E1, E2, P7, NS2, NS3, NS4A, NS4B, NS5A, and NS5B.

29. A method for producing viral particles, comprising incubating a cell comprising the replication competent hepatitis C virus genotype 1a replicon of claim 1 under conditions allowing the polynucleotide to replicate.

30. The method of claim 29 further comprising isolating the viral particles.

31. A method for using the viral particles of claim 29 in an assay.

32. The replication competent polynucleotide of claim 1 wherein the replication competent hepatitis C virus genotype 1a replicon replicates in Huh-7 cells.

33. The method of claim 9 wherein the replication competent hepatitis C virus genotype 1a replicon replicates in Huh-7 cells.

34. The method of claim 17 wherein the cell is a Huh-7 cell.

35. The method of claim 22 wherein the cell is a Huh-7 cell.

36. The method of claim 26 wherein the cell is a human hepatoma cell.

37. The method of claim 36 wherein the cell is a Hnh-7 cell.

* * * * *

UNITED STATES PATENT AND TRADEMARK OFFICE
CERTIFICATE OF CORRECTION

| | | |
|---|---|---|
| PATENT NO. | : 8,026,092 B2 | Page 1 of 1 |
| APPLICATION NO. | : 10/580979 | |
| DATED | : September 27, 2011 | |
| INVENTOR(S) | : Lemon et al. | |

It is certified that error appears in the above-identified patent and that said Letters Patent is hereby corrected as shown below:

Face Page
Item (57) Abstract, 4th line, delete "malting" and insert --making--.

Signed and Sealed this
Tenth Day of July, 2012

David J. Kappos
*Director of the United States Patent and Trademark Office*

SEQUENCE LISTING

<160> NUMBER OF SEQ ID NOS: 14

<210> SEQ ID NO 1
<211> LENGTH: 9599
<212> TYPE: DNA
<213> ORGANISM: Artificial Sequence
<220> FEATURE:
<223> OTHER INFORMATION: Nucleotide sequence of Hepatitis C virus
      strain H77

<400> SEQUENCE: 1

```
gccagccccc tgatgggggc gacactccac catgaatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag     180
gacgaccggg tcctttcttg gataaacccg ctcaatgcct ggagatttgg gcgtgccccc     240
gcaagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaacgt aacaccaacc gtcgcccaca ggacgtcaag ttcccgggtg     420
gcggtcagat cgttggtgga gtttacttgt tgccgcgcag gggccctaga ttgggtgtgc     480
gcgcgacgag gaagacttcc gagcggtcgc aacctcgagg tagacgtcag cctatcccca     540
aggcacgtcg gcccgagggc aggacctggg ctcagcccgg gtaccttggg ccctctatg     600 gcaatgaggg ttgcgggtgg gcgggatggc tcctgtctcc ccgtggctct cggcctagct     660
ggggccccac agaccccggg cgtaggtcgc gcaatttggg taaggtcatc gatacccta     720 cgtgcggctt cgccgacctc atggggtaca taccgctcgt cggcgcccct cttgaggcg     780 ctgccagggc cctggcgcat ggcgtccggg ttctggaaga cggcgtgaac tatgcaacag     840
ggaaccttcc tggttgctct ttctctatct tccttctggc cctgctctct tgcctgactg     900
tgcccgcttc agcctaccaa gtgcgcaatt cctcggggct ttaccatgtc accaatgatt     960
gccctaactc gagtattgtg tacgaggcgg ccgatgccat cctgcacact ccggggtgtg    1020
tcccttgcgt tcgcgagggt aacgcctcga ggtgttgggt ggcggtgacc cccacggtgg    1080
ccaccaggga cggcaaactc cccacaaacgc agcttcgacg tcatatcgat ctgcttgtcg    1140
ggagcgccac cctctgctcg gccctctacg tgggggacct gtgcgggtct gtctttcttg    1200
```

```
ttggtcaact gtttaccttc tctcccaggc gccactggac gacgcaagac tgcaattgtt    1260
ctatctatcc cggccatata acgggtcatc gcatggcatg ggatatgatg atgaactggt    1320
cccctacggc agcgttggtg gtagctcagc tgctccggat cccacaagcc atcatggaca    1380
tgatcgctgg tgctcactgg ggagtcctgg cgggcatagc gtatttctcc atggtgggga    1440
actgggcgaa ggtcctggta gtgctgctgc tatttgccgg cgtcgacgcg gaaacccacg    1500
tcaccggggg aaatgccggc cgcaccacgg ctgggcttgt tggtctcctt acaccaggcg    1560
ccaagcagaa catccaactg atcaacacca acggcagttg gcacatcaat agcacggcct    1620
tgaattgcaa tgaaagcctt aacaccggct ggttagcagg gctcttctat caacacaaat    1680
tcaactcttc aggctgtcct gagaggttgg ccagctgccg acgccttacc gattttgccc    1740
agggctgggg tcctatcagt tatgccaacg gaagcggcct cgacgaacgc ccctactgct    1800
ggcactaccc tccaagacct tgtggcattg tgcccgcaaa gagcgtgtgt ggcccggtat    1860
attgcttcac tcccagcccc gtggtggtgg gaacgaccga caggtcgggc gcgcctacct    1920
acagctgggg tgcaaatgat acggatgtct tcgtccttaa caacaccagg ccaccgctgg    1980
gcaattggtt cggttgtacc tggatgaact caactggatt caccaaagtg tgcggagcgc    2040 cccccttgtgt catcggaggg gtgggcaaca acaccttgct ctgccccact gattgcttcc    2100
gcaaacatcc ggaagccaca tactctcggt gcggctccgg tcctggatt acacccaggt    2160 gcatggtcga ctacccgtat aggctttggc actatccttg taccatcaat tacaccatat    2220
tcaaagtcag gatgtacgtg ggaggggtcg agcacaggct ggaagcggcc tgcaactgga    2280
cgcggggcga acgctgtgat ctggaagaca gggacaggtc cgagctcagc ccgttgctgc    2340
tgtccaccac acagtggcag gtccttccgt gttctttcac gaccctgcca gccttgtcca    2400
ccggcctcat ccacctccac cagaacattg tggacgtgca gtacttgtac ggggtagggt    2460
caagcatcgc gtcctgggcc attaagtggg agtacgtcgt tctcctgttc cttctgcttg    2520
cagacgcgcg cgtctgctcc tgcttgtgga tgatgttact catatcccaa gcggaggcgg    2580 cttttggagaa cctcgtaata ctcaatgcag catccctggc cgggacgcac ggtcttgtgt    2640
ccttcctcgt gttcttctgc tttgcgtggt atctgaaggg taggtgggtg cccggagcgg    2700
tctacgccct ctacgggatg tggcctctcc tcctgctcct gctggcgttg cctcagcggg    2760
catacgcact ggacacggag gtggccgcgt cgtgtggcgg cgttgttctt gtcgggttaa    2820
tggcgctgac tctgtcgcca tattacaagc gctatatcag ctggtgcatg tggtggcttc    2880
agtattttct gaccagagta gaagcgcaac tgcacgtgtg ggttccccccc ctcaacgtcc    2940 gggggggggcg cgatgccgtc atcttactca tgtgtgtagt acacccgacc ctggtatttg    3000
acatcaccaa actactcctg gccatcttcg gaccccttg gattcttcaa gccagtttgc    3060
ttaaagtccc ctacttcgtg cgcgttcaag gccttctccg gatctgcgcg ctagcgcgga    3120
agatagccgg aggtcattac gtgcaaatgg ccatcatcaa gttaggggcg cttactggca    3180
cctatgtgta taaccatctc acccctcttc gagactgggc gcacaacggc ctgcgagatc    3240
tggccgtggc tgtggaacca gtcgtcttct cccgaatgga gaccaagctc atcacgtggg    3300
gggcagatac cgccgcgtgc ggtgacatca tcaacggctt gccgtctct gcccgtaggg    3360 gccaggagat actgcttggg ccagccgacg gaatggtctc caaggggtgg aggttgctgg    3420
cgcccatcac ggcgtacgcc cagcagacga gaggcctcct agggtgtata atcaccagcc    3480
tgactggccg ggacaaaaac caagtggagg gtgaggtcca gatcgtgtca actgctaccc    3540 aaacccttcct ggcaacgtgc atcaatgggg tatgctggac tgtctaccac ggggccggaa    3600
```

```
cgaggaccat cgcatcaccc aagggtcctg tcatccagat gtataccaat gtggaccaag    3660
accttgtggg ctggcccgct cctcaaggtt cccgctcatt gacaccctgt acctgcggct    3720
cctcggacct ttacctggtc acgaggcacg ccgatgtcat tcccgtgcgc cggcgaggtg    3780
atagcagggg tagcctgctt tcgccccggc ccatttccta cttgaaaggc tcctcggggg    3840
gtccgctgtt gtgccccgcg ggacacgccg tgggcctatt cagggccgcg gtgtgcaccc    3900
gtggagtggc taaagcggtg gactttatcc ctgtggagaa cctagggaca accatgagat    3960
ccccggtgtt cacggacaac tcctctccac cagcagtgcc ccagagcttc caggtggccc    4020
acctgcatgc tcccaccggc agcggtaaga gcaccaaggt cccggctgcg tacgcagccc    4080
agggctacaa ggtgttggtg ctcaaccccct ctgttgctgc aacgctgggc tttggtgctt    4140
acatgtccaa ggcccatggg gttgatccta atatcaggac cggggtgaga acaattacca    4200
ctggcagccc catcacgtac tccacctacg gcaagttcct tgccgacggc gggtgctcag    4260
gaggtgctta tgacataata atttgtgacg agtgccactc cacggatgcc acatccatct    4320
tgggcatcgg cactgtcctt gaccaagcag agactgcggg ggcgagactg gttgtgctcg    4380
ccactgctac ccctccgggc tccgtcactg tgtcccatcc taacatcgag gaggttgctc    4440
tgtccaccac cggagagatc ccctttttacg gcaaggctat cccctcgag gtgatcaagg    4500 ggggaagaca tctcatcttc tgccactcaa agaagaagtg cgacgagctc gccgcgaagc    4560
tggtcgcatt gggcatcaat gccgtggcct actaccgcgg tcttgacgtg tctgtcatcc    4620
cgaccagcgg cgatgttgtc gtcgtgtcga ccgatgctct catgactggc tttaccggcg    4680
acttcgactc tgtgatagac tgcaacacgt gtgtcactca gacagtcgat ttcagccttg    4740
accctacctt taccattgag acaaccacgc tcccccagga tgctgtctcc aggactcaac    4800
gccggggcag gactggcagg gggaagccag gcatctatag atttgtggca ccgggggagc    4860
gcccctccgg catgttcgac tcgtccgtcc tctgtgagtg ctatgacgcg ggctgtgctt    4920
ggtatgagct cacgcccgcc gagactacag ttaggctacg agcgtacatg aacaccccgg    4980
ggcttcccgt gtgccaggac catcttgaat tttgggaggg cgtctttacg ggcctcactc    5040
atatagatgc ccacttttta tcccagacaa agcagagtgg ggagaacttt ccttacctgg    5100
tagcgtacca agccaccgtg tgcgctaggg ctcaagcccc tcccccatcg tgggaccaga    5160
tgtggaagtg tttgatccgc cttaaaccca ccctccatgg gccaacaccc ctgctataca    5220
gactgggcgc tgttcagaat gaagtcaccc tgacgcaccc aatcaccaaa tacatcatga    5280
catgcatgtc ggccgacctg gaggtcgtca cgagcacctg ggtgctcgtt ggcggcgtcc    5340
tggctgctct ggccgcgtat tgcctgtcaa caggctgcgt ggtcatagtg gcaggatcg    5400 tcttgtccgg gaagccggca attataccctg acagggaggt tctctaccag gagttcgatg    5460
agatggaaga gtgctctcag cacttaccgt acatcgagca agggatgatg ctcgctgagc    5520
agttcaagca gaaggccctc ggcctcctgc agaccgcgtc ccgccatgca gaggttatca    5580
cccctgctgt ccagaccaac tggcagaaac tcgaggtctt tttgggcgaag cacatgtgga    5640 atttcatcag tgggatacaa tacttggcgg gcctgtcaac gctgcctggt aaccccgcca    5700
ttgcttcatt gatggctttt acagctgccg tcaccagccc actaaccact ggccaaaccc    5760
tcctcttcaa catattgggg gggtgggtgg ctgcccagct cgccgccccc ggtgccgcta    5820
ctgcctttgt gggtgctggc ctagctggcg ccgccatcgg cagcgttgga ctggggaagg    5880
tcctcgtgga cattcttgca gggtatgcg cgggcgtggc gggagctctt gtagcattca    5940
agatcatgag cggtgaggtc ccctccacgg aggacctggt caatctgctg cccgccatcc    6000
```

```
tctcgcctgg agcccttgta gtcggtgtgg tctgcgcagc aatactgcgc cggcacgttg    6060
gcccgggcga gggggcagtg caatggatga accggctaat agccttcgcc tcccggggga    6120
accatgtttc ccccacgcac tacgtgccgg agagcgatgc agccgcccgc gtcactgcca    6180
tactcagcag cctcactgta acccagctcc tgaggcgact gcatcagtgg ataagctcgg    6240
agtgtaccac tccatgctcc ggttcctggc taagggacat ctgggactgg atatgcgagg    6300
tgctgagcga ctttaagacc tggctgaaag ccaagctcat gccacaactg cctgggattc    6360
cctttgtgtc ctgccagcgc gggtataggg gggtctggcg aggagacggc attatgcaca    6420
ctcgctgcca ctgtggagct gagatcactg gacatgtcaa aaacgggacg atgaggatcg    6480
tcggtcctag gacctgcagg aacatgtgga gtgggacgtt ccccattaac gcctacacca    6540
cgggcccctg tactcccctt cctgcgccga actataagtt cgcgctgtgg agggtgtctg    6600
cagaggaata cgtggagata aggcgggtgg gggacttcca ctacgtatcg ggtatgacta    6660
ctgacaatct taaatgcccg tgccagatcc catcgcccga atttttcaca gaattggacg    6720
gggtgcgcct acacaggttt gcgcccccct tgcaagccct tctgcgggag gaggtatcat    6780
tcagagtagg actccacgag tacccggtgg ggtcgcaatt accttgcgag cccgaaccgg    6840
acgtagccgt gttgacgtcc atgctcactg atccctccca tataacagca gaggcggccg    6900
ggagaaggtt ggcgagaggg tcacccccttcatgggccag ctcctcggct agccagctgt    6960
ccgctccatc tctcaaggca acttgcaccg ccaaccatga ctccctgac gccgagctca    7020 tagaggctaa cctcctgtgg aggcaggaga tgggcggcaa catcaccagg gttgagtcag    7080
agaacaaagt ggtgattctg gactccttcg atccgcttgt ggcagaggag gatgagcggg    7140
aggtctccgt acctgcagaa attctgcgga agtctcggag attcgcccgg gccctgcccg    7200
tctgggcgcg gccggactac aaccccccgc tagtagagac gtggaaaaag cctgactacg    7260
aaccacctgt ggtccatggc tgcccgctac cacctccacg gtcccctcct gtgcctccgc    7320
ctcggaaaaa gcgtacggtg gtcctcaccg aatcaaccct atctactgcc ttggccgagc    7380
ttgccaccaa aagttttggc agctcctcaa cttccggcat tacgggcgac aatacgacaa    7440
catcctctga gcccgcccct tctggctgcc ccccgactc cgacgttgag tcctattctt    7500
ccatgccccc cctggagggg gagcctgggg atccggatct cagcgacggg tcatggtcga    7560
cggtcagtag tgggccgac acggaagatg tcgtgtgctg ctcaatgtct tattcctgga    7620
caggcgcact cgtcaccccg tgcgctgcgg aagaacaaaa actgcccatc aacgcactga    7680
gcaactcgtt gctacgccat cacaatctgg tgtattccac cacttcacgc agtgcttgcc    7740
aaaggcagaa gaaagtcaca tttgacagac tgcaagttct ggacagccat taccaggacg    7800
tgctcaagga ggtcaaagca gcggcgtcaa aagtgaaggc taacttgcta tccgtagagg    7860
aagcttgcag cctgacgccc ccacattcag ccaaatccaa gtttggctat ggggcaaaag    7920
acgtccgttg ccatgccaga aaggccgtag cccacatcaa ctccgtgtgg aaagaccttc    7980
tggaagacag tgtaacacca atagacacta ccatcatggc caagaacgag gttttctgcg    8040
ttcagcctga agggggggt cgtaagccag ctcgtctcat cgtgttcccc gacctgggcg    8100
tgcgcgtgtg cgagaagatg gccctgtacg acgtggttag caagctcccc ctggccgtga    8160
tgggaagctc ctacgattc caatactcac caggacagcg ggttgaattc ctcgtgcaag    8220
cgtggaagtc caagaagacc ccgatggggt tctcgtatga tacccgctgt tttgactcca    8280
cagtcactga gagcgacatc cgtacggagg aggcaattta ccaatgttgt gacctggacc    8340
cccaagcccg cgtggccatc aagtccctca ctgagaggct ttatgttggg ggccctctta    8400
```

```
ccaattcaag gggggaaaac tgcggctacc gcaggtgccg cgcgagcggc gtactgacaa    8460
ctagctgtgg taacaccctc acttgctaca tcaaggcccg ggcagcctgt cgagccgcag    8520
ggctccagga ctgcaccatg ctcgtgtgtg cgacgactt agtcgttatc tgtgaaagtg     8580
cgggggtcca ggaggacgcg gcgagcctga gagccttcac ggaggctatg accaggtact    8640 ccgcccccc cggggacccc ccacaaccag aatacgactt ggagcttata acatcatgct     8700
cctccaacgt gtcagtcgcc cacgacggcg ctggaaagag ggtctactac cttacccgtg    8760
accctacaac ccccctcgcg agagccgcgt gggagacagc aagacacact ccagtcaatt    8820
cctggctagg caacataatc atgtttgccc ccacactgtg ggcgaggatg atactgatga    8880
cccatttctt tagcgtcctc atagccaggg atcagcttga acaggctctt aactgtgaga    8940
tctacggagc ctgctactcc atagaaccac tggatctacc tccaatcatt caaagactcc    9000
atggcctcag cgcatttca ctccacagtt actctccagg tgaaatcaat agggtggccg     9060
catgcctcag aaaacttggg gtcccgccct tgcgagcttg gagacaccgg gcccggagcg    9120
tccgcgctag gcttctgtcc agaggaggca gggctgccat atgtggcaag tacctcttca    9180
actgggcagt aagaacaaag ctcaaactca ctccaatagc ggccgctggc cggctggact    9240
tgtccggttg gttcacggct ggctacagcg ggggagacat ttatcacagc gtgtctcatg    9300
cccggccccg ctggttctgg ttttgcctac tcctgctcgc tgcagggta ggcatctacc     9360 tcctccccaa ccgatgaagg ttggggtaaa cactccggcc tcttaagcca tttcctgttt    9420 ttttttttt ttttttttt tttttcttt tttttttctt tcctttcctt ctttttttcc      9480 tttcttttc ccttctttaa tggtggctcc atcttagccc tagtcacggc tagctgtgaa     9540
aggtccgtga gccgcatgac tgcagagagt gctgatactg gcctctctgc agatcatgt    9599
```

<210> SEQ ID NO 2
<211> LENGTH: 3011
<212> TYPE: PRT
<213> ORGANISM: Artificial Sequence
<220> FEATURE:
<223> OTHER INFORMATION: Amino acid sequence of HCV polyprotein encoded
      by nucleotides 342 - 9377 of SEQ ID NO:1.

<400> SEQUENCE: 2

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
```

```
                145                 150                 155                 160
Gly Val Asn Tyr Ala Thr Gly Asn Leu Pro Gly Cys Ser Phe Ser Ile
                    165                 170                 175
Phe Leu Leu Ala Leu Leu Ser Cys Leu Thr Val Pro Ala Ser Ala Tyr
                180                 185                 190
Gln Val Arg Asn Ser Ser Gly Leu Tyr His Val Thr Asn Asp Cys Pro
                195                 200                 205
Asn Ser Ser Ile Val Tyr Glu Ala Ala Asp Ala Ile Leu His Thr Pro
            210                 215                 220
Gly Cys Val Pro Cys Val Arg Glu Gly Asn Ala Ser Arg Cys Trp Val
225                 230                 235                 240
Ala Val Thr Pro Thr Val Ala Thr Arg Asp Gly Lys Leu Pro Thr Thr
                245                 250                 255
Gln Leu Arg Arg His Ile Asp Leu Leu Val Gly Ser Ala Thr Leu Cys
            260                 265                 270
Ser Ala Leu Tyr Val Gly Asp Leu Cys Gly Ser Val Phe Leu Val Gly
            275                 280                 285
Gln Leu Phe Thr Phe Ser Pro Arg Arg His Trp Thr Thr Gln Asp Cys
        290                 295                 300
Asn Cys Ser Ile Tyr Pro Gly His Ile Thr Gly His Arg Met Ala Trp
305                 310                 315                 320
Asp Met Met Met Asn Trp Ser Pro Thr Ala Ala Leu Val Val Ala Gln
                325                 330                 335
Leu Leu Arg Ile Pro Gln Ala Ile Met Asp Met Ile Ala Gly Ala His
                340                 345                 350
Trp Gly Val Leu Ala Gly Ile Ala Tyr Phe Ser Met Val Gly Asn Trp
            355                 360                 365
Ala Lys Val Leu Val Val Leu Leu Leu Phe Ala Gly Val Asp Ala Glu
        370                 375                 380
Thr His Val Thr Gly Gly Asn Ala Gly Arg Thr Thr Ala Gly Leu Val
385                 390                 395                 400
Gly Leu Leu Thr Pro Gly Ala Lys Gln Asn Ile Gln Leu Ile Asn Thr
                405                 410                 415
Asn Gly Ser Trp His Ile Asn Ser Thr Ala Leu Asn Cys Asn Glu Ser
                420                 425                 430
Leu Asn Thr Gly Trp Leu Ala Gly Leu Phe Tyr Gln His Lys Phe Asn
            435                 440                 445
Ser Ser Gly Cys Pro Glu Arg Leu Ala Ser Cys Arg Arg Leu Thr Asp
        450                 455                 460
Phe Ala Gln Gly Trp Gly Pro Ile Ser Tyr Ala Asn Gly Ser Gly Leu
465                 470                 475                 480
Asp Glu Arg Pro Tyr Cys Trp His Tyr Pro Arg Pro Cys Gly Ile
                485                 490                 495
Val Pro Ala Lys Ser Val Cys Gly Pro Val Tyr Cys Phe Thr Pro Ser
                500                 505                 510
Pro Val Val Val Gly Thr Thr Asp Arg Ser Gly Ala Pro Thr Tyr Ser
                515                 520                 525
Trp Gly Ala Asn Asp Thr Asp Val Phe Val Leu Asn Asn Thr Arg Pro
        530                 535                 540
Pro Leu Gly Asn Trp Phe Gly Cys Thr Trp Met Asn Ser Thr Gly Phe
545                 550                 555                 560
Thr Lys Val Cys Gly Ala Pro Pro Cys Val Ile Gly Gly Val Gly Asn
                565                 570                 575
```

-continued

```
Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
        595                 600                 605

Val Asp Tyr Pro Tyr Arg Leu Trp His Tyr Pro Cys Thr Ile Asn Tyr
610                 615                 620

Thr Ile Phe Lys Val Arg Met Tyr Val Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Ser Thr Thr Gln Trp
                660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
        690                 695                 700

Val Gly Ser Ser Ile Ala Ser Trp Ala Ile Lys Trp Glu Tyr Val Val
705                 710                 715                 720

Leu Leu Phe Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
            755                 760                 765

Leu Val Phe Phe Cys Phe Ala Trp Tyr Leu Lys Gly Arg Trp Val Pro
        770                 775                 780

Gly Ala Val Tyr Ala Leu Tyr Gly Met Trp Pro Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
            835                 840                 845

Phe Leu Thr Arg Val Glu Ala Gln Leu His Val Trp Val Pro Pro Leu
850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Ile
        915                 920                 925

Ala Gly Gly His Tyr Val Gln Met Ala Ile Ile Lys Leu Gly Ala Leu
        930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Gln
            995                     1000                1005
```

```
Glu Ile Leu Leu Gly Pro Ala Asp Gly Met Val Ser Lys Gly Trp
    1010            1015            1020

Arg Leu Leu Ala Pro Ile Thr Ala Tyr Ala Gln Gln Thr Arg Gly
    1025            1030            1035

Leu Leu Gly Cys Ile Ile Thr Ser Leu Thr Gly Arg Asp Lys Asn
    1040            1045            1050

Gln Val Glu Gly Glu Val Gln Ile Val Ser Thr Ala Thr Gln Thr
    1055            1060            1065

Phe Leu Ala Thr Cys Ile Asn Gly Val Cys Trp Thr Val Tyr His
    1070            1075            1080

Gly Ala Gly Thr Arg Thr Ile Ala Ser Pro Lys Gly Pro Val Ile
    1085            1090            1095

Gln Met Tyr Thr Asn Val Asp Gln Asp Leu Val Gly Trp Pro Ala
    1100            1105            1110

Pro Gln Gly Ser Arg Ser Leu Thr Pro Cys Thr Cys Gly Ser Ser
    1115            1120            1125

Asp Leu Tyr Leu Val Thr Arg His Ala Asp Val Ile Pro Val Arg
    1130            1135            1140

Arg Arg Gly Asp Ser Arg Gly Ser Leu Leu Ser Pro Arg Pro Ile
    1145            1150            1155

Ser Tyr Leu Lys Gly Ser Ser Gly Gly Pro Leu Leu Cys Pro Ala
    1160            1165            1170

Gly His Ala Val Gly Leu Phe Arg Ala Ala Val Cys Thr Arg Gly
    1175            1180            1185

Val Ala Lys Ala Val Asp Phe Ile Pro Val Glu Asn Leu Gly Thr
    1190            1195            1200

Thr Met Arg Ser Pro Val Phe Thr Asp Asn Ser Ser Pro Pro Ala
    1205            1210            1215

Val Pro Gln Ser Phe Gln Val Ala His Leu His Ala Pro Thr Gly
    1220            1225            1230

Ser Gly Lys Ser Thr Lys Val Pro Ala Ala Tyr Ala Ala Gln Gly
    1235            1240            1245

Tyr Lys Val Leu Val Leu Asn Pro Ser Val Ala Ala Thr Leu Gly
    1250            1255            1260

Phe Gly Ala Tyr Met Ser Lys Ala His Gly Val Asp Pro Asn Ile
    1265            1270            1275

Arg Thr Gly Val Arg Thr Ile Thr Thr Gly Ser Pro Ile Thr Tyr
    1280            1285            1290

Ser Thr Tyr Gly Lys Phe Leu Ala Asp Gly Gly Cys Ser Gly Gly
    1295            1300            1305

Ala Tyr Asp Ile Ile Ile Cys Asp Glu Cys His Ser Thr Asp Ala
    1310            1315            1320

Thr Ser Ile Leu Gly Ile Gly Thr Val Leu Asp Gln Ala Glu Thr
    1325            1330            1335

Ala Gly Ala Arg Leu Val Val Leu Ala Thr Ala Thr Pro Pro Gly
    1340            1345            1350

Ser Val Thr Val Ser His Pro Asn Ile Glu Glu Val Ala Leu Ser
    1355            1360            1365

Thr Thr Gly Glu Ile Pro Phe Tyr Gly Lys Ala Ile Pro Leu Glu
    1370            1375            1380

Val Ile Lys Gly Gly Arg His Leu Ile Phe Cys His Ser Lys Lys
    1385            1390            1395

Lys Cys Asp Glu Leu Ala Ala Lys Leu Val Ala Leu Gly Ile Asn
```

-continued

```
            1400            1405            1410
Ala Val Ala Tyr Tyr Arg Gly Leu Asp Val Ser Val Ile Pro Thr
    1415                    1420                    1425
Ser Gly Asp Val Val Val Ser Thr Asp Ala Leu Met Thr Gly
    1430                    1435                    1440
Phe Thr Gly Asp Phe Asp Ser Val Ile Asp Cys Asn Thr Cys Val
    1445                    1450                    1455
Thr Gln Thr Val Asp Phe Ser Leu Asp Pro Thr Phe Thr Ile Glu
    1460                    1465                    1470
Thr Thr Thr Leu Pro Gln Asp Ala Val Ser Arg Thr Gln Arg Arg
    1475                    1480                    1485
Gly Arg Thr Gly Arg Gly Lys Pro Gly Ile Tyr Arg Phe Val Ala
    1490                    1495                    1500
Pro Gly Glu Arg Pro Ser Gly Met Phe Asp Ser Ser Val Leu Cys
    1505                    1510                    1515
Glu Cys Tyr Asp Ala Gly Cys Ala Trp Tyr Glu Leu Thr Pro Ala
    1520                    1525                    1530
Glu Thr Thr Val Arg Leu Arg Ala Tyr Met Asn Thr Pro Gly Leu
    1535                    1540                    1545
Pro Val Cys Gln Asp His Leu Glu Phe Trp Glu Gly Val Phe Thr
    1550                    1555                    1560
Gly Leu Thr His Ile Asp Ala His Phe Leu Ser Gln Thr Lys Gln
    1565                    1570                    1575
Ser Gly Glu Asn Phe Pro Tyr Leu Val Ala Tyr Gln Ala Thr Val
    1580                    1585                    1590
Cys Ala Arg Ala Gln Ala Pro Pro Pro Ser Trp Asp Gln Met Trp
    1595                    1600                    1605
Lys Cys Leu Ile Arg Leu Lys Pro Thr Leu His Gly Pro Thr Pro
    1610                    1615                    1620
Leu Leu Tyr Arg Leu Gly Ala Val Gln Asn Glu Val Thr Leu Thr
    1625                    1630                    1635
His Pro Ile Thr Lys Tyr Ile Met Thr Cys Met Ser Ala Asp Leu
    1640                    1645                    1650
Glu Val Val Thr Ser Thr Trp Val Leu Val Gly Gly Val Leu Ala
    1655                    1660                    1665
Ala Leu Ala Ala Tyr Cys Leu Ser Thr Gly Cys Val Val Ile Val
    1670                    1675                    1680
Gly Arg Ile Val Leu Ser Gly Lys Pro Ala Ile Ile Pro Asp Arg
    1685                    1690                    1695
Glu Val Leu Tyr Gln Glu Phe Asp Glu Met Glu Glu Cys Ser Gln
    1700                    1705                    1710
His Leu Pro Tyr Ile Glu Gln Gly Met Met Leu Ala Glu Gln Phe
    1715                    1720                    1725
Lys Gln Lys Ala Leu Gly Leu Leu Gln Thr Ala Ser Arg His Ala
    1730                    1735                    1740
Glu Val Ile Thr Pro Ala Val Gln Thr Asn Trp Gln Lys Leu Glu
    1745                    1750                    1755
Val Phe Trp Ala Lys His Met Trp Asn Phe Ile Ser Gly Ile Gln
    1760                    1765                    1770
Tyr Leu Ala Gly Leu Ser Thr Leu Pro Gly Asn Pro Ala Ile Ala
    1775                    1780                    1785
Ser Leu Met Ala Phe Thr Ala Ala Val Thr Ser Pro Leu Thr Thr
    1790                    1795                    1800
```

-continued

```
Gly Gln Thr Leu Leu Phe Asn Ile Leu Gly Gly Trp Val Ala Ala
1805                1810                1815

Gln Leu Ala Ala Pro Gly Ala Thr Ala Phe Val Gly Ala Gly
1820                1825                1830

Leu Ala Gly Ala Ala Ile Gly Ser Val Gly Leu Gly Lys Val Leu
1835                1840                1845

Val Asp Ile Leu Ala Gly Tyr Gly Ala Gly Val Ala Gly Ala Leu
1850                1855                1860

Val Ala Phe Lys Ile Met Ser Gly Glu Val Pro Ser Thr Glu Asp
1865                1870                1875

Leu Val Asn Leu Leu Pro Ala Ile Leu Ser Pro Gly Ala Leu Val
1880                1885                1890

Val Gly Val Val Cys Ala Ala Ile Leu Arg Arg His Val Gly Pro
1895                1900                1905

Gly Glu Gly Ala Val Gln Trp Met Asn Arg Leu Ile Ala Phe Ala
1910                1915                1920

Ser Arg Gly Asn His Val Ser Pro Thr His Tyr Val Pro Glu Ser
1925                1930                1935

Asp Ala Ala Arg Val Thr Ala Ile Leu Ser Ser Leu Thr Val
1940                1945                1950

Thr Gln Leu Leu Arg Arg Leu His Gln Trp Ile Ser Ser Glu Cys
1955                1960                1965

Thr Thr Pro Cys Ser Gly Ser Trp Leu Arg Asp Ile Trp Asp Trp
1970                1975                1980

Ile Cys Glu Val Leu Ser Asp Phe Lys Thr Trp Leu Lys Ala Lys
1985                1990                1995

Leu Met Pro Gln Leu Pro Gly Ile Pro Phe Val Ser Cys Gln Arg
2000                2005                2010

Gly Tyr Arg Gly Val Trp Arg Gly Asp Gly Ile Met His Thr Arg
2015                2020                2025

Cys His Cys Gly Ala Glu Ile Thr Gly His Val Lys Asn Gly Thr
2030                2035                2040

Met Arg Ile Val Gly Pro Arg Thr Cys Arg Asn Met Trp Ser Gly
2045                2050                2055

Thr Phe Pro Ile Asn Ala Tyr Thr Thr Gly Pro Cys Thr Pro Leu
2060                2065                2070

Pro Ala Pro Asn Tyr Lys Phe Ala Leu Trp Arg Val Ser Ala Glu
2075                2080                2085

Glu Tyr Val Glu Ile Arg Arg Val Gly Asp Phe His Tyr Val Ser
2090                2095                2100

Gly Met Thr Thr Asp Asn Leu Lys Cys Pro Cys Gln Ile Pro Ser
2105                2110                2115

Pro Glu Phe Phe Thr Glu Leu Asp Gly Val Arg Leu His Arg Phe
2120                2125                2130

Ala Pro Pro Cys Lys Pro Leu Leu Arg Glu Glu Val Ser Phe Arg
2135                2140                2145

Val Gly Leu His Glu Tyr Pro Val Gly Ser Gln Leu Pro Cys Glu
2150                2155                2160

Pro Glu Pro Asp Val Ala Val Leu Thr Ser Met Leu Thr Asp Pro
2165                2170                2175

Ser His Ile Thr Ala Glu Ala Ala Gly Arg Arg Leu Ala Arg Gly
2180                2185                2190

Ser Pro Pro Ser Met Ala Ser Ser Ser Ala Ser Gln Leu Ser Ala
2195                2200                2205
```

```
Pro Ser Leu Lys Ala Thr Cys Thr Ala Asn His Asp Ser Pro Asp
    2210                2215                2220

Ala Glu Leu Ile Glu Ala Asn Leu Leu Trp Arg Gln Glu Met Gly
    2225                2230                2235

Gly Asn Ile Thr Arg Val Glu Ser Glu Asn Lys Val Val Ile Leu
    2240                2245                2250

Asp Ser Phe Asp Pro Leu Val Ala Glu Glu Asp Glu Arg Glu Val
    2255                2260                2265

Ser Val Pro Ala Glu Ile Leu Arg Lys Ser Arg Arg Phe Ala Arg
    2270                2275                2280

Ala Leu Pro Val Trp Ala Arg Pro Asp Tyr Asn Pro Pro Leu Val
    2285                2290                2295

Glu Thr Trp Lys Lys Pro Asp Tyr Glu Pro Pro Val Val His Gly
    2300                2305                2310

Cys Pro Leu Pro Pro Arg Ser Pro Pro Val Pro Pro Pro Arg
    2315                2320                2325

Lys Lys Arg Thr Val Val Leu Thr Glu Ser Thr Leu Ser Thr Ala
    2330                2335                2340

Leu Ala Glu Leu Ala Thr Lys Ser Phe Gly Ser Ser Ser Thr Ser
    2345                2350                2355

Gly Ile Thr Gly Asp Asn Thr Thr Thr Ser Ser Glu Pro Ala Pro
    2360                2365                2370

Ser Gly Cys Pro Pro Asp Ser Asp Val Glu Ser Tyr Ser Ser Met
    2375                2380                2385

Pro Pro Leu Glu Gly Glu Pro Gly Asp Pro Asp Leu Ser Asp Gly
    2390                2395                2400

Ser Trp Ser Thr Val Ser Ser Gly Ala Asp Thr Glu Asp Val Val
    2405                2410                2415

Cys Cys Ser Met Ser Tyr Ser Trp Thr Gly Ala Leu Val Thr Pro
    2420                2425                2430

Cys Ala Ala Glu Glu Gln Lys Leu Pro Ile Asn Ala Leu Ser Asn
    2435                2440                2445

Ser Leu Leu Arg His His Asn Leu Val Tyr Ser Thr Thr Ser Arg
    2450                2455                2460

Ser Ala Cys Gln Arg Gln Lys Lys Val Thr Phe Asp Arg Leu Gln
    2465                2470                2475

Val Leu Asp Ser His Tyr Gln Asp Val Leu Lys Glu Val Lys Ala
    2480                2485                2490

Ala Ala Ser Lys Val Lys Ala Asn Leu Leu Ser Val Glu Glu Ala
    2495                2500                2505

Cys Ser Leu Thr Pro Pro His Ser Ala Lys Ser Lys Phe Gly Tyr
    2510                2515                2520

Gly Ala Lys Asp Val Arg Cys His Ala Arg Lys Ala Val Ala His
    2525                2530                2535

Ile Asn Ser Val Trp Lys Asp Leu Leu Glu Asp Ser Val Thr Pro
    2540                2545                2550

Ile Asp Thr Thr Ile Met Ala Lys Asn Glu Val Phe Cys Val Gln
    2555                2560                2565

Pro Glu Lys Gly Gly Arg Lys Pro Ala Arg Leu Ile Val Phe Pro
    2570                2575                2580

Asp Leu Gly Val Arg Val Cys Glu Lys Met Ala Leu Tyr Asp Val
    2585                2590                2595

Val Ser Lys Leu Pro Leu Ala Val Met Gly Ser Ser Tyr Gly Phe
```

```
                    2600                2605                2610
Gln Tyr  Ser Pro Gly Gln Arg  Val Glu Phe Leu Val  Gln Ala Trp
    2615                2620                2625
Lys Ser  Lys Lys Thr Pro Met  Gly Phe Ser Tyr Asp  Thr Arg Cys
    2630                2635                2640
Phe Asp  Ser Thr Val Thr Glu  Ser Asp Ile Arg Thr  Glu Glu Ala
    2645                2650                2655
Ile Tyr  Gln Cys Cys Asp Leu  Asp Pro Gln Ala Arg  Val Ala Ile
    2660                2665                2670
Lys Ser  Leu Thr Glu Arg Leu  Tyr Val Gly Gly Pro  Leu Thr Asn
    2675                2680                2685
Ser Arg  Gly Glu Asn Cys Gly  Tyr Arg Arg Cys Arg  Ala Ser Gly
    2690                2695                2700
Val Leu  Thr Thr Ser Cys Gly  Asn Thr Leu Thr Cys  Tyr Ile Lys
    2705                2710                2715
Ala Arg  Ala Ala Cys Arg Ala  Ala Gly Leu Gln Asp  Cys Thr Met
    2720                2725                2730
Leu Val  Cys Gly Asp Asp Leu  Val Val Ile Cys Glu  Ser Ala Gly
    2735                2740                2745
Val Gln  Glu Asp Ala Ala Ser  Leu Arg Ala Phe Thr  Glu Ala Met
    2750                2755                2760
Thr Arg  Tyr Ser Ala Pro Pro  Gly Asp Pro Pro Gln  Pro Glu Tyr
    2765                2770                2775
Asp Leu  Glu Leu Ile Thr Ser  Cys Ser Ser Asn Val  Ser Val Ala
    2780                2785                2790
His Asp  Gly Ala Gly Lys Arg  Val Tyr Tyr Leu Thr  Arg Asp Pro
    2795                2800                2805
Thr Thr  Pro Leu Ala Arg Ala  Ala Trp Glu Thr Ala  Arg His Thr
    2810                2815                2820
Pro Val  Asn Ser Trp Leu Gly  Asn Ile Ile Met Phe  Ala Pro Thr
    2825                2830                2835
Leu Trp  Ala Arg Met Ile Leu  Met Thr His Phe Phe  Ser Val Leu
    2840                2845                2850
Ile Ala  Arg Asp Gln Leu Glu  Gln Ala Leu Asn Cys  Glu Ile Tyr
    2855                2860                2865
Gly Ala  Cys Tyr Ser Ile Glu  Pro Leu Asp Leu Pro  Pro Ile Ile
    2870                2875                2880
Gln Arg  Leu His Gly Leu Ser  Ala Phe Ser Leu His  Ser Tyr Ser
    2885                2890                2895
Pro Gly  Glu Ile Asn Arg Val  Ala Ala Cys Leu Arg  Lys Leu Gly
    2900                2905                2910
Val Pro  Pro Leu Arg Ala Trp  Arg His Arg Ala Arg  Ser Val Arg
    2915                2920                2925
Ala Arg  Leu Leu Ser Arg Gly  Gly Arg Ala Ala Ile  Cys Gly Lys
    2930                2935                2940
Tyr Leu  Phe Asn Trp Ala Val  Arg Thr Lys Leu Lys  Leu Thr Pro
    2945                2950                2955
Ile Ala  Ala Ala Gly Arg Leu  Asp Leu Ser Gly Trp  Phe Thr Ala
    2960                2965                2970
Gly Tyr  Ser Gly Gly Asp Ile  Tyr His Ser Val Ser  His Ala Arg
    2975                2980                2985
Pro Arg  Trp Phe Trp Phe Cys  Leu Leu Leu Leu Ala  Ala Gly Val
    2990                2995                3000
```

Gly Ile Tyr Leu Leu Pro Asn Arg
     3005              3010

<210> SEQ ID NO 3
<211> LENGTH: 9416
<212> TYPE: DNA
<213> ORGANISM: Artificial Sequence
<220> FEATURE:
<223> OTHER INFORMATION: Nucleotide sequence of Hepatitis C virus
      strain H

<400> SEQUENCE: 3

| | | | | | |
|---|---|---|---|---|---|
| gccagccccc | tgatggggc | gacactccac | catgaatcac | tccctgtga | ggaactactg | 60 |
| tcttcacgca | gaaagcgtct | agccatggcg | ttagtatgag | tgtcgtgcag | cctccaggac | 120 |
| ccccctccc | gggagagcca | tagtggtctg | cggaaccggt | gagtacaccg | gaattgccag | 180 |
| gacgaccggg | tcctttcttg | gataaaccg | ctcaatgcct | ggagatttgg | gcgtgccccc | 240 |
| gcaagactgc | tagccgagta | gtgttgggtc | gcgaaaggcc | ttgtggtact | gcctgatagg | 300 |
| gtgcttgcga | gtgccccggg | aggtctcgta | gaccgtgcac | catgagcacg | aatcctaaac | 360 |
| ctcaaagaaa | aaccaaacgt | aacaccaacc | gtcgcccaca | ggacgtcaag | ttcccgggtg | 420 |
| gcggtcagat | cgttggtgga | gtttacttgt | tgccgcgcag | gggccctaga | ttgggtgtgc | 480 |
| gcgcgacgag | gaagacttcc | gagcggtcgc | aacctcgagg | tagacgtcag | cctatcccca | 540 |
| aggcacgtcg | gcccgagggc | aggacctggg | ctcagcccgg | gtaccttgg | ccctctatg | 600 |
| gcaatgaggg | ttgcgggtgg | gcgggatggc | tcctgtctcc | ccgtggctct | cggcctagct | 660 |
| ggggccccac | agaccccgg | cgtaggtcgc | gcaatttggg | taaggtcatc | gataccctta | 720 |
| cgtgcggctt | cgccgacctc | atggggtaca | taccgctcgt | cggcgcccct | cttggaggcg | 780 |
| ctgccagggc | cctggcgcat | ggcgtccggg | ttctggaaga | cggcgtgaac | tatgcaacag | 840 |
| ggaaccttcc | tggttgctct | ttctctatct | tccttctggc | cctgctctct | tgcctgactg | 900 |
| tgcccgcttc | agcctaccaa | gtgcgcaatt | cctcgggct | ttaccatgtc | accaatgatt | 960 |
| gccctaactc | gagtgttgtg | tacgaggcgg | ccgatgccat | cctgcacact | ccggggtgtg | 1020 |
| tcccttgcgt | tcgcgagggt | aacgcctcga | ggtgttgggt | ggcggtgacc | ccacggtgg | 1080 |
| ccaccaggga | cggcaaactc | cccacaacgc | agcttcgacg | tcatatcgat | ctgcttgtcg | 1140 |
| ggagcgccac | cctctgctcg | gccctctacg | tgggggacct | gtgcgggtct | gtctttcttg | 1200 |
| ttggtcaact | gtttaccttc | tctcccaggc | accactggac | gacgcaagac | tgcaattgtt | 1260 |
| ctatctatcc | cggccatata | acgggtcatc | gcatggcatg | gaatatgatg | atgaactggt | 1320 |
| cccctacggc | agcgttggtg | gtagctcagc | tgctccgaat | cccacaagcc | atcatggaca | 1380 |
| tgatcgctgg | cgcccactgg | ggagtcctgg | cgggcataaa | gtatttctcc | atggtgggga | 1440 |
| actgggcgaa | ggtcctggta | gtgctgctgc | tatttgccgg | cgtcgacgcg | gaaacccacg | 1500 |
| tcaccggggg | aaatgccggc | cgcaccacg | ctgggcttgt | tggtctccctt | acaccaggcg | 1560 |
| ccaagcagaa | catccaactg | atcaacacca | acggcagttg | gcacatcaat | agcacggcct | 1620 |
| tgaactgcaa | tgaaagcctt | aacaccggct | ggttagcagg | gctcttctat | cagcacaaat | 1680 |
| tcaactcttc | aggctgtcct | gagaggttgg | ccagctgccg | acgccttacc | gattttgccc | 1740 |
| agggctgggg | tcctatcagt | tatgccaacg | gaagcggcct | cgacgaacgc | ccctactgct | 1800 |
| ggcactaccc | tccaagacct | gtggcattg | tgcccgcaaa | gagcgtgtgt | ggcccggtat | 1860 |
| attgcttcac | tccagccccc | gtggtggtgg | gaacgaccga | caggtcgggc | gcgcctacct | 1920 |
| acagctgggg | tgcaaatgat | acggatgtct | tcgtccttaa | caacaccagg | ccaccgctgg | 1980 |

```
gcaattggtt cggttgtacc tggatgaact caactggatt caccaaagtg tgcggagcgc    2040 cccccttgtgt catcggaggg gtgggcaaca acaccttgct ctgccccact gattgcttcc    2100
gcaaatatcc ggaagccaca tactctcggt gcggctccgg tcccaggatt acacccaggt    2160
gcatggtcga ctacccgtat aggctttggc actatccttg taccatcaat tacaccatat    2220
tcaaagtcag gatgtacgtg ggaggggtcg agcacaggct ggaagcggcc tgcaactgga    2280
cgcggggcga acgctgtgat ctggaagaca gggacaggtc cgagctcagc ccgttgctgc    2340
tgtccaccac acagtggcag gtccttccgt gttctttcac gaccctgcca gccttgtcca    2400
ccggcctcat ccacctccac cagaacattg tggacgtgca gtacttgtac ggggtagggt    2460
caagcatcgc gtcctgggcc attaagtggg agtacgtcgt tctcctgttc cttctgcttg    2520
cagacgcgcg cgtctgttcc tgcttgtgga tgatgttact catatcccaa gcggaggcgg    2580
ctttggagaa cctcgtaata ctcaatgcag catccctggc cgggacgcat ggtcttgtgt    2640
ccttcctcgt gttcttctgc tttgcgtggt atctgaaggg taggtgggtg cccggagcgg    2700
tctacgccct ctacgggatg tggcctctcc tcctgctcct gctggcgttg cctcagcggg    2760
catacgcact ggacacggag gtggccgcgt cgtgtggcgg cgttgttctt gtcgggttaa    2820
tggcgctgac tctgtcgcca tattacaagc gctatatcag ctggtgcatg tggtggcttc    2880
agtattttct gaccagagta gaagcgcaac tgcacgtgtg ggttcccccc ctcaacgtcc    2940 gggggggggcg cgatgccgtc atcttactca cgtgtgtagt acacccggcc ctggtatttg    3000
acatcaccaa actactcctg gccatcttcg accccttttg gattcttcaa gccagttttgc    3060 ttaaagtccc ctacttcgtg cgcgttcaag gccttctccg gatctgcgcg ctagcgcgga    3120
agatagccgg aggtcattac gtgcaaatgg ccatcatcaa gttagggggcg cttactggca    3180 cctgtgtgta taaccatctc gctcctcttc gagactgggc gcacaacggc ctgcgagatc    3240
tggccgtggc tgtggaacca gtcgtcttct cccgaatgga gaccaagctc atcacgtggg    3300
gggcagatac cgccgcgtgc ggtgacatca tcaacggctt gcccgtctct gcccgtaggg    3360
gccaggagat actgcttggg ccagccgacg gaatggtctc caaggggtgg aggttgctgg    3420
cgcccatcac ggcgtacgcc cagcagacga gaggcctcct agggtgtata atcaccagcc    3480
tgactggccg ggacaaaaac caagtggagg gtgaggtcca gatcgtgtca actgctaccc    3540
agaccttcct ggcaacgtgc atcaatgggt atgctggac tgtctaccac ggggccggaa    3600
cgaggaccat cgcatcaccc aagggtcctg tcatccagac gtataccaat gtggatcaag    3660
acctcgtggg ctggccccgct cctcaaggtt cccgctcatt gacaccctgc acctgcggct    3720
cctcggacct ttacctggtc acgaggcacg ccgatgtcat tcccgtgcgc cggcgaggtg    3780
atagcagggg tagcctgctt tcgccccggc ccatttccta cttgaaaggc tcctcggggg    3840
gtccgctgtt gtgccccacg ggacacgccg tgggcctatt cagggccgcg gtgtgcaccc    3900
gtggagtggc taaggcggtg gactttatcc ctgtggagaa cctagagaca accatgagat    3960
ccccggtgtt cacggacaac tcctctccac cagcagtgcc ccagagcttc caggtggccc    4020
acctgcatgc tccaccggc agcggtaaga gcaccaaggt cccggctgcg tacgcagcca    4080
agggctacaa ggtgttggtg ctcaaccccct ctgttgctgc aacactgggc tttggtgctt    4140
acatgtccaa ggcccatggg gttgatccta atatcaggac cggggtgaga acaattacca    4200
ctggcagccc catcacgtac tccacctacg gcaagttcct tgccgacgcc gggtgctcag    4260
gaggtgctta tgacataata atttgtgacg agtgccactc cacggatgcc acatccatct    4320
cgggcatcgg cactgtcctt gaccaagcag agactgcggg ggcgagactg gttgtgctcg    4380
```

-continued

```
ccactgctac ccctccgggc tccgtcactg tgtcccatcc taacatcgag gaggttgctc    4440
tgtccaccac cggagagatc cccttttacg gcaaggctat cccctcgag  gtgatcaagg    4500
ggggaagaca tctcatcttc tgccactcaa agaagaagtg cgacgagctc gccgcgaagc    4560
tggtcgcatt gggcatcaat gccgtggcct actaccgcgg tcttgacgtg tctgtcatcc    4620
cgaccagcgg cgatgttgtc gtcgtgtcga ccgatgctct catgactggc tttaccggcg    4680
acttcgactc tgtgatagac tgcaacacgt gtgtcactca gacagtcgat tttagccttg    4740
accctacctt taccattgag acaaccacgc tcccccagga tgctgtctcc aggactcaac    4800
gccggggcag gactggcagg gggaagccag gcatctatag atttgtggca ccggggagc     4860
gcccctccgg catgttcgac tcgtccgtcc tctgtgagtg ctatgacgcg ggctgtgctt    4920
ggtatgagct cacgcccgcc gagactacag ttaggctacg agcgtacatg aacaccccgg    4980
ggcttcccgt gtgccaggac catcttggat tttgggaggg cgtctttacg ggcctcactc    5040
atatagatgc ccacttttcta tcccagacaa agcagagtgg ggagaacttt ccttacctgg   5100
tagcgtacca agccaccgtg tgcgctaggg ctcaagcccc tcccccatcg tgggaccaga    5160
tgcggaagtg ttttgatccgc cttaaaccca ccctccatgg ccaacaccc  ctgctataca    5220
gactgggcgc tgttcagaat gaagtcaccc tgacgcaccc aatcaccaaa tacatcatga    5280
catgcatgtc ggccgacctg gaggtcgtca cgagcacctg ggtgctcgtt ggcggcgtcc    5340
tggctgctct ggccgcgtat tgcctgtcaa caggctgcgt ggtcatagtg ggcaggatcg    5400
tcttgtccgg gaagccggca attataacctg acagggaggt tctctaccag gagttcgatg   5460
agatggaaga gtgctctcag cacttaccgt acatcgagca agggatgatg ctcgctgagc    5520
agttcaagca gaaggccctc ggcctcctgc agaccgcgtc ccgccatgca gaggttatca    5580
cccctgctgt ccagaccaac tggcagaaac tcgaggtctt ttgggcgaag cacatgtgga    5640
atttcatcag tgggatacaa tacttggcgg gcctgtcaac gctgcctggt aaccccgcca    5700
ttgcttcatt gatggcttttt acagctgccg tcaccagccc actaaccact ggccaaaccc   5760
tcctcttcaa catattgggg gggtgggtgg ctgcccagct cgccgccccc ggtgccgcta    5820
ccgccttttgt gggcgctggc ttagctgcgc ccgcactcga cagcgttgga ctggggaagg   5880
tcctcgtgga cattcttgca ggctatggcg cgggcgtggc gggagctctt gtggcattca    5940
agatcatgag cggtgaggtc ccctccacgg aggacctggt caatctgctg cccgccatcc    6000
tctcacctgg agcccttgca gtcggtgtgg tctttgcatc aatactgcgc cggcgtgttg    6060
gcccgggcga ggggcagtg  caatggatga accggctaat agccttcgcc tcccggggga    6120
accatgtttc ccccacacac tacgtgccgg agagcgatgc agccgcccgc gtcactgcca    6180
tactcagcag cctcactgta acccagctcc tgaggcgact gcatcagtgg ataagctcgg    6240
agtgtaccac tccatgctcc ggttcctggc taagggacat ctgggactgg atatgcgagg    6300
tgctgagcga ctttaagacc tggctgaaag ccaagctcat gccacaactg cctgggattc    6360
cctttgtgtc ctgccagcgc gggtataggg gggtctggcg aggagacggc attatgcaca    6420
ctcgctgcca ctgtggagct gagatcactg gacatgtcaa aaacgggacg atgaggatcg    6480
tcggtcctag gacctgcaag aacatgtgga gtgggacgtt cttcattaat gcctacacca    6540
cgggcccctg tactccccctt cctgcgccga actataagtt cgcgctgtgg agggtgtctg    6600
cagaggaata cgtggagata aggcgggtgg gggacttcca ctacgtatcg gcatgactac    6660
ctgacaatct caaatgcccg tgccagatcc catcgcccga ttttttcaca gaattggacg    6720
gggtgcgcct acataggttt gcgccccctt gcaagcccct gctgcgggag gaggtatcat    6780
```

```
tcagagtagg actccacgag tacccggtgg ggtcgcaatt accttgcgag cccgaaccgg    6840
acgtagccgt gttgacgtcc atgctcactg atccctccca tataacagca gaggcggccg    6900
ggagaaggtt ggcgagaggg tcaccccctt ctatggccag ctcctcggct agccagctgt    6960
ccgctccatc tctcaaggca acttgcaccg ccaaccatga ctcccctgac gccgagctca    7020
tagaggctaa cctcctgtgg aggcaggaga tgggcggcaa catcaccagg gttgagtcag    7080
agaacaaagt ggtgattctg gactccttcg atccgcttgt ggcagaggag gatgagcggg    7140
aggtctccgt acccgcagaa attctgcgga gtctcggag attcgcccca gccctgcccg    7200
tctgggcgcg gccggactac aaccccctgc tagtagagac gtggaaaaag cctgactacg    7260
aaccacctgt ggtccatggc tgcccgctac cacctccacg gtcccctcct gtgcctccgc    7320
ctcggaaaaa gcgtacggtg gtcctcaccg aatcaaccct acctactgcc ttggccgagc    7380
ttgccaccaa aagttttggc agctcctcaa cttccggcat tacgggcgac aatacgacaa    7440
catcctctga gcccgcccct tctggctgcc ccccgactc cgacgttgag tcctattctt    7500
ccatgccccc cctggagggg gagcctgggg atccggatct cagcgacggg tcatggtcga    7560
cggtcagtag tgggccgac acggaagatg tcgtgtgctg ctcaatgtct tattcctgga    7620
caggcgcact cgtcaccccg tgcgctgcgg aggaacaaaa actgcccatc aacgcactga    7680
gcaactcgtt gctacgccat cacaatctgg tgtattccac cacttcacgc agtgcttgcc    7740
aaaggaagaa gaaagtcaca tttgacagac tgcaagttct ggacagccat taccaggacg    7800
tgctcaagga ggtcaaagca gcggcgtcaa aagtgaaggc taacttgcta tccgtagagg    7860
aagcttgcag cctggcgccc ccacattcag ccaaatccaa gtttggctat ggggcaaaag    7920
acgtccgttg ccatgccaga aaggccgtag cccacatcaa ctccgtgtgg aaagaccttc    7980
tggaagacag tgtaacacca atagacacta ccatcatggc caagaacgag gttttctgcg    8040
ttcagcctga aaggggggt cgtaagccag ctcgtctcat cgtgttcccc gacctgggcg    8100
tgcgcgtgtg cgagaagatg gccctgtacg acgtggttag caagctcccc ttggccgtga    8160
tgggaagctc ctacggattc caatactcac caggacagcg ggttgaattc ctcgtgcaag    8220
cgtggaagtc caagaagacc ccgatggggc tctcgtatga tacccgctgt tttgactcca    8280
cagtcactga gagcgacatc cgtacggagg aggcaatttta ccaatgttgt gacctggacc    8340
cccaagcccg cgtggccatc aagtccctca ctgagaggct ttatgttggg ggccctctta    8400
ctaattcaag gggggaaaac tgcggctacc gcaggtgccg cgcgagcaga gtactgacaa    8460
ctagctgtgg taacaccctc actcgctaca tcaaggcccg ggcagcctgt cgagccgcag    8520
ggctccagga ctgcaccatg ctcgtgtgtg cgacgactt agtcgttatc tgtgaaagtg    8580
cgggggtcca ggaggacgcg gcgagcctga gagccttcac ggaggctatg accaggtact    8640 ccgcccccc cggggacccc ccacaaccag aatacgactt ggagcttata acatcatgct    8700
cctccaacgt gtcagtcgcc cacgacgcg ctggaaagag ggtctactac cttacccgtg    8760
accctacaac ccccctcgcg agagccgcgt gggagacagc aagacacact ccagtcaatt    8820
cctggctagg caacataatc atgtttgccc ccacactgtg ggcgaggatg atactgatga    8880
cccacttctt tagcgtcctc atagccaggg atcagcttga acaggctctc aactgcgaga    8940 tctacgagc ctgctactcc atagaaccac tggatctacc tccaatcatt caaagactcc    9000
atggcctcag cgcattttca ctccacagtt actctccagg tgaaattaat agggtggccg    9060
catgcctcag aaaacttggg gtcccgcct tgcgagcttg gagacaccgg gcctggagcg    9120
tccgcgctag gcttctggcc agaggaggca aggctgccat atgtggcaag tacctcttca    9180
```

```
actgggcagt aagaacaaag ctcaaactca ctccgataac ggccgctggc cggctggact    9240
tgtccggctg gttcacggct ggctacagcg ggggagacat ttatcacagc gtgtctcatg    9300
cccggccccg ctggttctgg ttttgcctac tcctgcttgc tgcaggggta ggcatctacc    9360
tcctccccaa ccgatgaaga ttgggctaac cactccaggc caataggcca ttccct        9416
```

<210> SEQ ID NO 4
<211> LENGTH: 3011
<212> TYPE: PRT
<213> ORGANISM: Artificial Sequence
<220> FEATURE:
<223> OTHER INFORMATION: Amino acid sequence of HCV polyprotein
      encoded by nucleotides 342 - 9377 of SEQ ID NO:3.

<400> SEQUENCE: 4

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Val Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg His His Trp Thr Thr Gln Asp Cys
    290                 295                 300

Asn Cys Ser Ile Tyr Pro Gly His Ile Thr Gly His Arg Met Ala Trp
305                 310                 315                 320

Asn Met Met Met Asn Trp Ser Pro Thr Ala Ala Leu Val Val Ala Gln
```

```
                    325                 330                 335
Leu Leu Arg Ile Pro Gln Ala Ile Met Asp Met Ile Ala Gly Ala His
                340                 345                 350

Trp Gly Val Leu Ala Gly Ile Lys Tyr Phe Ser Met Val Gly Asn Trp
                355                 360                 365

Ala Lys Val Leu Val Leu Leu Phe Ala Gly Val Asp Ala Glu
370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
                420                 425                 430

Leu Asn Thr Gly Trp Leu Ala Gly Leu Phe Tyr Gln His Lys Phe Asn
                435                 440                 445

Ser Ser Gly Cys Pro Glu Arg Leu Ala Ser Cys Arg Arg Leu Thr Asp
                450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Arg Pro Cys Gly Ile
                485                 490                 495

Val Pro Ala Lys Ser Val Cys Gly Pro Val Tyr Cys Phe Thr Pro Ser
                500                 505                 510

Pro Val Val Val Gly Thr Thr Asp Arg Ser Gly Ala Pro Thr Tyr Ser
                515                 520                 525

Trp Gly Ala Asn Asp Thr Asp Val Phe Val Leu Asn Asn Thr Arg Pro
530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Val Gly Asn
                565                 570                 575

Asn Thr Leu Leu Cys Pro Thr Asp Cys Phe Arg Lys Tyr Pro Glu Ala
                580                 585                 590

Thr Tyr Ser Arg Cys Gly Ser Gly Pro Arg Ile Thr Pro Arg Cys Met
                595                 600                 605

Val Asp Tyr Pro Tyr Arg Leu Trp His Tyr Pro Cys Thr Ile Asn Tyr
                610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
                660                 665                 670

Gln Val Leu Pro Cys Ser Phe Thr Thr Leu Pro Ala Leu Ser Thr Gly
                675                 680                 685

Leu Ile His Leu His Gln Asn Ile Val Asp Val Gln Tyr Leu Tyr Gly
                690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
                740                 745                 750
```

-continued

```
Ile Leu Asn Ala Ala Ser Leu Ala Gly Thr His Gly Leu Val Ser Phe
        755                 760                 765
Leu Val Phe Phe Cys Phe Ala Trp Tyr Leu Lys Gly Arg Trp Val Pro
770                 775                 780
Gly Ala Val Tyr Ala Leu Tyr Gly Met Trp Pro Leu Leu Leu Leu Leu
785                 790                 795                 800
Leu Ala Leu Pro Gln Arg Ala Tyr Ala Leu Asp Thr Glu Val Ala Ala
                805                 810                 815
Ser Cys Gly Gly Val Val Leu Val Gly Leu Met Ala Leu Thr Leu Ser
                820                 825                 830
Pro Tyr Tyr Lys Arg Tyr Ile Ser Trp Cys Met Trp Trp Leu Gln Tyr
                835                 840                 845
Phe Leu Thr Arg Val Glu Ala Gln Leu His Val Trp Val Pro Pro Leu
850                 855                 860
Asn Val Arg Gly Gly Arg Asp Ala Val Ile Leu Leu Thr Cys Val Val
865                 870                 875                 880
His Pro Ala Leu Val Phe Asp Ile Thr Lys Leu Leu Leu Ala Ile Phe
                    885                 890                 895
Gly Pro Leu Trp Ile Leu Gln Ala Ser Leu Leu Lys Val Pro Tyr Phe
            900                 905                 910
Val Arg Val Gln Gly Leu Leu Arg Ile Cys Ala Leu Ala Arg Lys Ile
            915                 920                 925
Ala Gly Gly His Tyr Val Gln Met Ala Ile Ile Lys Leu Gly Ala Leu
930                 935                 940
Thr Gly Thr Cys Val Tyr Asn His Leu Ala Pro Leu Arg Asp Trp Ala
945                 950                 955                 960
His Asn Gly Leu Arg Asp Leu Ala Val Ala Val Glu Pro Val Val Phe
                965                 970                 975
Ser Arg Met Glu Thr Lys Leu Ile Thr Trp Gly Ala Asp Thr Ala Ala
                980                 985                 990
Cys Gly Asp Ile Ile Asn Gly Leu Pro Val Ser Ala Arg Arg Gly Gln
            995                 1000                1005
Glu Ile Leu Leu Gly Pro Ala Asp Gly Met Val Ser Lys Gly Trp
    1010                1015                1020
Arg Leu Leu Ala Pro Ile Thr Ala Tyr Ala Gln Gln Thr Arg Gly
    1025                1030                1035
Leu Leu Gly Cys Ile Ile Thr Ser Leu Thr Gly Arg Asp Lys Asn
    1040                1045                1050
Gln Val Glu Gly Glu Val Gln Ile Val Ser Thr Ala Thr Gln Thr
    1055                1060                1065
Phe Leu Ala Thr Cys Ile Asn Gly Val Cys Trp Thr Val Tyr His
    1070                1075                1080
Gly Ala Gly Thr Arg Thr Ile Ala Ser Pro Lys Gly Pro Val Ile
    1085                1090                1095
Gln Thr Tyr Thr Asn Val Asp Gln Asp Leu Val Gly Trp Pro Ala
    1100                1105                1110
Pro Gln Gly Ser Arg Ser Leu Thr Pro Cys Thr Cys Gly Ser Ser
    1115                1120                1125
Asp Leu Tyr Leu Val Thr Arg His Ala Asp Val Ile Pro Val Arg
    1130                1135                1140
Arg Arg Gly Asp Ser Arg Gly Ser Leu Leu Ser Pro Arg Pro Ile
    1145                1150                1155
Ser Tyr Leu Lys Gly Ser Ser Gly Gly Pro Leu Leu Cys Pro Thr
    1160                1165                1170
```

```
Gly His Ala Val Gly Leu Phe Arg Ala Ala Val Cys Thr Arg Gly
        1175                1180                1185

Val Ala Lys Ala Val Asp Phe Ile Pro Val Glu Asn Leu Glu Thr
        1190                1195                1200

Thr Met Arg Ser Pro Val Phe Thr Asp Asn Ser Ser Pro Pro Ala
        1205                1210                1215

Val Pro Gln Ser Phe Gln Val Ala His Leu His Ala Pro Thr Gly
        1220                1225                1230

Ser Gly Lys Ser Thr Lys Val Pro Ala Ala Tyr Ala Ala Lys Gly
        1235                1240                1245

Tyr Lys Val Leu Val Leu Asn Pro Ser Val Ala Ala Thr Leu Gly
        1250                1255                1260

Phe Gly Ala Tyr Met Ser Lys Ala His Gly Val Asp Pro Asn Ile
        1265                1270                1275

Arg Thr Gly Val Arg Thr Ile Thr Thr Gly Ser Pro Ile Thr Tyr
        1280                1285                1290

Ser Thr Tyr Gly Lys Phe Leu Ala Asp Ala Gly Cys Ser Gly Gly
        1295                1300                1305

Ala Tyr Asp Ile Ile Ile Cys Asp Glu Cys His Ser Thr Asp Ala
        1310                1315                1320

Thr Ser Ile Ser Gly Ile Gly Thr Val Leu Asp Gln Ala Glu Thr
        1325                1330                1335

Ala Gly Ala Arg Leu Val Val Leu Ala Thr Ala Thr Pro Pro Gly
        1340                1345                1350

Ser Val Thr Val Ser His Pro Asn Ile Glu Glu Val Ala Leu Ser
        1355                1360                1365

Thr Thr Gly Glu Ile Pro Phe Tyr Gly Lys Ala Ile Pro Leu Glu
        1370                1375                1380

Val Ile Lys Gly Gly Arg His Leu Ile Phe Cys His Ser Lys Lys
        1385                1390                1395

Lys Cys Asp Glu Leu Ala Ala Lys Leu Val Ala Leu Gly Ile Asn
        1400                1405                1410

Ala Val Ala Tyr Tyr Arg Gly Leu Asp Val Ser Val Ile Pro Thr
        1415                1420                1425

Ser Gly Asp Val Val Val Val Ser Thr Asp Ala Leu Met Thr Gly
        1430                1435                1440

Phe Thr Gly Asp Phe Asp Ser Val Ile Asp Cys Asn Thr Cys Val
        1445                1450                1455

Thr Gln Thr Val Asp Phe Ser Leu Asp Pro Thr Phe Thr Ile Glu
        1460                1465                1470

Thr Thr Thr Leu Pro Gln Asp Ala Val Ser Arg Thr Gln Arg Arg
        1475                1480                1485

Gly Arg Thr Gly Arg Gly Lys Pro Gly Ile Tyr Arg Phe Val Ala
        1490                1495                1500

Pro Gly Glu Arg Pro Ser Gly Met Phe Asp Ser Ser Val Leu Cys
        1505                1510                1515

Glu Cys Tyr Asp Ala Gly Cys Ala Trp Tyr Glu Leu Thr Pro Ala
        1520                1525                1530

Glu Thr Thr Val Arg Leu Arg Ala Tyr Met Asn Thr Pro Gly Leu
        1535                1540                1545

Pro Val Cys Gln Asp His Leu Gly Phe Trp Glu Gly Val Phe Thr
        1550                1555                1560

Gly Leu Thr His Ile Asp Ala His Phe Leu Ser Gln Thr Lys Gln
```

-continued

```
            1565                1570                1575

Ser Gly Glu Asn Phe Pro Tyr Leu Val Ala Tyr Gln Ala Thr Val
1580                1585                1590

Cys Ala Arg Ala Gln Ala Pro Pro Pro Ser Trp Asp Gln Met Arg
1595                1600                1605

Lys Cys Leu Ile Arg Leu Lys Pro Thr Leu His Gly Pro Thr Pro
1610                1615                1620

Leu Leu Tyr Arg Leu Gly Ala Val Gln Asn Glu Val Thr Leu Thr
1625                1630                1635

His Pro Ile Thr Lys Tyr Ile Met Thr Cys Met Ser Ala Asp Leu
1640                1645                1650

Glu Val Val Thr Ser Thr Trp Val Leu Val Gly Gly Val Leu Ala
1655                1660                1665

Ala Leu Ala Ala Tyr Cys Leu Ser Thr Gly Cys Val Val Ile Val
1670                1675                1680

Gly Arg Ile Val Leu Ser Gly Lys Pro Ala Ile Ile Pro Asp Arg
1685                1690                1695

Glu Val Leu Tyr Gln Glu Phe Asp Glu Met Glu Glu Cys Ser Gln
1700                1705                1710

His Leu Pro Tyr Ile Glu Gln Gly Met Met Leu Ala Glu Gln Phe
1715                1720                1725

Lys Gln Lys Ala Leu Gly Leu Leu Gln Thr Ala Ser Arg His Ala
1730                1735                1740

Glu Val Ile Thr Pro Ala Val Gln Thr Asn Trp Gln Lys Leu Glu
1745                1750                1755

Val Phe Trp Ala Lys His Met Trp Asn Phe Ile Ser Gly Ile Gln
1760                1765                1770

Tyr Leu Ala Gly Leu Ser Thr Leu Pro Gly Asn Pro Ala Ile Ala
1775                1780                1785

Ser Leu Met Ala Phe Thr Ala Ala Val Thr Ser Pro Leu Thr Thr
1790                1795                1800

Gly Gln Thr Leu Leu Phe Asn Ile Leu Gly Gly Trp Val Ala Ala
1805                1810                1815

Gln Leu Ala Ala Pro Gly Ala Ala Thr Ala Phe Val Gly Ala Gly
1820                1825                1830

Leu Ala Gly Ala Ala Leu Asp Ser Val Gly Leu Gly Lys Val Leu
1835                1840                1845

Val Asp Ile Leu Ala Gly Tyr Gly Ala Gly Val Ala Gly Ala Leu
1850                1855                1860

Val Ala Phe Lys Ile Met Ser Gly Glu Val Pro Ser Thr Glu Asp
1865                1870                1875

Leu Val Asn Leu Leu Pro Ala Ile Leu Ser Pro Gly Ala Leu Ala
1880                1885                1890

Val Gly Val Val Phe Ala Ser Ile Leu Arg Arg Arg Val Gly Pro
1895                1900                1905

Gly Glu Gly Ala Val Gln Trp Met Asn Arg Leu Ile Ala Phe Ala
1910                1915                1920

Ser Arg Gly Asn His Val Ser Pro Thr His Tyr Val Pro Glu Ser
1925                1930                1935

Asp Ala Ala Ala Arg Val Thr Ala Ile Leu Ser Ser Leu Thr Val
1940                1945                1950

Thr Gln Leu Leu Arg Arg Leu His Gln Trp Ile Ser Ser Glu Cys
1955                1960                1965
```

-continued

Thr Thr Pro Cys Ser Gly Ser Trp Leu Arg Asp Ile Trp Asp Trp
1970            1975                1980

Ile Cys Glu Val Leu Ser Asp Phe Lys Thr Trp Leu Lys Ala Lys
1985            1990                1995

Leu Met Pro Gln Leu Pro Gly Ile Pro Phe Val Ser Cys Gln Arg
2000            2005                2010

Gly Tyr Arg Gly Val Trp Arg Gly Asp Gly Ile Met His Thr Arg
2015            2020                2025

Cys His Cys Gly Ala Glu Ile Thr Gly His Val Lys Asn Gly Thr
2030            2035                2040

Met Arg Ile Val Gly Pro Arg Thr Cys Lys Asn Met Trp Ser Gly
2045            2050                2055

Thr Phe Phe Ile Asn Ala Tyr Thr Thr Gly Pro Cys Thr Pro Leu
2060            2065                2070

Pro Ala Pro Asn Tyr Lys Phe Ala Leu Trp Arg Val Ser Ala Glu
2075            2080                2085

Glu Tyr Val Glu Ile Arg Arg Val Gly Asp Phe His Tyr Val Ser
2090            2095                2100

Gly Met Thr Thr Asp Asn Leu Lys Cys Pro Cys Gln Ile Pro Ser
2105            2110                2115

Pro Glu Phe Phe Thr Glu Leu Asp Gly Val Arg Leu His Arg Phe
2120            2125                2130

Ala Pro Pro Cys Lys Pro Leu Leu Arg Glu Glu Val Ser Phe Arg
2135            2140                2145

Val Gly Leu His Glu Tyr Pro Val Gly Ser Gln Leu Pro Cys Glu
2150            2155                2160

Pro Glu Pro Asp Val Ala Val Leu Thr Ser Met Leu Thr Asp Pro
2165            2170                2175

Ser His Ile Thr Ala Glu Ala Ala Gly Arg Arg Leu Ala Arg Gly
2180            2185                2190

Ser Pro Pro Ser Met Ala Ser Ser Ser Ala Ser Gln Leu Ser Ala
2195            2200                2205

Pro Ser Leu Lys Ala Thr Cys Thr Ala Asn His Asp Ser Pro Asp
2210            2215                2220

Ala Glu Leu Ile Glu Ala Asn Leu Leu Trp Arg Gln Glu Met Gly
2225            2230                2235

Gly Asn Ile Thr Arg Val Glu Ser Glu Asn Lys Val Val Ile Leu
2240            2245                2250

Asp Ser Phe Asp Pro Leu Val Ala Glu Glu Asp Glu Arg Glu Val
2255            2260                2265

Ser Val Pro Ala Glu Ile Leu Arg Lys Ser Arg Arg Phe Ala Pro
2270            2275                2280

Ala Leu Pro Val Trp Ala Arg Pro Asp Tyr Asn Pro Leu Leu Val
2285            2290                2295

Glu Thr Trp Lys Lys Pro Asp Tyr Glu Pro Pro Val Val His Gly
2300            2305                2310

Cys Pro Leu Pro Pro Arg Ser Pro Pro Val Pro Pro Pro Arg
2315            2320                2325

Lys Lys Arg Thr Val Val Leu Thr Glu Ser Thr Leu Pro Thr Ala
2330            2335                2340

Leu Ala Glu Leu Ala Thr Lys Ser Phe Gly Ser Ser Ser Thr Ser
2345            2350                2355

Gly Ile Thr Gly Asp Asn Thr Thr Thr Ser Ser Glu Pro Ala Pro
2360            2365                2370

-continued

Ser Gly Cys Pro Pro Asp Ser Asp Val Glu Ser Tyr Ser Ser Met
    2375            2380                2385

Pro Pro Leu Glu Gly Glu Pro Gly Asp Pro Asp Leu Ser Asp Gly
    2390            2395                2400

Ser Trp Ser Thr Val Ser Ser Gly Ala Asp Thr Glu Asp Val Val
    2405            2410                2415

Cys Cys Ser Met Ser Tyr Ser Trp Thr Gly Ala Leu Val Thr Pro
    2420            2425                2430

Cys Ala Ala Glu Glu Gln Lys Leu Pro Ile Asn Ala Leu Ser Asn
    2435            2440                2445

Ser Leu Leu Arg His His Asn Leu Val Tyr Ser Thr Thr Ser Arg
    2450            2455                2460

Ser Ala Cys Gln Arg Lys Lys Lys Val Thr Phe Asp Arg Leu Gln
    2465            2470                2475

Val Leu Asp Ser His Tyr Gln Asp Val Leu Lys Glu Val Lys Ala
    2480            2485                2490

Ala Ala Ser Lys Val Lys Ala Asn Leu Leu Ser Val Glu Glu Ala
    2495            2500                2505

Cys Ser Leu Ala Pro Pro His Ser Ala Lys Ser Lys Phe Gly Tyr
    2510            2515                2520

Gly Ala Lys Asp Val Arg Cys His Ala Arg Lys Ala Val Ala His
    2525            2530                2535

Ile Asn Ser Val Trp Lys Asp Leu Leu Glu Asp Ser Val Thr Pro
    2540            2545                2550

Ile Asp Thr Thr Ile Met Ala Lys Asn Glu Val Phe Cys Val Gln
    2555            2560                2565

Pro Glu Lys Gly Gly Arg Lys Pro Ala Arg Leu Ile Val Phe Pro
    2570            2575                2580

Asp Leu Gly Val Arg Val Cys Glu Lys Met Ala Leu Tyr Asp Val
    2585            2590                2595

Val Ser Lys Leu Pro Leu Ala Val Met Gly Ser Ser Tyr Gly Phe
    2600            2605                2610

Gln Tyr Ser Pro Gly Gln Arg Val Glu Phe Leu Val Gln Ala Trp
    2615            2620                2625

Lys Ser Lys Lys Thr Pro Met Gly Leu Ser Tyr Asp Thr Arg Cys
    2630            2635                2640

Phe Asp Ser Thr Val Thr Glu Ser Asp Ile Arg Thr Glu Glu Ala
    2645            2650                2655

Ile Tyr Gln Cys Cys Asp Leu Asp Pro Gln Ala Arg Val Ala Ile
    2660            2665                2670

Lys Ser Leu Thr Glu Arg Leu Tyr Val Gly Gly Pro Leu Thr Asn
    2675            2680                2685

Ser Arg Gly Glu Asn Cys Gly Tyr Arg Arg Cys Arg Ala Ser Arg
    2690            2695                2700

Val Leu Thr Thr Ser Cys Gly Asn Thr Leu Thr Arg Tyr Ile Lys
    2705            2710                2715

Ala Arg Ala Ala Cys Arg Ala Ala Gly Leu Gln Asp Cys Thr Met
    2720            2725                2730

Leu Val Cys Gly Asp Asp Leu Val Val Ile Cys Glu Ser Ala Gly
    2735            2740                2745

Val Gln Glu Asp Ala Ala Ser Leu Arg Ala Phe Thr Glu Ala Met
    2750            2755                2760

Thr Arg Tyr Ser Ala Pro Pro Gly Asp Pro Pro Gln Pro Glu Tyr

```
            2765                2770                2775
Asp Leu Glu Leu Ile Thr Ser Cys Ser Ser Asn Val Ser Val Ala
            2780                2785                2790

His Asp Gly Ala Gly Lys Arg Val Tyr Tyr Leu Thr Arg Asp Pro
            2795                2800                2805

Thr Thr Pro Leu Ala Arg Ala Ala Trp Glu Thr Ala Arg His Thr
            2810                2815                2820

Pro Val Asn Ser Trp Leu Gly Asn Ile Ile Met Phe Ala Pro Thr
            2825                2830                2835

Leu Trp Ala Arg Met Ile Leu Met Thr His Phe Phe Ser Val Leu
            2840                2845                2850

Ile Ala Arg Asp Gln Leu Glu Gln Ala Leu Asn Cys Glu Ile Tyr
            2855                2860                2865

Gly Ala Cys Tyr Ser Ile Glu Pro Leu Asp Leu Pro Pro Ile Ile
            2870                2875                2880

Gln Arg Leu His Gly Leu Ser Ala Phe Ser Leu His Ser Tyr Ser
            2885                2890                2895

Pro Gly Glu Ile Asn Arg Val Ala Ala Cys Leu Arg Lys Leu Gly
            2900                2905                2910

Val Pro Pro Leu Arg Ala Trp Arg His Arg Ala Trp Ser Val Arg
            2915                2920                2925

Ala Arg Leu Leu Ala Arg Gly Gly Lys Ala Ala Ile Cys Gly Lys
            2930                2935                2940

Tyr Leu Phe Asn Trp Ala Val Arg Thr Lys Leu Lys Leu Thr Pro
            2945                2950                2955

Ile Thr Ala Ala Gly Arg Leu Asp Leu Ser Gly Trp Phe Thr Ala
            2960                2965                2970

Gly Tyr Ser Gly Gly Asp Ile Tyr His Ser Val Ser His Ala Arg
            2975                2980                2985

Pro Arg Trp Phe Trp Phe Cys Leu Leu Leu Leu Ala Ala Gly Val
            2990                2995                3000

Gly Ile Tyr Leu Leu Pro Asn Arg
            3005                3010

<210> SEQ ID NO 5
<211> LENGTH: 86
<212> TYPE: PRT
<213> ORGANISM: Artificial Sequence
<220> FEATURE:
<223> OTHER INFORMATION: HIV tat polypeptide

<400> SEQUENCE: 5

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
            85

<210> SEQ ID NO 6
```

```
<211> LENGTH: 14
<212> TYPE: PRT
<213> ORGANISM: Artificial Sequence
<220> FEATURE:
<223> OTHER INFORMATION: NS3 recognition site

<400> SEQUENCE: 6

Gly Ala Asp Thr Glu Asp Val Val Cys Cys Ser Met Ser Tyr
1               5                   10

<210> SEQ ID NO 7
<211> LENGTH: 2239
<212> TYPE: DNA
<213> ORGANISM: Artificial Sequence
<220> FEATURE:
<223> OTHER INFORMATION: Nucleotide sequence of HIV SEAP, HIV long
      terminal repeat (LTR) is depicted at nucleotides 1-719, and
      secretory alkaline phosphatase is encoded by the nucleotides
      748-2239.

<400> SEQUENCE: 7
acctggaaaa acatggagca atcacaagta gcaatacagc agctaccaat gctgcttgtg      60
cctggctaga agcacaagag gaggaggagg tgggttttcc agtcacacct caggtacctt    120
taagaccaat gacttacaag gcagctgtag atcttagcca cttttaaaa gaaaagggg     180 gactggaagg gctaattcac tcccaaagaa gacaagatat ccttgatctg tggatctacc    240
acacacaagg ctacttccct gattagcaga actacacacc agggccaggg gtcagatatc    300
cactgacctt tggatggtgc tacaagctag taccagttga gccagataag atagaagagg    360
ccaataaagg agagaacacc agcttgttac accctgtgag cctgcatggg atggatgacc    420
cggagagaga agtgttagag tggaggtttg acagccgcct agcatttcat cacgtggccc    480
gagagctgca tccggagtac ttcaagaact gctgacatcg agcttgctac aagggacttt    540
ccgctgggga ctttccaggg aggcgtggcc tgggcgggac tggggagtgg cgagccctca    600
gatcctgcat ataagcagct gcttttgcc tgtactgggt ctctctggtt agaccagatc    660
tgagcctggg agctctctgg ctaactaggg aacccactgc ttaagcctca ataaagcttc    720
tgcatgctgc tgctgctgct gctgctgggc ctgaggctac agctctccct gggcatcatc    780
ccagttgagg aggagaaccc ggacttctgg aaccgcgagg cagccgaggc cctgggtgcc    840
gccaagaagc tgcagcctgc acagacagcc gccaagaacc tcatcatctt cctgggcgat    900
gggatggggg tgtctacggt gacagctgcc aggatcctaa aagggcagaa gaaggacaaa    960
ctggggcctg agatacccct ggccatggac cgcttccat atgtggctct gtccaagaca   1020
tacaatgtag acaaacatgt gccagacagt ggagccacag ccacggccta cctgtgcggg   1080
gtcaagggca acttccagac cattggcttg agtgcagccg cccgctttaa ccagtgcaac   1140
acgacacgcg gcaacgaggt catctccgtg atgaatcggg ccaagaaagc agggaagtca   1200
gtgggagtgg taaccaccac acgagtgcag cacgcctcgc cagccggcac ctacgcccac   1260
acggtgaacc gcaactggta ctcggacgcc gacgtgcctg cctcggcccg ccaggagggg   1320
tgccaggaca tcgctacgca gctcatctcc aacatggaca ttgacgtgat cctaggtgga   1380
ggccgaaagt acatgttttc catgggaacc ccagaccctg agtacccaga tgactacagc   1440
caaggtggga ccaggctgga cggaagaat ctggtgcagg aatggctggc gaagcgccag   1500
ggtgcccggt atgtgtggaa ccgcactgag ctcatgcagg cttccctgga cccgtctgtg   1560
acccatctca tgggtctctt tgagcctgga gacatgaaat acgagatcca ccgagactcc   1620
acactggacc cctcccctga tggagatgaca gaggctgccc tgcgcctgct gagcaggaac   1680
```

-continued

```
ccccgcggct tcttcctctt cgtggagggt ggtcgcatcg accatggtca tcatgaaagc   1740
agggcttacc gggcactgac tgagacgatc atgttcgacg acgccattga gagggcgggc   1800
cagctcacca gcgaggagga cacgctgagc ctcgtcactg ccgaccactc ccacgtcttc   1860
tccttcggag gctacccccct gcgagggagc tccatcttcg ggctggcccc tggcaaggcc   1920
cgggacagga aggcctacac ggtcctccta tacggaaacg gtccaggcta tgtgctcaag   1980
gacggcgccc ggccggatgt taccgagagc gagagcggga gccccgagta tcggcagcag   2040
tcagcagtgc ccctggacga agagacccac gcaggcgagg acgtggcggt gttcgcgcgc   2100
ggcccgcagg cgcacctggt tcacggcgtg caggagcaga ccttcatagc gcacgtcatg   2160
gccttcgccg cctgcctgga gccctacacc gcctgcgacc tggcgccccc cgccggcacc   2220
accgacgccg cgcacccgg                                                2239
```

<210> SEQ ID NO 8
<211> LENGTH: 225
<212> TYPE: DNA
<213> ORGANISM: Artificial Sequence
<220> FEATURE:
<223> OTHER INFORMATION: Nucleotide sequence of a 3' NTR.

<400> SEQUENCE: 8

```
tgaaggttgg ggtaaacact ccggcctctt aagccatttc ctgttttttt tttttttttt     60
tttttttttt tctttttttt tttctttcct ttccttcttt ttttcctttc tttttccctt    120
ctttaatggt ggctccatct tagccctagt cacggctagc tgtgaaaggt ccgtgagccg    180
catgactgca gagagtgctg atactggcct ctctgcagat catgt                    225
```

<210> SEQ ID NO 9
<211> LENGTH: 341
<212> TYPE: DNA
<213> ORGANISM: Artificial Sequence
<220> FEATURE:
<223> OTHER INFORMATION: Nucleotide sequence of a 5' NTR

<400> SEQUENCE: 9

```
gccagccccc tgatgggggc gacactccac catgaatcac tcccctgtga ggaactactg     60
tcttcacgca gaaagcgtct agccatggcg ttagtatgag tgtcgtgcag cctccaggac    120
ccccccctccc gggagagcca tagtggtctg cggaaccggt gagtacaccg gaattgccag   180
gacgaccggg tcctttcttg gataaacccg ctcaatgcct ggagatttgg gcgtgccccc    240
gcaagactgc tagccgagta gtgttgggtc gcgaaaggcc ttgtggtact gcctgatagg    300
gtgcttgcga gtgccccggg aggtctcgta gaccgtgcac c                        341
```

<210> SEQ ID NO 10
<211> LENGTH: 86
<212> TYPE: PRT
<213> ORGANISM: Artificial Sequence
<220> FEATURE:
<223> OTHER INFORMATION: HIV tat polypeptide

<400> SEQUENCE: 10

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Pro Pro Gln Gly Ser Gln Thr
```

```
                   50                  55                  60
His Gln Val Ser Leu Ser Lys Gln Pro Thr Ser Gln Ser Arg Gly Asp
 65                  70                  75                  80

Pro Thr Gly Pro Lys Glu
             85

<210> SEQ ID NO 11
<211> LENGTH: 9599
<212> TYPE: DNA
<213> ORGANISM: Artificial Sequence
<220> FEATURE:
<223> OTHER INFORMATION: genomic length hepatitis C virus, genotype 1a

<400> SEQUENCE: 11
gccagccccc tgatggggc gacactccac catgaatcac tccctgtga ggaactactg       60 tcttcacgca gaaagcgtct agccatggcg ttagtatgag tgtcgtgcag cctccaggac     120 ccccctccc gggagagcca tagtggtctg cggaaccggt gagtacaccg gaattgccag      180
gacgaccggg tcctttcttg gataaaccg ctcaatgcct ggagatttgg gcgtgccccc     240
gcaagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaacgt aacaccaacc gtcgcccaca ggacgtcaag ttccgggtg    420 gcggtcagat cgttggtgga gtttacttgt tgccgcgcag gggccctaga ttgggtgtgc    480
gcgcgacgag gaagacttcc gagcggtcgc aacctcgagg tagacgtcag cctatcccca    540
aggcacgtcg gcccgagggc aggacctggg ctcagcccgg gtaccttgg cccctctatg    600 gcaatgaggg ttgcgggtgg gcgggatggc tcctgtctcc ccgtggctct cggcctagct    660
ggggccccac agaccccccgg cgtaggtcgc gcaatttggg taaggtcatc gataccctta    720
cgtgcggctt cgccgacctc atggggtaca taccgctcgt cggcgcccct cttggaggcg    780
ctgccagggc cctggcgcat ggcgtccggg ttctggaaga cggcgtgaac tatgcaacag    840
ggaaccttcc tggttgctct ttctctatct tccttctggc cctgctctct tgcctgactg    900
tgcccgcttc agcctaccaa gtgcgcaatt cctcgggct ttaccatgtc accaatgatt    960
gccctaactc gagtattgtg tacgaggcgg ccgatgccat cctgcacact ccggggtgtg   1020
tcccttgcgt tcgcgagggt aacgcctcga ggtgttgggt ggcggtgacc ccacggtgg    1080 ccaccaggga cggcaaactc cccacaacgc agcttcgacg tcatatcgat ctgcttgtcg    1140
ggagcgccac cctctgctcg gccctctacg tgggggacct gtgcgggtct gtctttcttg    1200
ttggtcaact gtttaccttc tctcccaggc gccactggac gacgcaagac tgcaattgtt    1260
ctatctatcc cggccatata acgggtcatc gcatggcatg ggatatgatg atgaactggt    1320 ccctacggc agcgttggtg gtagctcagc tgctccggat cccacaagcc atcatggaca    1380
tgatcgctgg tgctcactgg ggagtcctgg cgggcatagc gtatttctcc atggtgggga    1440
actgggcgaa ggtcctggta gtgctgctgc tatttgccgg cgtcgacgcg gaaacccacg    1500
tcaccggggg aaatgccggc cgcaccacgg ctgggcttgt tggtctcctt acaccaggcg    1560
ccaagcagaa catccaactg atcaacacca acggcagttg gcacatcaat agcacggcct    1620
tgaattgcaa tgaaagcctt aacaccggct ggttagcagg gctcttctat caacacaaat    1680
tcaactcttc aggctgtcct gagaggttgg ccagctgccg acgccttacc gattttgccc    1740
agggctgggg tcctatcagt tatgccaacg gaagcggcct cgacgaacgc cctactgct    1800 ggcactaccc tccaagacct tgtggcattg tgccgcaaaa gagcgtgtgt ggcccggtat   1860
```

-continued

| | |
|---|---|
| attgcttcac tcccagcccc gtggtggtgg gaacgaccga caggtcgggc gcgcctacct | 1920 |
| acagctgggg tgcaaatgat acggatgtct tcgtccttaa caacaccagg ccaccgctgg | 1980 |
| gcaattggtt cggttgtacc tggatgaact caactggatt caccaaagtg tgcggagcgc | 2040 |
| ccccttgtgt catcggaggg gtgggcaaca acaccttgct ctgccccact gattgcttcc | 2100 |
| gcaaacatcc ggaagccaca tactctcggt gcggctccgg tccctggatt acacccaggt | 2160 |
| gcatggtcga ctacccgtat aggctttggc actatccttg taccatcaat tacaccatat | 2220 |
| tcaaagtcag gatgtacgtg ggaggggtcg agcacaggct ggaagcggcc tgcaactgga | 2280 |
| cgcggggcga acgctgtgat ctggaagaca gggacaggtc cgagctcagc ccgttgctgc | 2340 |
| tgtccaccac acagtggcag gtccttccgt gttctttcac gaccctgcca gccttgtcca | 2400 |
| ccggcctcat ccacctccac cagaacattg tggacgtgca gtacttgtac ggggtagggt | 2460 |
| caagcatcgc gtcctgggcc attaagtggg agtacgtcgt tctcctgttc cttctgcttg | 2520 |
| cagacgcgcg cgtctgctcc tgcttgtgga tgatgttact catatcccaa gcggaggcgg | 2580 |
| ctttggagaa cctcgtaata ctcaatgcag catccctggc cgggacgcac ggtcttgtgt | 2640 |
| ccttcctcgt gttcttctgc tttgcgtggt atctgaaggg taggtgggtg cccggagcgg | 2700 |
| tctacgccct ctacgggatg tggcctctcc tcctgctcct gctggcgttg cctcagcggg | 2760 |
| catacgcact ggacacggag gtggccgcgt cgtgtggcgg cgttgttctt gtcgggttaa | 2820 |
| tggcgctgac tctgtcgcca tattacaagc gctatatcag ctggtgcatg tggtggcttc | 2880 |
| agtattttct gaccagagta gaagcgcaac tgcacgtgtg ggttcccccc ctcaacgtcc | 2940 |
| gggggggggcg cgatgccgtc atcttactca tgtgtgtagt acacccgacc ctggtatttg | 3000 |
| acatcaccaa actactcctg gccatcttcg gaccccttgt gattcttcaa gccagttttgc | 3060 |
| ttaaagtccc ctacttcgtg cgcgttcaag gccttctccg gatctgcgcg ctagcgcgga | 3120 |
| agatagccgg aggtcattac gtgcaaatgg ccatcatcaa gttaggggcg cttactggca | 3180 |
| cctatgtgta taaccatctc acccctcttc gagactgggc gcacaacggc ctgcgagatc | 3240 |
| tggccgtggc tgtggaacca gtcgtcttct cccgaatgga gaccaagctc atcacgtggg | 3300 |
| gggcagatac cgccgcgtgc ggtgacatca tcaacggctt gccegtctct gcccgtaggg | 3360 |
| gccaggagat actgcttggg ccagccgacg gaatggtctc caaggggtgg aggttgctgg | 3420 |
| cgcccatcac ggcgtacgcc cagcagacga gaggcctcct agggtgtata atcaccagcc | 3480 |
| tgactggccg ggacaaaaac caagtggagg gtgaggtcca gatcgtgtca actgctaccc | 3540 |
| aaaccttcct ggcaacgtgc atcaatgggg tatgctggac tgtctaccac ggggccggaa | 3600 |
| cgaggaccat cgcatcaccc aagggtcctg tcatccagat gtataccaat gtggaccaag | 3660 |
| accttgtggg ctggccegct cctcaaggtt ccegctcatt gacaccctgt acctgcggct | 3720 |
| cctcggacct ttacctggtc acgaggcacg ccgatgtcat tcccgtgcgc cggcgaggtg | 3780 |
| atagcagggg tagcctgctt tcgccccggc ccatttccta cttgaaaggc cctcggggg | 3840 |
| gtccgctgtt gtgccccgcg ggacacgccg tgggcctatt cagggccgcg tgtgcacccc | 3900 |
| gtggagtggc taaagcggtg gactttatcc ctgtggagaa cctagggaca accatgagat | 3960 |
| ccccggtgtt cacggacaac tcctctccac cagcagtgcc ccagagcttc caggtggccc | 4020 |
| acctgcatgc tcccaccggc agcggtaaga gcaccaaggt cccggctgcg tacgcagccc | 4080 |
| agggctacaa ggtgttggtg ctcaacccct ctgttgctgc aacgctgggc tttggtgctt | 4140 |
| acatgtccaa ggcccatggg gttgatccta atatcaggac cggggtgaga acaattacca | 4200 |
| ctggcagccc catcacgtac tccacctacg gcaagttcct tgccgacggc gggtgctcag | 4260 |

```
gaggtgctta tgacataata atttgtgacg agtgccactc cacggatgcc acatccatct   4320
tgggcatcgg cactgtcctt gaccaagcag agactgcggg ggcgagactg gttgtgctcg   4380
ccactgctac ccctccgggc tccgtcactg tgtcccatcc taacatcgag gaggttgctc   4440
tgtccaccac cggagagatc ccctttacg gcaaggctat ccccctcgag gtgatcaagg    4500
ggggaagaca tctcatcttc tgccactcaa agaagaagtg cgacgagctc gccgcgaagc   4560
tggtcgcatt gggcatcaat gccgtggcct actaccgcgg tcttgacgtg tctgtcatcc   4620
cgaccagcgg cgatgttgtc gtcgtgtcga ccgatgctct catgactggc tttaccggcg   4680
acttcgactc tgtgatagac tgcaacacgt gtgtcactca gacagtcgat ttcagccttg   4740
accctacctt taccattgag acaaccacgc tcccccagga tgctgtctcc aggactcaac   4800
gccggggcag gactggcagg gggaagccag gcatctatag atttgtggca ccggggagc    4860
gcccctccgg catgttcgac tcgtccgtcc tctgtgagtg ctatgacgcg ggctgtgctt   4920
ggtatgagct cacgcccgcc gagactacag ttaggctacg agcgtacatg aacaccccgg   4980
ggcttcccgt gtgccaggac catcttgaat tttgggaggg cgtctttacg ggcctcactc   5040
atatagatgc ccactttta tcccagacaa agcagagtgg ggagaacttt ccttacctgg    5100
tagcgtacca agccaccgtg tgcgctaggg ctcaagcccc tcccccatcg tgggaccaga   5160
tgtggaagtt tttgatccgc cttaaaccca ccctccatgg gccaacaccc ctgctataca   5220
gactgggcgc tgttcagaat gaagtcaccc tgacgcaccc aatcaccaaa tacatcatga   5280
catgcatgtc ggccgacctg gaggtcgtca cgagcacctg ggtgctcgtt ggcggcgtcc   5340
tggctgctct ggccgcgtat tgcctgtcaa caggctgcgt ggtcatagtg ggcaggatcg   5400
tcttgtccgg gaagccggca attataccta cagggaggt tctctaccag gagttcgatg    5460
agatggaaga gtgctctcag cacttaccgt acatcgagca agggatgatg ctcgctgagc   5520
agttcaagca gaaggccctc ggcctcctgc agaccgcgtc cgccatgca gaggttatca    5580
cccctgctgt ccagaccaac tggcagaaac tcgaggtctt tgggcgaag cacatgtgga    5640
atttcatcag tggatacaa tacttggcgg gcctgtcaac gctgcctggt aaccccgcca    5700
ttgcttcatt gatggcttt acagctgccg tcaccagccc actaaccact ggccaaaccc    5760
tcctcttcaa catattgggg gggtgggtgg ctgcccagct cgccgccccc ggtgccgcta   5820
ctgccttgt gggtgctggc ctagctgcg ccgccatcgg cagcgttgga ctggggaagg    5880
tcctcgtgga cattcttgca gggtatggcg cgggcgtggc gggagctctt gtagcattca   5940
agatcatgag cggtgaggtc ccctccacgg aggacctggt caatctgctg cccgccatcc   6000
tctcgcctgg agcccttgta gtcggtgtgg tctgcgcagc aatactgcgc cggcacgttg   6060
gcccgggcga gggggcagtg caatggatga accggctaat agccttcgcc tcccggggga   6120
accatgtttc ccccacgcac tacgtgccgg agagcgatgc agccgcccgc gtcactgcca   6180
tactcagcag cctcactgta acccagctcc tgaggcgact gcatcagtgg ataagctcgg   6240
agtgtaccac tccatgctcc ggttcctggc taagggacat ctgggactgg atatgcgagg   6300
tgctgagcga ctttaagacc tggctgaaag ccaagctcat gccacaactg cctgggattc   6360
cctttgtgtc ctgccagcgc gggtataggg gggtctggcg aggagacggc attatgcaca   6420
ctcgctgcca ctgtggagct gagatcactg gacatgtcaa aaacgggacg atgaggatcg   6480
tcggtcctag gacctgcagg aacatgtgga gtgggacgtt cccattaac gcctacacca   6540
cgggcccctg tactcccctt cctgcgccga ctataagtt cgcgctgtgg agggtgtctg   6600
cagaggaata cgtggagata aggcgggtgg gggacttcca ctacgtatcg ggtatgacta   6660
```

-continued

```
ctgacaatct taaatgcccg tgccagatcc catcgcccga attttttcaca gaattggacg    6720 gggtgcgcct acacaggttt gcgccccctt gcaagccctt gctgcgggag gaggtatcat    6780
tcagagtagg actccacgag tacccggtgg ggtcgcaatt accttgcgag cccgaaccgg    6840
acgtagccgt gttgacgtcc atgctcactg atccctccca tataacagca gaggcggccg    6900
ggagaaggtt ggcgagaggg tcaccccctt ctatggccag ctcctcggct agccagctgt    6960
ccgctccatc tctcaaggca acttgcaccg ccaaccatga ctcccctgac gccgagctca    7020
tagaggctaa cctcctgtgg aggcaggaga tgggcggcaa catcaccagg gttgagtcag    7080
agaacaaagt ggtgattctg gactccttcg atccgcttgt ggcagaggag gatgagcggg    7140
aggtctccgt acctgcagaa attctgcgga agtctcggag attcgcccgg gccctgcccg    7200
tctgggcgcg gccggactac aacccccgc tagtagagac gtggaaaaag cctgactacg    7260
aaccacctgt ggtccatggc tgcccgctac cacctccacg gtccctcct gtgcctccgc    7320 ctcggaaaaa gcgtacggtg gtcctcaccg aatcaaccct atctactgcc ttggccgagc    7380
ttgccaccaa aagttttggc agctcctcaa cttccggcat tacgggcgac aatacgacaa    7440
catcctctga gcccgcccct tctggctgcc ccccgactc cgacgttgag tcctattctt    7500
ccatgccccc cctggagggg gagcctgggg atccggatct cagcgacggg tcatggtcga    7560
cggtcagtag tgggggccgac acggaagatg tcgtgtgctg ctcaatgtct tattcctgga    7620
caggcgcact cgtcaccccg tgcgctgcgg aagaacaaaa actgcccatc aacgcactga    7680
gcaactcgtt gctacgccat cacaatctgg tgtattccac cacttcacgc agtgcttgcc    7740
aaaggcagaa gaaagtcaca tttgacagac tgcaagttct ggacagccat taccaggacg    7800
tgctcaagga ggtcaaagca gcggcgtcaa aagtgaaggc taacttgcta tccgtagagg    7860
aagcttgcag cctgacgccc ccacattcag ccaaatccaa gtttggctat ggggcaaaag    7920
acgtccgttg ccatgccaga aaggccgtag cccacatcaa ctccgtgtgg aaagaccttc    7980
tggaagacag tgtaacacca atagacacta ccatcatggc caagaacgag gttttctgcg    8040
ttcagcctga gaagggggt cgtaagccaa ctcgtctcat cgtgttcccc gacctgggcg    8100
tgcgcgtgtg cgagaagatg gccctgtacg acgtggttag caagctcccc ctggccgtga    8160
tgggaagctc ctacggattc caatactcac caggacagcg ggttgaattc ctcgtgcaag    8220
cgtggaagtc caagaagacc ccgatggggt tctcgtatga tacccgctgt tttgactcca    8280
cagtcactga gagcgacatc cgtacggagg aggcaattta ccaatgttgt gacctggacc    8340
cccaagcccg cgtggccatc aagtccctca ctgagaggct ttatgttggg ggccctctta    8400
ccaattcaag gggggaaaac tgcggctacc gcaggtgccg cgcgagcggc gtactgacaa    8460
ctagctgtgg taacaccctc acttgctaca tcaaggcccg ggcagcctgt cgagccgcag    8520
ggctccagga ctgcaccatg ctcgtgtgtg gcgacgactt agtcgttatc tgtgaaagtg    8580
cgggggtcca ggaggacgcg gcgagcctga gagccttcac ggaggctatg accaggtact    8640
ccgccccccc cggggacccc ccacaaccag aatacgactt ggagcttata acatcatgct    8700
cctccaacgt gtcagtcgcc cacgacgcg ctggaaagag ggtctactac cttacccgtg    8760
accctacaac cccctcgcg agagccgcgt gggagacagc aagcacact ccagtcaatt    8820 cctggctagg caacataatc atgtttgccc ccacactgtg ggcgaggatg atactgatga    8880
cccatttctt tagcgtcctc atagccaggg atcagcttga acaggctctt aactgtgaga    8940 tctacgagc ctgctactcc atagaaccac tggatctacc tccaatcatt caaagactcc    9000
atggcctcag cgcattttca ctccacagtt actctccagg tgaaatcaat agggtggccg    9060
```

```
catgcctcag aaaacttggg gtcccgccct tgcgagcttg agacaccgg gcccggagcg      9120 tccgcgctag gcttctgtcc agaggaggca gggctgccat atgtggcaag tacctcttca      9180
actgggcagt aagaacaaag ctcaaactca ctccaatagc ggccgctggc cggctggact      9240
tgtccggttg gttcacggct ggctacagcg ggggagacat ttatcacagc gtgtctcatg      9300
cccggccccg ctggttctgg ttttgcctac tcctgctcgc tgcaggggta ggcatctacc      9360
tcctccccaa ccgatgaagg ttggggtaaa cactccggcc tcttaagcca tttcctgttt      9420
tttttttttt tttttttttt tttttctttt tttttttctt tcctttcctt ctttttttcc      9480 tttcttttc ccttctttaa tggtggctcc atcttagccc tagtcacggc tagctgtgaa        9540
aggtccgtga gccgcatgac tgcagagagt gctgatactg gcctctctgc agatcatgt       9599
```

<210> SEQ ID NO 12
<211> LENGTH: 3011
<212> TYPE: PRT
<213> ORGANISM: Artificial Sequence
<220> FEATURE:
<223> OTHER INFORMATION: HCV polyprotein encoded by the coding region
      present in SEQ ID NO:11.

<400> SEQUENCE: 12

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270
```

```
Ser Ala Leu Tyr Val Gly Asp Leu Cys Gly Ser Val Phe Leu Val Gly
            275                 280                 285

Gln Leu Phe Thr Phe Ser Pro Arg Arg His Trp Thr Thr Gln Asp Cys
290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
                340                 345                 350

Trp Gly Val Leu Ala Gly Ile Ala Tyr Phe Ser Met Val Gly Asn Trp
            355                 360                 365

Ala Lys Val Leu Val Val Leu Leu Leu Phe Ala Gly Val Asp Ala Glu
370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
            435                 440                 445

Ser Ser Gly Cys Pro Glu Arg Leu Ala Ser Cys Arg Arg Leu Thr Asp
450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Arg Pro Cys Gly Ile
                485                 490                 495

Val Pro Ala Lys Ser Val Cys Gly Pro Val Tyr Cys Phe Thr Pro Ser
                500                 505                 510

Pro Val Val Val Gly Thr Thr Asp Arg Ser Gly Ala Pro Thr Tyr Ser
            515                 520                 525

Trp Gly Ala Asn Asp Thr Asp Val Phe Val Leu Asn Asn Thr Arg Pro
530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Val Gly Asn
                565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
            595                 600                 605

Val Asp Tyr Pro Tyr Arg Leu Trp His Tyr Pro Cys Thr Ile Asn Tyr
610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
                660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700
```

-continued

```
Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Arg Trp Val Pro
    770                 775                 780

Gly Ala Val Tyr Ala Leu Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
        835                 840                 845

Phe Leu Thr Arg Val Glu Ala Gln Leu His Val Trp Val Pro Pro Leu
    850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910

Val Arg Val Gln Gly Leu Arg Ile Cys Ala Leu Ala Arg Lys Ile
        915                 920                 925

Ala Gly Gly His Tyr Val Gln Met Ala Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Gln
        995                 1000                1005

Glu Ile Leu Leu Gly Pro Ala Asp Gly Met Val Ser Lys Gly Trp
    1010                1015                1020

Arg Leu Leu Ala Pro Ile Thr Ala Tyr Ala Gln Gln Thr Arg Gly
    1025                1030                1035

Leu Leu Gly Cys Ile Ile Thr Ser Leu Thr Gly Arg Asp Lys Asn
    1040                1045                1050

Gln Val Glu Gly Glu Val Gln Ile Val Ser Thr Ala Thr Gln Thr
    1055                1060                1065

Phe Leu Ala Thr Cys Ile Asn Gly Val Cys Trp Thr Val Tyr His
    1070                1075                1080

Gly Ala Gly Thr Arg Thr Ile Ala Ser Pro Lys Gly Pro Val Ile
    1085                1090                1095

Gln Met Tyr Thr Asn Val Asp Gln Asp Leu Val Gly Trp Pro Ala
    1100                1105                1110

Pro Gln Gly Ser Arg Ser Leu Thr Pro Cys Thr Cys Gly Ser Ser
```

-continued

```
        1115                1120                1125

Asp Leu Tyr Leu Val Thr Arg His Ala Asp Val Ile Pro Val Arg
        1130                1135                1140

Arg Arg Gly Asp Ser Arg Gly Ser Leu Leu Ser Pro Arg Pro Ile
        1145                1150                1155

Ser Tyr Leu Lys Gly Ser Ser Gly Gly Pro Leu Leu Cys Pro Ala
        1160                1165                1170

Gly His Ala Val Gly Leu Phe Arg Ala Ala Val Cys Thr Arg Gly
        1175                1180                1185

Val Ala Lys Ala Val Asp Phe Ile Pro Val Glu Asn Leu Gly Thr
        1190                1195                1200

Thr Met Arg Ser Pro Val Phe Thr Asp Asn Ser Ser Pro Pro Ala
        1205                1210                1215

Val Pro Gln Ser Phe Gln Val Ala His Leu His Ala Pro Thr Gly
        1220                1225                1230

Ser Gly Lys Ser Thr Lys Val Pro Ala Ala Tyr Ala Ala Gln Gly
        1235                1240                1245

Tyr Lys Val Leu Val Leu Asn Pro Ser Val Ala Ala Thr Leu Gly
        1250                1255                1260

Phe Gly Ala Tyr Met Ser Lys Ala His Gly Val Asp Pro Asn Ile
        1265                1270                1275

Arg Thr Gly Val Arg Thr Ile Thr Thr Gly Ser Pro Ile Thr Tyr
        1280                1285                1290

Ser Thr Tyr Gly Lys Phe Leu Ala Asp Gly Gly Cys Ser Gly Gly
        1295                1300                1305

Ala Tyr Asp Ile Ile Ile Cys Asp Glu Cys His Ser Thr Asp Ala
        1310                1315                1320

Thr Ser Ile Leu Gly Ile Gly Thr Val Leu Asp Gln Ala Glu Thr
        1325                1330                1335

Ala Gly Ala Arg Leu Val Val Leu Ala Thr Ala Thr Pro Pro Gly
        1340                1345                1350

Ser Val Thr Val Ser His Pro Asn Ile Glu Glu Val Ala Leu Ser
        1355                1360                1365

Thr Thr Gly Glu Ile Pro Phe Tyr Gly Lys Ala Ile Pro Leu Glu
        1370                1375                1380

Val Ile Lys Gly Gly Arg His Leu Ile Phe Cys His Ser Lys Lys
        1385                1390                1395

Lys Cys Asp Glu Leu Ala Ala Lys Leu Val Ala Leu Gly Ile Asn
        1400                1405                1410

Ala Val Ala Tyr Tyr Arg Gly Leu Asp Val Ser Val Ile Pro Thr
        1415                1420                1425

Ser Gly Asp Val Val Val Ser Thr Asp Ala Leu Met Thr Gly
        1430                1435                1440

Phe Thr Gly Asp Phe Asp Ser Val Ile Asp Cys Asn Thr Cys Val
        1445                1450                1455

Thr Gln Thr Val Asp Phe Ser Leu Asp Pro Thr Phe Thr Ile Glu
        1460                1465                1470

Thr Thr Thr Leu Pro Gln Asp Ala Val Ser Arg Thr Gln Arg Arg
        1475                1480                1485

Gly Arg Thr Gly Arg Gly Lys Pro Gly Ile Tyr Arg Phe Val Ala
        1490                1495                1500

Pro Gly Glu Arg Pro Ser Gly Met Phe Asp Ser Ser Val Leu Cys
        1505                1510                1515
```

```
Glu Cys Tyr Asp Ala Gly Cys Ala Trp Tyr Glu Leu Thr Pro Ala
1520                1525                1530

Glu Thr Thr Val Arg Leu Arg Ala Tyr Met Asn Thr Pro Gly Leu
1535                1540                1545

Pro Val Cys Gln Asp His Leu Glu Phe Trp Glu Gly Val Phe Thr
1550                1555                1560

Gly Leu Thr His Ile Asp Ala His Phe Leu Ser Gln Thr Lys Gln
1565                1570                1575

Ser Gly Glu Asn Phe Pro Tyr Leu Val Ala Tyr Gln Ala Thr Val
1580                1585                1590

Cys Ala Arg Ala Gln Ala Pro Pro Pro Ser Trp Asp Gln Met Trp
1595                1600                1605

Lys Cys Leu Ile Arg Leu Lys Pro Thr Leu His Gly Pro Thr Pro
1610                1615                1620

Leu Leu Tyr Arg Leu Gly Ala Val Gln Asn Glu Val Thr Leu Thr
1625                1630                1635

His Pro Ile Thr Lys Tyr Ile Met Thr Cys Met Ser Ala Asp Leu
1640                1645                1650

Glu Val Val Thr Ser Thr Trp Val Leu Val Gly Gly Val Leu Ala
1655                1660                1665

Ala Leu Ala Ala Tyr Cys Leu Ser Thr Gly Cys Val Val Ile Val
1670                1675                1680

Gly Arg Ile Val Leu Ser Gly Lys Pro Ala Ile Ile Pro Asp Arg
1685                1690                1695

Glu Val Leu Tyr Gln Glu Phe Asp Glu Met Glu Glu Cys Ser Gln
1700                1705                1710

His Leu Pro Tyr Ile Glu Gln Gly Met Met Leu Ala Glu Gln Phe
1715                1720                1725

Lys Gln Lys Ala Leu Gly Leu Leu Gln Thr Ala Ser Arg His Ala
1730                1735                1740

Glu Val Ile Thr Pro Ala Val Gln Thr Asn Trp Gln Lys Leu Glu
1745                1750                1755

Val Phe Trp Ala Lys His Met Trp Asn Phe Ile Ser Gly Ile Gln
1760                1765                1770

Tyr Leu Ala Gly Leu Ser Thr Leu Pro Gly Asn Pro Ala Ile Ala
1775                1780                1785

Ser Leu Met Ala Phe Thr Ala Ala Val Thr Ser Pro Leu Thr Thr
1790                1795                1800

Gly Gln Thr Leu Leu Phe Asn Ile Leu Gly Gly Trp Val Ala Ala
1805                1810                1815

Gln Leu Ala Ala Pro Gly Ala Ala Thr Ala Phe Val Gly Ala Gly
1820                1825                1830

Leu Ala Gly Ala Ala Ile Gly Ser Val Gly Leu Gly Lys Val Leu
1835                1840                1845

Val Asp Ile Leu Ala Gly Tyr Gly Ala Gly Val Ala Gly Ala Leu
1850                1855                1860

Val Ala Phe Lys Ile Met Ser Gly Glu Val Pro Ser Thr Glu Asp
1865                1870                1875

Leu Val Asn Leu Leu Pro Ala Ile Leu Ser Pro Gly Ala Leu Val
1880                1885                1890

Val Gly Val Val Cys Ala Ala Ile Leu Arg Arg His Val Gly Pro
1895                1900                1905

Gly Glu Gly Ala Val Gln Trp Met Asn Arg Leu Ile Ala Phe Ala
1910                1915                1920
```

```
Ser Arg Gly Asn His Val Ser Pro Thr His Tyr Val Pro Glu Ser
    1925            1930                1935

Asp Ala Ala Ala Arg Val Thr Ala Ile Leu Ser Ser Leu Thr Val
    1940            1945                1950

Thr Gln Leu Leu Arg Arg Leu His Gln Trp Ile Ser Ser Glu Cys
    1955            1960                1965

Thr Thr Pro Cys Ser Gly Ser Trp Leu Arg Asp Ile Trp Asp Trp
    1970            1975                1980

Ile Cys Glu Val Leu Ser Asp Phe Lys Thr Trp Leu Lys Ala Lys
    1985            1990                1995

Leu Met Pro Gln Leu Pro Gly Ile Pro Phe Val Ser Cys Gln Arg
    2000            2005                2010

Gly Tyr Arg Gly Val Trp Arg Gly Asp Gly Ile Met His Thr Arg
    2015            2020                2025

Cys His Cys Gly Ala Glu Ile Thr Gly His Val Lys Asn Gly Thr
    2030            2035                2040

Met Arg Ile Val Gly Pro Arg Thr Cys Arg Asn Met Trp Ser Gly
    2045            2050                2055

Thr Phe Pro Ile Asn Ala Tyr Thr Thr Gly Pro Cys Thr Pro Leu
    2060            2065                2070

Pro Ala Pro Asn Tyr Lys Phe Ala Leu Trp Arg Val Ser Ala Glu
    2075            2080                2085

Glu Tyr Val Glu Ile Arg Arg Val Gly Asp Phe His Tyr Val Ser
    2090            2095                2100

Gly Met Thr Thr Asp Asn Leu Lys Cys Pro Cys Gln Ile Pro Ser
    2105            2110                2115

Pro Glu Phe Phe Thr Glu Leu Asp Gly Val Arg Leu His Arg Phe
    2120            2125                2130

Ala Pro Pro Cys Lys Pro Leu Leu Arg Glu Glu Val Ser Phe Arg
    2135            2140                2145

Val Gly Leu His Glu Tyr Pro Val Gly Ser Gln Leu Pro Cys Glu
    2150            2155                2160

Pro Glu Pro Asp Val Ala Val Leu Thr Ser Met Leu Thr Asp Pro
    2165            2170                2175

Ser His Ile Thr Ala Glu Ala Ala Gly Arg Arg Leu Ala Arg Gly
    2180            2185                2190

Ser Pro Pro Ser Met Ala Ser Ser Ser Ala Ser Gln Leu Ser Ala
    2195            2200                2205

Pro Ser Leu Lys Ala Thr Cys Thr Ala Asn His Asp Ser Pro Asp
    2210            2215                2220

Ala Glu Leu Ile Glu Ala Asn Leu Leu Trp Arg Gln Glu Met Gly
    2225            2230                2235

Gly Asn Ile Thr Arg Val Glu Ser Glu Asn Lys Val Val Ile Leu
    2240            2245                2250

Asp Ser Phe Asp Pro Leu Val Ala Glu Glu Asp Glu Arg Glu Val
    2255            2260                2265

Ser Val Pro Ala Glu Ile Leu Arg Lys Ser Arg Arg Phe Ala Arg
    2270            2275                2280

Ala Leu Pro Val Trp Ala Arg Pro Asp Tyr Asn Pro Pro Leu Val
    2285            2290                2295

Glu Thr Trp Lys Lys Pro Asp Tyr Glu Pro Pro Val Val His Gly
    2300            2305                2310

Cys Pro Leu Pro Pro Pro Arg Ser Pro Pro Val Pro Pro Pro Arg
```

```
    2315                2320                2325

Lys Lys  Arg Thr Val Val Leu  Thr Glu Ser Thr Leu  Ser Thr Ala
    2330                2335                2340

Leu Ala  Glu Leu Ala Thr Lys  Ser Phe Gly Ser Ser  Ser Thr Ser
    2345                2350                2355

Gly Ile  Thr Gly Asp Asn Thr  Thr Thr Ser Ser Glu  Pro Ala Pro
    2360                2365                2370

Ser Gly  Cys Pro Pro Asp Ser  Asp Val Glu Ser Tyr  Ser Ser Met
    2375                2380                2385

Pro Pro  Leu Glu Gly Glu Pro  Gly Asp Pro Asp Leu  Ser Asp Gly
    2390                2395                2400

Ser Trp  Ser Thr Val Ser Ser  Gly Ala Asp Thr Glu  Asp Val Val
    2405                2410                2415

Cys Cys  Ser Met Ser Tyr Ser  Trp Thr Gly Ala Leu  Val Thr Pro
    2420                2425                2430

Cys Ala  Ala Glu Glu Gln Lys  Leu Pro Ile Asn Ala  Leu Ser Asn
    2435                2440                2445

Ser Leu  Leu Arg His His Asn  Leu Val Tyr Ser Thr  Thr Ser Arg
    2450                2455                2460

Ser Ala  Cys Gln Arg Gln Lys  Lys Val Thr Phe Asp  Arg Leu Gln
    2465                2470                2475

Val Leu  Asp Ser His Tyr Gln  Asp Val Leu Lys Glu  Val Lys Ala
    2480                2485                2490

Ala Ala  Ser Lys Val Lys Ala  Asn Leu Leu Ser Val  Glu Glu Ala
    2495                2500                2505

Cys Ser  Leu Thr Pro Pro His  Ser Ala Lys Ser Lys  Phe Gly Tyr
    2510                2515                2520

Gly Ala  Lys Asp Val Arg Cys  His Ala Arg Lys Ala  Val Ala His
    2525                2530                2535

Ile Asn  Ser Val Trp Lys Asp  Leu Leu Glu Asp Ser  Val Thr Pro
    2540                2545                2550

Ile Asp  Thr Thr Ile Met Ala  Lys Asn Glu Val Phe  Cys Val Gln
    2555                2560                2565

Pro Glu  Lys Gly Gly Arg Lys  Pro Ala Arg Leu Ile  Val Phe Pro
    2570                2575                2580

Asp Leu  Gly Val Arg Val Cys  Glu Lys Met Ala Leu  Tyr Asp Val
    2585                2590                2595

Val Ser  Lys Leu Pro Leu Ala  Val Met Gly Ser Ser  Tyr Gly Phe
    2600                2605                2610

Gln Tyr  Ser Pro Gly Gln Arg  Val Glu Phe Leu Val  Gln Ala Trp
    2615                2620                2625

Lys Ser  Lys Lys Thr Pro Met  Gly Phe Ser Tyr Asp  Thr Arg Cys
    2630                2635                2640

Phe Asp  Ser Thr Val Thr Glu  Ser Asp Ile Arg Thr  Glu Glu Ala
    2645                2650                2655

Ile Tyr  Gln Cys Cys Asp Leu  Asp Pro Gln Ala Arg  Val Ala Ile
    2660                2665                2670

Lys Ser  Leu Thr Glu Arg Leu  Tyr Val Gly Gly Pro  Leu Thr Asn
    2675                2680                2685

Ser Arg  Gly Glu Asn Cys Gly  Tyr Arg Arg Cys Arg  Ala Ser Gly
    2690                2695                2700

Val Leu  Thr Thr Ser Cys Gly  Asn Thr Leu Thr Cys  Tyr Ile Lys
    2705                2710                2715
```

| | | | | | | | | | | |
|---|---|---|---|---|---|---|---|---|---|---|
| Ala | Arg | Ala | Ala | Cys | Arg | Ala | Ala | Gly | Leu | Gln | Asp | Cys | Thr | Met |
| | 2720 | | | | 2725 | | | | 2730 | |
| Leu | Val | Cys | Gly | Asp | Asp | Leu | Val | Val | Ile | Cys | Glu | Ser | Ala | Gly |
| | 2735 | | | | 2740 | | | | 2745 | |
| Val | Gln | Glu | Asp | Ala | Ala | Ser | Leu | Arg | Ala | Phe | Thr | Glu | Ala | Met |
| | 2750 | | | | 2755 | | | | 2760 | |
| Thr | Arg | Tyr | Ser | Ala | Pro | Pro | Gly | Asp | Pro | Pro | Gln | Pro | Glu | Tyr |
| | 2765 | | | | 2770 | | | | 2775 | |
| Asp | Leu | Glu | Leu | Ile | Thr | Ser | Cys | Ser | Ser | Asn | Val | Ser | Val | Ala |
| | 2780 | | | | 2785 | | | | 2790 | |
| His | Asp | Gly | Ala | Gly | Lys | Arg | Val | Tyr | Tyr | Leu | Thr | Arg | Asp | Pro |
| | 2795 | | | | 2800 | | | | 2805 | |
| Thr | Thr | Pro | Leu | Ala | Arg | Ala | Ala | Trp | Glu | Thr | Ala | Arg | His | Thr |
| | 2810 | | | | 2815 | | | | 2820 | |
| Pro | Val | Asn | Ser | Trp | Leu | Gly | Asn | Ile | Ile | Met | Phe | Ala | Pro | Thr |
| | 2825 | | | | 2830 | | | | 2835 | |
| Leu | Trp | Ala | Arg | Met | Ile | Leu | Met | Thr | His | Phe | Phe | Ser | Val | Leu |
| | 2840 | | | | 2845 | | | | 2850 | |
| Ile | Ala | Arg | Asp | Gln | Leu | Glu | Gln | Ala | Leu | Asn | Cys | Glu | Ile | Tyr |
| | 2855 | | | | 2860 | | | | 2865 | |
| Gly | Ala | Cys | Tyr | Ser | Ile | Glu | Pro | Leu | Asp | Leu | Pro | Pro | Ile | Ile |
| | 2870 | | | | 2875 | | | | 2880 | |
| Gln | Arg | Leu | His | Gly | Leu | Ser | Ala | Phe | Ser | Leu | His | Ser | Tyr | Ser |
| | 2885 | | | | 2890 | | | | 2895 | |
| Pro | Gly | Glu | Ile | Asn | Arg | Val | Ala | Ala | Cys | Leu | Arg | Lys | Leu | Gly |
| | 2900 | | | | 2905 | | | | 2910 | |
| Val | Pro | Pro | Leu | Arg | Ala | Trp | Arg | His | Arg | Ala | Arg | Ser | Val | Arg |
| | 2915 | | | | 2920 | | | | 2925 | |
| Ala | Arg | Leu | Leu | Ser | Arg | Gly | Gly | Arg | Ala | Ala | Ile | Cys | Gly | Lys |
| | 2930 | | | | 2935 | | | | 2940 | |
| Tyr | Leu | Phe | Asn | Trp | Ala | Val | Arg | Thr | Lys | Leu | Lys | Leu | Thr | Pro |
| | 2945 | | | | 2950 | | | | 2955 | |
| Ile | Ala | Ala | Ala | Gly | Arg | Leu | Asp | Leu | Ser | Gly | Trp | Phe | Thr | Ala |
| | 2960 | | | | 2965 | | | | 2970 | |
| Gly | Tyr | Ser | Gly | Gly | Asp | Ile | Tyr | His | Ser | Val | Ser | His | Ala | Arg |
| | 2975 | | | | 2980 | | | | 2985 | |
| Pro | Arg | Trp | Phe | Trp | Phe | Cys | Leu | Leu | Leu | Leu | Ala | Ala | Gly | Val |
| | 2990 | | | | 2995 | | | | 3000 | |
| Gly | Ile | Tyr | Leu | Leu | Pro | Asn | Arg | | | | | | | |
| | 3005 | | | | 3010 | | | | | |

<210> SEQ ID NO 13
<211> LENGTH: 11240
<212> TYPE: DNA
<213> ORGANISM: Artificial Sequence
<220> FEATURE:
<223> OTHER INFORMATION: nucleotide sequence of Htat2ANeo

<400> SEQUENCE: 13

```
gccagccccc tgatgggggc gacactccac catgaatcac tccctgtga ggaactactg      60
tcttcacgca gaaagcgtct agccatggcg ttagtatgag tgtcgtgcag cctccaggac    120
ccccctccc gggagagcca tagtggtctg cggaaccggt gagtacaccg gaattgccag    180
gacgaccggg tcctttcttg ataaacccg ctcaatgcct ggagatttgg gcgtgccccc    240
gcaagactgc tagccgagta gtgttgggtc gcgaaaggcc ttgtggtact gcctgatagg    300
```

```
gtgcttgcga gtgccccggg aggtctcgta gaccgtgcac catggagcca gtagatccta    360
gactagagcc ctggaagcat ccaggaagtc agcctaaaac tgcttgtacc aattgctatt    420
gtaaaaagtg ttgctttcat tgccaagttt gtttcataac aaaagcctta ggcatctcct    480
atggcaggaa gaagcggaga cagcgacgaa gacctcctca aggcagtcag actcatcaag    540
tttctctatc aaagcaaccc acctcccaat cccgagggga cccgacaggc ccgaaggaag    600
aattcgacct tcttaagctt gcgggagacg tcgagtccaa ccctgggccc ggatctgtta    660
acatgattga acaagatgga ttgcacgcag gttctccggc cgcttgggtg gagaggctat    720
tcggctatga ctgggcacaa cagacaatcg gctgctctga tgccgccgtg ttccggctgt    780
cagcgcaggg gcgcccggtt cttttgtca agaccgacct gtccggtgcc ctgaatgaac    840
tgcaggacga ggcagcgcgg ctatcgtggc tggccacgac gggcgttcct tgcgcagctg    900
tgctcgacgt tgtcactgaa gcgggaaggg actggctgct attgggcgaa gtgccggggc    960
aggatctcct gtcatctcac cttgctcctg ccgagaaagt atccatcatg gctgatgcaa   1020
tgcggcggct gcatacgctt gatccggcta cctgcccatt cgaccaccaa gcgaaacatc   1080
gcatcgagcg agcacgtact cggatggaag ccggtcttgt cgatcaggat gatctggacg   1140
aagagcatca ggggctcgcg ccagccgaac tgttcgccag gctcaaggcg cgcatgcccg   1200
acggcgagga tctcgtcgtg acccatggcg atgcctgctt gccgaatatc atggtggaaa   1260
atggccgctt ttctggattc atcgactgtg gccggctggg tgtggcggac cgctatcagg   1320
acatagcgtt ggctacccgt gatattgctg aagagcttgg cggcgaatgg gctgaccgct   1380
tcctcgtgct ttacggtatc gccgctcccg attcgcagcg catcgccttc tatcgccttc   1440
ttgacgagtt cttctgagtt taaacagacc acaacggttt ccctctagcg ggatcaattc   1500
cgcccctctc cctccccccc ccctaacgtt actggccgaa gccgcttgga ataaggccgg   1560
tgtgcgtttg tctatatgtt attttccacc atattgccgt cttttggcaa tgtgagggcc   1620
cggaaacctg gccctgtctt cttgacgagc attcctaggg gtctttcccc tctcgccaaa   1680
ggaatgcaag gtctgttgaa tgtcgtgaag gaagcagttc ctctggaagc ttcttgaaga   1740
caaacaacgt ctgtagcgac cctttgcagg cagcggaacc ccccacctgg cgacaggtgc   1800
ctctgcggcc aaaagccacg tgtataagat acacctgcaa aggcggcaca accccagtgc   1860
cacgttgtga gttggatagt tgtggaaaga gtcaaatggc tctcctcaag cgtattcaac   1920
aaggggctga aggatgccca gaaggtaccc cattgtatgg gatctgatct ggggcctcgg   1980
tgcacatgct ttacatgtgt ttagtcgagg ttaaaaaacg tctaggcccc ccgaaccacg   2040
gggacgtggt tttcctttga aaaacacgat aataccatgg cgcccatcac ggcgtacgcc   2100
cagcagacga gaggcctcct agggtgtata atcaccagcc tgactggccg ggacaaaaac   2160
caagtggagg gtgaggtcca gatcgtgtca actgctaccc aaaccttcct ggcaacgtgc   2220
atcaatgggg tatgctggac tgtctaccac ggggccggaa cgaggaccat cgcatcaccc   2280
aagggtcctg tcatccagat gtataccaat gtggaccaag accttgtggg ctggcccgct   2340
cctcaaggtt cccgctcatt gacaccctgt acctgcggct cctcggacct ttacctggtc   2400
acgaggcacg ccgatgtcat tcccgtgcgc cggcgaggtg atagcagggg tagcctgctt   2460
tcgcccggc ccatttccta cttgaaaggc tcctcggggg gtccgctgtt gtgccccgcg   2520
ggacacgccg tgggcctatt cagggccgcg gtgtgcaccc gtggagtggc taaagcggtg   2580
gactttatcc ctgtggagaa cctagggaca accatgagat ccccggtgtt cacggacaac   2640
tcctctccac cagcagtgcc ccagagcttc caggtggccc acctgcatgc tcccaccggc   2700
```

```
agcggtaaga gcaccaaggt cccggctgcg tacgcagccc agggctacaa ggtgttggtg    2760
ctcaacccct ctgttgctgc aacgctgggc tttggtgctt acatgtccaa ggcccatggg    2820
gttgatccta atatcaggac cggggtgaga acaattacca ctggcagccc catcacgtac    2880
tccacctacg gcaagttcct tgccgacggc gggtgctcag gaggtgctta tgacataata    2940
atttgtgacg agtgccactc cacggatgcc acatccatct tgggcatcgg cactgtcctt    3000
gaccaagcag agactgcggg ggcgagactg gttgtgctcg ccactgctac ccctccgggc    3060
tccgtcactg tgtcccatcc taacatcgag gaggttgctc tgtccaccac cggagagatc    3120 ccctttttacg gcaaggctat cccctcgag gtgatcaagg ggggaagaca tctcatcttc    3180
tgccactcaa agaagaagtg cgacgagctc gccgcgaagc tggtcgcatt gggcatcaat    3240
gccgtggcct actaccgcgg tcttgacgtg tctgtcatcc cgaccagcgg cgatgttgtc    3300
gtcgtgtcga ccgatgctct catgactggc tttaccggcg acttcgactc tgtgatagac    3360
tgcaacacgt gtgtcactca gacagtcgat ttcagccttg accctacctt taccattgag    3420
acaaccacgc tcccccagga tgctgtctcc aggactcaac gccggggcag gactggcagg    3480
gggaagccag gcatctatag atttgtggca ccggggagc gcccctccgg catgttcgac    3540
tcgtccgtcc tctgtgagtg ctatgacgcg ggctgtgctt ggtatgagct cacgcccgcc    3600
gagactacag ttaggctacg agcgtacatg aacaccccgg ggcttcccgt gtgccaggac    3660
catcttgaat tttgggaggg cgtctttacg ggcctcactc atatagatgc ccactttttta    3720 tcccagacaa agcagagtgg ggagaacttt ccttacctgg tagcgtacca agccaccgtg    3780
tgcgctaggg ctcaagcccc tccccccatcg tgggaccaga tgtggaagtg tttgatccgc    3840
cttaaaccca ccctccatgg gccaacaccc ctgctataca gactgggcgc tgttcagaat    3900
gaagtcaccc tgacgcaccc aatcaccaaa tacatcatga catgcatgtc ggccgacctg    3960
gaggtcgtca cgagcacctg ggtgctcgtt ggcggcgtcc tggctgctct ggccgcgtat    4020
tgcctgtcaa caggctgcgt ggtcatagtg gcaggatcg tcttgtccgg gaagccggca    4080
attatacctg acagggaggt tctctaccag gagttcgatg agatggaaga gtgctctcag    4140
cacttaccgt acatcgagca agggatgatg ctcgctgagc agttcaagca gaaggccctc    4200
ggcctcctgc agaccgcgtc ccgccatgca gaggttatca cccctgctgt ccagaccaac    4260
tggcagaaac tcgaggtctt tgggcgaag cacatgtgga atttcatcag tgggatacaa    4320
tacttggcgg gcctgtcaac gctgcctggt aaccccgcca ttgcttcatt gatggctttt    4380
acagctgccg tcaccagccc actaaccact ggccaaaccc tcctcttcaa catattgggg    4440
gggtgggtgg ctgcccagct cgccgccccc ggtgccgcta ctgcctttgt gggtgctggc    4500
ctagctggcg ccgccatcgg cagcgttgga ctggggaagg tcctcgtgga cattcttgca    4560
gggtatggcg cgggcgtggc gggagctctt gtagcattca agatcatgag cggtgaggtc    4620
ccctccacgg aggacctggt caatctgctg ccgccatcc tctcgcctgg agcccttgta    4680
gtcggtgtgg tctgcgcagc aatactgcgc cggcacgttg gcccgggcga ggggcagtg    4740 caatggatga accggctaat agccttcgcc tcccggggga accatgtttc ccccacgcac    4800
tacgtgccgg agagcgatgc agccgcccgc gtcactgcca tactcagcag cctcactgta    4860
acccagctcc tgaggcgact gcatcagtgg ataagctcgg agtgtaccac tccatgctcc    4920
ggttcctggc taagggacat ctgggactgg atatgcgagg tgctgagcga ctttaagacc    4980
tggctgaaag ccaagctcat gccacaactg cctgggattc cctttgtgtc ctgccagcgc    5040
gggtataggg gggtctggcg aggagacggc attatgcaca ctcgctgcca ctgtggagct    5100
```

-continued

```
gagatcactg gacatgtcaa aaacgggacg atgaggatcg tcggtcctag gacctgcagg      5160
aacatgtgga gtgggacgtt ccccattaac gcctacacca cgggcccctg tactcccctt      5220
cctgcgccga actataagtt cgcgctgtgg agggtgtctg cagaggaata cgtggagata      5280
aggcgggtgg gggacttcca ctacgtatcg ggtatgacta ctgacaatct taaatgcccg      5340
tgccagatcc catcgcccga atttttcaca gaattggacg gggtgcgcct acacaggttt      5400 gcgcccctt gcaagccctt gctgcgggag gaggtatcat tcagagtagg actccacgag      5460
tacccggtgg ggtcgcaatt accttgcgag cccgaaccgg acgtagccgt gttgacgtcc      5520
atgctcactg atccctccca tataacagca gaggcggccg ggagaaggtt ggcgagaggg      5580
tcaccccctt ctatggccag ctcctcggct agccagctgt ccgctccatc tctcaaggca      5640
acttgcaccg ccaaccatga ctcccctgac gccgagctca tagaggctaa cctcctgtgg      5700
aggcaggaga tgggcggcaa catcaccagg gttgagtcag agaacaaagt ggtgattctg      5760
gactccttcg atccgcttgt ggcagaggag gatgagcggg aggtctccgt acctgcagaa      5820
attctgcgga agtctcggag attcgcccgg gccctgcccg tctgggcgcg gccggactac      5880
aaccccccgc tagtagagac gtggaaaaag cctgactacg aaccacctgt ggtccatggc      5940
tgcccgctac cacctccacg gtcccctcct gtgcctccgc ctcggaaaaa gcgtacggtg      6000
gtcctcaccg aatcaaccct atctactgcc ttggccgagc ttgccaccaa agttttggc      6060 agctcctcaa cttccggcat tacgggcgac aatacgacaa catcctctga gcccgcccct      6120
tctggctgcc cccccgactc cgacgttgag tcctattctt ccatgccccc cctggagggg      6180
gagcctgggg atccggatct cagcgacggg tcatggtcga cggtcagtag tggggccgac      6240
acggaagatg tcgtgtgctg ctcaatgtct tattcctgga caggcgcact cgtcaccccg      6300
tgcgctgcgg aagaacaaaa actgcccatc aacgcactga gcaactcgtt gctacgccat      6360
cacaatctgg tgtattccac cacttcacgc agtgcttgcc aaaggcagaa gaaagtcaca      6420
tttgacagac tgcaagttct ggacagccat taccaggacg tgctcaagga ggtcaaagca      6480
gcggcgtcaa aagtgaaggc taacttgcta tccgtagagg aagcttgcag cctgacgccc      6540
ccacattcag ccaaatccaa gtttggctat ggggcaaaag acgtccgttg ccatgccaga      6600
aaggccgtag cccacatcaa ctccgtgtgg aaagaccttc tggaagacag tgtaacacca      6660
atagacacta ccatcatggc caagaacgag gtttctgcg ttcagcctga aaggggggt       6720 cgtaagccag ctcgtctcat cgtgttcccc gacctgggcg tgcgcgtgtg cgagaagatg      6780
gccctgtacg acgtggttag caagctcccc ctggccgtga tgggaagctc ctacggattc      6840
caatactcac caggacagcg ggttgaattc ctcgtgcaag cgtggaagtc caagaagacc      6900
ccgatggggt tctcgtatga tacccgctgt tttgactcca cagtcactga gagcgacatc      6960
cgtacggagg aggcaatta ccaatgttgt gacctggacc cccaagcccg cgtggccatc       7020
aagtccctca ctgagaggct ttatgttggg ggccctctta ccaattcaag gggggaaaac      7080
tgcggctacc gcaggtgccg cgcgagcggc gtactgacaa ctagctgtgg taacaccctc      7140
acttgctaca tcaaggcccg ggcagcctgt cgagccgcag ggctccagga ctgcaccatg      7200
ctcgtgtgtg gcgacgactt agtcgttatc tgtgaaagtg cgggggtcca ggaggacgcg      7260
gcgagcctga gagccttcac ggaggctatg accaggtact ccgcccccc cggggacccc      7320 ccacaaccag aatacgactt ggagcttata acatcatgct cctccaacgt gtcagtcgcc      7380
cacgacggcg ctgaaagag ggtctactac cttacccgtg accctacaac ccccctcgcg      7440
agagccgcgt gggagacagc aagacacact ccagtcaatt cctggctagg caacataatc      7500
```

```
atgtttgccc ccacactgtg ggcgaggatg atactgatga cccatttctt tagcgtcctc    7560
atagccaggg atcagcttga acaggctctt aactgtgaga tctacggagc ctgctactcc    7620
atagaaccac tggatctacc tccaatcatt caaagactcc atggcctcag cgcattttca    7680
ctccacagtt actctccagg tgaaatcaat agggtggccg catgcctcag aaaacttggg    7740
gtcccgccct tgcgagcttg agacaccgg  gcccggagcg tccgcgctag gcttctgtcc    7800
agaggaggca gggctgccat atgtggcaag tacctcttca actgggcagt aagaacaaag    7860
ctcaaactca ctccaatagc ggccgctggc cggctggact tgtccggttg gttcacggct    7920
ggctacagcg ggggagacat ttatcacagc gtgtctcatg cccggccccg ctggttctgg    7980
ttttgcctac tcctgctcgc tgcaggggta ggcatctacc tcctccccaa ccgatgaagg    8040
ttggggtaaa cactccggcc tcttaagcca tttcctgttt ttttttttt tttttttttt    8100 ttttctttt ttttttttctt tcctttcctt cttttttcc tttcttttc ccttctttaa    8160 tggtggctcc atcttagccc tagtcacggc tagctgtgaa aggtccgtga ccgcatgac    8220 tgcagagagt gctgatactg gcctctctgc agatcatgtg ggtcggcatg gcatctccac    8280
ctcctcgcgg tccgacctgg gcatccgaag gaggacgcac gtccactcgg atggctaagg    8340
gagtctagac tggaattcgt cgacgagctc cctatagtga gtcgtattag aggccgactt    8400
ggccaaattc gtaatcatgg tcatagctgt ttcctgtgtg aaattgttat ccgctcacaa    8460
ttccacacaa catacgagcc ggaagcataa agtgtaaagc ctggggtgcc taatgagtga    8520
gctaactcac attaattgcg ttgcgctcac tgcccgcttt ccagtcggga aacctgtcgt    8580
gccagctgca ttaatgaatc ggccaacgcg cggggagagg cggtttgcgt attgggcgct    8640
cttccgcttc ctcgctcact gactcgctgc gctcggtcgt tcggctgcgg cgagcggtat    8700
cagctcactc aaaggcggta atacggttat ccacagaatc aggggataac gcaggaaaga    8760
acatgtgagc aaaaggccag caaaaggcca ggaaccgtaa aaaggccgcg ttgctggcgt    8820
ttttccatag gctccgcccc cctgacgagc atcacaaaaa tcgacgctca agtcagaggt    8880
ggcgaaaccc gacaggacta taaagatacc aggcgtttcc ccctggaagc tccctcgtgc    8940
gctctcctgt tccgaccctg ccgcttaccg gatacctgtc cgcctttctc ccttcgggaa    9000
gcgtggcgct ttctcatagc tcacgctgta ggtatctcag ttcggtgtag tcgttcgct    9060 ccaagctggg ctgtgtgcac gaaccccccg ttcagcccga ccgctgcgcc ttatccggta    9120
actatcgtct tgagtccaac ccggtaagac acgacttatc gccactggca gcagccactg    9180
gtaacaggat tagcagagcg aggtatgtag gcggtgctac agagttcttg aagtggtggc    9240
ctaactacgg ctacactaga aggacagtat ttggtatctg cgctctgctg aagccagtta    9300
ccttcggaaa aagagttggt agctcttgat ccggcaaaca aaccaccgct ggtagcggtg    9360
gtttttttgt ttgcaagcag cagattacgc gcagaaaaaa aggatctcaa gaagatcctt    9420
tgatcttttc tacggggtct gacgctcagt ggaacgaaaa ctcacgttaa gggattttgg    9480
tcatgagatt atcaaaaagg atcttcacct agatcctttt aaattaaaaa tgaagtttta    9540
aatcaatcta agtatatat  gagtaaactt ggtctgacag ttaccaatgc ttaatcagtg    9600
aggcacctat ctcagcgatc tgtctatttc gttcatccat agttgcctga ctccccgtcg    9660
tgtagataac tacgatacgg gagggcttac catctggccc cagtgctgca atgataccgc    9720
gagacccacg ctcaccggct ccagatttat cagcaataaa ccagccagcc ggaagggccg    9780
agcgcagaag tggtcctgca actttatccg cctccatcca gtctattaat tgttgccggg    9840
aagctagagt aagtagttcg ccagttaata gtttgcgcaa cgttgttgcc attgctacag    9900
```

-continued

```
gcatcgtggt gtcacgctcg tcgtttggta tggcttcatt cagctccggt tcccaacgat    9960
caaggcgagt tacatgatcc cccatgttgt gcaaaaaagc ggttagctcc ttcggtcctc   10020
cgatcgttgt cagaagtaag ttggccgcag tgttatcact catggttatg cagcactgc    10080 ataattctct tactgtcatg ccatccgtaa gatgcttttc tgtgactggt gagtactcaa   10140
ccaagtcatt ctgagaatag tgtatgcggc gaccgagttg ctcttgcccg cgtcaatac    10200 gggataatac cgcgccacat agcagaactt taaaagtgct catcattgga aaacgttctt   10260
cggggcgaaa actctcaagg atcttaccgc tgttgagatc cagttcgatg taacccactc   10320
gtgcacccaa ctgatcttca gcatctttta ctttcaccag cgtttctggg tgagcaaaaa   10380
caggaaggca aaatgccgca aaaaagggaa taagggcgac acggaaatgt tgaatactca   10440
tactcttcct ttttcaatat tattgaagca tttatcaggg ttattgtctc atgagcggat   10500
acatatttga atgtatttag aaaaataaac aaataggggt tccgcgcaca tttccccgaa   10560
aagtgccacc tgacgcgccc tgtagcgcg cattaagcgc ggcgggtgtg gtggttacgc    10620
gcagcgtgac cgctacactt gccagcgccc tagcgcccgc tcctttcgct ttcttccctt   10680
cctttctcgc cacgttcgcc ggctttcccc gtcaagctct aaatcggggc atccctttag   10740
ggttccgatt tagtgcttta cggcacctcg accccaaaaa acttgattag ggtgatggtt   10800
cacgtagtgg gccatcgccc tgatagacgg ttttcgccc tttgacgttg gagtccacgt    10860
tctttaatag tggactcttg ttccaaactg gaacaacact caaccctatc tcggtctatt   10920
cttttgattt ataagggatt ttgccgattt cggcctattg gttaaaaaat gagctgattt   10980
aacaaaaatt taacgcgaat tttaacaaaa tattaacaaa atattaacgt ttacaatttc   11040
ccattcgcca ttcaggctgc gcaactgttg ggaagggcga tcggtgcggg cctcttcgct   11100
attacgccag ctggcgaaag ggggatgtgc tgcaaggcga ttaagttggg taacgccagg   11160
gttttcccag tcacgacgtt gtaaaacgac ggccagtgcc aagctgactt ggtcagcggc   11220
cgctaatacg actcactata                                                11240
```

<210> SEQ ID NO 14
<211> LENGTH: 1986
<212> TYPE: PRT
<213> ORGANISM: Artificial Sequence
<220> FEATURE:
<223> OTHER INFORMATION: HCV polyprotein encoded by the coding region present in SEQ ID NO:13.

<400> SEQUENCE: 14

```
Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Thr Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ser Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125
```

```
Ser Pro Arg Pro Ile Ser Tyr Leu Lys Gly Ser Ser Gly Pro Leu
    130                 135                 140

Leu Cys Pro Ala Gly His Ala Val Gly Leu Phe Arg Ala Ala Val Cys
145                 150                 155                 160

Thr Arg Gly Val Ala Lys Ala Val Asp Phe Ile Pro Val Glu Asn Leu
                165                 170                 175

Gly Thr Thr Met Arg Ser Pro Val Phe Thr Asp Asn Ser Ser Pro Pro
                180                 185                 190

Ala Val Pro Gln Ser Phe Gln Val Ala His Leu His Ala Pro Thr Gly
                195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Val Asp Pro Asn Ile Arg Thr Gly
                245                 250                 255

Val Arg Thr Ile Thr Thr Gly Ser Pro Ile Thr Tyr Ser Thr Tyr Gly
                260                 265                 270

Lys Phe Leu Ala Asp Gly Gly Cys Ser Gly Gly Ala Tyr Asp Ile Ile
    275                 280                 285

Ile Cys Asp Glu Cys His Ser Thr Asp Ala Thr Ser Ile Leu Gly Ile
290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Ser His Pro Asn
                325                 330                 335

Ile Glu Glu Val Ala Leu Ser Thr Thr Gly Ile Pro Phe Tyr Gly
                340                 345                 350

Lys Ala Ile Pro Leu Glu Val Ile Lys Gly Gly Arg His Leu Ile Phe
    355                 360                 365

Cys His Ser Lys Lys Lys Cys Asp Glu Leu Ala Ala Lys Leu Val Ala
    370                 375                 380

Leu Gly Ile Asn Ala Val Ala Tyr Tyr Arg Gly Leu Asp Val Ser Val
385                 390                 395                 400

Ile Pro Thr Ser Gly Asp Val Val Val Ser Thr Asp Ala Leu Met
                405                 410                 415

Thr Gly Phe Thr Gly Asp Phe Asp Ser Val Ile Asp Cys Asn Thr Cys
                420                 425                 430

Val Thr Gln Thr Val Asp Phe Ser Leu Asp Pro Thr Phe Thr Ile Glu
    435                 440                 445

Thr Thr Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
                500                 505                 510

Arg Leu Arg Ala Tyr Met Asn Thr Pro Gly Leu Pro Val Cys Gln Asp
    515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Phe Pro Tyr
```

```
                545                 550                 555                 560
Leu Val Ala Tyr Gln Ala Thr Val Cys Ala Arg Ala Gln Ala Pro Pro
                    565                 570                 575

Pro Ser Trp Asp Gln Met Trp Lys Cys Leu Ile Arg Leu Lys Pro Thr
                580                 585                 590

Leu His Gly Thr Pro Leu Leu Tyr Arg Leu Gly Ala Val Gln Asn
            595                 600                 605

Glu Val Thr Leu Thr His Pro Ile Thr Lys Tyr Ile Met Thr Cys Met
610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
                660                 665                 670

Arg Glu Val Leu Tyr Gln Glu Phe Asp Glu Met Glu Glu Cys Ser Gln
            675                 680                 685

His Leu Pro Tyr Ile Glu Gln Gly Met Met Leu Ala Glu Gln Phe Lys
            690                 695                 700

Gln Lys Ala Leu Gly Leu Leu Gln Thr Ala Ser Arg His Ala Glu Val
705                 710                 715                 720

Ile Thr Pro Ala Val Gln Thr Asn Trp Gln Lys Leu Glu Val Phe Trp
                725                 730                 735

Ala Lys His Met Trp Asn Phe Ile Ser Gly Ile Gln Tyr Leu Ala Gly
                740                 745                 750

Leu Ser Thr Leu Pro Gly Asn Pro Ala Ile Ala Ser Leu Met Ala Phe
            755                 760                 765

Thr Ala Ala Val Thr Ser Pro Leu Thr Thr Gly Gln Thr Leu Leu Phe
770                 775                 780

Asn Ile Leu Gly Gly Trp Val Ala Ala Gln Leu Ala Ala Pro Gly Ala
785                 790                 795                 800

Ala Thr Ala Phe Val Gly Ala Gly Leu Ala Gly Ala Ala Ile Gly Ser
                805                 810                 815

Val Gly Leu Gly Lys Val Leu Val Asp Ile Leu Ala Gly Tyr Gly Ala
                820                 825                 830

Gly Val Ala Gly Ala Leu Val Ala Phe Lys Ile Met Ser Gly Glu Val
            835                 840                 845

Pro Ser Thr Glu Asp Leu Val Asn Leu Leu Pro Ala Ile Leu Ser Pro
850                 855                 860

Gly Ala Leu Val Val Gly Val Val Cys Ala Ala Ile Leu Arg Arg His
865                 870                 875                 880

Val Gly Pro Gly Glu Gly Ala Val Gln Trp Met Asn Arg Leu Ile Ala
                885                 890                 895

Phe Ala Ser Arg Gly Asn His Val Ser Pro Thr His Tyr Val Pro Glu
            900                 905                 910

Ser Asp Ala Ala Ala Arg Val Thr Ala Ile Leu Ser Ser Leu Thr Val
            915                 920                 925

Thr Gln Leu Leu Arg Arg Leu His Gln Trp Ile Ser Ser Glu Cys Thr
            930                 935                 940

Thr Pro Cys Ser Gly Ser Trp Leu Arg Asp Ile Trp Asp Trp Ile Cys
945                 950                 955                 960

Glu Val Leu Ser Asp Phe Lys Thr Trp Leu Lys Ala Lys Leu Met Pro
                965                 970                 975
```

-continued

```
Gln Leu Pro Gly Ile Pro Phe Val Ser Cys Gln Arg Gly Tyr Arg Gly
            980                 985                 990

Val Trp Arg Gly Asp Gly Ile Met His Thr Arg Cys His Cys Gly Ala
        995                1000                1005

Glu Ile Thr Gly His Val Lys Asn Gly Thr Met Arg Ile Val Gly
    1010                1015                1020

Pro Arg Thr Cys Arg Asn Met Trp Ser Gly Thr Phe Pro Ile Asn
    1025                1030                1035

Ala Tyr Thr Thr Gly Pro Cys Thr Pro Leu Pro Ala Pro Asn Tyr
    1040                1045                1050

Lys Phe Ala Leu Trp Arg Val Ser Ala Glu Glu Tyr Val Glu Ile
    1055                1060                1065

Arg Arg Val Gly Asp Phe His Tyr Val Ser Gly Met Thr Thr Asp
    1070                1075                1080

Asn Leu Lys Cys Pro Cys Gln Ile Pro Ser Pro Glu Phe Phe Thr
    1085                1090                1095

Glu Leu Asp Gly Val Arg Leu His Arg Phe Ala Pro Pro Cys Lys
    1100                1105                1110

Pro Leu Leu Arg Glu Glu Val Ser Phe Arg Val Gly Leu His Glu
    1115                1120                1125

Tyr Pro Val Gly Ser Gln Leu Pro Cys Glu Pro Glu Pro Asp Val
    1130                1135                1140

Ala Val Leu Thr Ser Met Leu Thr Asp Pro Ser His Ile Thr Ala
    1145                1150                1155

Glu Ala Ala Gly Arg Arg Leu Ala Arg Gly Ser Pro Pro Ser Met
    1160                1165                1170

Ala Ser Ser Ser Ala Ser Gln Leu Ser Ala Pro Ser Leu Lys Ala
    1175                1180                1185

Thr Cys Thr Ala Asn His Asp Ser Pro Asp Ala Glu Leu Ile Glu
    1190                1195                1200

Ala Asn Leu Leu Trp Arg Gln Glu Met Gly Gly Asn Ile Thr Arg
    1205                1210                1215

Val Glu Ser Glu Asn Lys Val Val Ile Leu Asp Ser Phe Asp Pro
    1220                1225                1230

Leu Val Ala Glu Glu Asp Glu Arg Glu Val Ser Val Pro Ala Glu
    1235                1240                1245

Ile Leu Arg Lys Ser Arg Arg Phe Ala Arg Ala Leu Pro Val Trp
    1250                1255                1260

Ala Arg Pro Asp Tyr Asn Pro Pro Leu Val Glu Thr Trp Lys Lys
    1265                1270                1275

Pro Asp Tyr Glu Pro Pro Val His Gly Cys Pro Leu Pro Pro
    1280                1285                1290

Pro Arg Ser Pro Pro Val Pro Pro Arg Lys Lys Arg Thr Val
    1295                1300                1305

Val Leu Thr Glu Ser Thr Leu Ser Thr Ala Leu Ala Glu Leu Ala
    1310                1315                1320

Thr Lys Ser Phe Gly Ser Ser Ser Thr Ser Gly Ile Thr Gly Asp
    1325                1330                1335

Asn Thr Thr Thr Ser Ser Glu Pro Ala Pro Ser Gly Cys Pro Pro
    1340                1345                1350

Asp Ser Asp Val Glu Ser Tyr Ser Ser Met Pro Pro Leu Glu Gly
    1355                1360                1365

Glu Pro Gly Asp Pro Asp Leu Ser Asp Gly Ser Trp Ser Thr Val
    1370                1375                1380
```

```
Ser Ser Gly Ala Asp Thr Glu Asp Val Val Cys Cys Ser Met Ser
    1385            1390            1395

Tyr Ser Trp Thr Gly Ala Leu Val Thr Pro Cys Ala Ala Glu Glu
    1400            1405            1410

Gln Lys Leu Pro Ile Asn Ala Leu Ser Asn Ser Leu Leu Arg His
    1415            1420            1425

His Asn Leu Val Tyr Ser Thr Thr Ser Arg Ser Ala Cys Gln Arg
    1430            1435            1440

Gln Lys Lys Val Thr Phe Asp Arg Leu Gln Val Leu Asp Ser His
    1445            1450            1455

Tyr Gln Asp Val Leu Lys Glu Val Lys Ala Ala Ser Lys Val
    1460            1465            1470

Lys Ala Asn Leu Leu Ser Val Glu Glu Ala Cys Ser Leu Thr Pro
    1475            1480            1485

Pro His Ser Ala Lys Ser Lys Phe Gly Tyr Gly Ala Lys Asp Val
    1490            1495            1500

Arg Cys His Ala Arg Lys Ala Val Ala His Ile Asn Ser Val Trp
    1505            1510            1515

Lys Asp Leu Leu Glu Asp Ser Val Thr Pro Ile Asp Thr Thr Ile
    1520            1525            1530

Met Ala Lys Asn Glu Val Phe Cys Val Gln Pro Glu Lys Gly Gly
    1535            1540            1545

Arg Lys Pro Ala Arg Leu Ile Val Phe Pro Asp Leu Gly Val Arg
    1550            1555            1560

Val Cys Glu Lys Met Ala Leu Tyr Asp Val Val Ser Lys Leu Pro
    1565            1570            1575

Leu Ala Val Met Gly Ser Ser Tyr Gly Phe Gln Tyr Ser Pro Gly
    1580            1585            1590

Gln Arg Val Glu Phe Leu Val Gln Ala Trp Lys Ser Lys Lys Thr
    1595            1600            1605

Pro Met Gly Phe Ser Tyr Asp Thr Arg Cys Phe Asp Ser Thr Val
    1610            1615            1620

Thr Glu Ser Asp Ile Arg Thr Glu Glu Ala Ile Tyr Gln Cys Cys
    1625            1630            1635

Asp Leu Asp Pro Gln Ala Arg Val Ala Ile Lys Ser Leu Thr Glu
    1640            1645            1650

Arg Leu Tyr Val Gly Gly Pro Leu Thr Asn Ser Arg Gly Glu Asn
    1655            1660            1665

Cys Gly Tyr Arg Arg Cys Arg Ala Ser Gly Val Leu Thr Thr Ser
    1670            1675            1680

Cys Gly Asn Thr Leu Thr Cys Tyr Ile Lys Ala Arg Ala Ala Cys
    1685            1690            1695

Arg Ala Ala Gly Leu Gln Asp Cys Thr Met Leu Val Cys Gly Asp
    1700            1705            1710

Asp Leu Val Val Ile Cys Glu Ser Ala Gly Val Gln Glu Asp Ala
    1715            1720            1725

Ala Ser Leu Arg Ala Phe Thr Glu Ala Met Thr Arg Tyr Ser Ala
    1730            1735            1740

Pro Pro Gly Asp Pro Pro Gln Pro Glu Tyr Asp Leu Glu Leu Ile
    1745            1750            1755

Thr Ser Cys Ser Ser Asn Val Ser Val Ala His Asp Gly Ala Gly
    1760            1765            1770

Lys Arg Val Tyr Tyr Leu Thr Arg Asp Pro Thr Thr Pro Leu Ala
```

-continued

```
             1775                1780                1785
Arg Ala Ala Trp Glu Thr Ala Arg His Thr Pro Val Asn Ser Trp
    1790                1795                1800

Leu Gly Asn Ile Ile Met Phe Ala Pro Thr Leu Trp Ala Arg Met
    1805                1810                1815

Ile Leu Met Thr His Phe Phe Ser Val Leu Ile Ala Arg Asp Gln
    1820                1825                1830

Leu Glu Gln Ala Leu Asn Cys Glu Ile Tyr Gly Ala Cys Tyr Ser
    1835                1840                1845

Ile Glu Pro Leu Asp Leu Pro Pro Ile Ile Gln Arg Leu His Gly
    1850                1855                1860

Leu Ser Ala Phe Ser Leu His Ser Tyr Ser Pro Gly Glu Ile Asn
    1865                1870                1875

Arg Val Ala Ala Cys Leu Arg Lys Leu Gly Val Pro Pro Leu Arg
    1880                1885                1890

Ala Trp Arg His Arg Ala Arg Ser Val Arg Ala Arg Leu Leu Ser
    1895                1900                1905

Arg Gly Gly Arg Ala Ala Ile Cys Gly Lys Tyr Leu Phe Asn Trp
    1910                1915                1920

Ala Val Arg Thr Lys Leu Lys Leu Thr Pro Ile Ala Ala Ala Gly
    1925                1930                1935

Arg Leu Asp Leu Ser Gly Trp Phe Thr Ala Gly Tyr Ser Gly Gly
    1940                1945                1950

Asp Ile Tyr His Ser Val Ser His Ala Arg Pro Arg Trp Phe Trp
    1955                1960                1965

Phe Cys Leu Leu Leu Leu Ala Ala Gly Val Gly Ile Tyr Leu Leu
    1970                1975                1980

Pro Asn Arg
    1985
```